US012435151B2

(12) United States Patent
Zhou et al.

(10) Patent No.: US 12,435,151 B2
(45) Date of Patent: Oct. 7, 2025

(54) ANTI-TNFR2 ANTIBODIES AND USES THEREOF

(71) Applicants: Merrimack Pharmaceuticals, Inc., Cambridge, MA (US); The Regents of the University of California, Oakland, CA (US)

(72) Inventors: Yu Zhou, San Francisco, CA (US); James D. Marks, Kensington, CA (US); Marco Muda, New Haven, CT (US); James Frank Sampson, Medford, MA (US); Eric M. Tam, Cooperstown, NY (US); Ross Bane Fulton, Southborough, MA (US)

(73) Assignee: Merrimack Pharmaceuticals, Inc., Massachusetts (MA)

( * ) Notice: Subject to any disclaimer, the term of this patent is extended or adjusted under 35 U.S.C. 154(b) by 1050 days.

(21) Appl. No.: 17/434,340

(22) PCT Filed: Feb. 28, 2020

(86) PCT No.: PCT/US2020/020456

§ 371 (c)(1),
(2) Date: Aug. 26, 2021

(87) PCT Pub. No.: WO2020/180712

PCT Pub. Date: Sep. 10, 2020

(65) Prior Publication Data

US 2022/0281990 A1 Sep. 8, 2022

Related U.S. Application Data

(60) Provisional application No. 62/902,164, filed on Sep. 18, 2019, provisional application No. 62/812,875, filed on Mar. 1, 2019.

(51) Int. Cl.

| | |
|---|---|
| ***C07K 16/28*** | (2006.01) |
| ***A61K 39/395*** | (2006.01) |
| ***A61K 47/42*** | (2017.01) |
| ***A61P 35/00*** | (2006.01) |
| ***A61P 37/00*** | (2006.01) |

(52) U.S. Cl.

CPC .......... *C07K 16/2878* (2013.01); *A61K 47/42* (2013.01); *A61P 35/00* (2018.01); *A61P 37/00* (2018.01); *C07K 2317/24* (2013.01); *C07K 2317/52* (2013.01); *C07K 2317/732* (2013.01); *C07K 2317/75* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 2018/0161370 | A1 | 6/2018 | Faustman |
| 2019/0135929 | A1 | 5/2019 | Faustman |

FOREIGN PATENT DOCUMENTS

| | | |
|---|---|---|
| KR | 20130126550 | 11/2013 |
| WO | 2016187068 | 11/2016 |
| WO | 2017040312 | 3/2017 |
| WO | 2017083525 | 5/2017 |

OTHER PUBLICATIONS

Li et al. (2024). Journal of Translational Medicine. 22(1):812; 19 pages.*

Medler (2019) "Tumor Expert Opinion on Therapeutic Targets", necrosis factor receptor—2 (TNFR2): an overview of an emerging drug target; pp. 295-307.

Raue et al. (2018) "MM-401: A novel antibody that targets TNFR2, a key regulator of the tumor immunosuppressive microenvironment" NCI Poster, 1 page.

Tam et al., (2019) "Antibody-mediated targeting of TNFR2 activates CD8+ T cells in mice and promotes antitumor immunity" Science Translational Medicine, pp. 1-15.

* cited by examiner

*Primary Examiner* — Christine J Saoud
*Assistant Examiner* — Jon M Lockard
(74) *Attorney, Agent, or Firm* — Brian E. Dayy; Bozicevic, Field & Francis LLP

(57) ABSTRACT

Disclosed herein are anti-TNFR2 antibodies, therapeutic compositions comprising the anti-TNFR2 antibodies, and methods of using such antibodies and compositions in the treatment of cancer and autoimmune diseases.

16 Claims, 67 Drawing Sheets

Specification includes a Sequence Listing.

| | $K_D$ (nM) |
|---|---|
| UC1 (S4-2 1B5) | 18.13 |
| UC1.1 (S4-2 1B5-1D9) | 2.59 |
| UC2 (S4-2 1D10) | 42.8 |
| UC2.3 (S4-2 1D10-1G9) | 8.88 |

PD-1 sensitive: Sa1/N (Sarcoma)

CT26

EMT6

Wehi164

A20

ANTI-TNFR2 ANTIBODIES AND USES THEREOF

RELATED APPLICATIONS

This application is a 35 U.S.C. 371 national stage filing of International Application No. PCT/US2020/020456, filed Feb. 28, 2020, which claims priority to, and the benefit of, U.S. Provisional Application 62/812,875, filed Mar. 1, 2019, and U.S. Provisional Application 62/902,164, filed Sep. 18, 2019. The contents of the aforementioned applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Aug. 26, 2021, is named MMJ_119US_Sequence_Listing.txt and is 268,295 bytes in size.

BACKGROUND

Recent studies have shown that enhancing the body's own ability to fight disease through the regulation of immune responses is an attractive alternative and/or complement to traditional therapeutic platforms. For example, studies have shown that enhancing the activity to T-lymphocytes to target and treat various diseases (e.g., cancer or infectious disease) is therapeutically beneficial. Inhibiting the ability of T-regulatory cells (Tregs) to suppress the activity of T-lymphocytes is one potential mechanism to increase immune responses against disease.

Tumor Necrosis Factor Receptor 2 (TNFR2), also known as TNFRSF1B and CD120b, is a co-stimulatory member of the tumor necrosis factor receptor superfamily (TNFRSF), which includes proteins such as GITR, OX40, CD27, CD40, and 4-1BB (CD137). TNFR2 is a cell-surface receptor that is expressed on T cells and has been shown to enhance the activation of effector T (Teff) cells and decrease Treg-mediated suppression. Through the regulation of TRAF2/3 and NF-kB signaling, TNFR2 can mediate the transcription of genes that promote cell survival and proliferation. TNFR2 can be expressed on cancer cells, tumor-infiltrating Tregs, and effector T cells. Given the ongoing need for improved strategies for targeting diseases such as cancer, benefits from enhanced immune responses, in particular, T cell responses, novel agents and methods that modulate Treg activity are highly desirable.

SUMMARY

Provided herein are isolated antibodies, such as recombinant monoclonal antibodies (e.g., human antibodies), that specifically bind to TNFR2 (e.g., human TNFR2) and have therapeutically desirable properties. Accordingly, the antibodies described herein can be used to, e.g., inhibit tumor growth, treat cancer, treat autoimmune diseases, treat graft-versus-host disease, and promote graft survival and/or reduce graft rejection.

In one embodiment, provided herein are antibodies (e.g., isolated monoclonal antibodies) which bind to human TNFR2 and comprise heavy and light chain CDRs of the heavy and light chain variable region pairs selected from the group consisting of:

(a) SEQ ID NOs: 48 and 49, respectively; [UC2.3]
(b) SEQ ID NOs: 71 and 72, respectively; [UC2.3.3]
(c) SEQ ID NOs: 94 and 95, respectively; [UC2.3.7]
(d) SEQ ID NOs: 117 and 118, respectively; [UC2.3.8]
(e) SEQ ID NOs: 140 and 141, respectively; [UC2.3.9]
(f) SEQ ID NOs: 163 and 164, respectively; [UC2.3.10]
(g) SEQ ID NOs: 186 and 187, respectively; [UC2.3.11]
(h) SEQ ID NOs: 209 and 210, respectively; [UC2.3.12]
(i) SEQ ID NOs: 232 and 233, respectively; [UC2.3.13]
(j) SEQ ID NOs: 255 and 256, respectively; [UC2.3.14]
(k) SEQ ID NOs: 278 and 279, respectively; [UC2.3.15]
(l) SEQ ID NOs: 301 and 302, respectively; [UC1]
(m) SEQ ID NOs: 322 and 323, respectively; [UC1.1]
(n) SEQ ID NOs: 343 and 344, respectively; [UC1.2]
(o) SEQ ID NOs: 364 and 364, respectively; [UC1.3]
(p) SEQ ID NOs: 25 and 26, respectively; [UC2]
(q) SEQ ID NOs: 385 and 386, respectively; [UC3]
(r) SEQ ID NOs: 406 and 407, respectively; [UC4]
(s) SEQ ID NOs: 427 and 428, respectively; [UC5]
(t) SEQ ID NOs: 448 and 449, respectively; [UC6]
(u) SEQ ID NOs: 469 and 470, respectively; [UC7] and
(v) SEQ ID NOs: 490 and 491, respectively. [UC8]

In another embodiment, provided herein are antibodies which bind to human TNFR2 and comprise:

(a) heavy chain CDR1, CDR2, and CDR3 sequences comprising SEQ ID NOs: 36-38, respectively, and light chain CDR1, CDR2, and CDR3 sequences comprising SEQ ID NOs: 39-41, respectively; [UC2.3]
(b) heavy chain CDR1, CDR2, and CDR3 sequences comprising SEQ ID NOs: 59-61, respectively, and light chain CDR1, CDR2, and CDR3 sequences comprising SEQ ID NOs: 62-64, respectively; [UC2.3.3]
(c) heavy chain CDR1, CDR2, and CDR3 sequences comprising SEQ ID NOs: 82-84, respectively, and light chain CDR1, CDR2, and CDR3 sequences comprising SEQ ID NOs: 85-87, respectively; [UC2.3.7]
(d) heavy chain CDR1, CDR2, and CDR3 sequences comprising SEQ ID NOs: 105-107, respectively, and light chain CDR1, CDR2, and CDR3 sequences comprising SEQ ID NOs: 108-110, respectively; [UC2.3.8]
(e) heavy chain CDR1, CDR2, and CDR3 sequences comprising SEQ ID NOs: 128-130, respectively, and light chain CDR1, CDR2, and CDR3 sequences comprising SEQ ID NOs: 131-133, respectively; [UC2.3.9]
(f) heavy chain CDR1, CDR2, and CDR3 sequences comprising SEQ ID NOs: 151-153, respectively, and light chain CDR1, CDR2, and CDR3 sequences comprising SEQ ID NOs: 154-156, respectively; [UC2.3.10]
(g) heavy chain CDR1, CDR2, and CDR3 sequences comprising SEQ ID NOs: 174-176, respectively, and light chain CDR1, CDR2, and CDR3 sequences comprising SEQ ID NOs: 177-179, respectively; [UC2.3.11]
(h) heavy chain CDR1, CDR2, and CDR3 sequences comprising SEQ ID NOs: 197-199, respectively, and light chain CDR1, CDR2, and CDR3 sequences comprising SEQ ID NOs: 200-202, respectively; [UC2.3.12]
(i) heavy chain CDR1, CDR2, and CDR3 sequences comprising SEQ ID NOs: 220-222, respectively, and light chain CDR1, CDR2, and CDR3 sequences comprising SEQ ID NOs: 223-225, respectively; [UC2.3.13]
(j) heavy chain CDR1, CDR2, and CDR3 sequences comprising SEQ ID NOs: 243-245, respectively, and light chain CDR1, CDR2, and CDR3 sequences comprising SEQ ID NOs: 246-248, respectively; [UC2.3.14]

(k) heavy chain CDR1, CDR2, and CDR3 sequences comprising SEQ ID NOs: 266-268, respectively, and light chain CDR1, CDR2, and CDR3 sequences comprising SEQ ID NOs: 269-271, respectively; [UC2.3.15]

(l) heavy chain CDR1, CDR2, and CDR3 sequences comprising SEQ ID NOs: 289-291, respectively, and light chain CDR1, CDR2, and CDR3 sequences comprising SEQ ID NOs: 292-294, respectively; [UC1]

(m) heavy chain CDR1, CDR2, and CDR3 sequences comprising SEQ ID NOs: 310-312, respectively, and light chain CDR1, CDR2, and CDR3 sequences comprising SEQ ID NOs: 313-315, respectively; [UC1.1]

(n) heavy chain CDR1, CDR2, and CDR3 sequences comprising SEQ ID NOs: 331-333, respectively, and light chain CDR1, CDR2, and CDR3 sequences comprising SEQ ID NOs: 334-336, respectively; [UC1.2]

(o) heavy chain CDR1, CDR2, and CDR3 sequences comprising SEQ ID NOs: 352-354, respectively, and light chain CDR1, CDR2, and CDR3 sequences comprising SEQ ID NOs: 355-357, respectively; [UC1.3]

(p) heavy chain CDR1, CDR2, and CDR3 sequences comprising SEQ ID NOs: 13-15, respectively, and light chain CDR1, CDR2, and CDR3 sequences comprising SEQ ID NOs: 16-18, respectively; [UC2]

(q) heavy chain CDR1, CDR2, and CDR3 sequences comprising SEQ ID NOs: 373-375, respectively, and light chain CDR1, CDR2, and CDR3 sequences comprising SEQ ID NOs: 376-378, respectively; [UC3]

(r) heavy chain CDR1, CDR2, and CDR3 sequences comprising SEQ ID NOs: 394-396, respectively, and light chain CDR1, CDR2, and CDR3 sequences comprising SEQ ID NOs: 397-399, respectively; [UC4]

(s) heavy chain CDR1, CDR2, and CDR3 sequences comprising SEQ ID NOs: 415-417, respectively, and light chain CDR1, CDR2, and CDR3 sequences comprising SEQ ID NOs: 418-420, respectively; [UC5]

(t) heavy chain CDR1, CDR2, and CDR3 sequences comprising SEQ ID NOs: 436-438, respectively, and light chain CDR1, CDR2, and CDR3 sequences comprising SEQ ID NOs: 439-441, respectively; [UC6]

(u) heavy chain CDR1, CDR2, and CDR3 sequences comprising SEQ ID NOs: 457-459, respectively, and light chain CDR1, CDR2, and CDR3 sequences comprising SEQ ID NOs: 460-462, respectively; or [UC7]

(v) heavy chain CDR1, CDR2, and CDR3 sequences comprising SEQ ID NOs: 478-480, respectively, and light chain CDR1, CDR2, and CDR3 sequences comprising SEQ ID NOs: 481-483, respectively. [UC8]

In another embodiment, provided herein are antibodies which bind to human TNFR2 and comprise a heavy chain variable region and a light chain variable region, wherein the heavy chain variable region comprises an amino acid sequence selected from the group consisting of SEQ ID NOs: 25, 48, 71, 94, 117, 140, 163, 186, 209, 232, 255, 278, 301, 322, 343, 364, 385, 406, 427, 448, 469, and 490, or an amino acid sequence which is at least 80% (e.g., at least 85%, 90%, 95%, 96%, 97%, 98%, or 99%) identical to an amino acid sequence selected from the group consisting of SEQ ID NOs: 25, 48, 71, 94, 117, 140, 163, 186, 209, 232, 255, 278, 301, 322, 343, 364, 385, 406, 427, 448, 469, and 490.

In another embodiment, provided herein are antibodies which bind to human TNFR2 and comprise a heavy chain variable region and a light chain variable region, wherein the light chain variable region comprises an amino acid sequence selected from the group consisting of SEQ ID NOs: 26, 49, 72, 95, 118, 141, 164, 187, 210, 233, 256, 279, 302, 323, 344, 365, 386, 407, 428, 449, 470, and 491, or an amino acid sequence which is at least 80% (e.g., at least 85%, 90%, 95%, 96%, 97%, 98%, or 99%) identical to an amino acid sequence selected from the group consisting of SEQ ID NOs: 26, 49, 72, 95, 118, 141, 164, 187, 210, 233, 256, 279, 302, 323, 344, 365, 386, 407, 428, 449, 470, and 491.

In another embodiment, provided herein are antibodies which bind to human TNFR2 and comprise a heavy chain variable region and a light chain variable region, wherein the heavy chain variable region comprises an amino acid sequence selected from the group consisting of SEQ ID NOs: 25, 48, 71, 94, 117, 140, 163, 186, 209, 232, 255, 278, 301, 322, 343, 364, 385, 406, 427, 448, 469, and 490, or an amino acid sequence which is at least 80% (e.g., 85%, 90%, 95%, 96%, 97%, 98%, or 99%) identical to an amino acid sequence selected from the group consisting of SEQ ID NOs: 25, 48, 71, 94, 117, 140, 163, 186, 209, 232, 255, 278, 301, 322, 343, 364, 385, 406, 427, 448, 469, and 490, and the light chain variable region comprises an amino acid sequence selected from the group consisting of SEQ ID NOs: 26, 49, 72, 95, 118, 141, 164, 187, 210, 233, 256, 279, 302, 323, 344, 365, 386, 407, 428, 449, 470, and 491, or an amino acid sequence which is at least 80% (e.g., at least 85%, 90%, 95%, 96%, 97%, 98%, or 99%) identical to an amino acid sequence selected from the group consisting of SEQ ID NOs: 26, 49, 72, 95, 118, 141, 164, 187, 210, 233, 256, 279, 302, 323, 344, 365, 386, 407,428, 449, 470, and 491.

In another embodiment, provided herein are antibodies which bind to human TNFR2 and comprises heavy and light chain variable region sequences which are at least 80% (e.g., 85%, 90%, 95%, 96%, 97%, 98%, or 99%) or 100% identical to the amino acid sequences selected from the group consisting of:

(a) SEQ ID NOs: 48 and 49, respectively; [UC2.3]
(b) SEQ ID NOs: 71 and 72, respectively; [UC2.3.3]
(c) SEQ ID NOs: 94 and 95, respectively; [UC2.3.7]
(d) SEQ ID NOs: 117 and 118, respectively; [UC2.3.8]
(e) SEQ ID NOs: 140 and 141, respectively; [UC2.3.9]
(f) SEQ ID NOs: 163 and 164, respectively; [UC2.3.10]
(g) SEQ ID NOs: 186 and 187, respectively; [UC2.3.11]
(h) SEQ ID NOs: 209 and 210, respectively; [UC2.3.12]
(i) SEQ ID NOs: 232 and 233, respectively; [UC2.3.13]
(j) SEQ ID NOs: 255 and 256, respectively; [UC2.3.14]
(k) SEQ ID NOs: 278 and 279, respectively; [UC2.3.15]
(l) SEQ ID NOs: 301 and 302, respectively; [UC1]
(m) SEQ ID NOs: 322 and 323, respectively; [UC1.1]
(n) SEQ ID NOs: 343 and 344, respectively; [UC1.2]
(o) SEQ ID NOs: 364 and 364, respectively; [UC1.3]
(p) SEQ ID NOs: 25 and 26, respectively; [UC2]
(q) SEQ ID NOs: 385 and 386, respectively; [UC3]
(r) SEQ ID NOs: 406 and 407, respectively; [UC4]
(s) SEQ ID NOs: 427 and 428, respectively; [UC5]
(t) SEQ ID NOs: 448 and 449, respectively; [UC6]
(u) SEQ ID NOs: 469 and 470, respectively; [UC7] and
(v) SEQ ID NOs: 490 and 491, respectively. [UC8]

In another embodiment, provided herein are antibodies which bind to human TNFR2 and comprises heavy and light chain sequences which are at least 80% (e.g., at least 85%, 90%, 95%, 96%, 97%, 98%, or 99%) or 100% identical to the amino acid sequences selected from the group consisting of:

(a) SEQ ID NOs: 50 and 51, respectively; [UC2.3]
(b) SEQ ID NOs: 73 and 74, respectively; [UC2.3.3]
(c) SEQ ID NOs: 96 and 97, respectively; [UC2.3.7]
(d) SEQ ID NOs: 119 and 120, respectively; [UC2.3.8]
(e) SEQ ID NOs: 142 and 143, respectively; [UC2.3.9]
(f) SEQ ID NOs: 165 and 166, respectively; [UC2.3.10]
(g) SEQ ID NOs: 188 and 189, respectively; [UC2.3.11]
(h) SEQ ID NOs: 211 and 212, respectively; [UC2.3.12]
(i) SEQ ID NOs: 234 and 235, respectively; [UC2.3.13]
(j) SEQ ID NOs: 257 and 258, respectively; [UC2.3.14]
(k) SEQ ID NOs: 280 and 281, respectively; [UC2.3.15] and
(l) SEQ ID NOs: 27 and 28, respectively. [UC2]

In some embodiments, the antibodies described herein are agonistic antibodies. For example, in some embodiments, the antibodies activate NF-κB signaling, promote T cell proliferation (e.g., CD4+ and CD8+ T cells), and/or co-stimulate T cells. In other embodiments, the antibodies decrease the abundance of regulatory T cells (e.g., in the T cell compartment). In other embodiments, the antibodies induce a long-term anti-cancer effect, for example, by inducing the development of anti-cancer memory T cells.

In some embodiments, the antibodies described herein are IgG2, IgG2, igG3, or IgG4, or variants thereof. In other embodiments, the antibodies comprise a variant Fc region. In other embodiments, the variant Fc region increases binding to Fcγ receptors (e.g., FcγRIIb receptor) relative to binding observed with the corresponding non-variant Fc region. In other embodiments, the variant Fc region increases antibody clustering relative to the corresponding non-variant Fc region. In other embodiments, the antibody co-stimulates T cells (e.g., CD8+ T cells). In other embodiments, the variant Fc region is a variant IgG1 Fc region. In other embodiments, the variant IgG1 Fc region comprises a substitution or substitutions selected from the group consisting of (a) S267E, (b) S267E/L328F, (c) G237D/P238D/P271G/A330R, (d) E233D/P238D/H268D/P271G/A330R, (e) G237D/P238D/H268D/P271G/A330R, and (f) E233D/G237D/P238D/H268D/P271G/A330R.

In some embodiments, the antibodies described herein are monoclonal antibodies. In other embodiments, the antibodies are human, humanized, or chimeric antibodies. In other embodiments, the antibodies are multi-specific antibodies (e.g., bispecific antibodies) or immunoconjugates comprising the antigen-binding domains (e.g., variable regions or heavy and light chains) of the anti-TNFR2 antibodies described herein. In other embodiments, the antibodies are selected from the group consisting of a single-chain antibody, Fab, Fab', F(ab')2, Fd, Fv, or domain antibody.

In another aspect, provided herein are nucleic acids encoding the heavy and/or light chain variable region(s) of the antibodies described herein. Also provided are expression vectors comprising the nucleic acids and cells (e.g., host cells) transformed with the expression vectors.

In another aspect, provided herein are compositions (e.g., pharmaceutical compositions), which comprise an antibody described herein, and a carrier (e.g., a pharmaceutically acceptable carrier). Also provided are kits comprising the antibodies described herein, and instructions for use.

In another aspect, provided herein are methods of increasing T cell proliferation, co-stimulating an effector T cell, and/or reducing or depleting the number of regulatory T cells in a subject comprising administering an effective amount of an antibody described herein to the subject to achieve increased T cell proliferation, effector T cell co-stimulation, and/or a reduction in or depletion of the number of regulatory T cells.

In another aspect, provided herein are methods of treating cancer comprising administering to a subject in need thereof a therapeutically effective amount of an anti-TNFR2 antibody described herein. In some embodiments, provided is the use of an anti-TNFR2 antibody described herein for the manufacture of a medicament for the treatment of a subject having cancer, or an anti-TNFR2 antibody described herein for use in the treatment of a subject having cancer.

In some embodiments, the cancer to be treated is non-small cell lung cancer, breast cancer, ovarian cancer, or colorectal cancer.

In some embodiments, one or more additional therapeutic agents (e.g., immunomodulatory drug, cytotoxic drug, targeted therapeutic, cancer vaccine) are administered in the methods of treating cancer described above. In other embodiments, the method, use, or antibody described herein induces a long-term anti-cancer effect. In other embodiments, the method, use, or antibody described herein induces the development of anti-cancer memory T cells.

In another aspect, provided herein are methods of treating autoimmune diseases or disorders comprising administering to a subject in need thereof a therapeutically effective amount of an anti-TNFR2 antibody described herein. In some embodiments, provided is the use of an anti-TNFR2 antibody described herein for the manufacture of a medicament for the treatment of a subject having an autoimmune disease or disorder, or an anti-TNFR2 antibody described herein for use in the treatment of a subject having an autoimmune disease or disorder.

In some embodiments, the autoimmune disease or disorder to be treated is graft-versus-host disease, rheumatoid arthritis, Crohn's disease, multiple sclerosis, colitis, psoriasis, autoimmune uveitis, pemphigus, epidermolysis bullosa, or type 1 diabetes. In other embodiments, one or more additional therapeutic agents are administered in the methods of treating autoimmune diseases or disorders.

In another aspect, provided herein are methods of promoting graft survival or reducing graft rejection in a subject who has received or will receive a cell, tissue, or organ transplant comprising administering to the subject an effective amount (e.g., a therapeutically effective amount) of an anti-TNFR2 antibody described herein to promote graft survival or reduce graft rejection. In some embodiments, provided is the use of an anti-TNFR2 antibody described herein for the manufacture of a medicament for promoting graft survival or reducing graft rejection in a subject who has received or will receive a cell, tissue, or organ transplant, or an anti-TNFR2 antibody described herein for use in promoting graft survival or reducing graft rejection in a subject who has received or will receive a cell, tissue, or organ transplant.

In some embodiments, the graft is an allograft (e.g., a cell, tissue, or organ allograft). In other embodiments, the graft rejection is in a recipient who has received or will receive a cell, tissue, or organ allograft. In other embodiments, one or more additional therapeutic agents are administered in the methods of promoting graft survival or reducing graft rejection.

In another aspect, provided herein are methods of treating, preventing, or reducing graft-versus-host disease in a subject who has or will receive a cell, tissue, or organ transplant comprising administering to the subject an effective amount (e.g., a therapeutically effective amount) of an anti-TNFR2 antibody described herein. In some embodiments, provided is the use of an anti-TNFR2 antibody described herein for the manufacture of a medicament for treating, preventing, or reducing graft-versus-host disease in a subject who has or will receive a cell, tissue, or organ transplant, or an anti-TNFR2 antibody described herein for use in treating, preventing, or reducing graft-versus-host disease in a subject who has or will receive a cell, tissue, or organ transplant. In other embodiments, one or more additional therapeutic agents are administered in the methods of treating, preventing, or reducing graft-versus-host disease.

Also provided herein are methods of detecting TNFR2 (e.g., human TNFR2) comprising contacting a sample (e.g., a biological sample) with an anti-TNFR2 antibody described herein under conditions that allow for formation of a complex between the antibody and TNFR2 protein, and detecting the complex. In some embodiments, provided is the use of an anti-TNFR2 antibody described herein for detecting TNFR2 (e.g., human TNFR2) in a sample (e.g., a biological sample), comprising contacting the sample with the anti-TNFR2 antibody under conditions that allow for formation of a complex between the antibody and TNFR2 proteins, and detecting the formation of the complex.

BRIEF DESCRIPTION OF THE DRAWINGS

FIG. 6A: $K_D$ values were 2.87 nM for 1B5-1D9, 0.57 nM for 1B5-1A5, and 0.64 nM for 1B5-1B3. FIG. 6B: $K_D$ values were 8.16 nM for 1D10-1G9, 1.35 nM for 1D10-1G9-1F10, 1.79 nM for 1D10-1G9-1F12, 0.63 nM for 1D10-1G9-1G2, 1.52 nM for 1D10-1G9-1G3 and 1.98 nM for 1D10-1G9-1H1. FIG. 6C: $K_D$ values were 8.16 nM for 1D10-1G9, 0.87 nM for 1D10-1G9-1G11, 0.65 nM for 1D10-1G9-1H11, and 0.78 nM for 1D10-1G9-1H12

FIG. 16B shows the gating strategy for the flow cytometry analysis.

FIGS. 18A and 18B show data from 3 individuals and are normalized to samples stimulated in the absence of any anti-TNFRSF antibody. Asterisks show statistical significance between isotype and UC2.3.8. FIG. 18C shows representative flow plots of CD4+ T cells stimulated with 20 ug/mL isotype, UC2.3.8, or anti-GITR antibody.

(FIG. 22A: IL-2, FIG. 22B: IFN-γ, FIG. 22C: TNF, FIG. 22D: LTα, FIG. 22E: IL-18, FIG. 22F: GM-CSF). Data are from a single donor and are representative of 4 individual donors. IgG1 was used as a negative control.

(FIG. 23A: IL-2, FIG. 23B: IFN-γ, FIG. 23C: TNF, FIG. 23D: LTα, FIG. 23E: IL-18, FIG. 23F: GM-CSF). Data are from a single donor and are representative of 2 individual donors. IgG1 was used as a negative control.

FIG. 32A) and aspartate aminotransferase (AST; FIG. 32B) in healthy mice.

FIG. 33A is a graph showing the effects of the indicated treatments on the proliferation of CD4+ T cells. FIG. 33B is a graph showing the effects of the indicated treatments on the proliferation of CD8+ T cells. FIG. 33C shows a series of dot plots describing the gating strategy for flow cytometry. FIG. 33D is a graph showing the effects of the indicated treatments on expression of CD86 (B7.2), a co-stimulatory molecule important in dendritic cell activation of T cells.

Figure 44A:
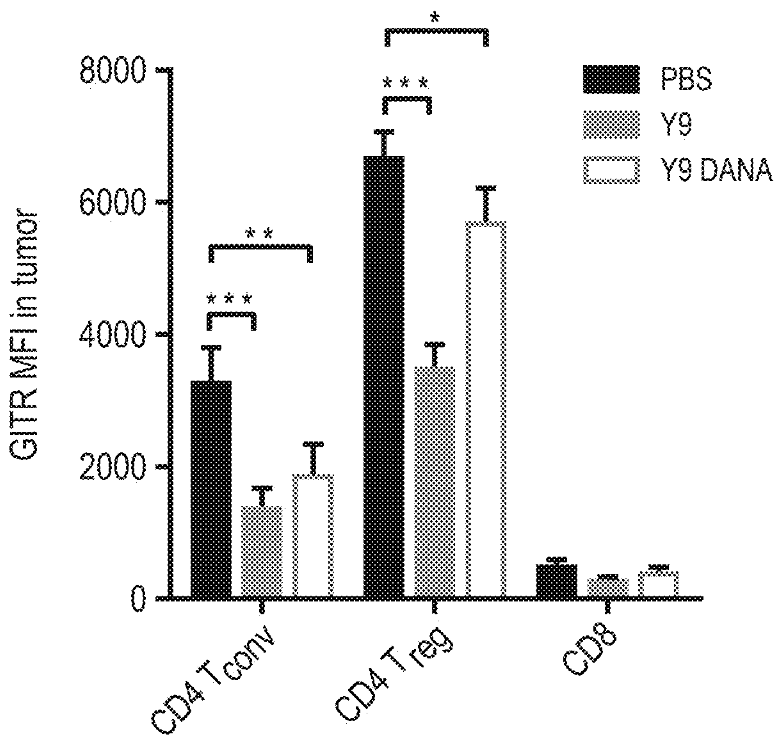
Figure 44B:
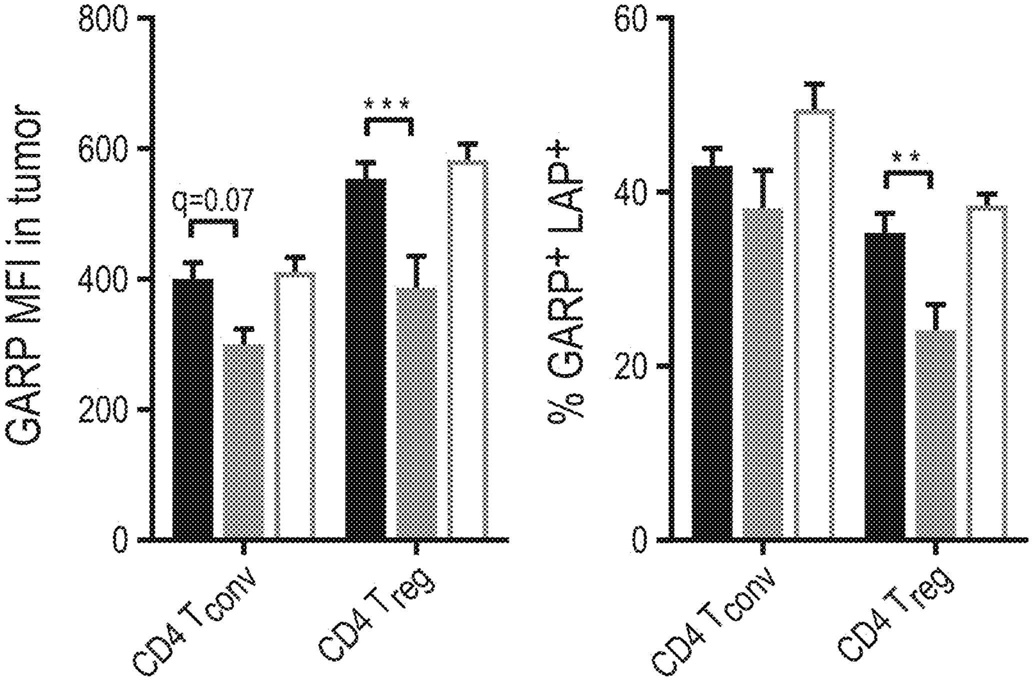
Figure 44C:
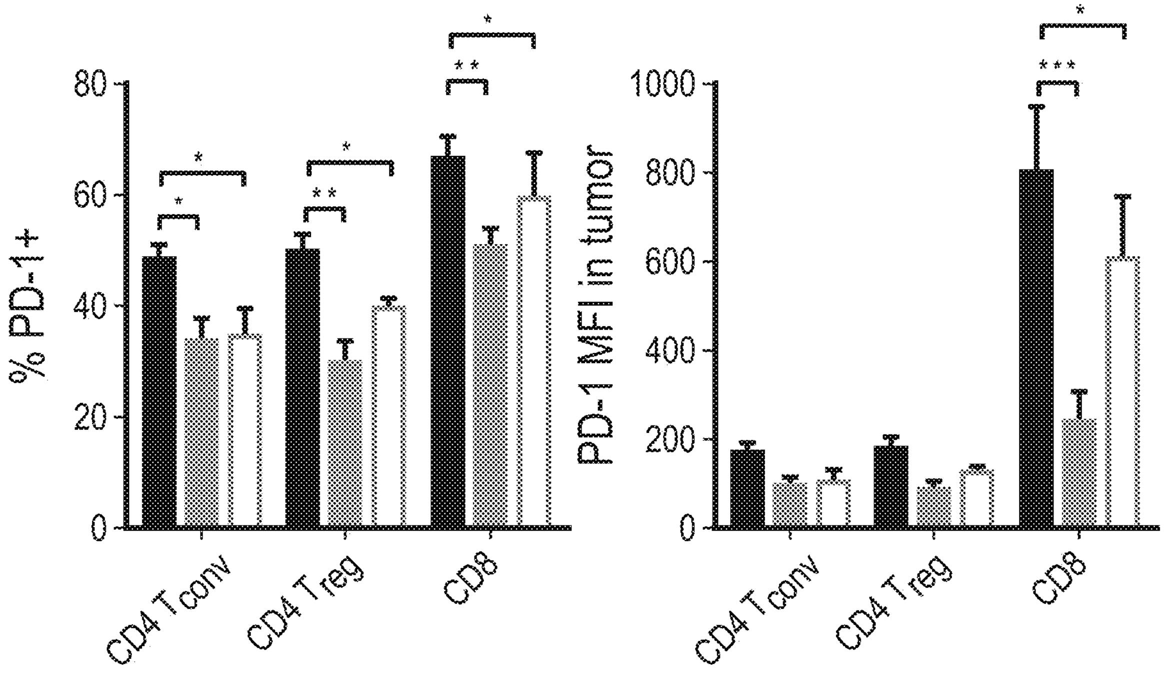

FIGS. 44A-44C are graphs showing the effects of antibody Y9 and Y9 DANA on GITR (FIG. 44A), GARP (FIG. 44B), and PD-1 (FIG. 44C) expression in CD4+ conventional T cells, Tregs, and CD8+ T cells in tumors of a EMT-6 syngeneic model.

Figure 45A:
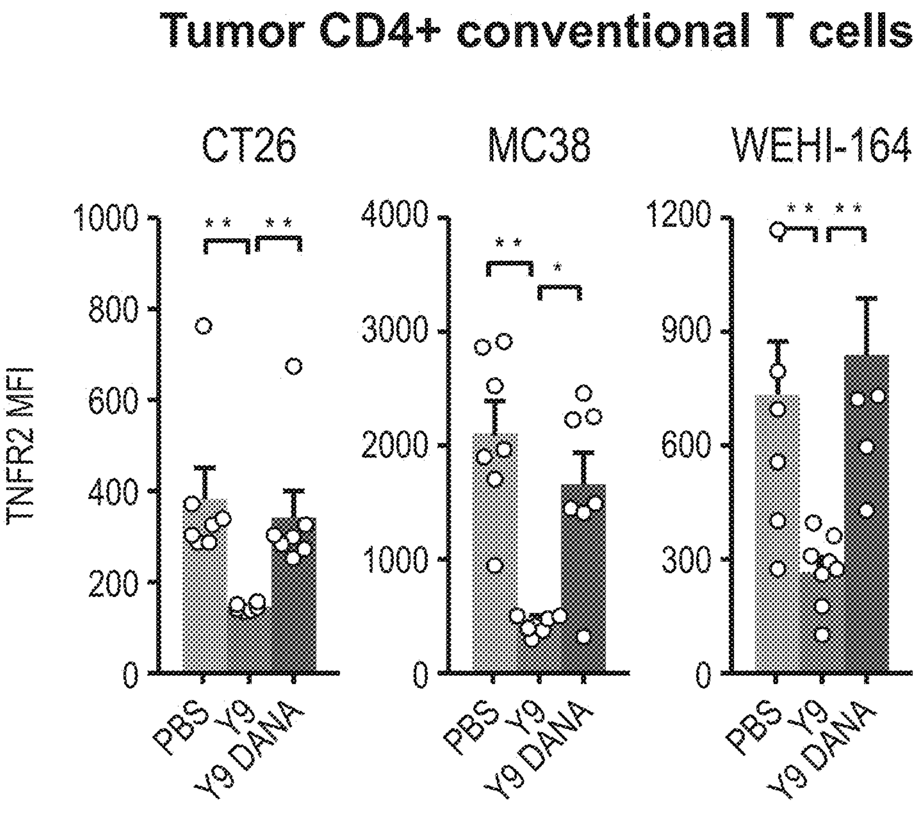
Figure 45B:
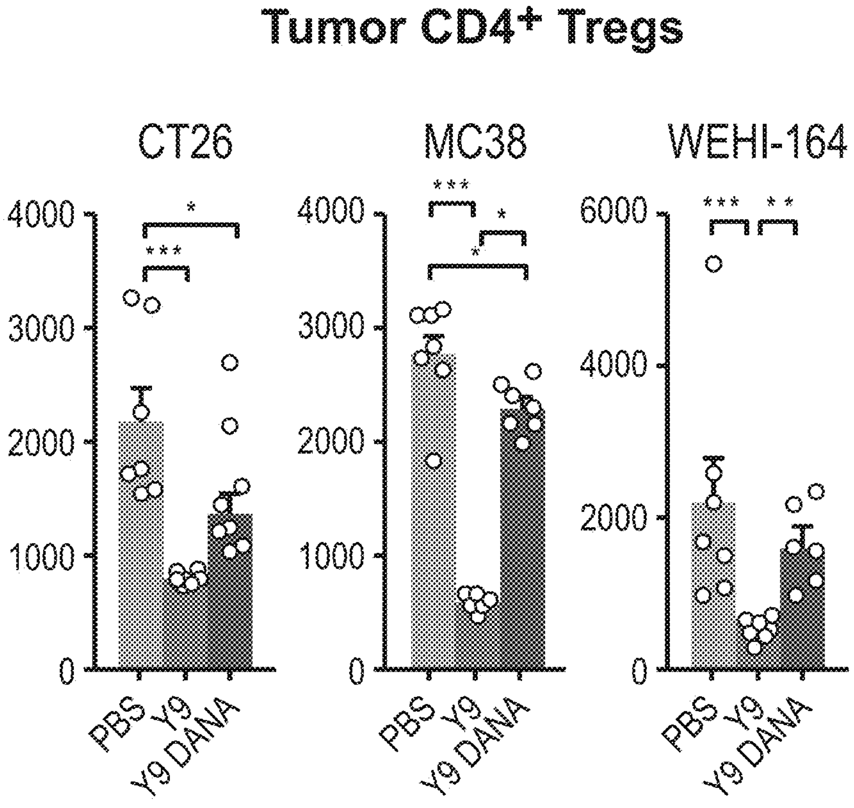
Figure 45C:
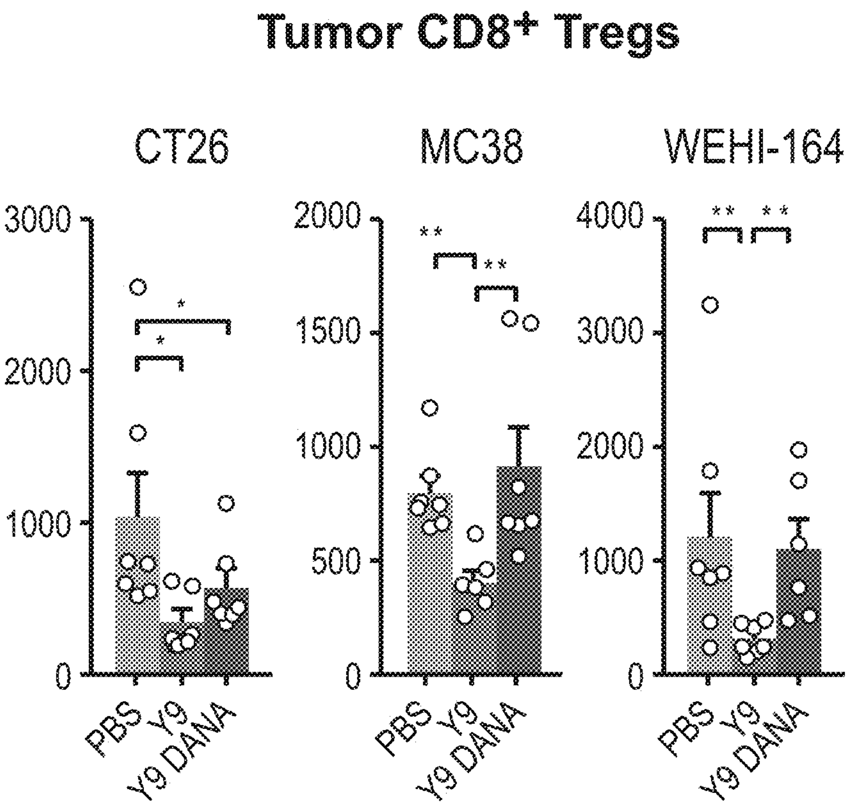

FIG. 45A-45C are graphs showing the effects of antibody Y9 and Y9 DANA on TNFR2 expression in CD4+ conventional T cells (FIG. 45A), Tregs (FIG. 45B), and CD8+ T cells (FIG. 45C) in tumors of CT26, MC38, and WEHI-164 syngeneic models.

DETAILED DESCRIPTION

I. Overview

Provided herein are isolated antibodies, particularly recombinant monoclonal antibodies, e.g., human monoclonal antibodies, which specifically bind to TNFR2 (e.g., human TNFR2).

Also provided herein are methods of making the antibodies, immunoconjugates and multispecific molecules and pharmaceutical compositions comprising the antibodies, as well as methods of inhibiting tumor growth, treating cancer, treating autoimmune diseases, treating graft-versus-host diseases, and promoting graft survival and/or reducing graft rejection using the antibodies.

II. Definitions

In order that the present description may be more readily understood, certain terms are first defined. Additional definitions are set forth throughout the detailed description.

The terms "tumor necrosis factor receptor 2," "TNFR2," "CD120b," "p75," "p75TNFR," "p80 TNF-alpha receptor," "TBPII," "TNFBR," "TNFR1B," "TNF-R75," and "TNFR80," are used interchangeably herein, are inclusive of all family members, mutants, alleles, fragments, and species, and refer to a protein having the amino acid sequences (human and mouse) set forth below. The extracellular domain of TNFR2 includes four cysteine-rich domains (CRD1-CRD4), the sequences of which are summarized in Table 1. The numbering of CRD regions in Table 1 is based on human and mouse TNFR2 with the leader sequence (i.e., SEQ ID NOs: 1 and 4).

```
Human TNFR2 (NP_001057) (leader sequence is
underlined):
                                        (SEQ ID NO: 1)
MAPVAVWAALAVGLELWAAAHALPAQVAFTPYAPEPGSTCRLREYYDQTA

QMCCSKCSPGQHAKVFCTKTSDTVCDSCEDSTYTQLWNWVPECLSCGSRC

SSDQVETQACTREQNRICTCRPGWYCALSKQEGCRLCAPLRKCRPGFGVA

RPGTETSDVVCKPCAPGTFSNTTSSTDICRPHQICNVVAIPGNASMDAVC

TSTSPTRSMAPGAVHLPQPVSTRSQHTQPTPEPSTAPSTSFLLPMGPSPP

AEGSTGDFALPVGLIVGVTALGLLIIGVVNCVIMTQVKKKPLCLQREAKV

PHLPADKARGTQGPEQQHLLITAPSSSSSSLESSASALDRRAPTRNQPQA

PGVEASGAGEARASTGSSDSSPGGHGTQVNVTCIVNVCSSSDHSSQCSSQ

ASSTMGDTDSSPSESPKDEQVPFSKEECAFRSQLETPETLLGSTEEKPLP

LGVPDAGMKPS
```

-continued

```
Mouse TNFR2 (NP_035740) (leader sequence is
underlined):
                                        (SEQ ID NO: 4)
MAPAALWVALVFELQLWATGHTVPAQVVLTPYKPEPGYECQISQEYYDRK

AQMCCAKCPPGQYVKHFCNKTSDTVCADCEASMYTQVWNQFRTCLSCSSS

CTTDQVEIRACTKQQNRVCACEAGRYCALKTHSGSCRQCMRLSKCGPGFG

VASSRAPNGNVLCKACAPGTFSDTTSSTDVCRPHRICSILAIPGNASTDA

VCAPESPTLSAIPRTLYVSQPEPTRSQPLDQEPGPSQTPSILTSLGSTPI

IEQSTKGGISLPIGLIVGVTSLGLLMLGLVNCIILVQRKKKPSCLQRDAK

VPHVPDEKSQDAVGLEQQHLLTTAPSSSSSSLESSASAGDRRAPPGGHPQ

ARVMAEAQGFQEARASSRISDSSHGSHGTHVNVTCIVNVCSSSDHSSQCS

SQASATVGDPDAKPSASPKDEQVPFSQEECPSQSPCETTETLQSHEKPLP

LGVPDMGMKPSQAGWFDQIAVKVA
```

TABLE 1

| Cysteine-rich domain (CRD) | Mouse amino acid residues[A] | Human amino acid residues[B] |
|---|---|---|
| CRD1 | 39-77 | 39-76 |
| CRD1 A1 | 40-55 | 40-53 |
| CRD1 B2 | 56-76 | 54-75 |
| CRD2 | 78-120 | 77-118 |
| CRD2 A1 | 79-94 | 78-93 |
| CRD2 B2 | 97-119 | 96-118 |
| CRD3 | 120-164 | 119-162 |
| CRD3 A2 | 121-139 | 120-137 |
| CRD3 B1 | 145-163 | 143-161 |
| CRD4 | 165-203 | 163-201 |
| CRD4 A1 | 166-180 | 164-179 |
| CRD4B1 | 187-202 | 185-200 |

[A]Mouse TNFR2 (UniProt ID: P25119)
[B]Human TNFR2 (UniProt ID: P20333)

TNFR2, together with TNFR1, mediate the activity of TNFα. TNFR1 is a 55 kD membrane-bound protein, whereas TNFR2 is a 75 kD membrane-bound protein. TNFR2 can regulate the binding of TNFα to TNFR1, and thus may regulate the levels of TNFα necessary to stimulate the action of NF-kB. TNFR2 can also be cleaved by metalloproteases (or be subjected to alternative splicing), generating soluble receptors that maintain affinity for TNFα.

The term "antibody" or "immunoglobulin," as used interchangeably herein, includes whole antibodies and any antigen binding fragment (antigen-binding portion) or single chain cognates thereof. An "antibody" comprises at least one heavy (H) chain and one light (L) chain. In naturally occurring IgGs, for example, these heavy and light chains are inter-connected by disulfide bonds and there are two paired heavy and light chains, these two also inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR) or Joining (J) regions (JH or JL in heavy and light chains respectively). Each $V_H$ and $V_L$ is composed of three CDRs, three FRs and a J domain, arranged from amino-terminus to carboxy-terminus in the following order: FR1, CDR1, FR2, CDR2, FR3, CDR3, J. The variable regions of the heavy and light chains bind with an antigen. The constant regions of the antibodies may mediate the binding of the immunoglobulin to host tissues or factors, including various cells of the immune system (e.g., effector cells) or humoral factors such as the first component (C1q) of the classical complement system. It has been shown that fragments of a full-length antibody can perform the antigen-binding function of an antibody. Examples of binding fragments denoted as an antigen-binding portion or fragment of an antibody include (i) a Fab fragment, a monovalent fragment consisting of the $V_L$, $V_H$, CL and CH1 domains; (ii) a $F(ab')_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including VH and VL domains; (vi) a dAb fragment (Ward et al. (1989) *Nature* 341, 544-546), which consists of a $V_H$ domain; (vii) a dAb which consists of a VH or a VL domain; and (viii) an isolated complementarity determining region (CDR) or (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions are paired to form monovalent molecules (such a single chain cognate of an immunoglobulin fragment is known as a single chain Fv (scFv). Such single chain antibodies are also intended to be encompassed within the term "antibody". Antibody fragments are obtained using conventional techniques known to those with skill in the art, and the fragments are screened for utility in the same general manner as are intact antibodies. Antigen-binding portions can be produced by recombinant DNA techniques, or by enzymatic or chemical cleavage of intact immunoglobulins. Unless otherwise specified, the numbering of amino acid positions in the antibodies described herein (e.g., amino acid residues in the Fc region) and identification of regions of interest, e.g., CDRs, use the Kabat system (Kabat, E. A., et al. (1991) Sequences of Proteins of Immunological Interest, Fifth Edition, U.S. Department of Health and Human Services, NIH Publication No. 91-3242).

The term "monoclonal antibody" as used herein refers to an antibody obtained from a population of substantially homogeneous antibodies, i.e., the individual antibodies comprising the population are identical except for possible naturally occurring mutations that may be present in minor amounts. Antigen binding fragments (including scFvs) of such immunoglobulins are also encompassed by the term "monoclonal antibody" as used herein. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. Monoclonal antibodies can be prepared using any art recognized technique and those described herein such as, for example, a hybridoma method, a transgenic animal, recombinant DNA methods (see, e.g., U.S. Pat. No. 4,816,567), or using phage antibody libraries using the techniques described in, for example, U.S. Pat. No. 7,388,088 and U.S. patent application Ser. No. 09/856,907 (PCT Int. Pub. No. WO 00/31246). Monoclonal antibodies include chimeric antibodies, human antibodies, and humanized antibodies and may occur naturally or be produced recombinantly.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "chimeric immunoglobulin" or "chimeric antibody" refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The term "humanized antibody" refers to an antibody that includes at least one humanized antibody chain (i.e., at least one humanized light or heavy chain). The term "humanized antibody chain" (i.e., a "humanized immunoglobulin light chain") refers to an antibody chain (i.e., a light or heavy chain, respectively) having a variable region that includes a variable framework region substantially from a human antibody and complementarity determining regions (CDRs) (e.g., at least one CDR, two CDRs, or three CDRs) substantially from a non-human antibody. In some embodiments, the humanized antibody chain further includes constant regions (e.g., one constant region or portion thereof, in the case of a light chain, and preferably three constant regions in the case of a heavy chain).

The term "human antibody," as used herein, is intended to include antibodies having variable regions in which both the framework and CDR regions are derived from human germline immunoglobulin sequences as described, for example, by Kabat et al. (See Kabat, et al. (1991) *Sequences of proteins of Immunological Interest, Fifth Edition*, U.S. Department of Health and Human Services, NIH Publication No. 91-3242). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The human antibody can have at least one or more amino acids replaced with an amino acid residue, e.g., an activity enhancing amino acid residue that is not encoded by the human germline immunoglobulin sequence. Typically, the human antibody can have up to twenty positions replaced with amino acid residues that are not part of the human germline immunoglobulin sequence. In a particular embodiment, these replacements are within the CDR regions as described in detail below.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., *J Immunol.* 148, 1547-1553 (1992).

"Isolated," as used herein, is intended to refer to an antibody that is substantially free of other antibodies having different antigenic specificities. In addition, an isolated antibody is typically substantially free of other cellular material and/or chemicals.

An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and downregulation of a cell surface receptor (e.g., the B cell receptor; BCR). Such effector functions generally require the Fc region to be combined with a binding domain (e.g., an antibody variable domain).

An "Fc region," "Fc domain," or "Fc" refers to the C-terminal region of the heavy chain of an antibody. Thus, an Fc region comprises the constant region of an antibody excluding the first constant region immunoglobulin domain (e.g., CH1 or CL).

An "antigen" is an entity (e.g., a proteinaceous entity or peptide) to which an antibody binds, e.g., TNFR2.

The terms "specific binding," "specifically binds," "selective binding," and "selectively binds," mean that an antibody exhibits appreciable affinity for a particular antigen or epitope and, generally, does not exhibit significant cross-reactivity with other antigens and epitopes. "Appreciable" or preferred binding includes binding with a $K_D$ of $10^{-7}$, $10^{-8}$, $10^{-9}$, or $10^{-10}$ M or better. The $K_D$ of an antibody antigen interaction (the affinity constant) indicates the concentration of antibody at which 50% of antibody and antigen molecules are bound together. Thus, at a suitable fixed antigen concentration, 50% of a higher (i.e., stronger) affinity antibody will bind antigen molecules at a lower antibody concentration than would be required to achieve the same percent binding with a lower affinity antibody. Thus a lower $K_D$ value indicates a higher (stronger) affinity. As used herein, "better" affinities are stronger affinities, and are of lower numeric value than their comparators, with a $K_D$ of $10^{-7}$ M being of lower numeric value and therefore representing a better affinity than a $K_D$ of $10^{-6}$ M. Affinities better (i.e., with a lower $K_D$ value and therefore stronger) than $10^{-7}$ M, preferably better than $10^{-8}$ M, are generally preferred. Values intermediate to those set forth herein are also contemplated, and a preferred binding affinity can be indicated as a range of affinities, for example preferred binding affinities for anti-TNFR2 antibodies disclosed herein are, $10^{-7}$ to $10^{-12}$ M, more preferably $10^{-8}$ to $10^{-12}$ M. An antibody that "does not exhibit significant cross-reactivity" or "does not bind with a physiologically-relevant affinity" is one that will not appreciably bind to an off-target antigen (e.g., a non-TNFR2 protein) or epitope. For example, in one embodiment, an antibody that specifically binds to TNFR2 will exhibit at least a two, and preferably three, or four or more orders of magnitude better binding affinity (i.e., binding exhibiting a two, three, or four or more orders of magnitude lower $K_D$ value) for TNFR2 than, e.g., a protein other than TNFR2. Specific or selective binding can be determined according to any art-recognized means for determining such binding, including, for example, according to Scatchard analysis, Biacore analysis, bio-layer interferometry, and/or competitive (competition) binding assays as described herein.

The term "$K_D$," as used herein, is intended to refer to the dissociation equilibrium constant of a particular antibody-antigen interaction or the affinity of an antibody for an antigen, which is obtained from the ratio of $k_d$ to $k_a$ (i.e., $k_d/k_a$) and is expressed as a molar concentration (M). $K_D$ values for antibodies can be determined using methods well established in the art. In some embodiments, an antibody binds an antigen with an affinity ($K_D$) of approximately less than $10^{-7}$ M, such as approximately less than $10^{-8}$ M, $10^{-9}$ M or $10^{-10}$ M or even lower when determined by bio-layer interferometery with a Pall ForteBio Octet RED96 Bio-Layer Interferometry system or surface plasmon resonance (SPR) technology in a BIACORE 3000 instrument using recombinant TNFR2 as the analyte and the antibody as the ligand, and binds to the predetermined antigen with an affinity that is at least two-fold greater than its affinity for binding to a non-specific antigen (e.g., BSA, casein) other than the predetermined antigen or a closely-related antigen. Other methods for determining $K_D$ include equilibrium binding to live cells expressing TNFR2 via flow cytometry (FACS) or in solution using KinExA® technology. $K_D$ values as used herein refer to monovalent $K_D$.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction.

The term "epitope" or "antigenic determinant" refers to a site on an antigen to which an immunoglobulin or antibody specifically binds. Epitopes can be formed both from contiguous amino acids (usually a linear epitope) or noncontiguous amino acids juxtaposed by tertiary folding of a protein (usually a conformational epitope). Epitopes formed from contiguous amino acids are typically, but not always, retained on exposure to denaturing solvents, whereas epitopes formed by tertiary folding are typically lost on treatment with denaturing solvents. Methods for determining what epitopes are bound by a given antibody (i.e., epitope mapping) are well known in the art and include, for example, immunoblotting and immunoprecipitation assays, wherein overlapping or contiguous peptides are tested for reactivity with a given antibody. Methods of determining spatial conformation of epitopes include techniques in the art, for example, x-ray crystallography, 2-dimensional nuclear magnetic resonance and HDX-MS (see, e.g., *Epitope Mapping Protocols in Methods in Molecular Biology*, Vol. 66, G. E. Morris, Ed. (1996)). The term "epitope mapping" refers to the process of identification of the molecular determinants for antibody-antigen recognition.

The term "binds to the same epitope" with reference to two or more antibodies means that the antibodies bind to the same segment of amino acid residues, as determined by a given method. Techniques for determining whether antibodies bind to the "same epitope on TNFR2" with the antibodies described herein include, for example, epitope mapping methods, such as, x-ray analyses of crystals of antigen: antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi:10.1101/pdb.prot4277 or in Chapter 11 of "Using Antibodies" by Ed Harlow and David Lane, Cold Spring Harbor Laboratory Press, Cold Spring Harbor, NY, USA 1999. Competing antibodies bind to the same epitope, an overlapping epitope or to adjacent epitopes (e.g., as evidenced by steric hindrance). Other competitive binding assays include: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

The term "nucleic acid molecule," as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody fragments (e.g., $V_H$, $V_L$, CDR3), is intended to refer to a nucleic acid molecule in which the nucleotide sequences are essentially free of other genomic nucleotide sequences, e.g., those encoding antibodies that bind antigens other than TNFR2, which other sequences may naturally flank the nucleic acid in human genomic DNA.

The term "modifying," or "modification," as used herein, refers to changing one or more amino acids in an antibody or antigen-binding portion thereof, or on a recombinant TNFR2 protein (e.g., for epitope mapping). The change can be produced by adding, substituting or deleting an amino acid at one or more positions. The change can be produced using known techniques, such as PCR mutagenesis. For example, in some embodiments, an antibody or an antigen-binding portion thereof identified using the methods provided herein can be modified, to thereby modify the binding affinity of the antibody or antigen-binding portion thereof to TNFR2.

"Conservative amino acid substitutions" in the sequences of the antibodies refer to nucleotide and amino acid sequence modifications which do not abrogate the binding of the antibody encoded by the nucleotide sequence or containing the amino acid sequence, to the antigen (e.g., TNFR2). Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted nonessential amino acid residue in an anti-TNFR2 antibody is preferably replaced with another amino acid residue from the same class. Methods of identifying nucleotide and amino acid conservative substitutions which do not eliminate antigen binding are well-known in the art.

The term "non-conservative amino acid substitution" refers to the substitution of an amino acid in one class with an amino acid from another class; for example, substitution of an Ala, a class II residue, with a class III residue such as Asp, Asn, Glu, or Gln.

Alternatively, in another embodiment, mutations (conservative or non-conservative) can be introduced randomly along all or part of an anti-TNFR2 antibody coding sequence, such as by saturation mutagenesis, and the resulting modified anti-TNFR2 antibodies can be screened for binding activity.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, other forms of expression vectors, such as viral vectors (e.g., replication defective retroviruses, adenoviruses and adeno-associated viruses), which serve equivalent functions are also contemplated.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

Also provided are "conservative sequence modifications" of the sequences set forth herein, i.e., amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into a sequence in Table 5 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-TNFR2 antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)). Alternatively, in another embodiment, mutations can be introduced randomly along all or part of an anti-TNFR2 antibody coding sequence, such as by saturation mutagenesis, and the resulting modified anti-TNFR2 antibodies can be screened for binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or two amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

The term "inhibition" as used herein, refers to any statistically significant decrease in biological activity, including partial and full blocking of the activity. For example, "inhibition" can refer to a statistically significant decrease of about 10%, 20%, 30%, 40%, 50%, 60%, 70%, 80%, 90%, 95%, 96%, 97%, 98%, 99%, or 100% in biological activity.

The phrase "inhibit TNFR2 ligand binding to TNFR2," as used herein, refers to the ability of an antibody to statistically significantly decrease the binding of an TNFR2 ligand (e.g., TNFα) to TNFR2, relative to the TNFR2 ligand binding in the absence of the antibody (control). In other words, in the presence of the antibody, the amount of the TNFR2 ligand that binds to TNFR2 relative to a control (no antibody), is statistically significantly decreased. The amount of an TNFR2 ligand which binds to TNFR2 may be decreased in the presence of an anti-TNFR2 antibody disclosed herein by at least about 10%, or at least about 20%, or at least about 30%, or at least about 40%, or at least about 50%, or at least about 60%, or at least about 70%, or at least about 80%, or at least about 90%, or about 100% relative to the amount in the absence of the antibody (control). A decrease in TNFR2 ligand binding can be measured using art-recognized techniques that measure the level of binding of labeled TNFR2 ligand (e.g., radiolabelled TNFα) to cells expressing TNFR2 in the presence or absence (control) of the antibody.

As used herein, the term "inhibits growth" of a tumor includes any measurable decrease in the growth of a tumor, e.g., the inhibition of growth of a tumor by at least about 10%, for example, at least about 20%, at least about 30%, at least about 40%, at least about 50%, at least about 60%, at least about 70%, at least about 80%, at least about 90%, at least about 99%, or about 100%.

The terms "treat," "treating," and "treatment," as used herein, refer to therapeutic or preventative measures described herein. The methods of "treatment" employ administration to a subject with a disease such as graft-versus-host disease, or a subject who is may develop the disease (e.g., a subject who will receive a cell or organ transplant) an anti-TNFR2 antibody (e.g., anti-human TNFR2 antibody) described herein, in order to prevent, cure, delay, reduce the severity of, or ameliorate one or more symptoms of the disease or disorder or recurring disease or disorder, or in order to prolong the survival of a subject beyond that expected in the absence of such treatment.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma and various types of head and neck cancer.

The phrase "long-term anti-cancer effect" as used herein, refers to the ability of an antibody to induce suppression of cancer growth for a sustained period of time (e.g, at least 6 or more months) after initial treatment with the antibody. The sustained anti-cancer effect may be assessed, e.g., by measuring tumor growth or by periodically testing blood samples of a subject in remission for the presence of memory T cells against the original cancer (e.g., testing for reactivity to original biopsy samples).

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

The term "therapeutic agent" in intended to encompass any and all compounds that have an ability to decrease or inhibit the severity of the symptoms of a disease or disorder, or increase the frequency and/or duration of symptom-free or symptom-reduced periods in a disease or disorder, or inhibit or prevent impairment or disability due to a disease or disorder affliction, or inhibit or delay progression of a disease or disorder, or inhibit or delay onset of a disease or disorder. Non-limiting examples of therapeutic agents include small organic molecules, monoclonal antibodies, bispecific antibodies, recombinantly engineered biologics, RNAi compounds, and commercial antibodies.

As used herein, "administering" refers to the physical introduction of a composition comprising a therapeutic agent to a subject, using any of the various methods and delivery systems known to those skilled in the art. Exemplary routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

The term "patient" includes human and other mammalian subjects that receive either prophylactic or therapeutic treatment.

The term "subject" includes any mammal. For example, the methods and compositions herein disclosed can be used to treat a subject having cancer. In a particular embodiment, the subject is a human.

The term "sample" refers to tissue, body fluid, or a cell (or a fraction of any of the foregoing) taken from a patient or a subject. Normally, the tissue or cell will be removed from the patient, but in vivo diagnosis is also contemplated. In the case of a solid tumor, a tissue sample can be taken from a surgically removed tumor and prepared for testing by conventional techniques. In the case of lymphomas and leukemias, lymphocytes, leukemic cells, or lymph tissues can be obtained (e.g., leukemic cells from blood) and appropriately prepared. Other samples, including urine, tears, serum, plasma, cerebrospinal fluid, feces, sputum, cell extracts etc. can also be useful for particular cancers.

As used herein, the term "about" means plus or minus 10% of a specified value.

As used herein, the term "and/or" includes any and all combinations of one or more of the associated listed items. For example, the phrase "A, B, and/or C" is intended to encompass A; B; C; A and B; A and C; B and C; and A, B, and C.

As used in the description of the invention and the appended claims, the singular forms "a," "an" and "the" are intended to include the plural forms as well, unless the context clearly indicates otherwise.

Various aspects of the disclosure are described in further detail in the following subsections.

III. Anti-TNFR2 Antibodies

Anti-TNFR2 antibodies (e.g., isolated anti-human TNFR2 antibodies) disclosed herein are characterized by particular functional and structural features (e.g., CDRs, variable regions, heavy and light chains).

Accordingly, in one embodiment, the antibody binds to human TNFR2 and comprises heavy and light chain CDR1, CDR2, and CDR3 sequences of the heavy and light chain variable region pairs selected from the group consisting of:

(a) SEQ ID NOs: 48 and 49, respectively; [UC2.3]
(b) SEQ ID NOs: 71 and 72, respectively; [UC2.3.3]
(c) SEQ ID NOs: 94 and 95, respectively; [UC2.3.7]
(d) SEQ ID NOs: 117 and 118, respectively; [UC2.3.8]
(e) SEQ ID NOs: 140 and 141, respectively; [UC2.3.9]
(f) SEQ ID NOs: 163 and 164, respectively; [UC2.3.10]
(g) SEQ ID NOs: 186 and 187, respectively; [UC2.3.11]
(h) SEQ ID NOs: 209 and 210, respectively; [UC2.3.12]
(i) SEQ ID NOs: 232 and 233, respectively; [UC2.3.13]
(j) SEQ ID NOs: 255 and 256, respectively; [UC2.3.14]
(k) SEQ ID NOs: 278 and 279, respectively; [UC2.3.15]
(l) SEQ ID NOs: 301 and 302, respectively; [UC1]
(m) SEQ ID NOs: 322 and 323, respectively; [UC1.1]
(n) SEQ ID NOs: 343 and 344, respectively; [UC1.2]
(o) SEQ ID NOs: 364 and 364, respectively; [UC1.3]
(p) SEQ ID NOs: 25 and 26, respectively; [UC2]
(q) SEQ ID NOs: 385 and 386, respectively; [UC3]
(r) SEQ ID NOs: 406 and 407, respectively; [UC4]
(s) SEQ ID NOs: 427 and 428, respectively; [UC5]
(t) SEQ ID NOs: 448 and 449, respectively; [UC6]
(u) SEQ ID NOs: 469 and 470, respectively; [UC7] and
(v) SEQ ID NOs: 490 and 491, respectively. [UC8]

In some embodiments, the CDR sequences are defined using Kabat numbering. In other embodiments, the CDR sequences are defined using Chothia numbering. In other embodiments, the CDR sequences are defined using IMGT numbering.

In some embodiments, the anti-TNFR2 antibody comprises:

(a) heavy chain CDR1, CDR2, and CDR3 sequences comprising SEQ ID NOs: 36-38, respectively, and light chain CDR1, CDR2, and CDR3 sequences comprising SEQ ID NOs: 39-41, respectively; [UC2.3]
(b) heavy chain CDR1, CDR2, and CDR3 sequences comprising SEQ ID NOs: 59-61, respectively, and light chain CDR1, CDR2, and CDR3 sequences comprising SEQ ID NOs: 62-64, respectively; [UC2.3.3]
(c) heavy chain CDR1, CDR2, and CDR3 sequences comprising SEQ ID NOs: 82-84, respectively, and light chain CDR1, CDR2, and CDR3 sequences comprising SEQ ID NOs: 85-87, respectively; [UC2.3.7]
(d) heavy chain CDR1, CDR2, and CDR3 sequences comprising SEQ ID NOs: 105-107, respectively, and light chain CDR1, CDR2, and CDR3 sequences comprising SEQ ID NOs: 108-110, respectively; [UC2.3.8]
(e) heavy chain CDR1, CDR2, and CDR3 sequences comprising SEQ ID NOs: 128-130, respectively, and light chain CDR1, CDR2, and CDR3 sequences comprising SEQ ID NOs: 131-133, respectively; [UC2.3.9]
(f) heavy chain CDR1, CDR2, and CDR3 sequences comprising SEQ ID NOs: 151-153, respectively, and light chain CDR1, CDR2, and CDR3 sequences comprising SEQ ID NOs: 154-156, respectively; [UC2.3.10]
(g) heavy chain CDR1, CDR2, and CDR3 sequences comprising SEQ ID NOs: 174-176, respectively, and light chain CDR1, CDR2, and CDR3 sequences comprising SEQ ID NOs: 177-179, respectively; [UC2.3.11]
(h) heavy chain CDR1, CDR2, and CDR3 sequences comprising SEQ ID NOs: 197-199, respectively, and light chain CDR1, CDR2, and CDR3 sequences comprising SEQ ID NOs: 200-202, respectively; [UC2.3.12]
(i) heavy chain CDR1, CDR2, and CDR3 sequences comprising SEQ ID NOs: 220-222, respectively, and light chain CDR1, CDR2, and CDR3 sequences comprising SEQ ID NOs: 223-225, respectively; [UC2.3.13]
(j) heavy chain CDR1, CDR2, and CDR3 sequences comprising SEQ ID NOs: 243-245, respectively, and light chain CDR1, CDR2, and CDR3 sequences comprising SEQ ID NOs: 246-248, respectively; [UC2.3.14]
(k) heavy chain CDR1, CDR2, and CDR3 sequences comprising SEQ ID NOs: 266-268, respectively, and light chain CDR1, CDR2, and CDR3 sequences comprising SEQ ID NOs: 269-271, respectively; [UC2.3.15]
(l) heavy chain CDR1, CDR2, and CDR3 sequences comprising SEQ ID NOs: 289-291, respectively, and light chain CDR1, CDR2, and CDR3 sequences comprising SEQ ID NOs: 292-294, respectively; [UC1]
(m) heavy chain CDR1, CDR2, and CDR3 sequences comprising SEQ ID NOs: 310-312, respectively, and light chain CDR1, CDR2, and CDR3 sequences comprising SEQ ID NOs: 313-315, respectively; [UC1.1]
(n) heavy chain CDR1, CDR2, and CDR3 sequences comprising SEQ ID NOs: 331-333, respectively, and light chain CDR1, CDR2, and CDR3 sequences comprising SEQ ID NOs: 334-336, respectively; [UC1.2]
(o) heavy chain CDR1, CDR2, and CDR3 sequences comprising SEQ ID NOs: 352-354, respectively, and light chain CDR1, CDR2, and CDR3 sequences comprising SEQ ID NOs: 355-357, respectively; [UC1.3]
(p) heavy chain CDR1, CDR2, and CDR3 sequences comprising SEQ ID NOs: 13-15, respectively, and light chain CDR1, CDR2, and CDR3 sequences comprising SEQ ID NOs: 16-18, respectively; [UC2]
(q) heavy chain CDR1, CDR2, and CDR3 sequences comprising SEQ ID NOs: 373-375, respectively, and light chain CDR1, CDR2, and CDR3 sequences comprising SEQ ID NOs: 376-378, respectively; [UC3]
(r) heavy chain CDR1, CDR2, and CDR3 sequences comprising SEQ ID NOs: 394-396, respectively, and light chain CDR1, CDR2, and CDR3 sequences comprising SEQ ID NOs: 397-399, respectively; [UC4]
(s) heavy chain CDR1, CDR2, and CDR3 sequences comprising SEQ ID NOs: 415-417, respectively, and light chain CDR1, CDR2, and CDR3 sequences comprising SEQ ID NOs: 418-420, respectively; [UC5]
(t) heavy chain CDR1, CDR2, and CDR3 sequences comprising SEQ ID NOs: 436-438, respectively, and light chain CDR1, CDR2, and CDR3 sequences comprising SEQ ID NOs: 439-441, respectively; [UC6]
(u) heavy chain CDR1, CDR2, and CDR3 sequences comprising SEQ ID NOs: 457-459, respectively, and light chain CDR1, CDR2, and CDR3 sequences comprising SEQ ID NOs: 460-462, respectively; or [UC7]
(v) heavy chain CDR1, CDR2, and CDR3 sequences comprising SEQ ID NOs: 478-480, respectively, and light chain CDR1, CDR2, and CDR3 sequences comprising SEQ ID NOs: 481-483, respectively. [UC8]

In some embodiments, the anti-TNFR2 antibody comprises:

(a) heavy chain CDR1, CDR2, and CDR3 sequences comprising SEQ ID NOs: 30-32, respectively, and light chain CDR1, CDR2, and CDR3 sequences comprising SEQ ID NOs: 33-35, respectively; [UC2.3]

(b) heavy chain CDR1, CDR2, and CDR3 sequences comprising SEQ ID NOs: 53-55, respectively, and light chain CDR1, CDR2, and CDR3 sequences comprising SEQ ID NOs: 56-58, respectively; [UC2.3.3]

(c) heavy chain CDR1, CDR2, and CDR3 sequences comprising SEQ ID NOs: 76-78, respectively, and light chain CDR1, CDR2, and CDR3 sequences comprising SEQ ID NOs: 79-81, respectively; [UC2.3.7]

(d) heavy chain CDR1, CDR2, and CDR3 sequences comprising SEQ ID NOs: 99-101, respectively, and light chain CDR1, CDR2, and CDR3 sequences comprising SEQ ID NOs: 102-104, respectively; [UC2.3.8]

(e) heavy chain CDR1, CDR2, and CDR3 sequences comprising SEQ ID NOs: 122-124, respectively, and light chain CDR1, CDR2, and CDR3 sequences comprising SEQ ID NOs: 125-127, respectively; [UC2.3.9]

(f) heavy chain CDR1, CDR2, and CDR3 sequences comprising SEQ ID NOs: 145-147, respectively, and light chain CDR1, CDR2, and CDR3 sequences comprising SEQ ID NOs: 148-150, respectively; [UC2.3.10]

(g) heavy chain CDR1, CDR2, and CDR3 sequences comprising SEQ ID NOs: 168-170, respectively, and light chain CDR1, CDR2, and CDR3 sequences comprising SEQ ID NOs: 171-173, respectively; [UC2.3.11]

(h) heavy chain CDR1, CDR2, and CDR3 sequences comprising SEQ ID NOs: 191-193, respectively, and light chain CDR1, CDR2, and CDR3 sequences comprising SEQ ID NOs: 194-196, respectively; [UC2.3.12]

(i) heavy chain CDR1, CDR2, and CDR3 sequences comprising SEQ ID NOs: 214-216, respectively, and light chain CDR1, CDR2, and CDR3 sequences comprising SEQ ID NOs: 217-219, respectively; [UC2.3.13]

(j) heavy chain CDR1, CDR2, and CDR3 sequences comprising SEQ ID NOs: 237-239, respectively, and light chain CDR1, CDR2, and CDR3 sequences comprising SEQ ID NOs: 240-242, respectively; [UC2.3.14]

(k) heavy chain CDR1, CDR2, and CDR3 sequences comprising SEQ ID NOs: 260-262, respectively, and light chain CDR1, CDR2, and CDR3 sequences comprising SEQ ID NOs: 263-265, respectively; [UC2.3.15]

(l) heavy chain CDR1, CDR2, and CDR3 sequences comprising SEQ ID NOs: 283-285, respectively, and light chain CDR1, CDR2, and CDR3 sequences comprising SEQ ID NOs: 286-288, respectively; [UC1]

(m) heavy chain CDR1, CDR2, and CDR3 sequences comprising SEQ ID NOs: 304-306, respectively, and light chain CDR1, CDR2, and CDR3 sequences comprising SEQ ID NOs: 307-309, respectively; [UC1.1]

(n) heavy chain CDR1, CDR2, and CDR3 sequences comprising SEQ ID NOs: 325-327, respectively, and light chain CDR1, CDR2, and CDR3 sequences comprising SEQ ID NOs: 328-330, respectively; [UC1.2]

(o) heavy chain CDR1, CDR2, and CDR3 sequences comprising SEQ ID NOs: 346-348, respectively, and light chain CDR1, CDR2, and CDR3 sequences comprising SEQ ID NOs: 349-351, respectively; [UC1.3]

(p) heavy chain CDR1, CDR2, and CDR3 sequences comprising SEQ ID NOs: 7-9, respectively, and light chain CDR1, CDR2, and CDR3 sequences comprising SEQ ID NOs: 10-12, respectively; [UC2]

(q) heavy chain CDR1, CDR2, and CDR3 sequences comprising SEQ ID NOs: 367-369, respectively, and light chain CDR1, CDR2, and CDR3 sequences comprising SEQ ID NOs: 370-372, respectively; [UC3]

(r) heavy chain CDR1, CDR2, and CDR3 sequences comprising SEQ ID NOs: 388-390, respectively, and light chain CDR1, CDR2, and CDR3 sequences comprising SEQ ID NOs: 391-393, respectively; [UC4]

(s) heavy chain CDR1, CDR2, and CDR3 sequences comprising SEQ ID NOs: 409-411, respectively, and light chain CDR1, CDR2, and CDR3 sequences comprising SEQ ID NOs: 412-414, respectively; [UC5]

(t) heavy chain CDR1, CDR2, and CDR3 sequences comprising SEQ ID NOs: 430-432, respectively, and light chain CDR1, CDR2, and CDR3 sequences comprising SEQ ID NOs: 433-435, respectively; [UC6]

(u) heavy chain CDR1, CDR2, and CDR3 sequences comprising SEQ ID NOs: 451-453, respectively, and light chain CDR1, CDR2, and CDR3 sequences comprising SEQ ID NOs: 454-456, respectively; or [UC7]

(v) heavy chain CDR1, CDR2, and CDR3 sequences comprising SEQ ID NOs: 472-474, respectively, and light chain CDR1, CDR2, and CDR3 sequences comprising SEQ ID NOs: 475-477, respectively. [UC8]

In some embodiments, the anti-TNFR2 antibody comprises:

(a) heavy chain CDR1, CDR2, and CDR3 sequences comprising SEQ ID NOs: 42-44, respectively, and light chain CDR1, CDR2, and CDR3 sequences comprising SEQ ID NOs: 45-47, respectively; [UC2.3]

(b) heavy chain CDR1, CDR2, and CDR3 sequences comprising SEQ ID NOs: 65-67, respectively, and light chain CDR1, CDR2, and CDR3 sequences comprising SEQ ID NOs: 68-70, respectively; [UC2.3.3]

(c) heavy chain CDR1, CDR2, and CDR3 sequences comprising SEQ ID NOs: 88-90, respectively, and light chain CDR1, CDR2, and CDR3 sequences comprising SEQ ID NOs: 91-93, respectively; [UC2.3.7]

(d) heavy chain CDR1, CDR2, and CDR3 sequences comprising SEQ ID NOs: 111-113, respectively, and light chain CDR1, CDR2, and CDR3 sequences comprising SEQ ID NOs: 114-116, respectively; [UC2.3.8]

(e) heavy chain CDR1, CDR2, and CDR3 sequences comprising SEQ ID NOs: 134-136, respectively, and light chain CDR1, CDR2, and CDR3 sequences comprising SEQ ID NOs: 137-139, respectively; [UC2.3.9]

(f) heavy chain CDR1, CDR2, and CDR3 sequences comprising SEQ ID NOs: 157-159, respectively, and light chain CDR1, CDR2, and CDR3 sequences comprising SEQ ID NOs: 160-162, respectively; [UC2.3.10]

(g) heavy chain CDR1, CDR2, and CDR3 sequences comprising SEQ ID NOs: 180-182, respectively, and light chain CDR1, CDR2, and CDR3 sequences comprising SEQ ID NOs: 183-185, respectively; [UC2.3.11]

(h) heavy chain CDR1, CDR2, and CDR3 sequences comprising SEQ ID NOs: 203-205, respectively, and light chain CDR1, CDR2, and CDR3 sequences comprising SEQ ID NOs: 206-208, respectively; [UC2.3.12]

(i) heavy chain CDR1, CDR2, and CDR3 sequences comprising SEQ ID NOs: 226-228, respectively, and light chain CDR1, CDR2, and CDR3 sequences comprising SEQ ID NOs: 229-231, respectively; [UC2.3.13]

(j) heavy chain CDR1, CDR2, and CDR3 sequences comprising SEQ ID NOs: 249-251, respectively, and light chain CDR1, CDR2, and CDR3 sequences comprising SEQ ID NOs: 252-254, respectively; [UC2.3.14]

(k) heavy chain CDR1, CDR2, and CDR3 sequences comprising SEQ ID NOs: 272-274, respectively, and light chain CDR1, CDR2, and CDR3 sequences comprising SEQ ID NOs: 275-277, respectively; [UC2.3.15]

(l) heavy chain CDR1, CDR2, and CDR3 sequences comprising SEQ ID NOs: 295-297, respectively, and light chain CDR1, CDR2, and CDR3 sequences comprising SEQ ID NOs: 298-300, respectively; [UC1]

(m) heavy chain CDR1, CDR2, and CDR3 sequences comprising SEQ ID NOs: 316-318, respectively, and light chain CDR1, CDR2, and CDR3 sequences comprising SEQ ID NOs: 319-321, respectively; [UC1.1]

(n) heavy chain CDR1, CDR2, and CDR3 sequences comprising SEQ ID NOs: 337-339, respectively, and light chain CDR1, CDR2, and CDR3 sequences comprising SEQ ID NOs: 340-342, respectively; [UC1.2]

(o) heavy chain CDR1, CDR2, and CDR3 sequences comprising SEQ ID NOs: 358-360, respectively, and light chain CDR1, CDR2, and CDR3 sequences comprising SEQ ID NOs: 361-363, respectively; [UC1.3]

(p) heavy chain CDR1, CDR2, and CDR3 sequences comprising SEQ ID NOs: 19-21, respectively, and light chain CDR1, CDR2, and CDR3 sequences comprising SEQ ID NOs: 22-24, respectively; [UC2]

(q) heavy chain CDR1, CDR2, and CDR3 sequences comprising SEQ ID NOs: 379-381, respectively, and light chain CDR1, CDR2, and CDR3 sequences comprising SEQ ID NOs: 382-384, respectively; [UC3]

(r) heavy chain CDR1, CDR2, and CDR3 sequences comprising SEQ ID NOs: 400-402, respectively, and light chain CDR1, CDR2, and CDR3 sequences comprising SEQ ID NOs: 403-405, respectively; [UC4]

(s) heavy chain CDR1, CDR2, and CDR3 sequences comprising SEQ ID NOs: 421-423, respectively, and light chain CDR1, CDR2, and CDR3 sequences comprising SEQ ID NOs: 424-426, respectively; [UC5]

(t) heavy chain CDR1, CDR2, and CDR3 sequences comprising SEQ ID NOs: 442-444, respectively, and light chain CDR1, CDR2, and CDR3 sequences comprising SEQ ID NOs: 445-447, respectively; [UC6]

(u) heavy chain CDR1, CDR2, and CDR3 sequences comprising SEQ ID NOs: 463-465, respectively, and light chain CDR1, CDR2, and CDR3 sequences comprising SEQ ID NOs: 466-468, respectively; or [UC7]

(v) heavy chain CDR1, CDR2, and CDR3 sequences comprising SEQ ID NOs: 484-486, respectively, and light chain CDR1, CDR2, and CDR3 sequences comprising SEQ ID NOs: 487-489, respectively. [UC8]

In some embodiments, the anti-TNFR2 antibody comprises the heavy chain CDR sequences above, and a constant region, e.g., a human IgG constant region (e.g., IgG1, IgG2, IgG3, or IgG4, or variants thereof). In some embodiments, a heavy chain variable region comprising the heavy chain CDR sequences described above may be linked to a constant domain to form a heavy chain (e.g., a full length heavy chain). Similarly, a light chain variable region comprising the light chain CDR sequences described above may be linked to a constant region to form a light chain (e.g., a full length light chain). A full length heavy chain (with the exception of the C-terminal lysine (K) or with the exception of the C-terminal glycine and lysine (GK), which may be absent or removed) and full length light chain combine to form a full length antibody.

In some embodiments, the anti-TNFR2 antibody comprises a heavy chain variable region and a light chain variable region, wherein the heavy chain variable region comprises an amino acid sequence selected from the group consisting of SEQ ID NOs: 25, 48, 71, 94, 117, 140, 163, 186, 209, 232, 255, 278, 301, 322, 343, 364, 385, 406, 427, 448, 469, and 490. In other embodiments, the anti-TNFR2 antibody comprises a heavy chain variable region and a light chain variable region, wherein the light chain variable region comprises an amino acid sequence selected from the group consisting of SEQ ID NOs: 26, 49, 72, 95, 118, 141, 164, 187, 210, 233, 256, 279, 302, 323, 344, 365, 386, 407, 428, 449, 470, and 491. In other embodiments, the anti-TNFR2 antibody comprises a heavy chain variable region and a light chain variable region, wherein the heavy chain variable region comprises an amino acid sequence selected from the group consisting of SEQ ID NOs: 25, 48, 71, 94, 117, 140, 163, 186, 209, 232, 255, 278, 301, 322, 343, 364, 385, 406, 427, 448, 469, and 490, and the light chain variable region comprises an amino acid sequence selected from the group consisting of SEQ ID NOs: 26, 49, 72, 95, 118, 141, 164, 187, 210, 233, 256, 279, 302, 323, 344, 365, 386, 407, 428, 449, 470, and 491. In other embodiments, the anti-TNFR2 antibody comprises a heavy chain variable region and a light chain variable region, wherein the heavy chain variable region and/or light chain variable region sequence is at least 80%, 85%, 90%, 95%, 96%, 97%, 98%, or 99% identical to the heavy chain and/or light chain variable region sequences described above (e.g., SEQ ID NOs: 25, 26, 48, 49, 71, 72, 94, 95, 117, 118, 140, 141, 163, 164, 186, 187, 209, 210, 232, 233, 255, 256, 278, 279, 301, 302, 322, 323, 343, 344, 364, 365, 385, 386, 406, 407, 427, 428, 448, 449, 469, 470, 490, and 491). In other embodiments, the heavy chain and/or light chain variable region sequences of any of SEQ ID NOs: 25, 26, 48, 49, 71, 72, 94, 95, 117, 118, 140, 141, 163, 164, 186, 187, 209, 210, 232, 233, 255, 256, 278, 279, 301, 302, 322, 323, 343, 344, 364, 365, 385, 386, 406, 407, 427, 428, 448, 449, 469, 470, 490, and 491 has 1, 2, 3, 4, 5, 1-2, 1-3, 1-4, or 1-5 amino acid substitutions (e.g., conservative amino acid substitutions).

In some embodiments, the anti-TNFR2 antibody comprises heavy and light chain variable region sequences which are at least 80%, at least 85%, at least 90%, at least 91%, at least 92%, at least 93%, at least 94%, at least 95%, at least 96%, at least 97%, at least 98%, at least 99%, or are 100% identical to the amino acid sequences selected from the group consisting of:

(a) SEQ ID NOs: 48 and 49, respectively; [UC2.3]

(b) SEQ ID NOs: 71 and 72, respectively; [UC2.3.3]

(c) SEQ ID NOs: 94 and 95, respectively; [UC2.3.7]

(d) SEQ ID NOs: 117 and 118, respectively; [UC2.3.8]

(e) SEQ ID NOs: 140 and 141, respectively; [UC2.3.9]

(f) SEQ ID NOs: 163 and 164, respectively; [UC2.3.10]

(g) SEQ ID NOs: 186 and 187, respectively; [UC2.3.11]

(h) SEQ ID NOs: 209 and 210, respectively; [UC2.3.12]

(i) SEQ ID NOs: 232 and 233, respectively; [UC2.3.13]

(j) SEQ ID NOs: 255 and 256, respectively; [UC2.3.14]

(k) SEQ ID NOs: 278 and 279, respectively; [UC2.3.15]

(l) SEQ ID NOs: 301 and 302, respectively; [UC1]

(m) SEQ ID NOs: 322 and 323, respectively; [UC1.1]

(n) SEQ ID NOs: 343 and 344, respectively; [UC1.2]

(o) SEQ ID NOs: 364 and 364, respectively; [UC1.3]

(p) SEQ ID NOs: 25 and 26, respectively; [UC2]
(q) SEQ ID NOs: 385 and 386, respectively; [UC3]
(r) SEQ ID NOs: 406 and 407, respectively; [UC4]
(s) SEQ ID NOs: 427 and 428, respectively; [UC5]
(t) SEQ ID NOs: 448 and 449, respectively; [UC6]
(u) SEQ ID NOs: 469 and 470, respectively; [UC7] and
(v) SEQ ID NOs: 490 and 491, respectively. [UC8]

In some embodiments, the heavy chain and/or light chain variable region sequences above have 1, 2, 3, 4, 5, 1-2, 1-3, 1-4, or 1-5 amino acid substitutions (e.g., conservative amino acid substitutions).

In some embodiments, antibodies comprising the heavy and light chain CDR sequences or heavy and light chain variable region sequences described herein are human, humanized, or chimeric antibodies (e.g., recombinant human, humanized, or chimeric antibodies).

In some embodiments, the anti-human TNFR2 antibody comprises the heavy chain variable region sequences above, and a constant region, e.g., a human IgG constant region (e.g., IgG1, IgG2, IgG3, or IgG4, or variants thereof) to form a heavy chain (e.g., a full length heavy chain). Similarly, a light chain variable region comprising the light chain variable region sequences described above may be linked to a constant region to form a light chain (e.g., a full length light chain). A full length heavy chain (with the exception of the C-terminal lysine (K) or with the exception of the C-terminal glycine and lysine (GK), which may be absent or removed) and full length light chain combine to form a full length antibody.

In some embodiments, the anti-TNFR2 antibody comprises heavy and light chain sequences which are at least 80%, at least 85%, at least 90%, at least 91%, at least 92%, at least 93%, at least 94%, at least 95%, at least 96%, at least 97%, at least 98%, at least 99%, or are 100% identical to the amino acid sequences selected from the group consisting of:

(a) SEQ ID NOs: 50 and 51, respectively; [UC2.3]
(b) SEQ ID NOs: 73 and 74, respectively; [UC2.3.3]
(c) SEQ ID NOs: 96 and 97, respectively; [UC2.3.7]
(d) SEQ ID NOs: 119 and 120, respectively; [UC2.3.8]
(e) SEQ ID NOs: 142 and 143, respectively; [UC2.3.9]
(f) SEQ ID NOs: 165 and 166, respectively; [UC2.3.10]
(g) SEQ ID NOs: 188 and 189, respectively; [UC2.3.11]
(h) SEQ ID NOs: 211 and 212, respectively; [UC2.3.12]
(i) SEQ ID NOs: 234 and 235, respectively; [UC2.3.13]
(j) SEQ ID NOs: 257 and 258, respectively; [UC2.3.14]
(k) SEQ ID NOs: 280 and 281, respectively; [UC2.3.15] and
(l) SEQ ID NOs: 27 and 28, respectively. [UC2]

In some embodiments, the heavy chain and/or light chain sequences above have 1, 2, 3, 4, 5, 1-2, 1-3, 1-4, or 1-5 amino acid substitutions (e.g., conservative amino acid substitutions).

In some embodiments, the anti-TNFR2 antibodies bind to TNFR2 (e.g., the extracellular domain of human TNFR2) with a $K_D$ of about 100 nM or less, about 75 nM or less, about 50 nM or less, about 25 nM or less, about 10 nM or less, about 1 nM or less, about 750 pM or less, about 500 pM or less, about 250 pM or less, about 100 pM or less, about 10 pM or less, about 1 pM or less, about 1 pM to about 100 nM, about 10 pM to about 100 nM, about 100 pM to about 100 nM, about 250 pM to about 100 nM, about 500 pM to about 100 nM, about 750 pM to about 100 nM, about 100 pM to about 10 nM, about 250 pM to about 10 nM, about 500 pM to about 10 nM, about 750 pM to about 10 nM, about 100 pM to about 10 nM, about 250 pM to about 10 nM, about 500 pM to about 10 nM, about 750 pM to about 10 nM, about 100 pM to about 1 nM, about 250 pM to about 750 pM, about 300 pM to about 600 pM, about 250 pM to about 1 nM, about 500 pM to about 1 nM, about 750 pM to about 1 nM, about 1 nM to about 100 nM, about 1 nM to about 75 nM, about 1 nM to about 50 nM, or about 1 nM to about 25 nM, as assessed by, e.g., bio-layer interferometry.

In some embodiments, the anti-TNFR2 antibodies bind to membrane-bound human TNFR2 (e.g., human TNFR2 expressed on cells) with an $EC_{50}$ of about 500 nM or less, about 250 nM or less, about 100 nM or less, about 50 nM or less, about 25 nM or less, about 10 nM or less, about 1 nM or less, about 100 pM or less, about 10 pM or less, about 100 pM to about 500 nM, about 100 pM to about 250 nM, about 100 pM to about 100 nM, about 1 pM to about 250 nM, about 1 pM to about 100 nM, about 500 pM to about 100 nM, about 1 nM to about 100 nM, as assessed by, e.g., flow cytometry.

In some embodiments, the anti-TNFR2 antibodies inhibit the binding of TNFR2 ligand (e.g., TNFα) to TNFR2. In some embodiments, the anti-TNFR2 antibodies inhibit the binding of TNFR2 ligand (e.g., TNFα) to TNFR2 by at least 10%, for example, by at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99%, relative to a control antibody (e.g., an antibody which does not bind to TNFR2). In some embodiments, the anti-TNFR2 antibodies inhibit the binding of TNFR2 ligand (e.g., TNFα) to membrane TNFR2 (e.g., human TNFR2 expressed on cells) with an $IC_{50}$ of about 250 nM or less, about 100 nM or less, about 50 nM or less, about 25 nM or less, about 10 nM or less, about 5 nM or less, about 1 nM or less, about 750 pM or less, about 500 pM or less, about 100 pM or less, about 10 pM to about 250 nM, about 10 pM to about 100 nM, about 10 pM to about 50 nM, about 50 pM to about 250 nM, about 50 pM to about 100 nM, about 50 pM to about 50 nM, about 75 pM to about 250 nM, about 75 pM to about 100 nM, about 75 pM to about 50 nM, about 100 pM to about 250 nM, about 100 pM to about 100 nM, about 100 pM to about 100 nM, about 500 pM to about 250 nM, about 500 pM to about 100 nM, about 500 pM to about 50 nM, about 500 pM to about 10 nM, about 1 nM to about 250 nM, about 1 nM to about 100 nM, or about 1 nM to about 50 nM, as assessed by, e.g., flow cytometry. Other art-recognized methods can be used to measure ligand competition, such as biolayer interferometry and surface plasmon resonance.

In some embodiments, the anti-TNFR2 antibodies are agonist antibodies, i.e., anti-TNFR2 antibodies that activate TNFR2 signaling pathways in cells.

In some embodiments, the anti-TNFR2 antibodies increase NF-kB activity, e.g., as assessed by NF-kB reporter cell lines (e.g., NF-kB reporter cell lines engineered to express human TNFR2). In other embodiments, the anti-TNFR2 antibodies increase NF-kB activity by, e.g., at least 2-fold, at least 3-fold, at least 4-fold, at least 5-fold, at least 10-fold, at least 15-fold, or at least 20-fold relative to a control (e.g., an isotype control antibody or the NF-kB reporter cell line which does not express human TNFR2).

In some embodiments, the anti-TNFR2 antibodies decrease the percentage of regulatory T cells (Tregs) within the CD4+ T cell compartment relative to a control (e.g., no antibody control or isotype antibody control). In other embodiments, the anti-TNFR2 antibodies decrease the percentage of Treg cells within the CD4+ T cell compartment by about 10%, about 20%, about 30%, about 40%, about 50%, about 60%, about 70%, or about 80% relative to a control (e.g., no antibody control or isotype antibody control).

In some embodiments, the anti-TNFR2 antibodies induce ADCC in the presence of NK cells.

In some embodiments, the anti-TNFR2 antibodies enhance T cell activation. In other embodiments, the anti-TNFR2 antibodies enhance the activation of CD4+ and CD8+ T cells, e.g., as reflected in the increased expression of activation markers (e.g., CD25, PD1), as assessed by, e.g., flow cytometry.

In some embodiments, the anti-TNFR2 antibodies increase T cell proliferation. In other embodiments, the anti-TNFR2 antibodies increase the proliferation of CD4+ T cells and CD8+ T cells.

In some embodiments, the anti-TNFR2 antibodies reduce (protect against) graft rejection, e.g., as assessed in a graft-versus-host disease (GvHD) model. Reduced graft rejection can be assessed, e.g., by comparison with a control (e.g., improved survival relative to treatment with a control antibody or vehicle or an unrelated antibody).

In some embodiments, the anti-TNFR2 antibodies inhibit tumor growth, for example, by 10% or more, 20% or more, 30% or more, 40% or more, 50% or more, 60% or more, 70% or more, 80% or more, 90% or more, or 95% or more, relative to a control therapy.

In some embodiments, the anti-TNFR2 antibodies inhibit tumor growth independent of the ability to agonize TNFR2 signaling.

In some embodiments, the anti-TNFR2 antibodies inhibit tumor growth independent of the ability to inhibit TNF-α binding to TNFR2.

In some embodiments, the anti-TNFR2 antibodies induce a long-term anti-cancer effect (e.g., inhibit and/or suppress tumor growth for a sustained period of time after treatment with the anti-TNFR2 antibodies). In a particular embodiment, the anti-TNFR2 antibodies induce the development of anti-cancer memory T cells, as compared to control (e.g., subjects not treated with anti-TNFR2 antibodies).

Also provided herein are methods of inducing a long-term anti-cancer effect comprising administering the anti-TNFR2 antibodies described herein to a subject with cancer.

In one embodiment, a long-term anti-cancer effect can be measured in mouse models of human cancer (e.g., transgenic models, humanized models, and/or chimeric, allograft, and xenograft models). Tumor recurrence (or suppression) can be monitored, e.g., for at least 6 months, in mice which exhibited tumor regression after initial treatment with anti-TNFR2 antibodies. In other embodiments, tumor recurrence (or suppression) can be monitored for at least 1 or more years or at least 2 or more years.

In another embodiment, to determine whether cytotoxic T lymphocytes (CTLs) have develop into memory T cells, various doses of the same tumor cells can be reinoculated into the tumor-regressed mice at different time points after the tumor regression, and then monitor tumor grow in the recipient mouse. Wildtype mice can be inoculated with the same tumor as controls. To determine the frequency of tumor specific memory T cells in tumor regressed mice, in vitro cytotoxicity assay can be performed using particular cancer cell antigens as targets.

In some embodiments, the anti-TNFR2 antibodies described herein are monoclonal antibodies, e.g., monoclonal human antibodies.

An antibody that exhibits one or more of the functional properties described above (e.g., biochemical, immunochemical, cellular, physiological or other biological activities, or the like) as determined according to methodologies known to the art and described herein, will be understood to relate to a statistically significant difference in the particular activity relative to that seen in the absence of the antibody (e.g., or when a control antibody of irrelevant specificity is present). Preferably, the anti-TNFR2 antibody-induced increases in a measured parameter effects a statistically significant increase by at least 10% of the measured parameter, more preferably by at least 20%, 30%, 40%, 50%, 60%, 70%, 80%, 90%, 95%, or 100% (i.e., 2-fold), 3-fold, 5-fold or 10-fold. Conversely, anti-TNFR2 antibody-induced decreases in a measured parameter (e.g., TNFα binding to TNFR2) effects a statistically significant decrease by at least 10%, 20%, 30%, 40%, 50%, 60%, 70%, 80%, 90%, 95%, 97%, 98%, 99%, or 100%.

Antibodies disclosed herein include all known forms of antibodies and other protein scaffolds with antibody-like properties. For example, the antibody can be a human antibody, a humanized antibody, a bispecific antibody, an immunoconjugate, a chimeric antibody, or a protein scaffold with antibody-like properties, such as fibronectin or ankyrin repeats. The antibody also can be a Fab, Fab'2, scFv, AFFIBODY, avimer, nanobody, or a domain antibody. The antibody also can have any isotype, including any of the following isotypes: IgG1, IgG2, IgG3, IgG4, IgM, IgA1, IgA2, IgAsec, IgD, and IgE. Full-length antibodies can be prepared from $V_H$ and $V_L$ sequences using standard recombinant DNA techniques and nucleic acid encoding the desired constant region sequences to be operatively linked to the variable region sequences.

In some embodiments, the anti-TNFR2 antibody binds to the same epitope on TNFR2 as the anti-TNFR2 antibodies described herein. In other embodiments, the antibody competes for binding to TNFR2 with the anti-TNFR2 antibodies described herein.

In some embodiments, the anti-TNFR2 antibodies are modified to enhance effector function relative to the same antibody in unmodified form. In other embodiments, the anti-TNFR2 antibodies exhibit increased anti-tumor activity relative to the same antibody in unmodified form.

Accordingly, the variable regions of the anti-TNFR antibodies may be linked to a non-naturally occurring Fc region, e.g., an Fc with enhanced binding to one or more activating Fc receptors (FcγI, FcγIIa or FcγIIIa). In general, the variable regions described herein may be linked to an Fc comprising one or more modification (e.g., an amino acid substitution, deletion, and/or insertion), typically to enhance one or more functional properties of the antibody, such as serum half-life, complement fixation, Fc receptor binding, antibody-dependent cell-mediated cytotoxicity (ADCC), and/or antibody-dependent cellular phagocytosis (ADCP), relative to a parent Fc sequence (e.g., the unmodified Fc polypeptide). Furthermore, an antibody may be chemically modified (e.g., one or more chemical moieties can be attached to the antibody) or be modified to alter its glycosylation, to alter one or more functional properties of the antibody. Each of these embodiments is described in further detail below. The numbering of residues in the Fc region is that of the EU index of Kabat.

Fcγ receptor engagement of therapeutic antibodies can be important for their activity (Clynes et al., Nat Med 2000; 6:443-6). Both mice and humans have activating Fcγ receptors (e.g., mFcγRI, mFcγRIII, or mFcγRIV in mice and hFcγRI, hFcγRIIa, hFcγRIIc, mFcγRIIIa, or mFcγRIIIb in humans) and inhibitory Fcγ receptors (mFcγRIIb in mice and hFcγRIIb in humans) (Nimmerjahn et al., Nat Rev Immunol 2008; 8:34-47). Fcγ receptor engagement can indicate: 1) contribution of effector functions of the antibody such as antibody-dependent cellular cytotoxicity (ADCC), Opsonization or antibody-dependent cellular phagocytosis (ADCP) via activating Fcγ receptors (Dahan et al., Cancer Cell 2015; 28:285-95); or 2) enhanced agonism via clustering of the antibody on Fcγ receptor-expressing cell types (Nimmerjahn et al., Trends in Immunology 2015; 36:325-36. Accordingly, in some embodiments, provided herein are anti-TNFR2 antibodies that mediate the agonistic activity and co-stimulation of T cells. For enhanced agonism, the inhibitory Fcγ receptor FcγRIIb has been described as most important to facilitate agonism (see, e.g., Dahan et al., Cancer Cell 2016; 29:820-31).

The various antibody IgG isotypes have different preferences for binding certain Fcγ receptors (Bruhns et al., Blood 2012; 119:5640-9). In humans, IgG1 antibodies are the preferred isotype for mediating effector functions such as ADCC or ADCP because of their high affinity for activating Fcγ receptors. Various mutations for antibody Fc have been described that alter the binding profile to the various Fcγ receptors, and hence can modulate the activity of an antibody. The N297A mutation (NA), D265A/N297A mutations (DANA), or the D265A/N297G mutations (DANG) reduce or ablate bind to all Fcγ receptors (Lo et al., J Biol Chem 2017; 292:3900-8) and hence reduce capacity for effector functions or enhanced agonism. L234A/L235A mutations (LALA) reduce or ablate bind to all Fcγ receptors (Arduin et al., Mol Immunol 2015; 63:456-63). Similarly, mutations with enhanced binding to FcγRIIb and hence increased agonistic activity have been described (see, e.g., Dahan et al., Cancer Cell 2016; 29:820-31), such as the S267E mutation (SE), the S267E and L328F mutations (SELF), the G237D/P238D/P271G/A330R mutations (V9), the E233D/P238D/H268D/P271G/A330R mutations (V10), the G237D/P238D/H268D/P271G/A330R mutations (V11), or the E233D/G237D/P238D/H268D/P271G/A330R mutations (V12) (Mimoto et al., Protein Eng Des Sel 2013; 26:589-98).

Accordingly, the anti-TNFR2 antibodies may comprise a variant Fc region (e.g., a variant IgG1 Fc region). In some embodiments, the variant Fc region increases binding to Fcγ receptors relative to binding observed with the corresponding non-variant version of the Fc region (e.g., if the variant Fc region is a variant IgG1 Fc region, then the corresponding non-variant version is the wild-type IgG1 Fc region). In some embodiments, the variant Fc region (e.g., variant IgG1 Fc region) increases binding to the FcγRIIb receptor. In some embodiments, the variant Fc region increases antibody clustering relative to the corresponding wild-type Fc region. In some embodiments, the antibody comprises a variant Fc region and exhibits increased agonistic activity relative to an antibody with a corresponding non-variant version of the Fc region. In some embodiments, the antibody co-stimulates T cells. In some embodiments, the variant Fc region is a variant IgG1 Fc region. In some embodiments, the Fc region has a 267E mutation (SE), S267E/L328F mutations (SELF), G237D/P238D/P271G/A330R mutations, E233D/P238D/H268D/P271G/A330R mutations, G237D/P238D/H268D/P271G/A330R mutations, or E233D/G237D/P238D/H268D/P271G/A330R mutations. Other exemplary modifications to the Fc region for altering effector function are described below.

Modifications can be made in the Fc region to generate an Fc variant that (a) has increased antibody-dependent cell-mediated cytotoxicity (ADCC), (b) has increased antibody-dependent cellular phagocytosis (ADCP), (c) has increased complement mediated cytotoxicity (CDC), (d) has increased affinity for C1q and/or (e) has increased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc. substitutions therein, e.g. of the specific Fc region positions identified herein.

In some embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320, and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in detail in U.S. Pat. Nos. 5,624,821 and 5,648,260, both by Winter et al.

In some embodiments, the Fc region may be modified to increase antibody dependent cellular cytotoxicity (ADCC) and/or to increase the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E. Exemplary combinations of substitutions include 239D/332E, 236A/332E, 236A/239D/332E, 268F/324T, 267E/268F, 267E/324T, and 267E/268F/324T. Other modifications for enhancing FcγR and complement interactions include, but are not limited to, substitutions 298A, 333A, 334A, 326A, 2471, 339D, 339Q, 280H, 290S, 298D, 298V, 243L, 292P, 300L, 396L, 305I, and 396L. These and other modifications are reviewed in Strohl et al., Current Opinion in Biotechnology 2009; 20:685-691.

Fc modifications that increase binding to an Fcγ receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 3338, 340, 360, 373, 376, 379, 382, 388, 389, 398, 414, 416, 419, 430, 434, 435, 437, 438, or 439 of the Fc region, wherein the numbering of the residues in the Fc region is that of the EU index as in Kabat (WO00/42072).

Fc variants that enhance affinity for an inhibitory receptor FcγRllb may also be used. Such variants may provide an Fc fusion protein with immunomodulatory activities related to FcγRllb$^+$ cells, including for example B cells and monocytes. In one embodiment, the Fc variants provide selectively enhanced affinity to FcγRllb relative to one or more activating receptors. Modifications for altering binding to FcγRllb include one or more modifications at a position selected from the group consisting of 234, 235, 236, 237, 239, 266, 267, 268, 325, 326, 327, 328, and 332, according to the EU index. Exemplary substitutions for enhancing FcγRllb affinity include, but are not limited to, 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Other Fc variants for enhancing binding to FcγRllb include 235Y/267E, 236D/267E, 239D/268D, 239D/267E, 267E/268D, 267E/268E, and 267E/328F.

The affinities and binding properties of an Fc region for its ligand may be determined by a variety of in vitro assay methods (biochemical or immunological based assays) known in the art including, but not limited to, equilibrium methods (e.g., enzyme-linked immunosorbent assay (ELISA), or radioimmunoassay (RIA)), or kinetics (e.g., BIACORE analysis), and other methods such as indirect binding assays, competitive inhibition assays, fluorescence resonance energy transfer (FRET), gel electrophoresis, and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

In certain embodiments, the antibody is modified to increase its biological half-life. For example, this may be done by increasing the binding affinity of the Fc region for FcRn by mutating one or more of the following residues: 252, 254, 256, 433, 435, 436, as described in U.S. Pat. No. 6,277,375. Specific exemplary substitutions include one or more of the following: T252L, T254S, and/or T256F. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary variants that increase binding to FcRn and/or improve pharmacokinetic properties include substitutions at positions 259, 308, 428, and 434, including for example 2591, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 307Q, 31 1A, 312A, 376A, 378Q, 380A, 382A, 434A (Shields et al, *Journal of Biological Chemistry,* 2001, 276 (9):6591-6604), 252F, 252T, 252Y, 252W, 254T, 256S, 256R, 256Q, 256E, 256D, 256T, 309P, 31 1 S, 433R, 433S, 4331, 433P, 433Q, 434H, 434F, 434Y, 252Y/254T/256E, 433K/434F/436H, 308T/309P/311S (Dall Acqua et al. Journal of Immunology, 2002, 169:5171-5180, Dall'Acqua et al., 2006, Journal of Biological Chemistry 281:23514-23524). Other modifications for modulating FcRn binding are described in Yeung et al., 2010, J Immunol, 182:7663-7671.

The binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding and ADCC activity: T256A/S298A, S298A/E333A, S298A/K224A, and S298A/E333A/K334A (Shields et al., supra). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys (Lazar et al., 2006). Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys (Lazar et al., 2006). In addition, IgG1 mutants containing L235V, F243L, R292P, Y300L, and P396L mutations which exhibited enhanced binding to FcγRIIIa and concomitantly enhanced ADCC activity in transgenic mice expressing human FcγRIIIa in models of B cell malignancies and breast cancer have been identified (Stavenhagen et al., 2007; Nordstrom et al., 2011). Other Fc mutants that may be used include: S298A/E333A/L334A, S239D/I332E, S239D/I332E/A330L, L235V/F243L/R292P/Y300L/P396L, and M428L/N434S.

In another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such an approach is described in further detail in U.S. Pat. Nos. 5,714,350 and 6,350,861 by Co et al. In one embodiment, glycosylation of the constant region on N297 may be prevented by mutating the N297 residue to another residue, e.g., N297A, and/or by mutating an adjacent amino acid, e.g., 298 to thereby reduce glycosylation on N297.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. In some embodiments, mutations can be made to restore effector function in aglycosylated antibody, e.g., as described in U.S. Pat. No. 8,815,237. Exemplary mutations include E269D, D270E, N297D, N297H, S298A, S298G, S298T, T299A, T299G, T299H, K326E, K326I, A327E, A327Y, L328A, and L328G.

A variant Fc region may also comprise sequence alterations wherein amino acids involved in disulfide bond formation are removed or replaced with other amino acids. Such removal may avoid reaction with other cysteine-containing proteins present in the host cell used to produce the antibodies. Even when cysteine residues are removed, single chain Fc domains can still form a dimeric Fc domain that is held together non-covalently.

IV. Antibodies which Bind to the Same Epitope as or Compete with Anti-TNFR2 Antibodies Also provided are antibodies which bind to the same epitope on TNFR2 as the anti-TNFR2 antibodies described herein. In some embodiments, the antibodies compete for binding to TNFR2 with the anti-TNFR2 antibodies described herein.

Cross-competing antibodies can be screened for based on their ability to cross-compete with the anti-TNFR2 antibodies described herein using standard binding assays (e.g., ELISA, Biacore).

Techniques for determining antibodies that bind to the "same epitope on TNFR2" with the antibodies described herein include x-ray analyses of crystals of antigen:antibody complexes, which provides atomic resolution of the epitope. Other methods monitor the binding of the antibody to antigen fragments or mutated variations of the antigen where loss of binding due to an amino acid modification within the antigen sequence indicates the epitope component. Methods may also rely on the ability of an antibody of interest to affinity isolate specific short peptides (either in native three-dimensional form or in denatured form) from combinatorial phage display peptide libraries or from a protease digest of the target protein. The peptides are then regarded as leads for the definition of the epitope corresponding to the antibody used to screen the peptide library. For epitope mapping, computational algorithms have also been developed that have been shown to map conformational discontinuous epitopes.

The epitope or region comprising the epitope can also be identified by screening for binding to a series of overlapping peptides spanning TNFR2. Alternatively, the method of Jespers et al. (1994) *Biotechnology* 12:899 may be used to guide the selection of antibodies having the same epitope and therefore similar properties to the anti-TNFR2 antibodies described herein. Using phage display, first, the heavy chain of the anti-TNFR2 antibody is paired with a repertoire of (e.g., human) light chains to select an TNFR2-binding antibody, and then the new light chain is paired with a repertoire of (e.g., human) heavy chains to select a (e.g., human) TNFR2-binding antibody having the same epitope or epitope region as an anti-TNFR2 antibody described herein. Alternatively, variants of an antibody described herein can be obtained by mutagenesis of cDNA sequences encoding the heavy and light chains of the antibody.

Alanine scanning mutagenesis, as described by Cunningham & Wells (1989) *Science* 244: 1081, or some other form of point mutagenesis of amino acid residues in TNFR2 may also be used to determine the functional epitope for an anti-TNFR2 antibody.

The epitope or epitope region (an "epitope region" is a region comprising the epitope or overlapping with the epitope) bound by a specific antibody may also be determined by assessing binding of the antibody to peptides comprising TNFR2 fragments. A series of overlapping peptides encompassing the TNFR2 sequence may be synthesized and screened for binding, e.g. in a direct ELISA, a competitive ELISA (where the peptide is assessed for its ability to prevent binding of an antibody to TNFR2 bound to a well of a microtiter plate), or on a chip. Such peptide screening methods may not be capable of detecting some discontinuous functional epitopes, i.e., functional epitopes that involve amino acid residues that are not contiguous along the primary sequence of the TNFR2 polypeptide chain.

An epitope may also be identified by MS-based protein footprinting, such as HDX-MS and Fast Photochemical Oxidation of Proteins (FPOP). HDX-MS may be conducted, e.g., as further described at Wei et al. (2014) *Drug Discovery Today* 19:95, the methods of which are specifically incorporated by reference herein. FPOP may be conducted as described, e.g., in Hambley & Gross (2005) *J. American Soc. Mass Spectrometry* 16:2057, the methods of which are specifically incorporated by reference herein.

The epitope bound by anti-TNFR2 antibodies may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in TNFR2 when free and when bound in a complex with an antibody of interest (Zinn-Justin et al. (1992) *Biochemistry* 31:11335; Zinn-Justin et al. (1993) *Biochemistry* 32:6884).

V. Nucleic Acid Molecules

Also provided herein are nucleic acid molecules that encode the antibodies described herein. The nucleic acids may be present in whole cells, in a cell lysate, or in a partially purified or substantially pure form. A nucleic acid described herein can be, for example, DNA or RNA and may or may not contain intronic sequences. In a certain embodiments, the nucleic acid is a cDNA molecule. The nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

In some embodiments, provided herein are nucleic acid molecules that encode the VH and/or VL sequences, or heavy and/or light chain sequences, of any of the anti-TFNR2 antibodies described herein. Host cells comprising the nucleotide sequences (e.g., nucleic acid molecules) described herein are encompassed herein.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

Also provided herein are nucleic acid molecules with conservative substitutions that do not alter the resulting amino acid sequence upon translation of the nucleic acid molecule.

VI. Methods for Screening and Producing Antibodies

The anti-TNFR2 antibodies (e.g., anti-human TNFR2 antibodies) provided herein typically are prepared by standard recombinant DNA techniques. Additionally, monoclonal antibodies can be produced using a variety of known techniques, such as the standard somatic cell hybridization technique, viral or oncogenic transformation of B lymphocytes, or yeast or phage display techniques using libraries of human antibody genes. In particular embodiments, the antibodies are fully human monoclonal antibodies.

In one embodiment, provided herein are methods for generating monoclonal anti-human TNFR2 antibodies. Monoclonal antibodies may be readily prepared using well-known techniques (see, e.g., Antibodies: A Laboratory Manual, Cold Spring Harbor Laboratory, 1988; incorporated herein by reference). Typically, this technique involves immunizing a suitable animal with a selected polypeptide (e.g., the extracellular domain of human TNFR2 or a polypeptide that includes a human TNFR2 epitope of interest) conjugated to a carrier protein (e.g., KLH, bovine serum albumin).

The immunizing composition is administered in a manner effective to stimulate antibody producing cells. Rodents such as mice and rats are preferred, however, the use of rabbit, sheep and frog cells is also possible. The use of rats may provide certain advantages (Goding, 1986, pp. 60-61; incorporated herein by reference), but mice are preferred, with the BALB/c mouse being most preferred as this is most routinely used and generally gives a higher percentage of stable fusions. Following immunization, B lymphocytes (B cells) are selected for use in the antibody generating protocol. These cells may be obtained from biopsied spleens, tonsils or lymph nodes, or from a peripheral blood sample. A panel of animals is typically immunized and the spleen of the animal with the highest antibody titer will be removed and the spleen lymphocytes obtained by homogenizing the spleen with a syringe. The anti-human TNFR2 antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Exemplary myeloma cells include, e.g., P3-X63/Ag8, X63-Ag8.653, NS1/1.Ag 4 1, Sp210-Ag14, FO, NSO/U, MPC-11, MPC11-X45-GTG 1.7 and S194/5XX0 Bul for mouse; R210.RCY3, Y3-Ag 1.2.3, IR983F, 4B210 or one of the above listed mouse cell lines for rats; and U-266, GM1500-GRG2, LICR-LON-HMy2 and UC729-6 are useful in connection with human cell fusions.

Producing Hybridomas

Methods for generating hybrids of antibody-producing spleen or lymph node cells and myeloma cells usually comprise mixing somatic cells with myeloma cells in a 4:1 proportion, although the proportion may vary from about 20:1 to about 1:1, respectively, in the presence of an agent or agents (chemical or electrical) that promote the fusion of cell membranes. Fusion methods using Sendai virus or polyethylene glycol (PEG), such as 37% (v/v) PEG, are known in the art. The use of electrically induced fusion methods is also appropriate.

Viable, fused hybrids are differentiated from the parental, unfused cells by culturing in a selective medium which typically contains an agent that blocks the de novo synthesis of nucleotides in the tissue culture media. Exemplary agents are aminopterin, methotrexate, and azaserine. Where aminopterin or methotrexate is used, the media is supplemented with hypoxanthine and thymidine as a source of nucleotides (HAT medium). Where azaserine is used, the media is supplemented with hypoxanthine. When HAT medium is used, only cells capable of operating nucleotide salvage pathways are able to survive in HAT medium. The myeloma cells are defective in key enzymes of the salvage pathway, e.g., hypoxanthine phosphoribosyl transferase (HPRT), and thus cannot survive. The only cells that can survive in the selective media are those hybrids formed from myeloma and B cells. This culturing process provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired anti-human TNFR2 reactivity. Exemplary assays include radioimmunoassays, enzyme immunoassays, cytotoxicity assays, plaque assays, dot immunobinding assays, bio-layer interferometry, and the like.

Selected hybridomas are serially diluted and cloned into individual anti-human TNFR2 antibody-producing cell lines, which clones can then be propagated indefinitely to provide monoclonal antibodies. The cell lines may be used for monoclonal antibody production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide monoclonal antibodies in high concentration. The individual cell lines could also be cultured in vitro, where the monoclonal antibodies are naturally secreted into the culture medium from which they can be readily obtained in high concentrations. Monoclonal antibodies produced by either means will generally be further purified, e.g., using filtration, centrifugation and various chromatographic methods, such as HPLC or affinity chromatography, all of which purification techniques are well known to those of skill in the art. These purification techniques each involve fractionation to separate the desired antibody from other components of a mixture. Analytical methods particularly suited to the preparation of antibodies include, for example, protein A-Sepharose and/or protein G-Sepharose chromatography.

High Throughput Screening of Anti-TNFR2 Antibodies

Also provided herein are methods for high throughput screening of libraries for molecules that bind to human TNFR2 epitopes (e.g., the same epitopes recognized by the anti-TNFR2 antibodies described herein), e.g., phage display, bacterial display, yeast display, mammalian display, ribosome display, mRNA display, and cDNA display.

In one embodiment, provided herein are methods for screening anti-human TNFR2 antibodies using phagemid libraries. Exemplary phage display protocols can be found, e.g., in U.S. Pat. Nos. 7,846,892, 8,846,867, WO1997/002342, and WO2007/13291, herein incorporated by reference. Recombinant technology now allows the preparation of antibodies having the desired specificity from recombinant genes encoding a range of antibodies. Certain recombinant techniques involve the isolation of the antibody genes by immunological screening of combinatorial immunoglobulin phage expression libraries prepared from RNA isolated from the spleen of an immunized animal (e.g., an animal immunized with the extracellular domain of human TNFR2 or a peptide that includes a human TNFR2 epitope of interest). For such methods, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination, which further increases the percentage of appropriate antibodies generated.

One method for the generation of a large repertoire of diverse antibody molecules in bacteria utilizes the bacteriophage lambda as the vector (Huse et al., 1989; incorporated herein by reference). Production of antibodies using the lambda vector involves the cloning of heavy and light chain populations of DNA sequences into separate starting vectors. The vectors are subsequently combined randomly to form a single vector that directs the co-expression of heavy and light chains to form antibody fragments. The heavy and light chain DNA sequences are obtained by amplification, preferably by PCR or a related amplification technique, of mRNA isolated from spleen cells (or hybridomas thereof) from an animal that has been immunized with a selected antigen (e.g., the extracellular domain of human TNFR2 or a peptide that includes a human TNFR2 epitope of interest). The heavy and light chain sequences are typically amplified using primers that incorporate restriction sites into the ends of the amplified DNA segment to facilitate cloning of the heavy and light chain segments into the starting vectors.

Another method for the generation and screening of large libraries of wholly or partially synthetic antibody combining sites, or paratopes, utilizes display vectors derived from filamentous phage such as M13, fl or fd. These filamentous phage display vectors, referred to as "phagemids", yield large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries. In a general sense, the method provides a system for the simultaneous cloning and screening of pre-selected ligand-binding specificities from antibody gene repertoires using a single vector system. Screening of isolated members of the library for a pre-selected ligand-binding capacity allows the correlation of the binding capacity of an expressed antibody molecule with a convenient means to isolate the gene that encodes the member from the library.

The diversity of a filamentous phage-based combinatorial antibody library can be increased by shuffling of the heavy and light chain genes, by altering one or more of the complementarity determining regions of the cloned heavy chain genes of the library, or by introducing random mutations into the library by error-prone polymerase chain reactions. Additional methods for screening phagemid libraries are described in U.S. Pat. Nos. 5,580,717; 5,427,908; 5,403,484; and 5,223,409, each incorporated herein by reference.

In another embodiment, provided herein are methods for screening anti-human TNFR2 antibodies using cell-based display techniques, such as yeast display (Boder et al., Nat Biotechnol 1997; 15:553) and bacterial display. Established procedures to generate and screen libraries of bacterial cells or yeast cells that express polypeptides, such as single-chain polypeptides, antibodies, or antibody fragments, containing randomized hypervariable regions can be found in, e.g., U.S. Pat. No. 7,749,501, US2013/0085072, de Bruin et al., Nat Biotechnol 1999; 17:397; the teachings of each which are incorporated herein by reference.

In another embodiment, provided herein are methods for screening anti-human TNFR2 antibodies using nucleotide display techniques, which use in vitro translation of randomized polynucleotide libraries encoding single-chain polypeptides, antibodies, or antigen-binding fragments that contain mutations within designated hypervariable regions (see, e.g., WO2006/072773, U.S. Pat. No. 7,074,557). Antibodies can also be generated using cDNA display, a technique analogous to mRNA display, with the exception that cDNA instead of mRNA is used. cDNA display techniques are described in, e.g., Ueno et al. Methods Mol. Biol. 2012; 805:113-135).

The in vitro display techniques described above can also be used to improve the affinity of the anti-TNFR2 antibodies described herein. For example, libraries of single-chain polypeptides, antibodies, and antigen-binding fragments thereof that have targeted mutations at specific sites within hypervariable regions of a particular anti-TNFR2 antibody can be used. Polynucleotides encoding these mutated antibodies or antigen-binding fragments thereof can then be used in ribosome display, mRNA display, cDNA display to screen for polypeptides that specifically bind to the human TNFR2 epitope of interest.

Combinatorial libraries of polypeptides can also be screened to identify anti-TNFR2 antibodies that bind to human TNFR2 epitopes of interest. Combinatorial polypeptide libraries, such as antibody or antibody fragment libraries, can be obtained, e.g., by expression of polynucleotides encoding randomized hypervariable regions of an antibody or antigen-binding fragment thereof in a eukaryotic or prokaryotic cell using art-recognized gene expression techniques. The resulting heterogeneous mixture of antibodies can be isolated from the cells using standard techniques and screened for the ability to bind to a peptide derived from TNFR2 immobilized to a surface. Non-binding antibodies are washed off using an appropriate buffer, and antibodies that remain bound can be detected using, an ELISA-based detection protocol. The sequence of an antibody fragment that specifically binds to the TNFR2 peptide can be determined by techniques known in the art, including, e.g., Edman degradation, tandem mass spectrometry, matrix-assisted laser-desorption time-of-flight mass spectrometry (MALDI-TOF MS), nuclear magnetic resonance (NMR), and 2D gel electrophoresis, among others (see, e.g., WO 2004/062553).

Producing Anti-TNFR2 Antibodies with Recombinant DNA Techniques, Host Cell Transfectomas, and Transgenic Animals Also provided herein are methods of producing anti-human TNFR2 antibodies in a host cell transfectoma using, for example, a combination of recombinant DNA techniques and gene transfection methods known in the art (Morrison, S. (1985) Science 229:1202). For example, to express antibodies, or antibody fragments thereof, DNAs encoding partial or full-length light and heavy chains can be obtained by standard molecular biology techniques (e.g., PCR amplification or cDNA cloning using a hybridoma (such as those described above) that expresses the antibody of interest) and the DNAs can be inserted into expression vectors such that the genes are operatively linked to transcriptional and translational control sequences. In this context, the term "operatively linked" means that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes are inserted into the same expression vector. The antibody genes are inserted into the expression vector(s) by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector.

For expression of light and heavy chains, the expression vector(s) encoding the heavy and light chains is transfected into a host cell by standard techniques. Although it is possible to express the antibodies described herein in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Preferred mammalian host cells for expressing the recombinant antibodies described herein include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

In yet another embodiment, human monoclonal antibodies directed against particular epitopes on human TNFR2 can be generated using transgenic or transchromosomic mice carrying parts of the human immune system rather than the mouse system (see e.g., U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.).

In another embodiment, human antibodies can be raised against particular epitopes on human TNFR2 (e.g., the same epitopes recognized by the anti-TNFR2 antibodies described herein) using a mouse that carries human immunoglobulin sequences on transgenes and transchomosomes, such as a mouse that carries a human heavy chain transgene and a human light chain transchromosome (see e.g., PCT Publication WO 02/43478 to Ishida et al.).

Still further, alternative transgenic animal systems expressing human immunoglobulin genes are available in the art and can be used to raise anti-human TNFR2 antibodies that recognize particular human TNFR2 epitopes (e.g., the same epitopes recognized by the anti-TNFR2 antibodies described herein). For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al. Another suitable transgenic animal system is the HuMAb mouse (Medarex, Inc), which contains human immunoglobulin gene miniloci that encode unrearranged human heavy (μ and γ) and x light chain immunoglobulin sequences, together with targeted mutations that inactivate the endogenous p and x chain loci (see e.g., Lonberg, et al. (1994) Nature 368(6474): 856-859). Yet another suitable transgenic animal system is the KM mouse, described in detail in PCT publication WO02/43478.

Alternative transchromosomic animal systems expressing human immunoglobulin genes are available in the art and can be used to raise anti-TNFR2 antibodies. For example, mice carrying both a human heavy chain transchromosome and a human light chain tranchromosome can be used. Furthermore, cows carrying human heavy and light chain transchromosomes have been described in the art and can be used to raise anti-TNFR2 antibodies.

In yet another embodiment, antibodies can be prepared using a transgenic plant and/or cultured plant cells (such as, for example, tobacco, maize and duckweed) that produce such antibodies. For example, transgenic tobacco leaves expressing antibodies can be used to produce such antibodies by, for example, using an inducible promoter. Also, transgenic maize can be used to express such antibodies and antigen binding portions thereof. Antibodies can also be produced in large amounts from transgenic plant seeds including antibody portions, such as single chain antibodies (scFv's), for example, using tobacco seeds and potato tubers.

In the above embodiments, the antigen used to immunize animals may be, for example, the extracellular domain of human TNFR2. When the extracellular domain of human TNFR2 is used as the antigen, the generated antibodies are further screened for the ability to selectively bind particular epitopes on human TNFR2 (e.g., the same epitopes recognized by the anti-TNFR2 antibodies described herein). Screening can be performed, e.g., using assays (e.g., ELISA) to assess binding to peptides that include the human TNFR2 epitope of interest, or binding assays using the TNFR2 chimeras described herein. Anti-human TNFR2 antibodies that share the epitope or TNFR2 chimera binding characteristics of the anti-TNFR2 antibodies described herein are then selected.

In another embodiment, the antigen used to immunize animals or target used to screen libraries (e.g., phagemid libraries, yeast surface display libraries) is a peptide that includes a human TNFR2 epitope recognized by the anti-TNFR2 antibodies described herein. Peptides that include these sequences can be used to immunize animals or screen libraries using the techniques listed above. Anti-human TNFR2 antibodies generated using this method can be screened for selectively binding to the peptide used as the immunogen.

Producing Humanized and/or Chimeric TNFR2 Antibodies

Chimeric and/or humanized antibodies can be generated based on the sequence of a murine monoclonal antibody, such as those described herein. DNA encoding the heavy and light chain immunoglobulins can be obtained from the murine hybridoma of interest and engineered to contain non-murine (e.g., human) immunoglobulin sequences using standard molecular biology techniques.

For example, chimeric antibodies and antigen-binding fragments thereof comprise portions from two or more different species (e.g., mouse and human). To create a chimeric antibody, the murine variable regions can be linked to human constant regions using methods known in the art (see e.g., U.S. Pat. No. 4,816,567 to Cabilly et al.). In this manner, non-human antibodies can be modified to make them more suitable for human clinical application (e.g., methods for treating or preventing a cancer in a human subject).

Alternatively, humanized antibodies are antibodies from non-human species whose protein sequences have been modified to increase their similarity to antibody variants produced naturally in humans. Humanized or CDR-grafted mAbs are particularly useful as therapeutic agents for humans because they are not cleared from the circulation as rapidly as mouse antibodies and do not typically provoke an adverse immune reaction.

Methods of preparing humanized antibodies are well known in the art. For example, humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)). Additionally, humanized TNFR2 antibodies described herein can be produced using a variety of techniques known in the art, including, but not limited to, CDR-grafting (see e.g., European Patent No. EP 239,400; International Publication No. WO 91/09967; and U.S. Pat. Nos. 4,816,567; 6,331,415, 5,225,539, 5,530,101, and 5,585,089, each of which is incorporated herein by reference), veneering or resurfacing (see, e.g., European Patent Nos. EP 592,106 and EP 519,596; Padlan, 1991, Molecular Immunology 28(4/5):489-498; Studnicka et al., 1994, Protein Engineering, 7(6):805-814; and Roguska et al., 1994, Proc. Natl. Acad. Sci., 91:969-973, each of which is incorporated herein by reference), chain shuffling (see, e.g., U.S. Pat. No. 5,565,332, which is incorporated herein by reference), and techniques disclosed in, e.g., U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al, Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein by reference. Often, framework (FW) residues in the FW regions will be substituted with the corresponding residue from the CDR donor antibody to alter, preferably improve, antigen binding. These FW substitutions are identified by methods well known in the art, e.g., by modeling of the interactions of the CDR and FW residues to identify FW residues important for antigen binding and sequence comparison to identify unusual FW residues at particular positions. (See, e.g., Queen et al., U.S. Pat. No. 5,585,089; and Riechmann et al, 1988, Nature, 332:323, which are incorporated herein by reference in their entireties.)

In some embodiments, humanized forms of non-human antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and/or chimeric antibodies can be modified to comprise residues that are not found in the recipient antibody or in the donor antibody in order to further improve antibody properties, such as, for example, affinity or effector function.

In such humanized chimeric antibodies, substantially less than an intact human variable domain has been substituted by the corresponding sequence from a nonhuman species. In practice, humanized antibodies are typically human antibodies in which some CDR residues and possibly some FW residues are substituted by residues from analogous sites in rodent antibodies. Humanization of anti-TNFR2 antibodies can also be achieved by veneering or resurfacing (EP 592,106; EP 519,596; Padlan, 1991, Molecular Immunology 28(4/5):489-498; Studnicka et al., Protein Engineering, 7(6): 805-814 (1994); and Roguska et al., Proc. Natl. Acad. Sci., 91:969-973 (1994)) or chain shuffling (U.S. Pat. No. 5,565,332), the contents of which are incorporated herein by reference in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequences which are most closely related to that of the rodent are then screened for the presence of specific residues that may be critical for antigen binding, appropriate structural formation and/or stability of the intended humanized mAb (Sims et al., J. Immunol., 151:2296 (1993); Chothia et al., J. Mol. Biol., 196:901 (1987), the contents of which are incorporated herein by reference in their entirety). The resulting FW sequences matching the desired criteria are then be used as the human donor FW regions for the humanized antibody.

Another method uses a particular FW derived from the consensus sequence of all human antibodies of a particular subgroup of light or heavy chains. The same FW may be used for several different humanized anti-TNFR2 antibodies (Carter et al., Proc. Natl. Acad. Sci. USA, 89:4285 (1992); Presta et al., J. Immunol., 151:2623 (1993), the contents of which are incorporated herein by reference in their entirety).

Anti-TNFR2 antibodies can be humanized with retention of high affinity for human TNFR2 and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind TNFR2. In this way, FW residues can be selected and combined from the recipient and import sequences so that the desired antibody characteristic, for example affinity for TNFR2, is achieved. In general, the CDR residues are directly and most substantially involved in influencing antigen binding.

The binding specificity of monoclonal antibodies (or portions thereof) that bind TNFR2 prepared using any technique including those disclosed herein, can be determined by immunoprecipitation or by an in vitro binding assay, such as radioimmunoassay (RIA), enzyme-linked immunoabsorbent assay (ELISA), bio-layer interferometry (e.g., ForteBio assay), and/or Scatchard analysis.

In certain embodiments, an anti-TNFR2 antibody produced using any of the methods discussed above may be further altered or optimized to achieve a desired binding specificity and/or affinity using art recognized techniques, such as those described herein.

VII. Multispecific Antibodies

Multispecific antibodies (e.g., bispecific antibodies) provided herein include at least a binding affinity for TNFR2 (e.g., human TNFR2) as described herein, and at least one other binding specificity. Multispecific antibodies can be prepared as full length antibodies or antibody fragments (e.g. $F(ab')_2$ antibodies).

Methods for making multispecific antibodies are well known in the art (see, e.g., WO 05117973 and WO 06091209). For example, production of full length multispecific antibodies can be based on the coexpression of two paired immunoglobulin heavy chain-light chains, where the two chains have different specificities. Various techniques for making and isolating multispecific antibody fragments directly from recombinant cell culture have also been described. For example, multispecific antibodies can be produced using leucine zippers. Another strategy for making multispecific antibody fragments by the use of single-chain Fv (sFv) dimers has also been reported.

In a particular embodiment, the multispecific antibody comprises a first antibody (or binding portion thereof) which binds to an epitope of interest on TNFR2 derivatized or linked to another functional molecule, e.g., another peptide or protein (e.g., another antibody or ligand for a receptor) to generate a multispecific molecule that binds to an epitope on TNFR2 and another target molecule. An antibody may be derivatized or linked to more than one other functional molecule to generate multispecific molecules that bind to more than two different binding sites and/or target molecules. To create a multispecific molecule, an antibody disclosed herein can be functionally linked (e.g., by chemical coupling, genetic fusion, noncovalent association or otherwise) to one or more other binding molecules, such as another antibody, antibody fragment, peptide or binding mimetic, such that a multispecific molecule results.

Accordingly, multispecific molecules comprising at least one first binding specificity for a particular epitope on TNFR2 (e.g., human TNFR2) and a second binding specificity for another target epitope are contemplated. In a particular embodiment, the second target epitope is an Fc receptor, e.g., human FcγRI (CD64) or a human Fcα receptor (CD89). Therefore, multispecific molecules capable of binding both to FcγR, FcαR or FcεR expressing effector cells (e.g., monocytes, macrophages or polymorphonuclear cells (PMNs)), and to target cells expressing TNFR2 are also provided. These multispecific molecules target TNFR2-expressing cells to effector cells and trigger Fc receptor-mediated effector cell activities, such as phagocytosis of TNFR2-expressing cells, antibody dependent cell-mediated cytotoxicity (ADCC), cytokine release, or generation of superoxide anion.

In one embodiment, the multispecific molecules comprise as a binding specificity at least one antibody, or an antibody fragment thereof, including, e.g., an Fab, Fab', $F(ab')_2$, Fv, or a single chain Fv. The antibody may also be a light chain or heavy chain dimer, or any minimal fragment thereof such as a Fv or a single chain construct as described in Ladner et al. U.S. Pat. No. 4,946,778.

The multispecific molecules can be prepared by conjugating the constituent binding specificities, e.g., the anti-FcR and anti-TNFR2 binding specificities, using methods known in the art. For example, each binding specificity of the multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC). Preferred conjugating agents are SATA and sulfo-SMCC, both available from Pierce Chemical Co. (Rockford, IL).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the multispecific molecule is a mAb×mAb, mAb×Fab, Fab×F$(ab')_2$ or ligand x Fab fusion protein. A multispecific molecule can be a single chain molecule comprising one single chain antibody and a binding determinant, or a single chain bispecific molecule comprising two binding determinants. Multispecific molecules may comprise at least two single chain molecules. Methods for preparing multispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the multispecific molecules to their specific targets can be confirmed by, for example, enzyme-linked immunosorbent assay (ELISA), radioimmunoassay (RIA), FACS analysis, bioassay (e.g., growth inhibition), or western blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA). The radioactive isotope can be detected by such means as the use of a α γ-β counter or a scintillation counter or by autoradiography.

VIII. Immunoconjugates

Immunoconjugates provided herein can be formed by conjugating the antibodies described herein (e.g., anti-human TNFR2 antibodies) to another therapeutic agent. Suitable agents include, for example, a cytotoxic agent (e.g., a chemotherapeutic agent), a toxin (e.g. an enzymatically active toxin of bacterial, fungal, plant or animal origin, or fragments thereof), and/or a radioactive isotope (i.e., a radioconjugate).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, neomycin, and the tricothecenes. Additional examples of cytotoxins or cytotoxic agents include, e.g., taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

A variety of radionuclides are available for the production of radioconjugated anti-TNFR2 antibodies. Examples include $^{212}$Bi, $^{131}$I, $^{131}$In, $^{90}$Y and $^{186}$Re.

Immunoconjugates can also be used to modify a given biological response, and the drug moiety is not to be construed as limited to classical chemical therapeutic agents. For example, the drug moiety may be a protein or polypeptide possessing a desired biological activity (e.g., lymphokines, tumor necrosis factor, IFNγ, growth factors).

Immunoconjugates can be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Carbon-14-labeled 1-isothiocyanatobenzyl-3-methyldiethylene triaminepentaacetic acid (MX-DTPA) is an exemplary chelating agent for conjugation of radionucleotide to the antibody (see, e.g., WO94/11026).

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

IX. Assays

Subsequent to producing antibodies (e.g., antibodies having the CDR sequences of the anti-TNFR2 antibodies disclosed herein), they can be screened or tested for various properties, such as those described herein (e.g., binding to TNFR2), using a variety of assays known in the art.

In one embodiment, the antibodies are screened or tested (e.g., by flow cytometry, ELISA, Biacore, or bio-layer interferometry) for the ability to bind to TNFR2 using, for example, purified TNFR2 (e.g., purified extracellular domain of human TNFR2) and/or TNFR2-expressing cells. Other methods monitor the binding of the antibody to antigen fragments or mutated variations of human TNFR2 where loss of binding due to a modification of an amino acid residue within the antigen sequence is often considered an indication of an epitope component.

In some embodiments, the antibodies are screened or tested for binding to TNFR2 by Western blotting. Briefly, cell extracts from cells expressing TNFR2 (e.g., the extracellular domain of TNFR2) can be prepared and subjected to sodium dodecyl sulfate polyacrylamide gel electrophoresis. After electrophoresis, the separated antigens will be transferred to nitrocellulose membranes, blocked with serum, and probed with the monoclonal antibodies to be tested. IgG binding can be detected using anti-IgG alkaline phosphatase and developed with BCIP/NBT substrate tablets (Sigma Chem. Co., St. Louis, MO).

Methods for analyzing binding affinity, cross-reactivity, and binding kinetics of various anti-TNFR2 antibodies include standard assays known in the art, for example, Biacore™ surface plasmon resonance (SPR) analysis using a Biacore™ 2000 SPR instrument (Biacore AB, Uppsala, Sweden) or bio-layer interferometry (e.g., ForteBio assay), as described in the Examples.

In some embodiments, the anti-TNFR2 antibodies are screened or tested for the ability to inhibit the binding of TNF-alpha to TNFR2 using art-recognized methods, such as flow cytometry, surface plasmon resonance, and biolayer interferometry, e.g., as described in Examples 1 and 2.

In some embodiments, the anti-TNFR2 antibodies are screened or tested for agonist activity. Agonist activity can be tested using reporter assays, e.g., NF-kB reporter assays. In some embodiments, the antibodies are contacted with reporter cell lines, and reporter activity is determined by flow cytometry, e.g., as described in Example 3. In some embodiments, the agonist activity of the anti-TNFR2 antibodies are determined by assessing the proliferation of and/or induction of activation marker expression in primary isolated T cells, for example, as described in Examples 7, 9, and 16.

The anti-TNFR2 antibodies described herein can also be screened or tested for their ability to induce ADCC. Briefly, effector cells (e.g., NK cells) are cultured together with target cells in the presence or absence of the antibody of interest (e.g., anti-TNFR2 antibody) and/or a control antibody (e.g., isotype control). Death of target cells are then assessed, e.g., based on the quantification of a detectable label (e.g., fluorescence if the target cells are fluorescently labeled) using, e.g., flow cytometry as described in Example 5.

Antibodies can also be screened or tested for their ability to promote or inhibit the proliferation or viability of cells, such as CD4+(e.g., Tregs) and CD8+ T cells (either in vivo or in vitro), using art recognized techniques, including the Cell Titer-Glo Assay, tritium-labeled thymidine incorporation assay, or flow cytometry.

X. Compositions

In another aspect, provided herein is a composition, e.g., a pharmaceutical composition, comprising an anti-TNFR2 antibody (e.g., an anti-human TNFR2 antibody) disclosed herein, formulated together with a pharmaceutically acceptable carrier. Pharmaceutical compositions are prepared using standard methods known in the art by mixing the active ingredient (e.g., anti-TNFR2 antibodies described herein) having the desired degree of purity with optional physiologically acceptable carriers, excipients or stabilizers (Remington's Pharmaceutical Sciences ($20^{th}$ edition), ed. A. Gennaro, 2000, Lippincott, Williams & Wilkins, Philadelphia, Pa.). Preferred pharmaceutical compositions are sterile compositions, compositions suitable for injection, and sterile compositions suitable for injection by a desired route of administration, such as by intravenous injection.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, may be coated in a material to protect the compound from the action of acids and other natural conditions that may inactivate the compound.

Compositions can be administered alone or in combination therapy, i.e., combined with other agents. For example, the combination therapy can include a composition provided herein with at least one or more additional therapeutic agents, e.g., other compounds, drugs, and/or agents used for the treatment of autoimmune disease (e.g., an immunosuppressant) or cancer (e.g., an anti-cancer agent(s)). Particular combinations of anti-TNFR2 antibodies may also be administered separately or sequentially, with or without additional therapeutic agents.

Compositions can be administered by a variety of methods known in the art. As will be appreciated by the skilled artisan, the route and/or mode of administration will vary depending upon the desired results. The antibodies can be prepared with carriers that will protect the antibodies against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

To administer compositions by certain routes of administration, it may be necessary to coat the constituents, e.g., antibodies, with, or co-administer the compositions with, a material to prevent its inactivation. For example, the compositions may be administered to a subject in an appropriate carrier, for example, liposomes, or a diluent. Acceptable diluents include saline and aqueous buffer solutions. Liposomes include water-in-oil-in-water CGF emulsions as well as conventional liposomes.

Acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional medium or agent is incompatible with the antibodies, use thereof in compositions provided herein is contemplated. Supplementary active constituents can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Including in the composition an agent that delays absorption, for example, monostearate salts and gelatin can bring about prolonged absorption of the injectable compositions.

Sterile injectable solutions can be prepared by incorporating the monoclonal antibodies in the required amount in an appropriate solvent with one or a combination of ingredients enumerated above, as required, followed by sterilization microfiltration. Generally, dispersions are prepared by incorporating the antibodies into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, human antibodies may be administered once or twice weekly by subcutaneous injection or once or twice monthly by subcutaneous injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of antibodies calculated to produce the desired therapeutic effect in association with the required pharmaceutical carrier. The specification for the dosage unit forms provided herein are dictated by and directly dependent on (a) the unique characteristics of the antibodies and the particular therapeutic effect to be achieved, and (b) the limitations inherent in the art of compounding such antibodies for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations include those suitable for oral, nasal, topical (including buccal and sublingual), rectal, and parenteral administration. Parenteral administration is the most common route of administration for therapeutic compositions comprising antibodies. The formulations may conveniently be presented in unit dosage form and may be prepared by any methods known in the art of pharmacy. The amount of antibodies that can be combined with a carrier material to produce a single dosage form will vary depending upon the subject being treated, and the particular mode of administration. This amount of antibodies will generally be an amount sufficient to produce a therapeutic effect. Generally, out of 100%, this amount will range from about 0.001% to about 90% of antibody by mass, preferably from about 0.005% to about 70%, most preferably from about 0.01% to about 30%.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Particular examples of adjuvants which are well-known in the art include, for example, inorganic adjuvants (such as aluminum salts, e.g., aluminum phosphate and aluminum hydroxide), organic adjuvants (e.g., squalene), oil-based adjuvants, virosomes (e.g., virosomes which contain a membrane-bound heagglutinin and neuraminidase derived from the influenza virus).

Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of one or more agents that delay absorption such as aluminum monostearate or gelatin.

When compositions are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, compositions provided herein, may be used in a suitable hydrated form, and they may be formulated into pharmaceutically acceptable dosage forms by conventional methods known to those of skill in the art.

Actual dosage levels of the antibodies in the pharmaceutical compositions provided herein may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the composition required. For example, the physician or veterinarian could start doses of the antibodies at levels lower than that required to achieve the desired therapeutic effect and gradually increasing the dosage until the desired effect is achieved. In general, a suitable daily dose of compositions provided herein will be that amount of the antibodies which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for antibodies to be administered alone, it is preferable to administer antibodies as a formulation (composition).

Dosages and frequency of administration may vary according to factors such as the route of administration and the particular antibody used, the nature and severity of the disease to be treated, and the size and general condition of the subject. Appropriate dosages can be determined by procedures known in the pertinent art, e.g. in clinical trials that may involve dose escalation studies.

Therapeutic compositions can be administered with medical devices known in the art, such as, for example, those disclosed in U.S. Pat. Nos. 5,399,163, 5,383,851, 5,312,335, 5,064,413, 4,941,880, 4,790,824, 4,596,556, 4,487,603, 4,486,194, 4,447,233, 4,447,224, 4,439,196, and 4,475,196.

The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

Uses of the above-described anti-TNFR2 antibodies and compositions comprising the same are provided in the manufacture of a medicament for the treatment of a disease associated with TNFR2-dependent signaling. For example, the anti-TNFR2 antibodies and compositions described herein are used to treat cancer (or used in the manufacture of a medicament for the treatment of cancer). In some embodiments, the cancer is a solid tumor. Exemplary cancers include, but are not limited to, lung cancer, renal cancer, breast cancer, ovarian cancer, hepatocellular carcinoma, renal cell carcinoma, lung carcinoma, cervical cancer, prostate cancer, melanoma, head and neck cancer, lymphoma, and colorectal cancer.

In some embodiments, the anti-TNFR2 antibodies and compositions described herein are used to treat an autoimmune disease or disorder (or used in the manufacture of a medicament for the treatment of autoimmune disease). Exemplary autoimmune diseases include, but are not limited to, graft-versus-host disease, rheumatoid arthritis, Crohn's disease, multiple sclerosis, colitis, psoriasis, autoimmune uveitis, pemphigus, epidermolysis bullosa, and type 1 diabetes.

In some embodiments, the anti-TNFR2 antibodies and compositions described herein are used to promote graft survival or reduce graft rejection in a subject who has received or will receive a cell, tissue, or organ transplant (or used in the manufacture of a medicament for promoting graft survival or reduce graft rejection). In other embodiments, the anti-TNFR2 antibodies and compositions described herein are used to treat, prevent, or reduce graft-versus-host disease (or used in the manufacture of a medicament for treating, preventing, or reducing graft-versus-host disease).

Additionally, contemplated compositions may further include, or be prepared for use as a medicament in combination therapy with, an additional therapeutic agent. Drug therapy (e.g., with antibody compositions disclosed herein) may be administered without other treatment, or in combination with other treatments.

A "therapeutically effective dosage" of an anti-TNFR2 antibody or composition described herein preferably results in a decrease in severity of disease symptoms, an increase in frequency and duration of disease symptom-free periods, or a prevention of impairment or disability due to the disease affliction. In the context of cancer, a therapeutically effective dose preferably results in increased survival, and/or prevention of further deterioration of physical symptoms associated with cancer. A therapeutically effective dose may prevent or delay onset of cancer, such as may be desired when early or preliminary signs of the disease are present. In the context of autoimmune disease, a therapeutically effective dose preferably results in the prevention of further deterioration of physical symptoms associated with autoimmune disease.

In the context of transplantation, a therapeutically effective dose preferably promotes graft survival and/or reduces graft rejection.

XI. Kits

Also provided are kits comprising the anti-TNFR2 antibodies, multispecific molecules, or immunoconjugates disclosed herein, optionally contained in a single vial or container, and include, e.g., instructions for use in treating or diagnosing a disease such as cancer. The kits may include a label indicating the intended use of the contents of the kit. The term label includes any writing, marketing materials or recorded material supplied on or with the kit, or which otherwise accompanies the kit. Such kits may comprise the antibody, multispecific molecule, or immunoconjugate in unit dosage form, such as in a single dose vial or a single dose pre-loaded syringe.

XII. Methods of Using Antibodies

The antibodies and compositions disclosed herein can be used in a broad variety of therapeutic and diagnostic applications, for example, to treat cancer (oncological applications), to treat autoimmune diseases or disorders, to promote graft survival and/or reduce graft rejection in a transplant recipient, or to treat, prevent, or reduce graft-versus-host disease.

Accordingly, in one embodiment, provided herein is a method of treating proliferation disorders, e.g., cancer, comprising administering to a subject an anti-TNFR2 antibody described herein in an amount effective (e.g., a therapeutically effective amount) to treat the disorder. In some embodiments, the disorder is cancer. Exemplary cancers include, but are not limited to, solid tumors, such as lung cancer, renal cancer, breast cancer, ovarian cancer, hepatocellular carcinoma, renal cell carcinoma, lung carcinoma, cervical cancer, prostate cancer, melanoma, head and neck cancer, lymphoma, and colorectal cancer. Subjects can be examined during therapy to monitor the efficacy of the anti-TNFR2 antibodies to attenuate the progression of cancer (e.g., as reflected in the reduction in volume of one or more tumors).

In some embodiments, the anti-TNFR2 antibodies described herein are capable of reducing the volume of a tumor by at least about 10%, at least about 20%, at least about 30%, at least about 40%, at least about 50%, at least about 60%, at least about 70%, at least about 80%, at least about 90%, at least about 95%, at least about 98%, or about 100%, relative to the volume of the tumor prior to initiating anti-TNFR2 antibody therapy.

In another embodiment, provided herein is a method for inhibiting the growth of a tumor comprising administering to a subject an anti-TNFR2 antibody described herein in an effective amount (e.g., a therapeutically effective amount) to inhibit the growth of the tumor.

In another embodiment, provided herein is a method for inhibiting the growth of tumor cells comprising administering to a subject an anti-TNFR2 antibody described herein in an effective amount (e.g., a therapeutically effective amount) to inhibit the growth of the tumor cells.

In some embodiments, the anti-TNFR2 antibodies described herein induce a long-term anti-cancer effect. In some embodiments, the anti-TNFR2 antibodies described herein induce the development of anti-cancer memory T cells.

In another embodiment, provided herein is a method of enhancing the anti-tumor activity of an antibody which binds to human TNFR2, comprising modifying the antibody to increase its effector function relative to the same antibody in unmodified form, for example, by introducing one or more amino acid substitutions in the Fc region. In some embodiments, the increased anti-tumor activity is independent of the epitope of human TNFR2 which the antibody binds to. In other embodiments, the inhibition of tumor growth is independent of the ability of the antibody to agonize TNFR2 signaling. In other embodiments, the inhibition of tumor growth is independent of the ability of the antibody to inhibit TNF-alpha binding to TNFR2.

In another embodiment, provided herein is a method of treating cancer comprising administering to a subject in need thereof a therapeutically effective amount of an anti-TNFR2 antibody, wherein the antibody has effector function and agonizes TNFR2 receptor signaling.

In the methods described herein, the anti-TNFR2 antibodies can be administered alone or with one or more therapeutic agents (e.g., anti-cancer agents) or standard cancer treatment that act in conjunction with or synergistically with the antibody to treat a subject with a tumor or cancer. For example, the anti-TNFR2 antibodies described herein can be used in combination with immune checkpoint blockers. Suitable immune checkpoint blockers for use in combination with the anti-TNFR2 antibodies described herein include, for example, an anti-PD1 antibody, an anti-PD-L1 antibody, an anti-LAG-3 antibody, an anti-CTLA-4 antibody, an anti-TIGIT antibody, or an anti-TIM3 antibody.

PD-1 and PD-L1 checkpoint inhibitors offer significant promise in the treatment of cancer (Brahmer et al., NEJM 2012; 366:2455-65; Topalian et al., NEJM 2012; 366:2443-54). Unfortunately, their activity remains limited to a subset of patients in indications such as metastatic bladder cancer, non-small cell lung cancer (NSCLC), melanoma and head and neck cancers, with many progressing over time (Swaika et al., Molecular Immunology 2015; 67:4-17; Grigg et al., Journal for ImmunoTherapy of Cancer 2016; 4:48). Combinations with chemotherapy or other immunotherapies, such as the CTLA4 inhibitor, ipilimumab, have been shown to improve efficacy, but often at the expenses of significant increases in many toxicities compared to the PD-1 inhibitor alone (Weber, Oncologist 2016; 21:1230-40; Paz-Ares et al., NEJM 2018 pub ahead of print—PMID: 30280635). As shown in Example 12, a TNFR2 agonist antibody (Y9) in combination with PD-1 or PD-L1 inhibitors improves anti-tumor activity significantly, without the toxicity observed with anti-CTLA4 antibody treatment upon chronic dosing (see, Example 13). This suggests that the combination of an agonistic TNFR2 mAb with PD-1 or PD-L1 inhibitors has a significantly greater therapeutic index than that of PD-1 inhibitors with CTLA4 inhibitors, such as ipilimumab.

The anti-TNFR2 antibodies and combination antibody therapies described herein may also be used in conjunction with other well-known therapies selected for their particular usefulness against the indication being treated (e.g., cancer).

For example, the anti-TNFR2 antibodies described herein can be used in combination (e.g., simultaneously or separately) with an additional treatment, such as irradiation, surgery, chemotherapy (e.g., using camptothecin (CPT-11), 5-fluorouracil (5-FU), cisplatin, doxorubicin, irinotecan, paclitaxel, gemcitabine, cisplatin, paclitaxel, carboplatin-paclitaxel (Taxol), doxorubicin, 5-fu, or camptothecin+apo2l/TRAIL (a 6× combo)), one or more proteasome inhibitors (e.g., bortezomib or MG132), one or more Bcl-2 inhibitors (e.g., BH3I-2' (bcl-xl inhibitor), indoleamine dioxygenase-1 inhibitor (e.g., INCB24360, indoximod, NLG-919, or F001287), AT-101 (R-(−)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda et al., *Nat Med* 2002; 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), anti-angiogenic agents targeting VEGF and VEGFR (e.g., Avastin), synthetic triterpenoids (see Hyer et al., Cancer Research 2005; 65:4799-808), c-FLIP (cellular FLICE-inhibitory protein) modulators (e.g., natural and synthetic ligands of PPARγ(peroxisome proliferator-activated receptor γ), 5809354 or 5569100), kinase inhibitors (e.g., Sorafenib), Trastuzumab, Cetuximab, Temsirolimus, mTOR inhibitors such as rapamycin and temsirolimus, Bortezomib, JAK2 inhibitors, HSP90 inhibitors, PI3K-AKT inhibitors, Lenalildomide, GSK30 inhibitors, IAP inhibitors, genotoxic drugs, targeted therapeutics, and/or cancer vaccines.

The anti-TNFR2 antibodies may also be used in combination with therapeutic antibodies useful for the treatment of cancer, such as Rituxan® (rituximab), Herceptin® (trastuzumab), Bexxar® (tositumomab), Zevalin® (ibritumomab), Campath® (alemtuzumab), Lymphocide® (eprtuzumab), Avastin® (bevacizumab), and Tarceva® (erlotinib), as well as antibodies that target a member of the TNF and TNFR family of molecules (ligands or receptors), such as CD40 and CD40L, OX-40, OX-40L, CD70, CD27L, CD30, CD30L, 4-1BBL, CD137, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TAC1, APRIL, BCMA, LTβR, LIGHT, DcR3, HVEM, VEGI/TL1A, TRAMP/DR3, EDA1, EDA2, TNFR1, Lymphotoxin α/TNFβ, TNFα, LTβR, Lymphotoxin α 1β2, FAS, FASL, RELT, DR6, TROY, and NGFR.

Cytotoxic agents that are useful for treating cancer in combination with the anti-TNFR2 antibodies described herein include alkylating agents, antimetabolites, and other art-recognized anti-proliferative agents. Exemplary alkylating agents include nitrogen mustards, ethylenimine derivatives, alkyl sulfonates, nitrosoureas and triazenes, for example Uracil mustard, Chlormethine, Cyclophosphamide (CYTOXAN™) fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide. Exemplary antimetabolites include folic acid antagonists, pyrimidine analogs, purine analogs and adenosine deaminase inhibitors, for example, Methotrexate, 5-Fluorouracil, Floxuridine, Cytarabine, 6-Mercaptopurine, 6-Thioguanine, Fludarabine phosphate, Pentostatine, and Gemcitabine. Other suitable anti-proliferative agents for use in combination with the anti-TNFR2 antibodies described herein include, e.g., taxanes, paclitaxel (paclitaxel is commercially available as TAXOL™), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone Bl, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discoderomolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

In cases where it is desirable to render aberrantly proliferative cells quiescent in conjunction with or prior to treatment with anti-TNFR2 antibodies described herein, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX™, can also be administered to the patient. When employing the methods or compositions described herein, other agents used in the modulation of tumor growth or metastasis in a clinical setting, such as antimimetics, can also be administered as desired.

The anti-TNFR2 antibodies described herein may be combined with an art-recognized vaccination protocol (e.g., cancer vaccine). Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, Cancer: Principles and Practice of Oncology, Fifth Edition). In some embodiments, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

The anti-TNFR2 antibodies described herein are also useful for the treatment of autoimmune disease and disorders. Accordingly, in one embodiment, provided herein is a method of treating autoimmune disease and disorders comprising administering to a subject an anti-TNFR2 antibody described herein in an amount effective (e.g., a therapeutically effective amount) to treat the autoimmune diseases and disorders. Exemplary autoimmune diseases and disorders for treatment with the anti-TNFR2 antibodies described herein include, for example, graft-versus-host disease, rheumatoid arthritis, Crohn's disease, multiple sclerosis, colitis, psoriasis, autoimmune uveitis, pemphigus, epidermolysis bullosa, and type 1 diabetes. Subjects can be examined during therapy to monitor the efficacy of the anti-TNFR2 antibodies to attenuate the symptoms or pathology of autoimmune disease. Efficacy of the treatment can be monitored by comparing the effects of the antibody and or combination treatment before and after administration.

The anti-TNFR2 antibodies described herein can be administered alone or with one or more therapeutic agents that act in conjunction with or synergistically with the antibody to treat a subject with autoimmune disease. For example, the anti-TNFR2 antibodies described herein can be used in combination with corticosteroids (e.g., prednisone, budesonide, prednisolone), calcineurin inhibitors (e.g., cyclosporine, tacrolimus); mTOR inhibitors (e.g., sirolimus, everolimus); EVIDH inhibitors (e.g., azathioprine, leflunomide, mycophenolate); biologics (e.g., abatacept, adalimumab, anakinra, certolizumab, etanercept, golimumab, infliximab, ixekizumab, natalizumab, rituximab, secukinumab, tocilizumab, ustekinumab, vedolizumab); and monoclonal antibodies (e.g., basiliximab, daclizumab, muromonab).

The anti-TNFR2 antibodies described herein are also useful in the context of transplantation (e.g., cell, tissue, or organ transplantation). Accordingly, in some embodiments, provided herein is a method of promoting graft survival and/or reducing graft rejection in a subject (e.g., a human graft recipient) who has received or will receive a cell, tissue, or organ transplant comprising administering to the subject an effective amount (e.g., a therapeutically effective amount) of an anti-TNFR2 described herein to promote graft survival and/or reduce graft rejection. In some embodiments, the graft is autologous, allogeneic, or xenogeneic to the recipient. In some embodiments, the anti-TNFR2 antibody (or combination treatment) can be administered prior to transplantation, at the time of transplantation, and/or after transplantation to promote graft survival and/or reduce graft rejection.

In some embodiments, the graft rejection is in a recipient of a cell, tissue, or organ allograft. In some embodiments, the graft recipient is a recipient of a hematopoietic cell or bone marrow transplant, an allogeneic transplant of pancreatic islet cells, or a solid organ transplant selected from the group consisting of a heart transplant, a kidney-pancreas transplant, a kidney transplant, a liver transplant, a lung transplant, and a pancreas transplant. Additional examples of grafts include but are not limited to allotransplanted cells, tissues, or organs such as vascular tissue, eye, cornea, lens, skin, bone marrow, muscle, connective tissue, gastrointestinal tissue, nervous tissue, bone, stem cells, cartilage, hepatocytes, or hematopoietic cells.

In some embodiments, the method of promoting graft survival and/or reducing graft rejection increases graft survival in the recipient by at least about 15%, by at least about 20%, by at least about 25%, by at least about 30%, by at least about 40%, or by at least about 50%, compared to the graft survival observed in a control recipient. A control recipient may be, for example, a graft recipient that does not receive a therapy post-transplant or that receives a monotherapy following transplant. In certain embodiments, a method of promoting graft survival promotes long-term graft survival (e.g., at least about 6 months, at least 1 year, at least 5 years, at least about 10 years, or longer post-transplantation.

Also provided herein is a method of treating, preventing, or reducing graft-versus-host disease (e.g., in a subject who has or will receive a cell, tissue, or organ transplant) comprising administering to a subject in need thereof an effective amount (e.g., a therapeutically effective amount) of an anti-TNFR2 described herein to treat, prevent, or reduce graft-versus-host disease. The anti-TNFR2 antibody (or combination treatment) can be administered prior to transplantation, at the time of transplantation, and/or after transplantation to treat, prevent, or reduce graft-versus-host disease.

The anti-TNFR2 antibodies described herein can be administered alone or with one or more therapeutic agents that act in conjunction with or synergistically with the antibody to promote graft survival and/or reduce graft rejection, or treat, prevent, or attenuate graft-versus-host disease. For example, the anti-TNFR2 antibodies described herein can be used in combination with an immunomodulatory or immunosuppressive agent, for example, adriamycin, azathiopurine, busulfan, bredinin, brequinar, leflunamide, cyclophosphamide, cyclosporine A, fludarabine, 5-fluorouracil, methotrexate, mycophenolate mofetil, 6-mercaptopurine, a corticosteroid, a nonsteroidal anti-inflammatory, sirolimus (rapamycin), tacrolimus (FK-506), anti-thymocyte globulin (ATG), muromonab-CD3, OKT3, alemtuzumab, basiliximab, daclizumab, rituximab, anti-thymocyte globulin and IVIg.

In the combination treatments described herein, the anti-TNFR2 antibodies described herein can be administered before, after, or concurrently with the one or more additional agents.

In some embodiments, provided herein is a method of blocking TNFα binding to TNFR2 in a cell comprising contacting the cell with an effective amount of an anti-TNFR2 antibody described herein.

In some embodiments, provided herein is a method of activating TNFR2-mediated signaling in a cell comprising contacting the cell with an effective amount of an anti-TNFR2 antibody described herein.

In some embodiments, provided herein is a method of activating NF-κB signaling in a cell or subject comprising contacting the cell with or administering to the subject an effective amount of an anti-TNFR2 antibody described herein to activate NF-κB signaling.

In some embodiments, provided herein is a method of promoting (e.g., increasing) T cell proliferation (e.g., CD4+ T cells, CD8+ T cells, or both CD4+ T cells and CD8+ T cells) in vitro (e.g., in culture) or in vivo (i.e., in a subject) comprising contacting cells (e.g., T cells) with or administering to the subject an effective amount of an anti-TNFR2 antibody described herein to promote T cell proliferation.

In some embodiments, provided herein is a method of co-stimulating T cells in vitro (e.g., in culture) or in vivo (i.e., in a subject) comprising contacting cells (e.g., T cells) with or administering to a subject an effective amount of an anti-TNFR2 antibody described herein to co-stimulate T cells.

In some embodiments, provided herein is a method of decreasing the abundance of regulatory T cells (e.g., in the T cell compartment) comprising contacting cells (e.g., T cells) with or administering to a subject an effective amount of an anti-TNFR2 antibody described herein to decrease the abundance of regulatory T cells. In some embodiments, the decrease in abundance of regulatory T cells involves ADCC. In other embodiments, the decrease in abundance of regulatory T cells involves inhibition or reduction of proliferation or induction of cell death.

Also provided herein are methods of detecting the presence of TNFR2 in a sample. In some embodiments, the method comprises contacting the sample with an anti-TNFR2 antibody described herein under conditions that allow for formation of a complex between the antibody and TNFR2 protein, and detecting the complex. In some embodiments, the anti-TNFR2 antibodies described herein can be used to detect the presence or expression levels of TNFR2 proteins on the surface of cells in cell culture or in a cell population. In another embodiment, the anti-TNFR2 antibodies described herein can be used to detect the amount of TNFR2 proteins in a biological sample (e.g., a biopsy). In yet another embodiment, the anti-TNFR2 antibodies described herein can be used in in vitro assays (e.g., immunoassays such as Western blot, radioimmunoassays, ELISA) to detect TNFR2 proteins. The anti-TNFR2 antibodies described herein can also be used for fluorescence activated cell sorting (FACS).

The present invention is further illustrated by the following examples which should not be construed as further limiting. The contents of Sequence Listing, figures and all references, patents and published patent applications cited throughout this application are expressly incorporated herein by reference.

EXAMPLES

Commercially available reagents referred to in the Examples below were used according to manufacturer's instructions unless otherwise indicated. The present invention uses art-recognized procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture,* 1987; Coligan et al., *Current Protocols in Immunology,* 1991.

Example 1. Generation of Human Anti-TNFR2 Antibodies

Human anti-TNFR2 antibodies were generated as follows. Human single chain Fv antibody phage libraries consisting of a naïve repertoire (6.7e9 members) (PMID: 9600934), natural diversity in HV3-23/KV1-33 pairings (2e9 members), and HV1-69/KV3-20 pairings (5e8 members) were individually panned against human TNFR2-Fc for two rounds. To enrich for binders to the CRD1 domain of human TNFR2, the final round of panning was performed on a chimera 4 TNFR2 construct consisting of the CRD1 of human TNFR2 (23-75) and CRD2-4 of mouse TNFR2 (77-258) fused to Fc.

Figure 1:
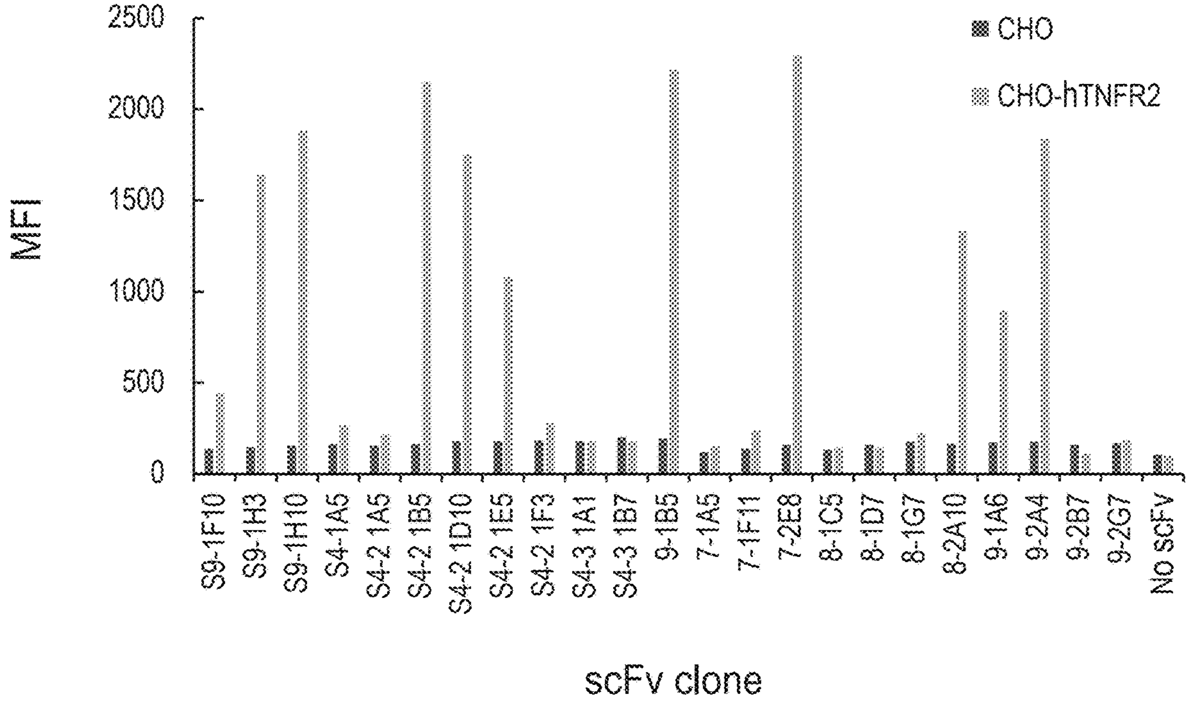
FIG. 1 is a graph showing the binding of soluble scFv clones (200 nM) to CHO-hTNFR2 cells and CHO cells, as measured by flow cytometry.
Figure 2:
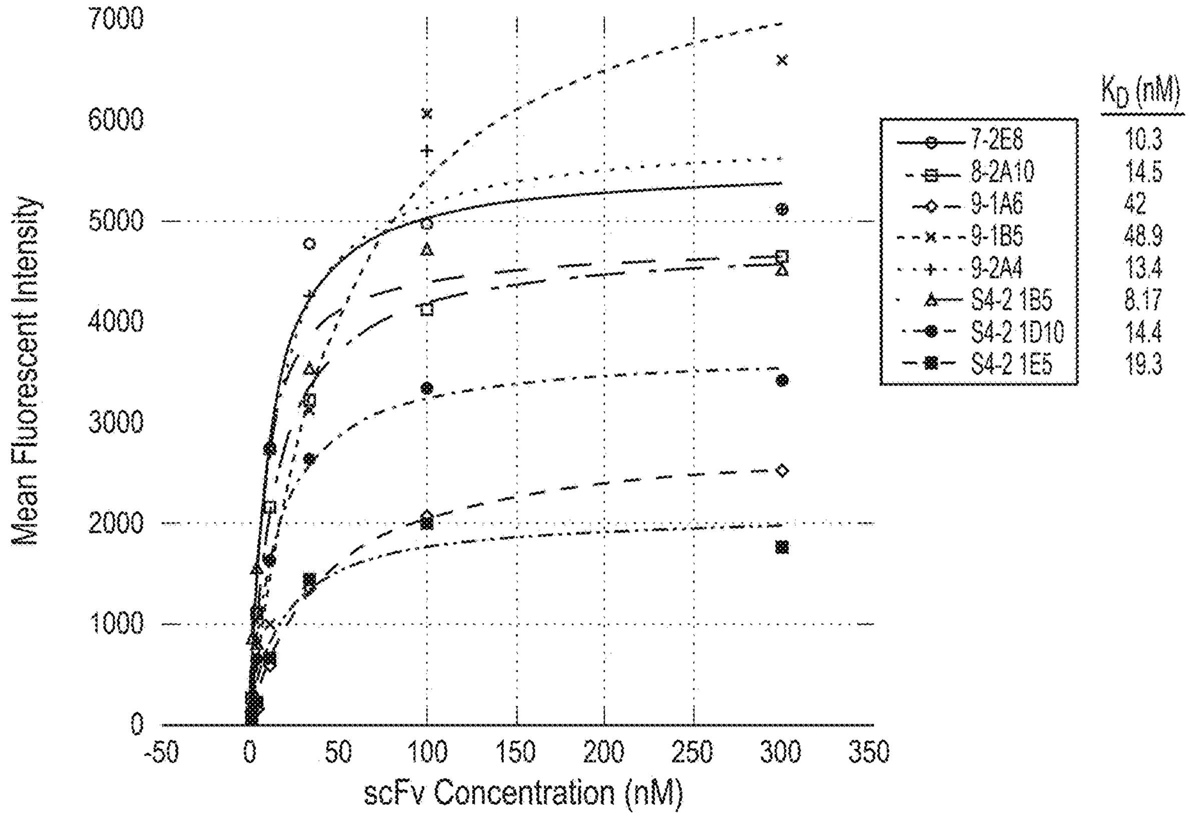
FIG. 2 is a graph showing the binding of a subset of soluble scFv clones from FIG. 1 to CHO-hTNFR2 cells as measured by flow cytometry. $K_D$ values were determined using one site binding non-linear fit.
Figure 3:
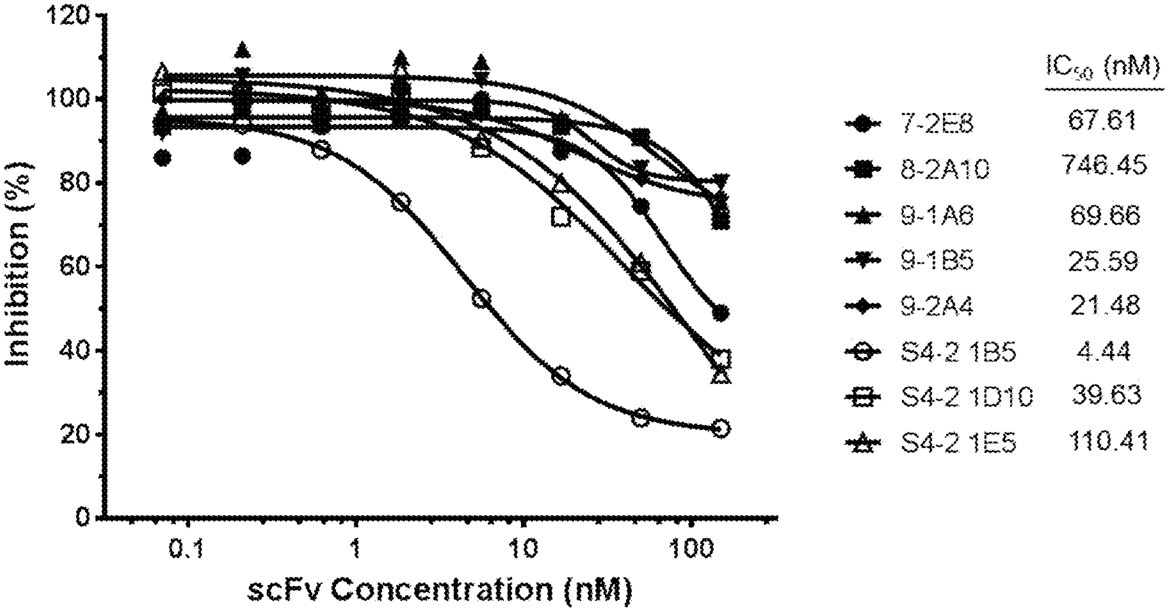
FIG. 3 is a graph showing the inhibition of TNF (1 nM) binding to CHO cells overexpressing human TNFR2 by soluble scFv clones. $IC_{50}$ values were determined using a four-parameter non-linear fit. $IC_{50}$ values were 67.61 nM for 7-2E8, 746.45 nM for 8-2A10, 69.66 nM for 9-1A6, 25.59 nM for 9-1B5, 21.48 nM for 9-2A4, 4.44 nM for S4-2 1B5, 39.63 nM for S4-2 1D10, and 110.41 nM for S4-2 1E5.

Clones selected from the final round of panning were enriched for that bound specifically to CHO cells overexpressing hTNFR2 (CHO-hTNFR2 cells) and not CHO cells (FIGS. 1 and 2) when expressed as a soluble scFv. A number of these clones were tested and shown to inhibit TNF binding to CHO-hTNFR2 cells (FIG. 3).

Example 2. Affinity Maturation of Human Anti-TNFR2 Antibodies

Figure 4:
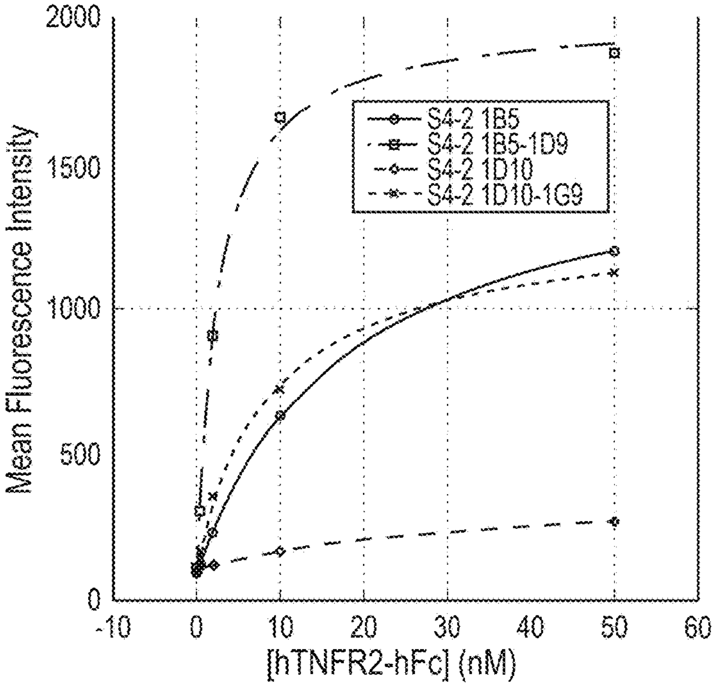
FIG. 4 shows binding of hTNFR2-Fc to the indicated mutant and wild-type scFv clones on yeast as measured by flow cytometry. $K_D$ values were determined using one site binding non-linear fit. $K_D$ values were 18.13 nM for UC1, 2.59 nM for UC1.1, 42.8 nM for UC2, and 8.88 nM for UC2.3.

Two scFv candidates (UC1) S4-2 1B5 and (UC2) S4-2 1D10 were mutated by error-prone PCR, cloned into the yeast display vector pYD3, and mutant scFv libraries were constructed. After two rounds of sorting with decreasing concentration of recombinant human TNFR2-hFc protein, one dominant affinity-matured variant was identified for each scFv. The variant scFvs, UC1.1 and UC2.3, bound the target with about 5-fold higher affinities as measured by flow cytometry (FIG. 4).

Figure 5A:
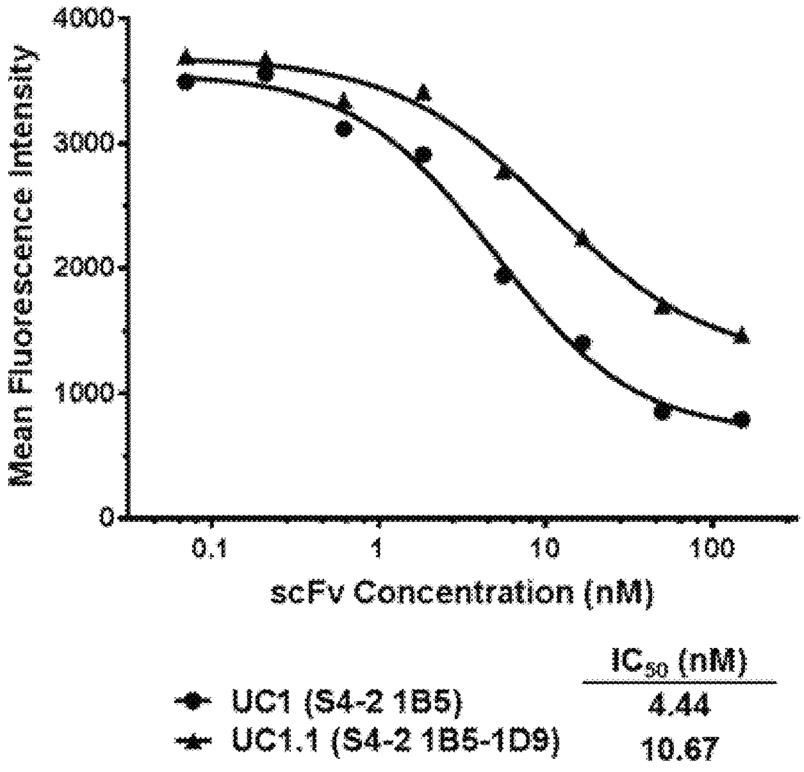
FIGS. 5A and 5B are graphs showing the inhibition of TNF (1 nM) binding to CHO-hTNFR2 cells by soluble parental (UC1 and UC2) and mutant (UC1.1 and UC2.3) scFvs. $IC_{50}$ values were determined using a four-parameter non-linear fit. $IC_{50}$ values were 4.44 nM for UC1, 10.67 nM for UC1.1, 39.63 nM for UC2, and 6.59 nM for UC2.3.
Figure 5B:
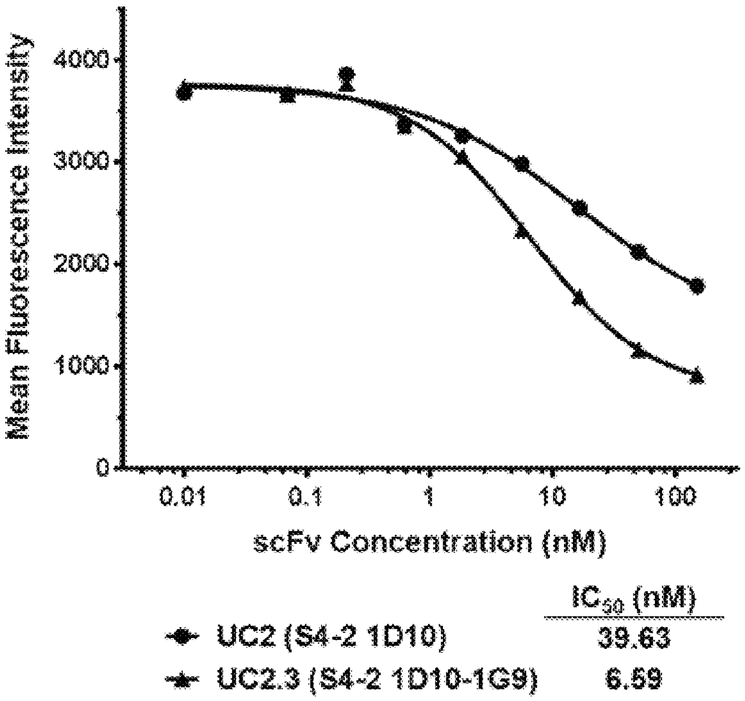
Figure 6A:
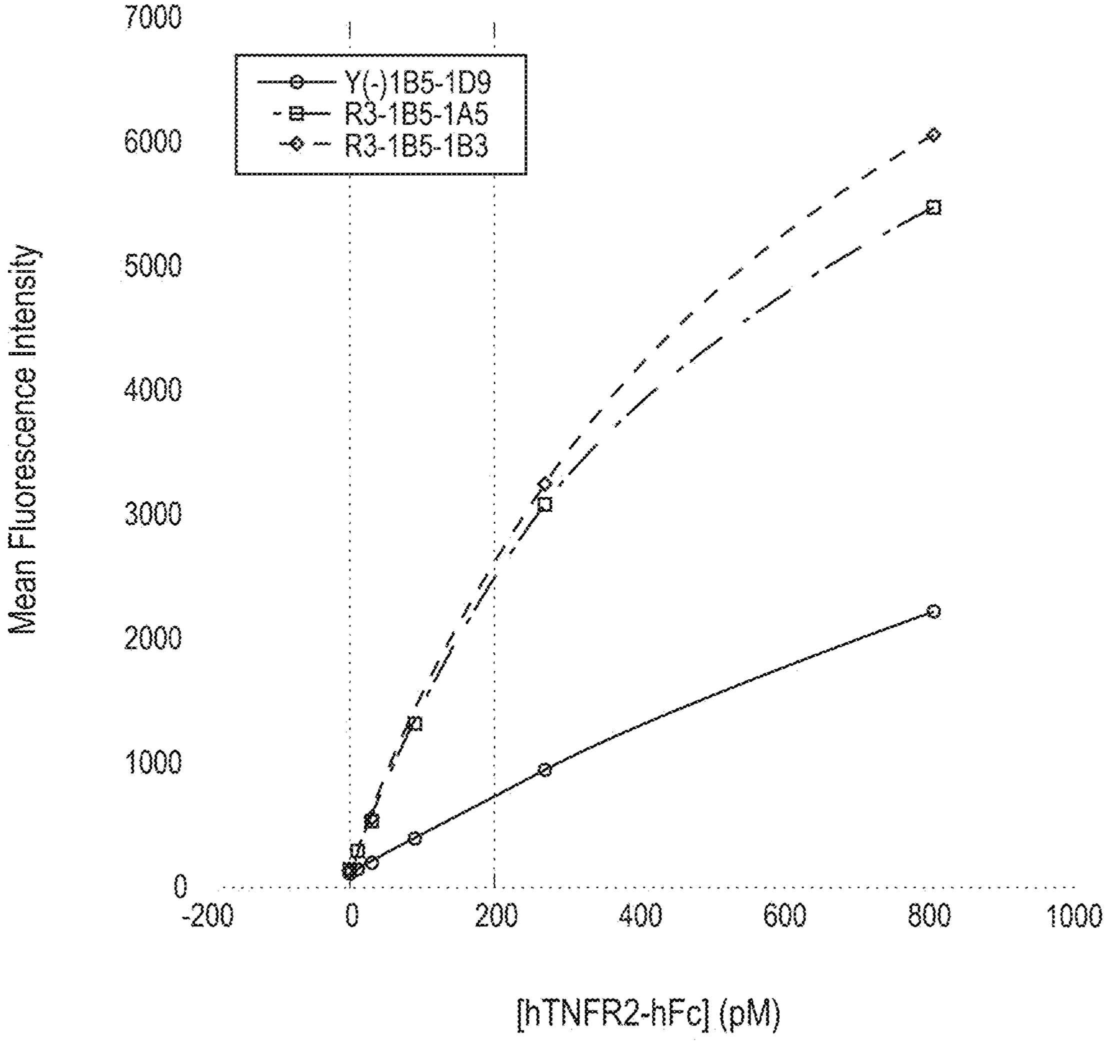
FIGS. 6A-6C are graphs showing the binding of hTNFR2-Fc to variant and wild-type scFv clones on yeast as measured by flow cytometry. $K_D$ values were determined using one site binding non-linear fit.
Figure 6B:
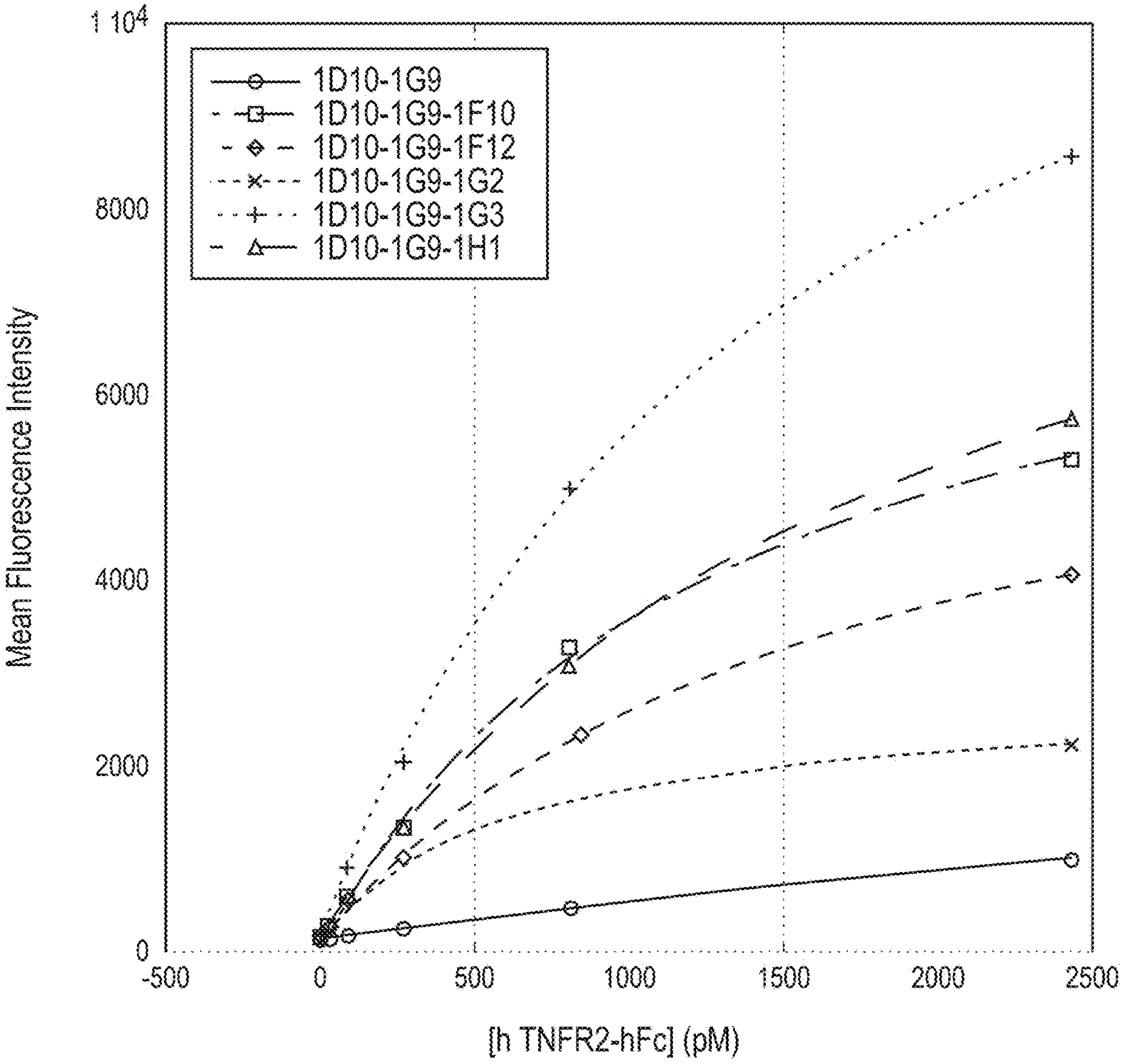
Figure 6C:
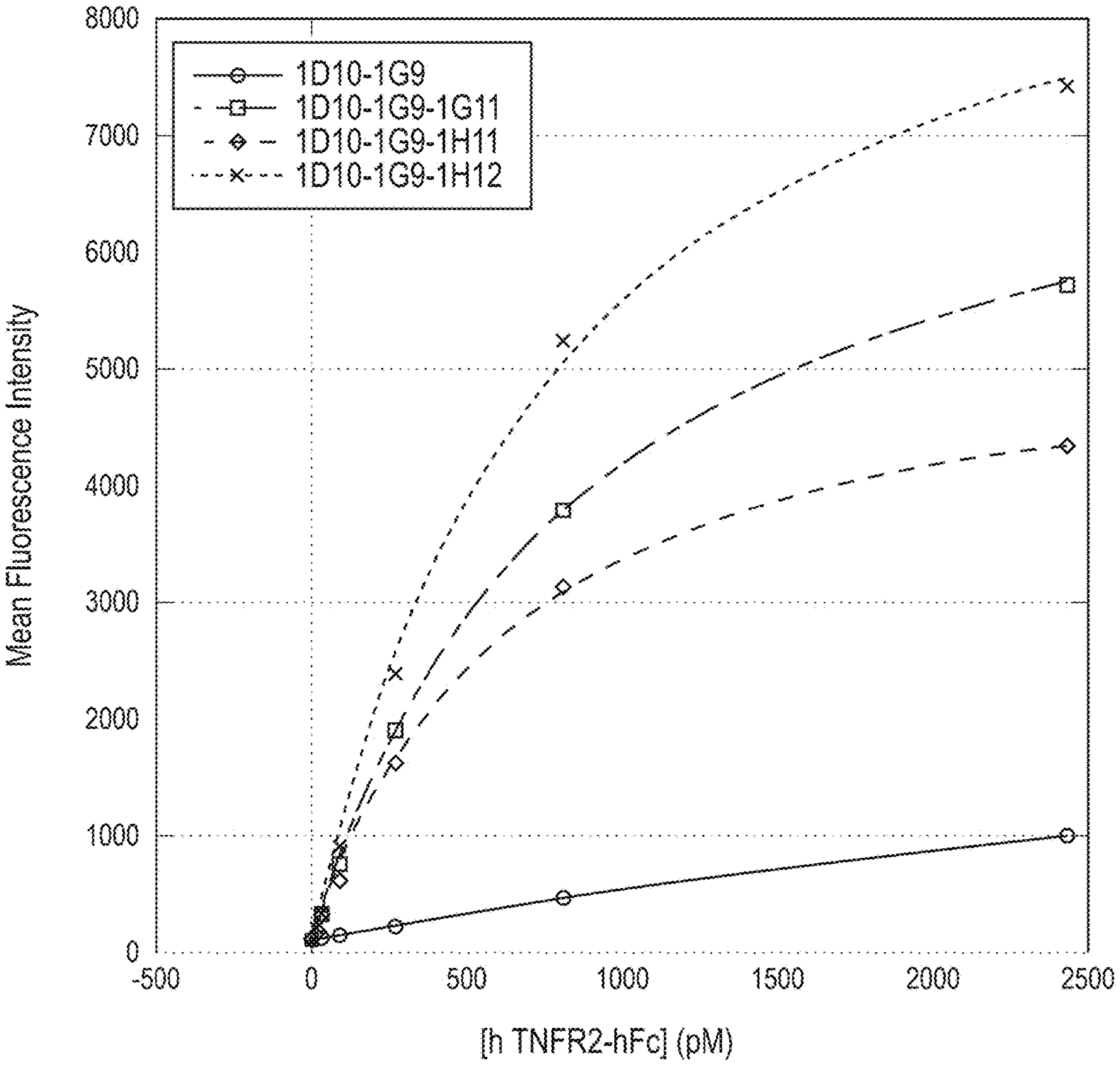
Figure 7:
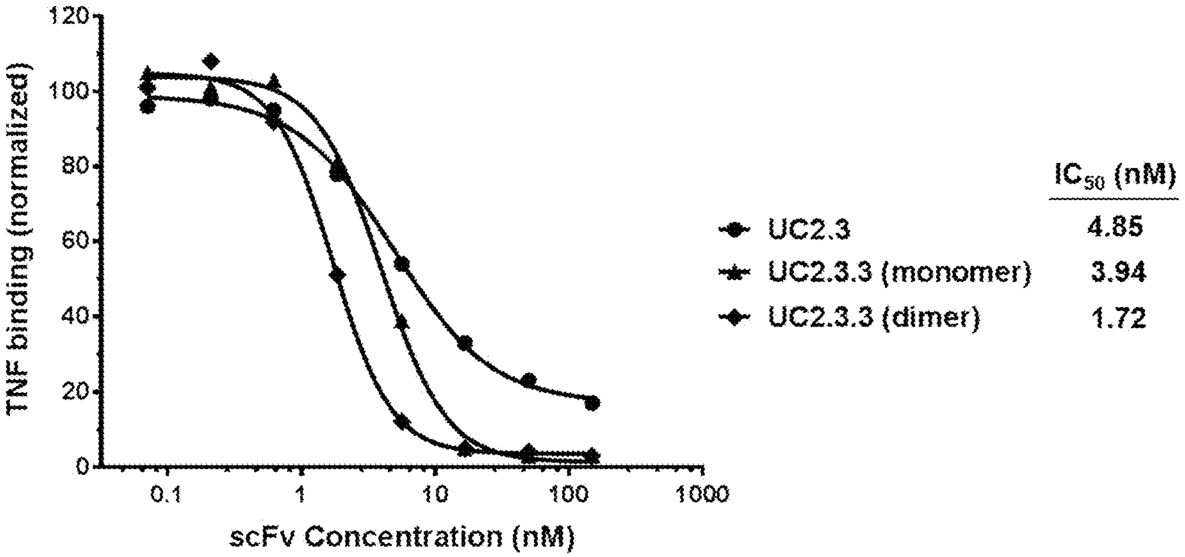
FIG. 7 is a graph showing the inhibition of TNF (1 nM) binding to CHO-hTNFR2 cells by soluble parental scFv clones (US2.3 (S4-2 1D10) and UC2.3.3 (S4-2 1D10-1G9). $IC_{50}$ values were determined using a four-parameter non-linear fit. $IC_{50}$ values were 4.85 nM for UC2.3, 3.94 nM for UC2.3.3 (monomer), and 1.72 nM for UC2.3.3 (dimer).

When expressed as soluble scFvs, these variants inhibited binding of human TNF to CHO cells overexpressing human TNFR2 (FIGS. 5A and 5B). To further improve binding affinities and inhibition of TNF binding, scFv candidates UC1 (S4-2 1B5) and UC2.3 (S4-2 1D10-1G9) were further mutated by error-prone PCR with a higher average mutation rate (5 amino acid changes per scFv), cloned into yeast display vector pYD3, and mutant scFv libraries were constructed. After four rounds of sorting with decreasing concentration of recombinant TNFR2-Fc protein, a number of variants were identified that bound the target with 10-fold higher affinities as measured by flow cytometry (FIGS. 6A-6C). Of these variants, UC2.3.3 was expressed as a soluble scFv and further evaluated for inhibition TNF binding to CHO-hTNFR2 cells. As shown in FIG. 7, UC2.3.3 scFv showed stronger inhibition of TNF binding to CHO-hTNFR2 cells than parental UC2.3 scFv.

Figure 8:
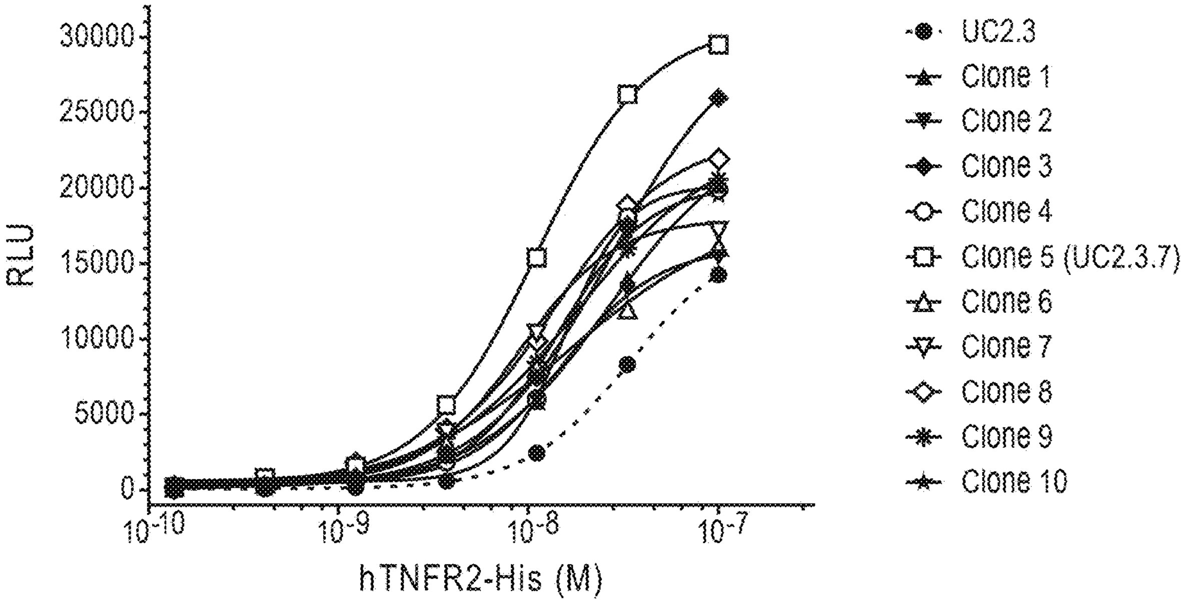
FIG. 8 is a graph showing the binding of hTNFR2-His by yeast display scFv clones as assessed by flow cytometry. $EC_{50}$ values were 33.89 nM for UC2.3, 26.14 nM for Clone 1, 15.06 nM for Clone 2, 27.22 nM for Clone 3, 15.67 nM for Clone 4, 11.03 nM for Clone 5, 16.47 nM for Clone 6, 8.97 nM for Clone 7, 13.70 nM for Clone 8, 17.74 nM for Clone 9 and 14.34 nM for Clone 10.

For saturation mutagenesis, positions 24-34 in CDR1 and 50-56 in CDR2 of the light chain of UC2.3 were randomized using mutagenic PCR primers containing degenerate codons NNS or VNS. The resulting mutant library was selected against recombinant human TNFR2-His for two rounds. Several scFv variants showing improved binding to TNFR2-His as measured on yeast surface were identified (FIG. 8).

Figure 9A:
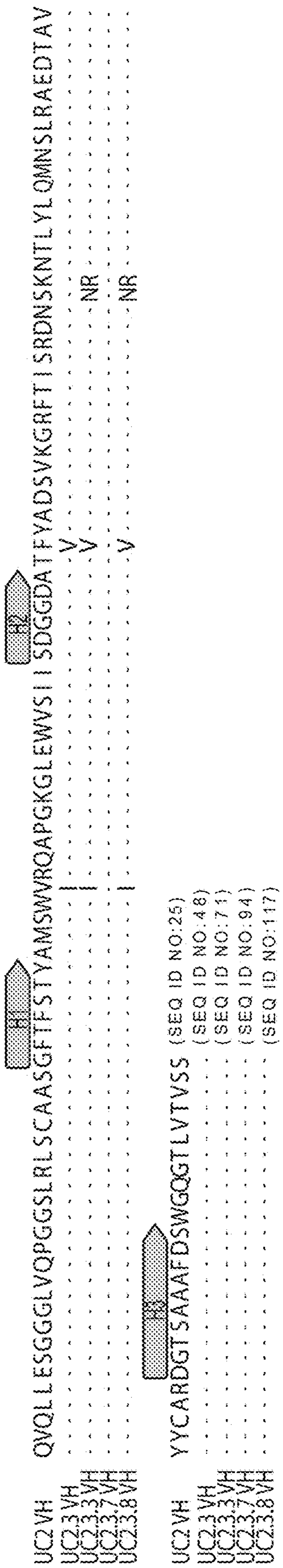
FIGS. 9A and 9B show sequence alignments of heavy and light chain variable region sequences, respectively, of the indicated anti-TNFR2 antibodies. The sequence for UC2 is shown in full while only changes from consensus sequence are represented for the affinity matured variants UC2.3, UC2.3.3, UC2.3.7, and UC2.3.8. CDRs are annotated using Chothia definition.
Figure 9B:
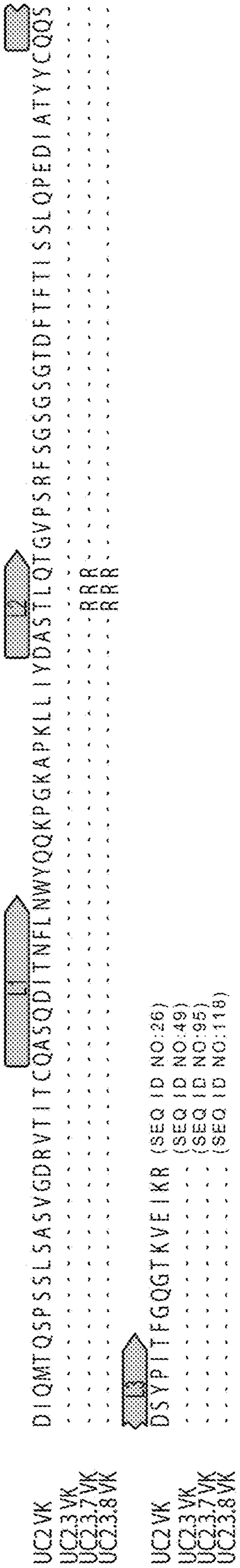
Figure 10:
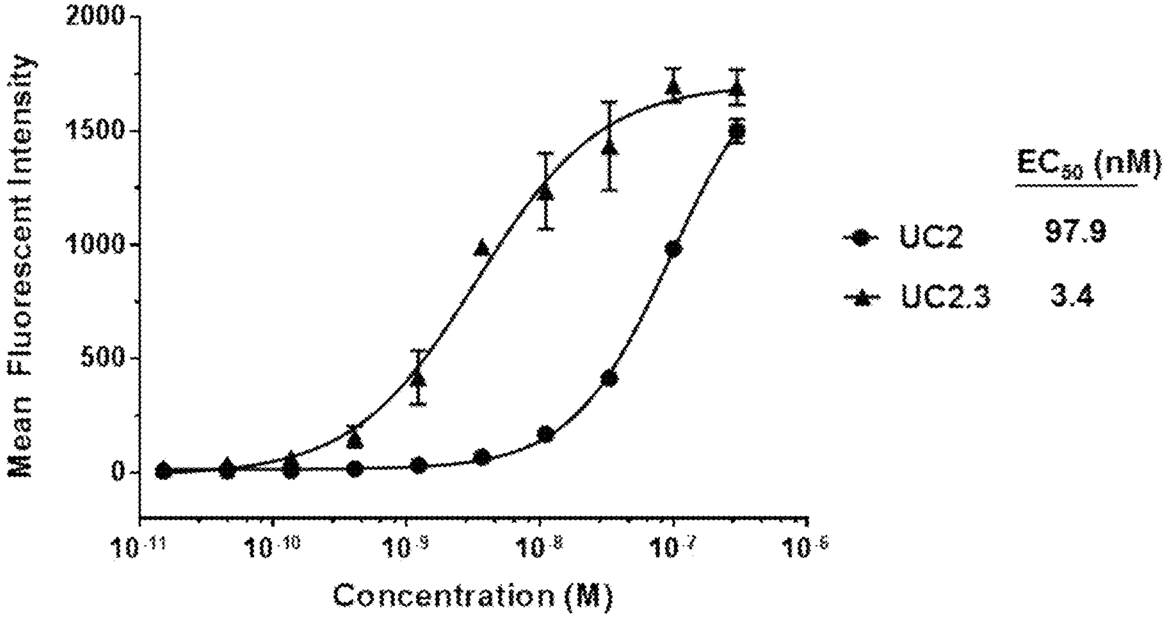
FIG. 10 is a graph showing the binding of anti-human TNFR2 IgGs UC2 and UC2.3 to CHO-hTNFR2 cells. $EC_{50}$ values were determined using four parameter non-linear fit. $EC_{50}$ values were 97.9 nM for UC2 and 3.4 nM for UC2.3.
Figure 11:
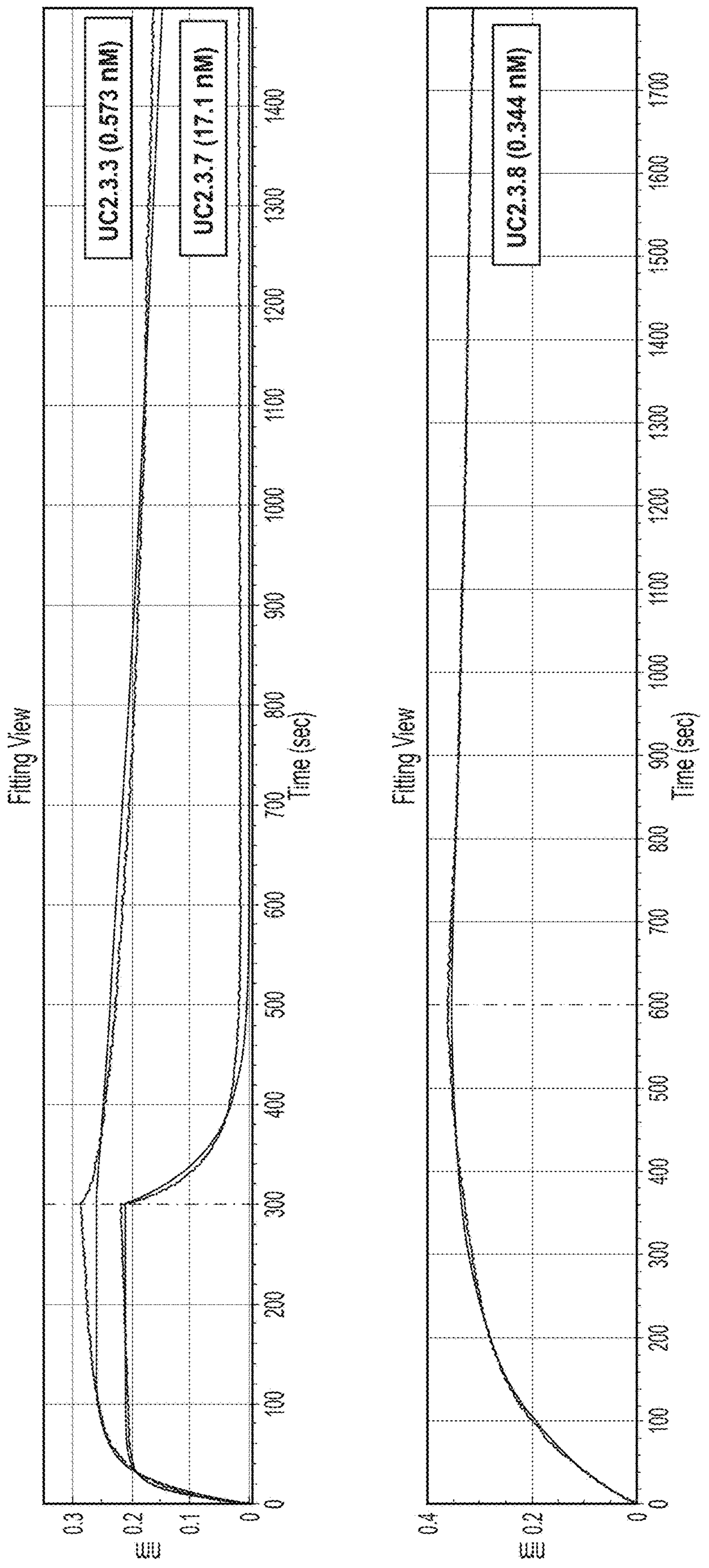
FIG. 11 shows sensorgrams and fits (smooth lines) for anti-human TNFR2 IgGs UC2.3.3, UC2.3.7, and UC2.3.8 by biolayer interferometry (BLI). $K_D$ values were 0.573 nM for UC2.3.3, 17.1 nM for UC2.3.7, and 0.344 nM for UC2.3.8.
Figure 12:
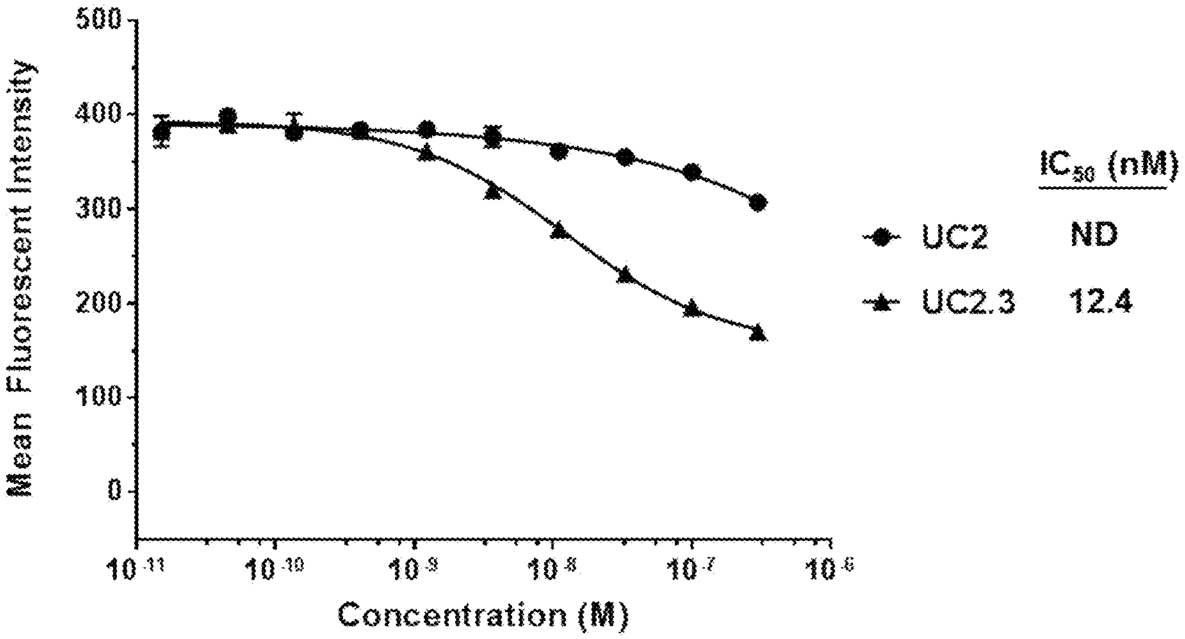
FIG. 12 is a graph showing the inhibition of TNF (1 nM) binding to CHO-hTNFR2 cells by anti-human TNFR2 IgGs: UC2 and UC2.3. $IC_{50}$ values were determined using a four-parameter non-linear fit. The $IC_{50}$ value was 12.4 nM for UC2.3 and could not be determined for UC2.
Figure 13A:
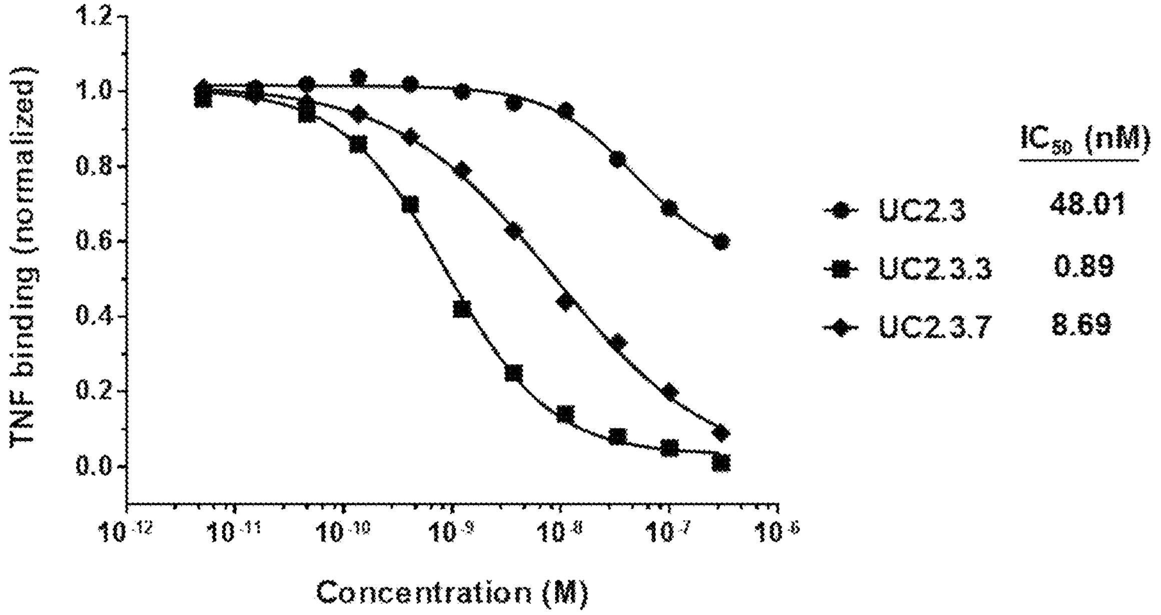
FIGS. 13A and 13B are graphs showing the inhibition of TNF (1 nM) binding to CHO-hTNFR2 cells by anti-human TNFR2 IgGs UC2.3, UC2.3.3, UC2.3.7, and UC2.3.8. IC50 values were determined using a four-parameter non-linear fit. $IC_{50}$ values in FIG. 13A are 48.01 nM for UC2.3, 0.89 nM for UC2.3.3, and 8.69 nM for UC2.3.7. $IC_{50}$ values in FIG. 13B are 0.68 for UC2.3.3 and 0.088 nM for UC2.3.8.
Figure 13B:
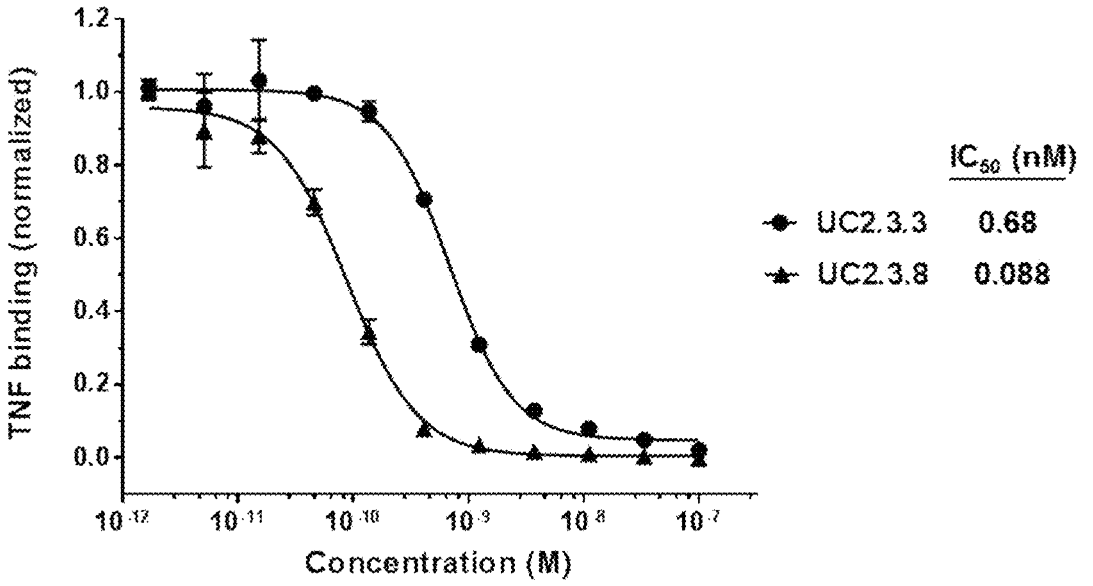

The most improved scFv variants from the two affinity maturation strategies, random mutagenesis (UC2.3.3) and saturation mutagenesis (UC2.3.7), were reformatted and expressed as full-length human IgG1 proteins. Since UC2.3.3 and UC2.3.7 contain only mutations in VH and VL regions, respectively (FIGS. 9A and 9B), the UC2.3.3 heavy chain was combined with the UC2.3.7 light chain to create a new variant, UC2.3.8. The affinity of the antibodies in IgG1 format for either CHO-hTNFR2 cells (FIG. 10; UC2 and UC2.3) or to TNFR2-His protein (FIG. 11; UC2.3.3, UC2.3.7, and UC2.3.8) were measured, as well as their ability to inhibit TNF binding to CHO-hTNFR2 cells (FIG. 12: UC2 and UC2.3; FIG. 13A: UC2.3, UC2.3.3, and UC2.3.7; FIG. 13B: UC2.3.3 and UC2.3.8)).

Example 3. Agonistic Activity of Human Anti-TNFR2 Antibodies

The agonistic activity of the human anti-TNFR2 antibodies was tested in a human TNFR2 reporter cell line as follows.

Briefly, GloResponse™ NF-kB-RE-luc2p HEK293 cell lines (Promega) were transfected with a full length human TNFR2 gene (Origene) using Lipofectamine 3000 (Thermofisher) and allowed to recover in DMEM/10% FBS. Two days following transfection, media was replaced with media containing Geneticin® (0.2 mg/ml). After 14 days of culture in geneticin-containing media, stable expression of human TNFR2 was confirmed by flow cytometry. To measure TNFR2-induced NF-kB signaling, human TNFR2 reporter cells and vector control cells ($1\times10^4$) were incubated with human UC2.3 (0.14-100 nM) for 5 hours at 37° C. ONE-Glo™ luciferase reagent was then added, and luminescence was measured on a SYNERGY H1 plate reader (BioTek).

Figure 14:
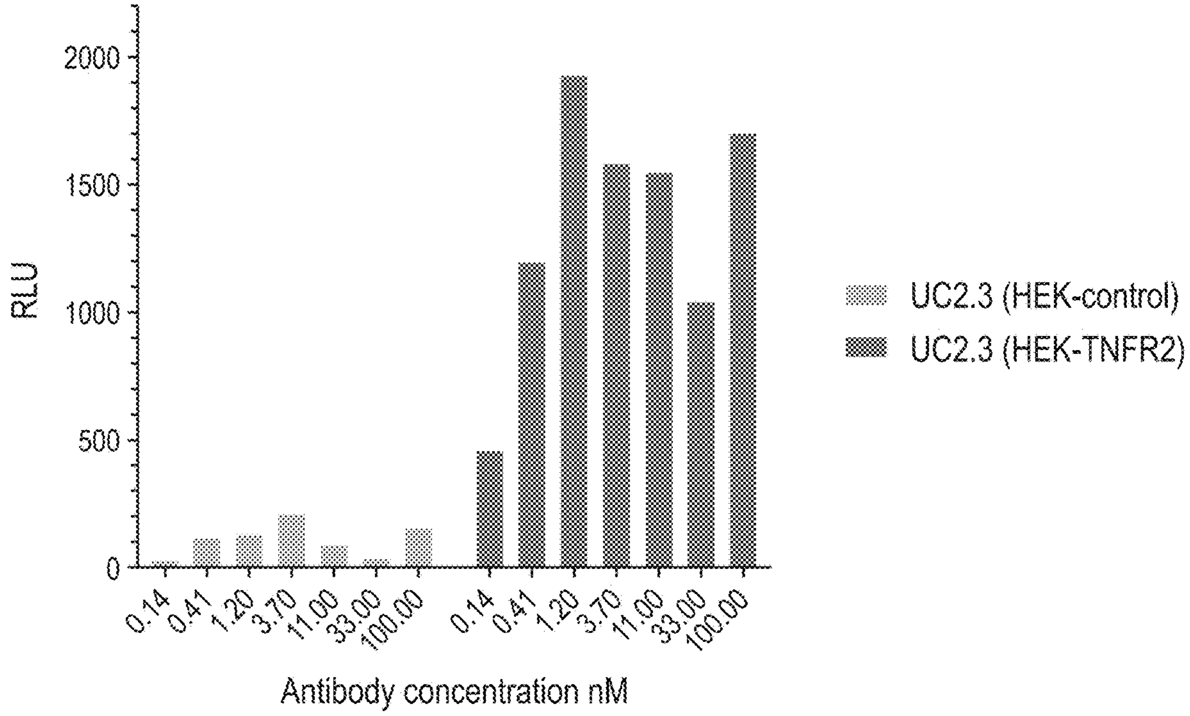
FIG. 14 is a graph showing the agonistic activity of the human anti-TNFR2 antibody UC2.3, as assessed by induction of NF-kB signaling in a reporter cell line.

As shown in FIG. 14, there was a dose-dependent increase in NF-kB signaling after incubation with the human anti-TNFR2 antibody UC2.3.

Example 4. UC2.3.8 Recognizes a Distinct Epitope on Human TNFR2

This Examples shows that UC2.3.8 binds to a distinct non-overlapping epitope relative to an antibody which binds to an epitope on human TNFR2 that includes positions Y24, Q26, Q29, M30, and K47 (comparator antibody).

Briefly, a BLI assay was performed in which biotin-labeled human TNFR2 (5 ug/ml) was captured using streptavidin biosensors followed by association with UC2.3.8 (20 ug/ml).

Figure 15:
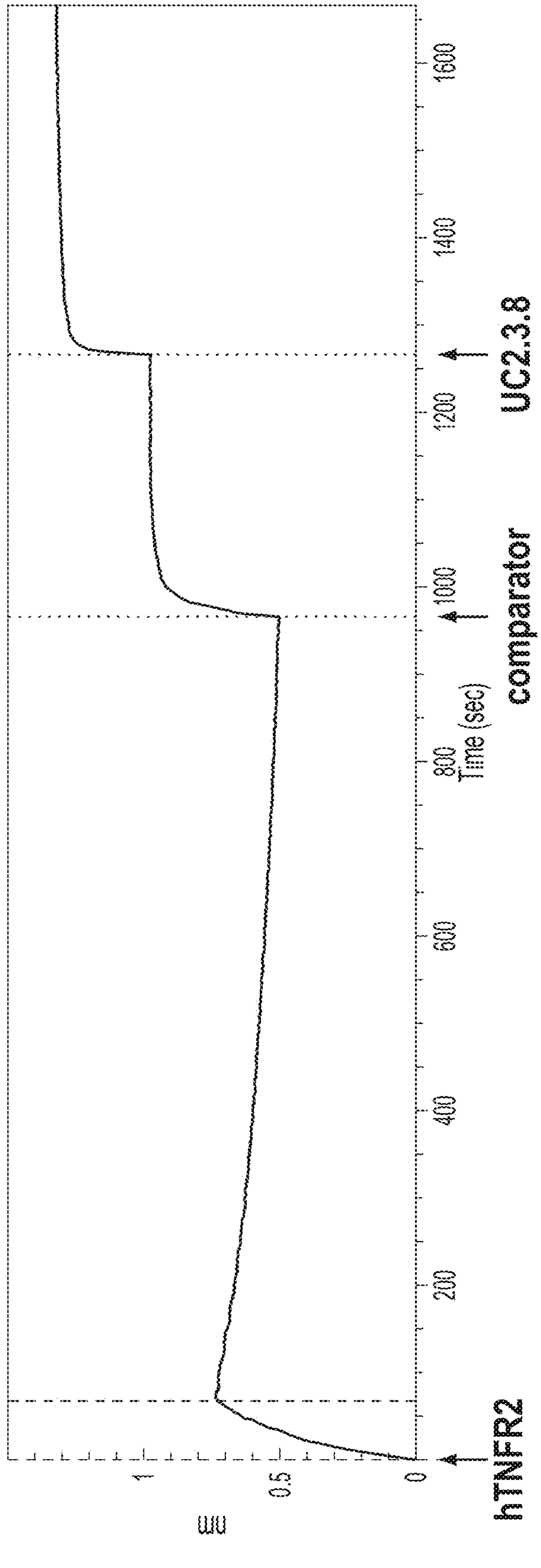
FIG. 15 shows a sensorgram demonstrating the concurrent binding of UC2.3.8 and a comparator antibody (20 μg/ml) to immobilized human TNFR2 (5 μg/mL). The comparator antibody binds to an epitope on human TNFR2 that includes positions Y24, Q26, Q29, M30, and K47 (numbering based on human TNFR2 without leader sequence).

As shown in FIG. 15, the comparator antibody and UC2.3.8 bind simultaneously to immobilized human TNFR2, suggesting that the antibodies bind to distinct non-overlapping epitopes.

Example 5. Effects of Human Anti-TNFR2 Antibodies on Tregs in Ovarian Cancer Ascites Regulatory T cells (Tregs) from patients with ovarian cancer have been reported to have high levels of TNFR2 and to be highly immunosuppressive. Others have shown that TNFR2 antagonism reduces the viability of ascites Treg cells (Torrey et al., *Sci Signal* 2017; 10:eaaf8608). In this Example, effects of the human anti-TNFR2 antibodies on Tregs were examined.

Briefly, ovarian cancer ascites were obtained and cultured with the indicated concentrations of anti-TNFR2 antibody UC2.3 for 48 hours. Flow cytometry was used to determine the relative abundance of Treg cells in the CD4+ T cell compartment following treatment using the antibodies shown in Table 2.

Figure 16A:
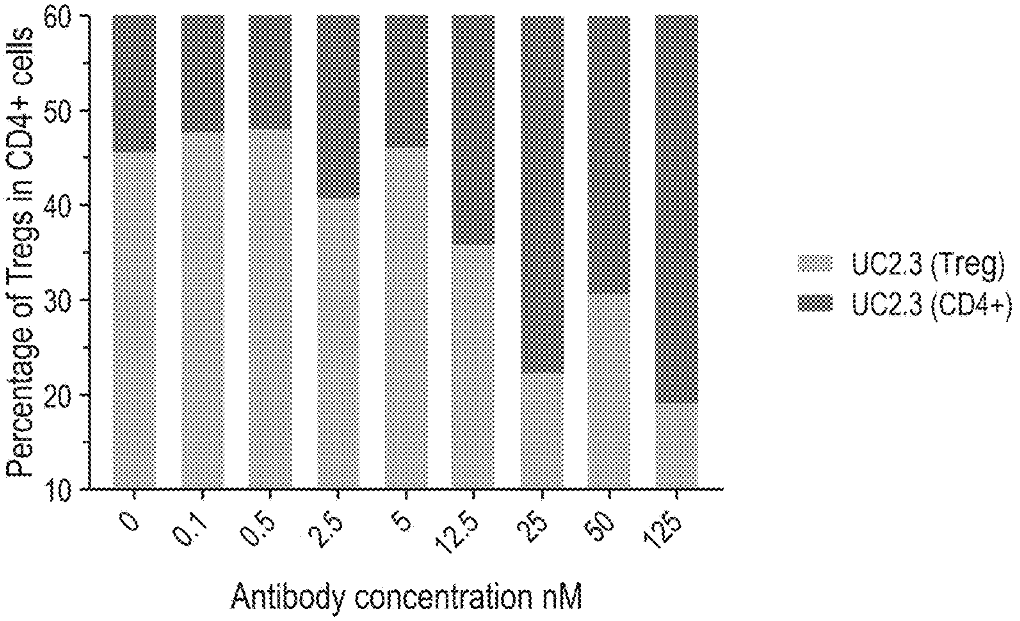
FIGS. 16A and 16B show the effect of antibody UC2.3 on T cell populations from ovarian cancer ascites.
Figure 16B:
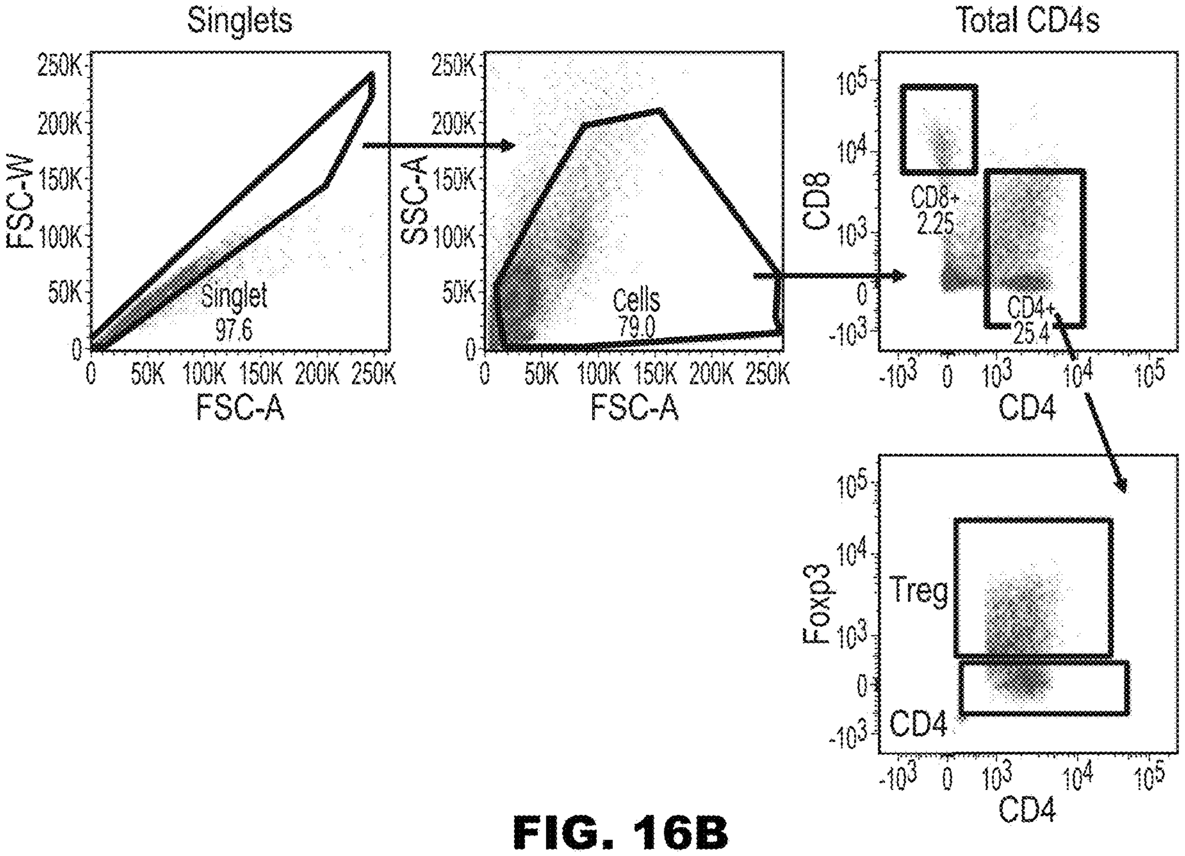

As shown in FIG. 16, UC2.3 decreased the percentage of cells expressing the Treg-lineage marker Foxp3 within the CD4 compartment, suggesting that UC2.3 selectively inhibits Treg cells but not effector CD4 T cells.

TABLE 2

| Target | Clone | Source | Fluorochrome | Laser | Dilution |
|---|---|---|---|---|---|
| Tru Stain Fcx | Poly | BioLegend | | | 100 |
| CD4 | OKT4 | BioLegend | BV785 | 405 | 200 |
| CD8 | SK1 | BioLegend | APC/Cy7 | 633 | 200 |
| TNFR2 | 3G7A02 | BioLegend | PE | 488 | 200 |
| Foxp3 | 206D | BioLegend | PE/Dazzle 594 | 488 | 100 |

Example 6. Effects of Human Anti-TNFR2 Antibodies on ADCC

The ability of human anti-TNFR2 antibodies to induce ADCC in human cells was tested as follows.

Briefly, NK cells (RosetteSep Human NK cell Enrichment Cocktail, StemCell) from peripheral blood of healthy donors were isolated and cultured with carboxyfluorescein succinimidyl ester (CFSE)-labeled JJN3 (plasma cell myeloma) target cells, which express high levels of TNFR2, at a 5:1 effector (NK cell) to target cell ratio for four hours in the presence or absence of UC2.3 at a concentration of 5 μg/mL. As target cells die, the cell membrane becomes permeable and intracellular proteins leak out, causing a drop in the per-cell fluorescence of CFSE that can be quantified by flow cytometry.

Figure 17A:
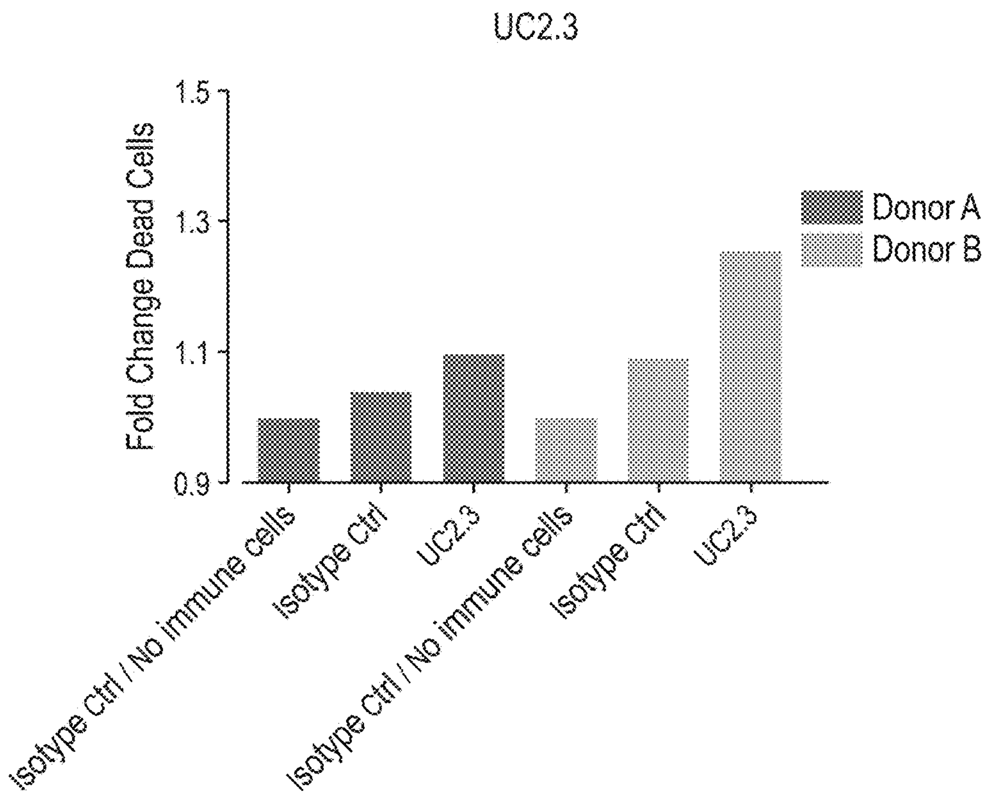
FIG. 17A shows the ADCC activity of UC2.3 and controls (isotype control and isotype control/no immune cells).
Figure 17B:
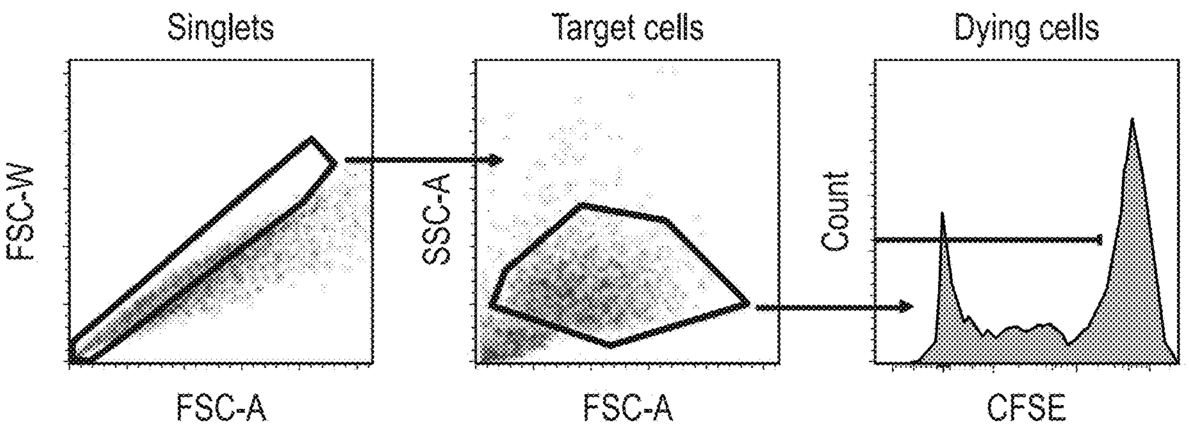
FIG. 17B shows the gating strategy for the flow cytometry analysis.

Across multiple donors, in the presence of NK cells, UC2.3 increased the number of dead cells compared to target cells alone with isotype control antibody, or target cells plus NK cells with isotype control antibody (FIGS. 17A and 17B). These data indicate that UC2.3 can mediate ADCC of human target cells.

Example 7. Effects of Human Anti-TNFR2 Antibodies on Co-Stimulatory Activity, Proliferation, and Functionality of CD4+ and CD8+ T Cells The effects of human anti-TNFR2 antibodies on various aspects of T cell function were tested as follows.

Briefly, 96-well flat bottom plates (Corning) were coated with titrated amounts of functional-grade anti-CD3 (clone OKT3, BioLegend) and human anti-TNFR2 antibodies. Mononuclear cells were isolated in 50 mL SepMate-50 tubes (StemCell Technologies) over a Ficoll-Paque Plus density gradient (GE Healthcare). Total CD8 T cells or naïve CD45RA+CD4 T cells were purified via negative selection (human CD8+ T cell isolation kit or Naïve CD4+ T cell isolation kit II, Miltenyi) and labelled with 5 μM CellTrace Violet (ThermoFisher Scientific). $2\text{-}5\times10^4$ cells (typically >85% purity for CD8 T cells and >90% for CD4 T cells) were added per well along with 1 μg/mL soluble anti-CD28

(clone CD28.2, BioLegend) in RPMI 1640 (Gibco) supplemented with 10% FBS, 5 mM HEPES (Gibco), pen/strep (Gibco), 50 μM β-ME (G-Biosciences), 2 mM L-glutamine (Gibco), and incubated at 37° C. for 72 or 96 hrs as indicated. The golgi inhibitor Brefeldin A (BioLegend) was added to CD8+ T cell cultures for the final 5 hrs. Cells were then stained for activation markers and intracellular cytokines and analyzed by flow cytometry. Cells were first incubated and stained with the following antibodies from BioLegend: CD4 (OKT4), CD8 (SK1 or HIT8a), CD25 (BC96), PD-1 (EH12.2H7). Single cell suspensions were first incubated with Fc Block (BD Biosciences) and live/dead Ghost Dye red710 (Tonbo Biosciences) in PBS for 10 min at 4° C. Cells were then stained for extracellular markers for 30 min at 4° C. in FACS buffer (PBS with 1% FBS and 0.02% sodium azide). When staining CD8+ T cells for intracellular cytosolic proteins, cells were permeabilized using BioLegend's Fixation and Intracellular Staining Perm Buffer. Samples were run on an LSR Fortessa flow cytometer (BD Biosciences) and data were analyzed using FlowJo analysis software (Tree Star) version 10.5.3. Data were analyzed using a two-way ANOVA with Dunnett's multiple comparisons post-test. Data were plotted as mean S.E.M. Statistically significant difference from Isotype is indicated (*p<0.05, p<0.01, *p<0.001).

Figure 18A:
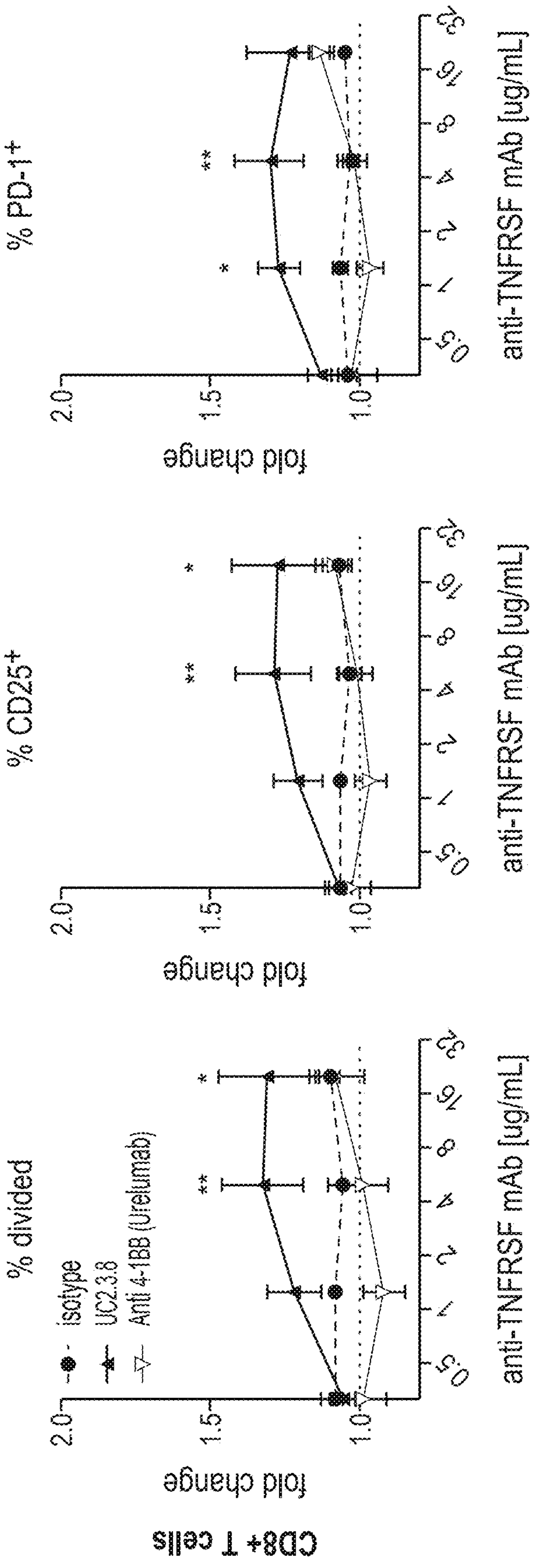
FIGS. 18A-18C show in vitro expansion, induction of activation markers, and cytokines on CD4+ T cells by human anti-TNFR2 antibody UC2.3.8. Naïve CD45RA+ CD8+ or CD4+ T cells were stimulated for 4 days with 5 ug/mL plate bound CD3, 1 ug/mL soluble CD28, and various concentrations of plate bound isotype control, anti-TNFR2 (UC2.3.8), anti-4-1BB (Urelumab), or anti-GITR (TRX518) mAb.
Figure 18B:
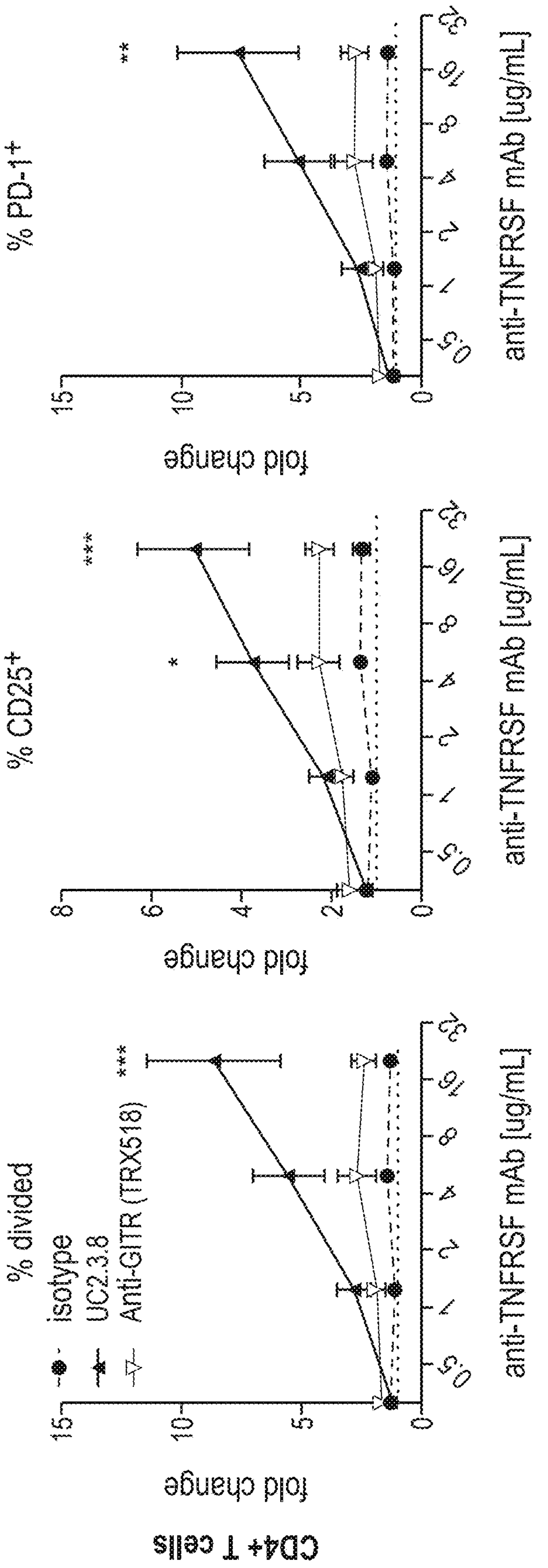
Figure 18C:
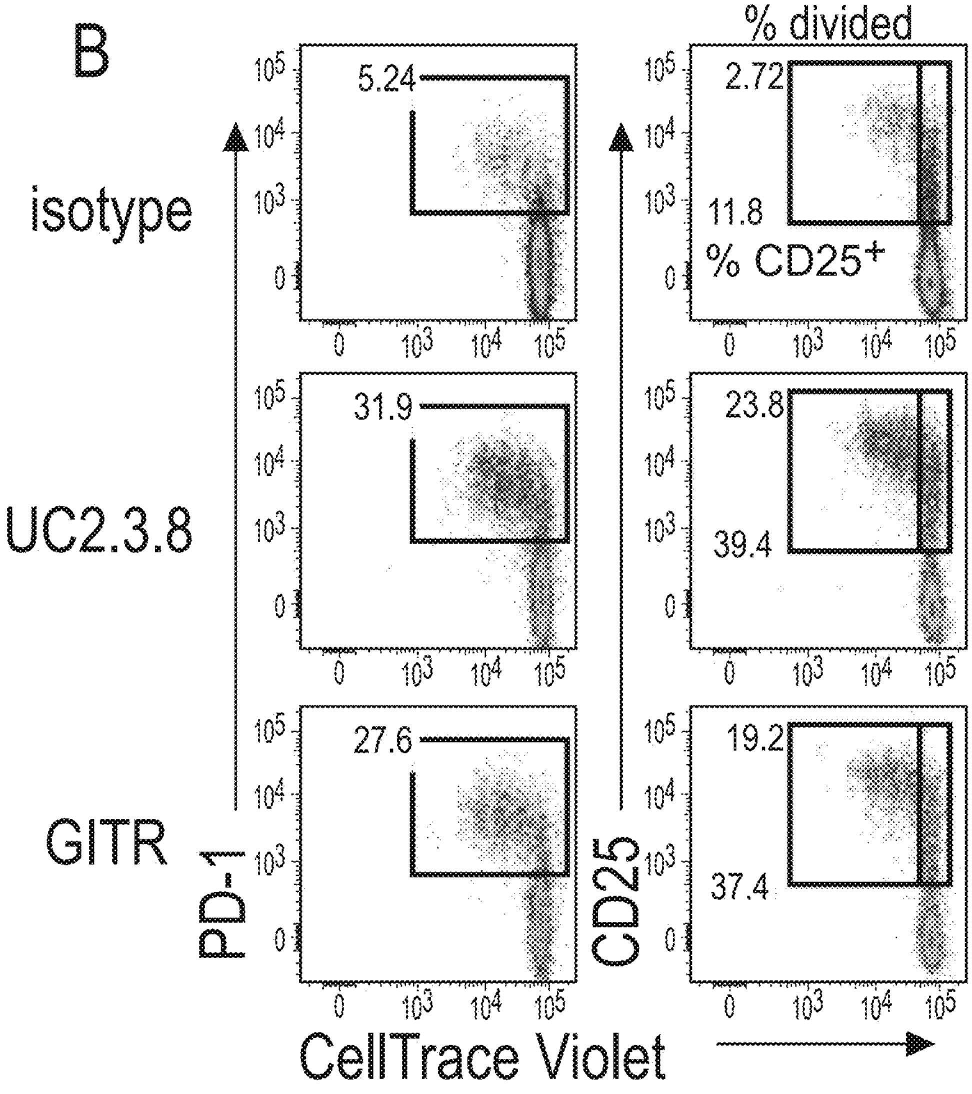

As shown in FIGS. 18A-18C, UC2.3.8 expanded and induced activation markers on $CD4^+$ and $CD8^+$ T cells in vitro. Moreover, UC2.3.8 lead to greater expansion and induction of activation markers than an anti-GITR antibody (TRX518) or anti-4-1BB antibody (Urelumab).

Example 8. Effects of Human Anti-TNFR2 Antibodies in a Graft-Versus-Host Disease Model The ability of human anti-TNFR2 antibodies to protect against disease was tested using a xenogenic GvHD model as follows.

Figure 19:
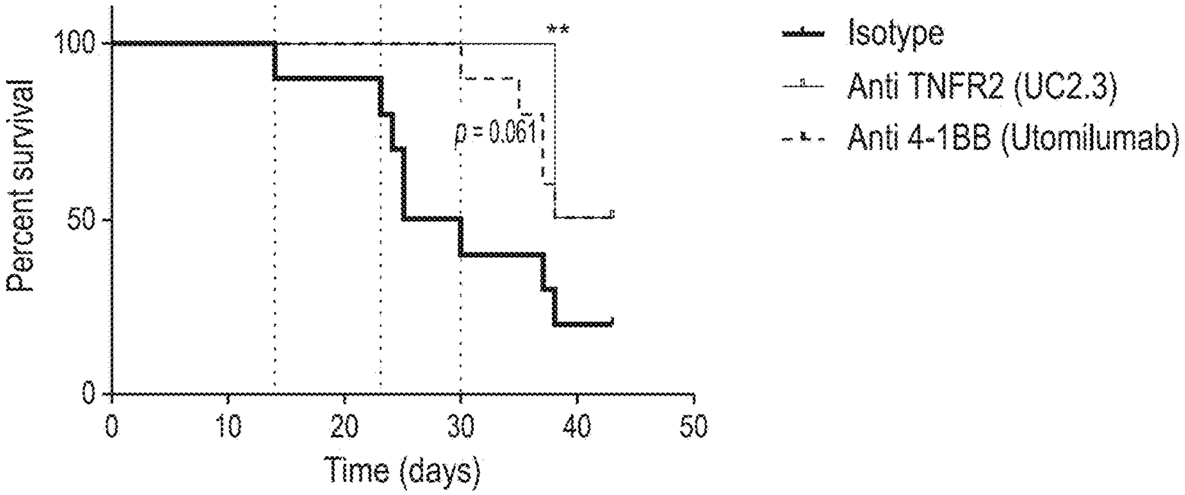
FIG. 19 shows the effect of antibody UC2.3-IgG1 on survival in a xenogeneic GvHD model.

Briefly, three to six-week-old female NSG-SGM3 (NOD Cg-Prkdc$^{scid}$ IL2rg$^{tm1Wji}$ Tg(CMV-IL-3, CSF2, KITLG) 1Eav/MloySz) mice were administered $10^7$ PBMCs from healthy donors i.v. and monitored daily for weight loss and changes in body condition. Animals were euthanized if >20% initial weight loss or significant deterioration in body condition were observed. On days 14, 23, and 30, mice were treated i.p. with 300 μg anti-TNFR2 (UC2.3), anti-4-1BB (Utomilumab), or isotype control antibody. Comparisons were made between control and treatment groups using the log rank test. Statistically significant difference from PBS is indicated (*p<0.05, p<0.01, *p<0.001). As shown in FIG. 19, UC2.3 increased survival in the xenogeneic GvHD model. The protective effect was greater than that of the agonistic anti-4-1BB antibody (Utomilumab).

Example 9. Human Anti-TNFR2 Antibodies in Mixed Lymphocyte Reaction Assay

To test the co-stimulatory activity of UC2.3.8 in a physiologically-relevant TCR stimulation context, we used a mixed lymphocyte reaction assay (MLR) (Bain et al., Fed. Proc. 1963; 22:4281). Mononuclear cells were isolated from healthy human blood (Research Blood Components; Watertown, MA) in 50 mL SepMate-50 tubes (StemCell Technologies) over a Ficoll-Paque Plus density gradient (GE Healthcare). For MLR, half of the cells from each donor were irradiated with 20 Gy from an X ray source (Faxitron) and were plated at $4\times10^5$ cells/well in RPMI 1640 (Gibco) supplemented with 10% FBS, 5 mM HEPES (Gibco), pen/strep (Gibco), 50 uM beta-ME (G-Biosciences), and 2 mM L-glutamine (Gibco) in a 96-well U-bottom plate to serve as stimulator cells, while the other half was labeled with 5 μM CellTrace Violet (ThermoFisher Scientific) and plated at $2\times10^5$ cells/well as responder cells. Cells were preincubated for 15 minutes with 50 ug/ml human IgG1 (BioXCell) of irrelevant specificity to block FcγRs. Varying concentrations of UC2.3.8 or isotype control (5 ug/ml) were then added. Cells were incubated for 7 days at 37° C., after which cells were stained for activation markers and analyzed by flow cytometry. Cells were stained with the following antibodies from BioLegend: CD4 (OKT4), CD8 (SK1), CD25 (BC96). Single cell suspensions were first incubated with Fc Block (BD Biosciences) and live/dead Ghost Dye red710 (Tonbo Biosciences) in PBS for 10 min at 4° C. Cells were then stained for extracellular markers for 30 min at 4° C. in FACS buffer (PBS with 1% FBS and 0.02% sodium azide). Samples were run on an LSR Fortessa flow cytometer (BD Biosciences) and data were analyzed using FlowJo analysis software (Tree Star) version 10.5.3. Data (plotted as mean S.E.M.) were analyzed using two-way ANOVA with Dunnett's multiple comparisons post-test.

Figure 20A:
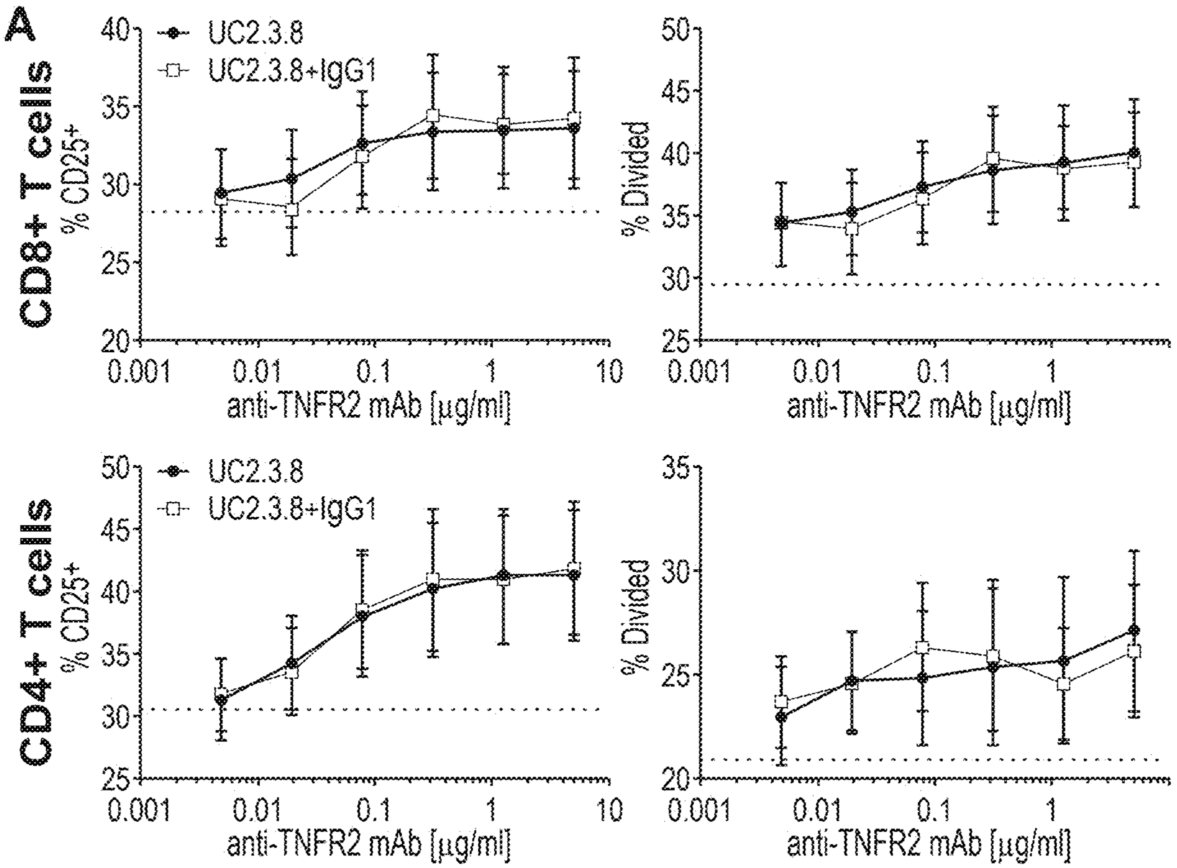
FIG. 20A is a series of graphs showing the effects of human anti-TNFR2 antibody UC2.3.8 on activating CD4+ and CD8+ T cells in a mixed lymphocyte reaction. Whole PBMCs were isolated from 4 individuals. Cells from all combination of donors were mixed at a 2:1 stimulator: responder ratio and cultured for 7 days in the presence of varying concentrations of soluble UC2.3.8 with or without 50 μg/ml irrelevant IgG1, or isotype control (5 μg/ml). Data are from 12 reactions among 4 individuals. Dotted horizontal line represents isotype control. No statistically significant difference was observed between UC2.3.8 and UC2.3.8 with IgG1.
Figure 20B:
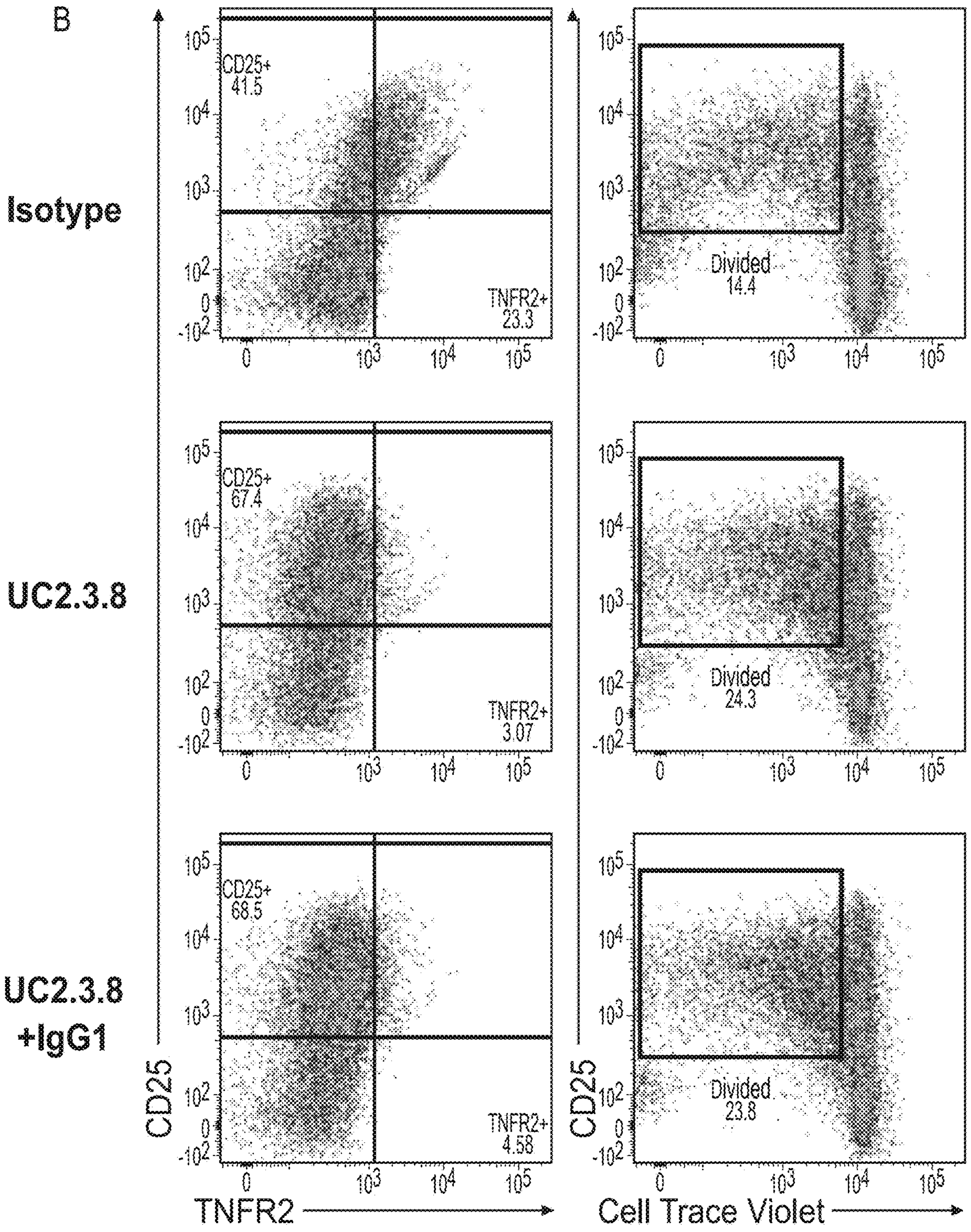
FIG. 20B shows representative flow plots of CD4 T cells stimulated with 5 μg/ml isotype, UC2.3.8 with or without IgG1.

As shown in FIGS. 20A and 20B, the human anti-TNFR2 antibody UC2.3.8 promoted the in vitro expansion of and CD25 induction on CD4+ and CD8+ T cells. This occurred independently of binding to FcγRs, since incubation with excess IgG1 did not diminish the effect.

Example 10. Superior T Cell Co-Stimulation by Human Anti-TNFR2 Antibody Relative to Comparator Prior Art Antibodies Various aspects of T cell co-stimulation were compared between a low affinity human anti-TNFR2 antibody (UC2.3), UC2.3.8, and comparator prior art anti-TNFR2 antibodies A-C.

Human naïve CD4 T cells from 3 healthy donors were enriched via negative selection using the human Naïve CD4+ T cell Isolation Kit II (Miltenyi) and then labeled with 5 mM CellTrace Violet. 96 well flat-bottom plates (Costar) were coated with 5 mg/mL anti-CD3 (clone OKT3, BioLegend) and titrated amounts of anti-TNFR2 antibody at 37° C. for 2 hrs. Plates were then washed with complete RPMI, blocked at room temperature for >10 min at room temperature, and $4\times10^4$ cells were added along with 1 mg/mL soluble anti-CD28 (BioLegend). Cells were stimulated for 4 days and then analyzed by flow cytometry. Live CD4+ T cells were assessed for proliferation, expansion, and upregulation of the acute activation marker PD-1.

To assess NF-kB activity, a human TNFR2 reporter cell line was generated using GloResponse™ NF-kB-RE-luc2p HEK293 cells (Promega) that were stably transfected with either full-length murine TNFR2 gene (Origene) using Lipofectamine 3000 (ThermoFisher) or vector control. Cells were maintained in DMEM/10% FBS containing geneticin (0.2 mg/mL). 96 well black-walled tissue culture plates were coated with titrated concentrations of anti-TNFR2 mAb for 2 hrs at 37° C. and then washed and blocked with complete culture media. $4\times10^4$ TNFR2-expressing or control HEK293 cells were added per well in a volume of 50 mL, cultured at 370 for 5 hrs, and 50 uL ONE-Glo luciferase reagent was then added per well. Luminescence was measure on a SYNERGY H1 plate reader (BioTek).

UC2.3.8 stimulated 62% of CD4+ T cells to divide compared to 15% for UC2.3, 30% for comparator A, 24% for comparator B, 32% for comparator C, and 15% for isotype control at the highest concentration tested (FIG.

Figure 21A:
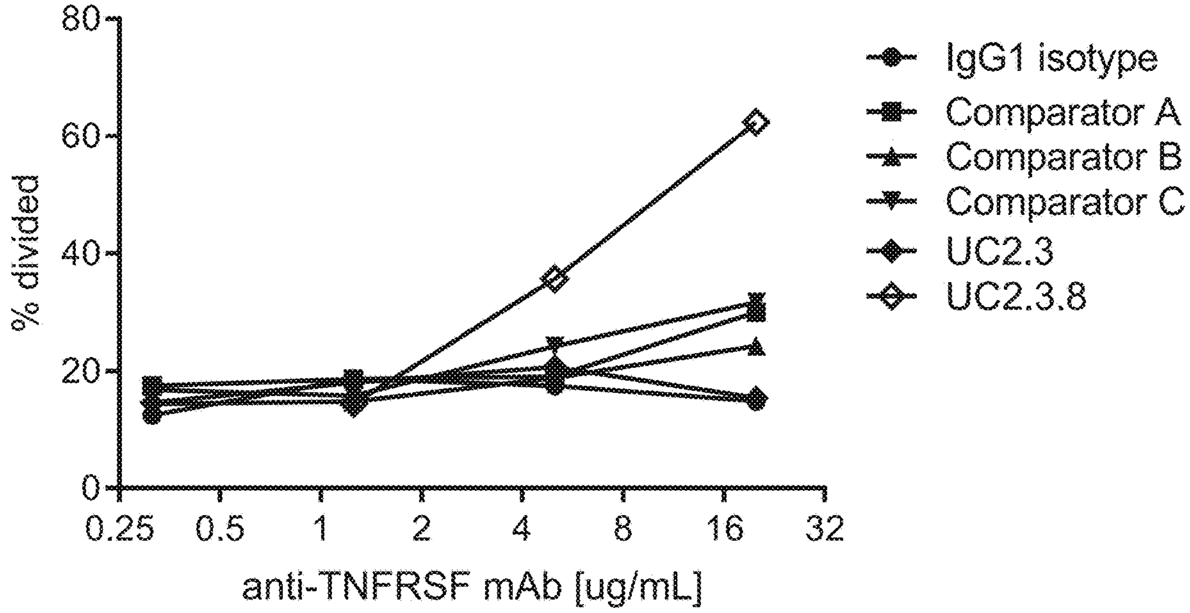
FIGS. 21A-21E are graphs showing the effects of antibodies UC2.3, UC2.3.8, and prior art comparator antibodies A-C on CD4+ T cell proliferation (FIGS. 21A and 21B), CD4+ T cell expansion (FIG. 21C), and percent PD-1-positive CD4+ T cells (FIG. 21D), as assessed by flow cytometry, and NF-kB activity (FIG. 21E), as assessed by reporter assay. IgG1 was used as a negative control.
Figure 21B:
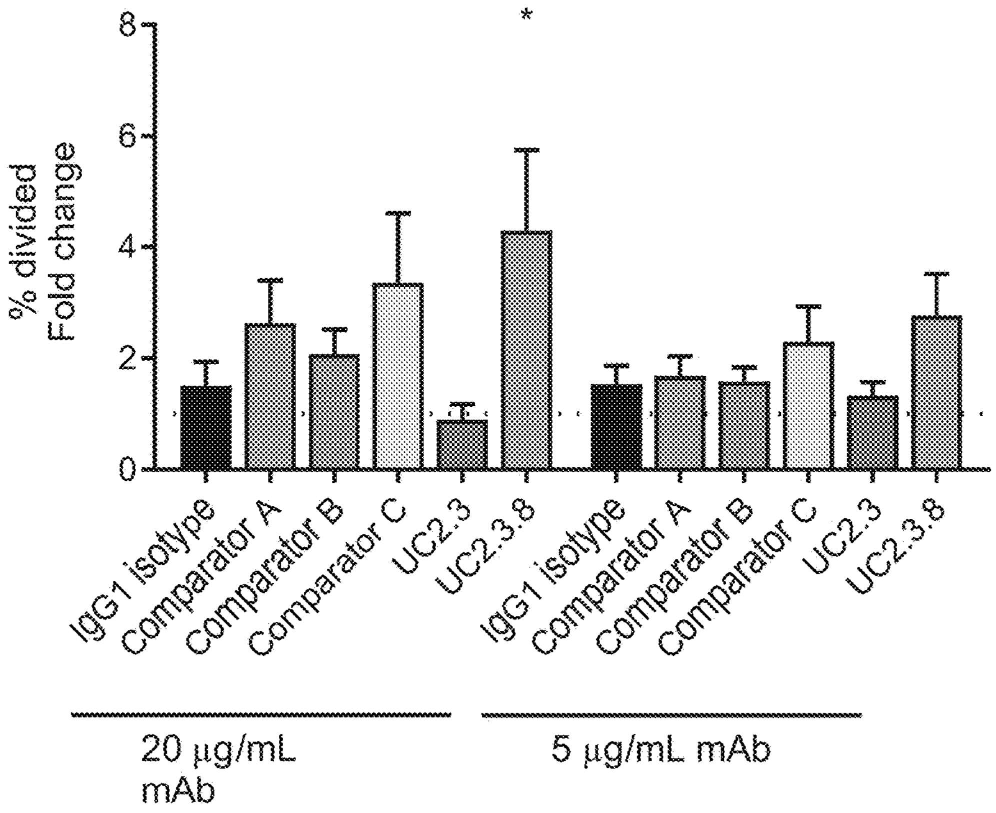

21A). The mean fold-change in cell proliferation induced by 20 μg/ml of UC2.3.8 (4.3-fold) compared to isotype control (1.5-fold) was determined to be significant ($p<0.05$) by two-way ANOVA. In contrast, the mean-fold change for UC2.3 (0.9-fold), comparator A (2.6-fold), comparator B (2.0-fold), and comparator C (3.3-fold) were not significant compared to isotype control (FIG. 21B).

Figure 21C:
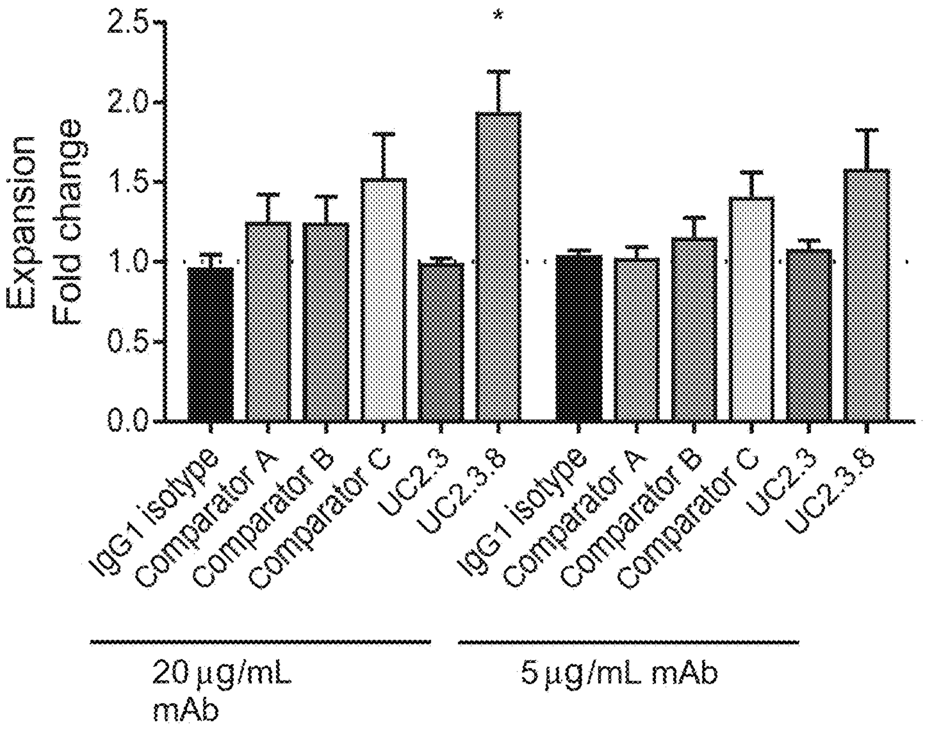

The mean fold-change in CD4+ T cell expansion induced by 20 μg/ml of UC2.3.8 (1.9-fold) compared to isotype control (0.96-fold) was determined to be significant ($p<0.05$) by two-way ANOVA. In contrast, the mean-fold change for UC2.3 (0.9-fold), comparator A (1.2-fold), comparator B (1.2-fold), and comparator C (1.5-fold) were not significant compared to isotype control (FIG. 21C).

Figure 21D:
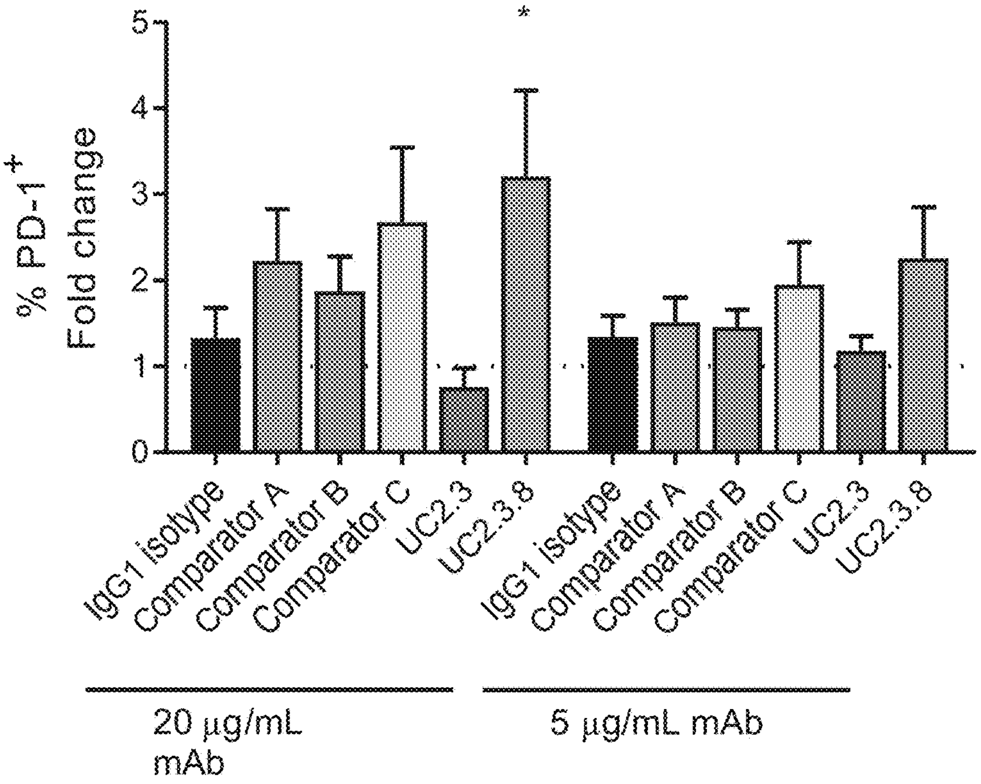

The mean fold-change in PD-1 upregulation on CD4+ T cells induced by 20 μg/ml of UC2.3.8 (3.2-fold) compared to isotype control (1.3-fold) was determined to be significant ($p<0.01$) by two-way ANOVA. In contrast, the mean-fold change for UC2.3 (0.7-fold), comparator A (2.2-fold), comparator B (1.8-fold), and comparator C (2.6-fold) were not significant compared to isotype control (FIG. 21D).

Figure 21E:
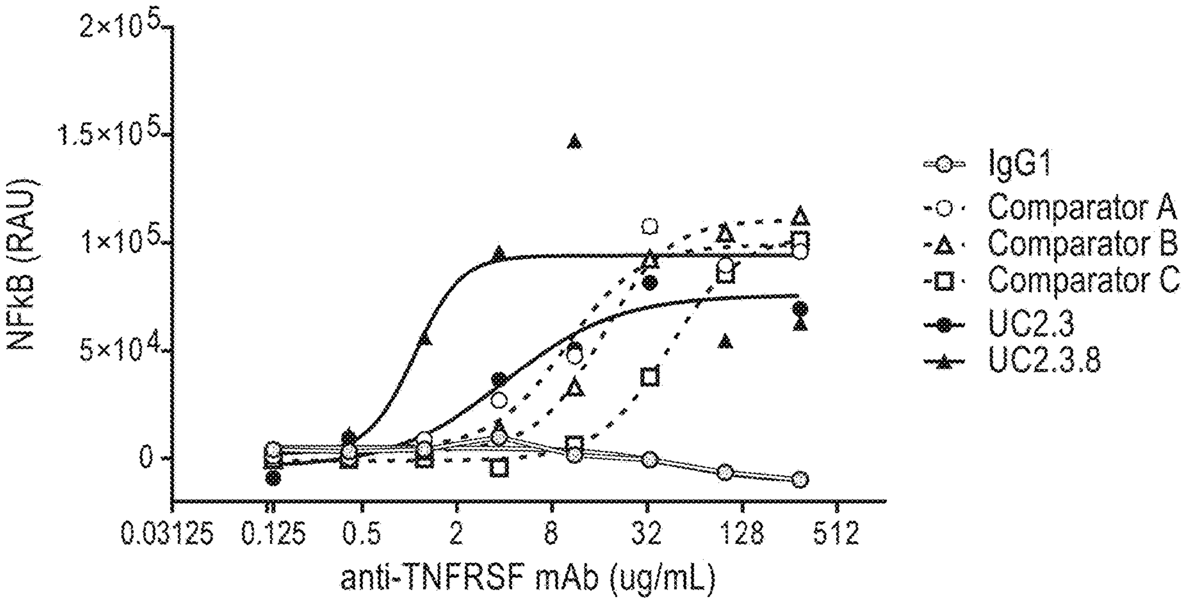
Figure 22A:
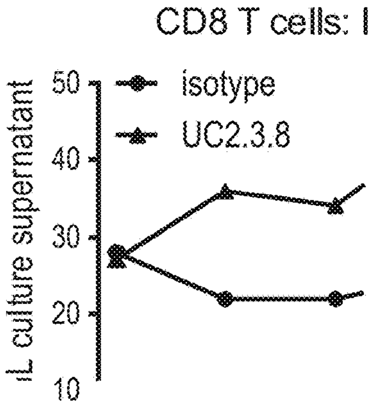
FIGS. 22A-22F are graphs showing the effects of antibody UC2.3.8 on cytokine production by CD8+ T cells, as assessed by the Luminex platform
Figure 22B:
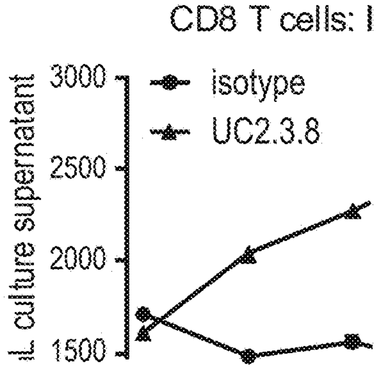
Figure 22C:
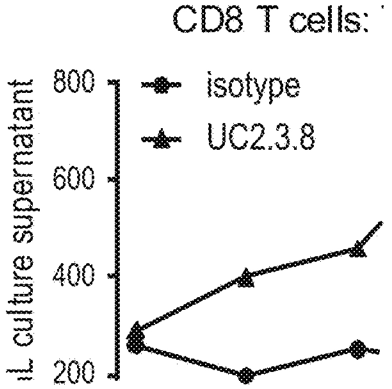
Figure 22D:
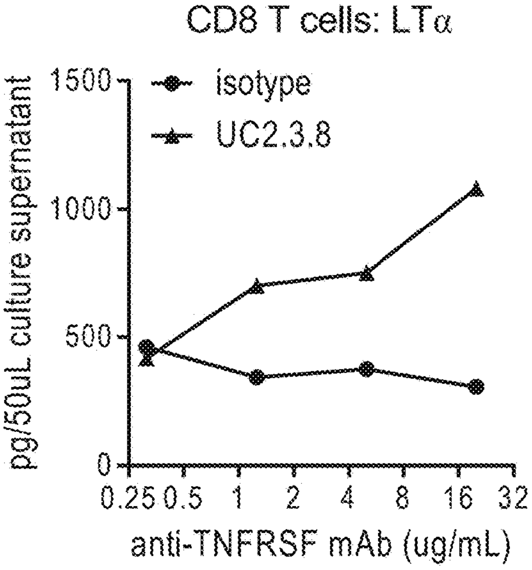
Figure 22E:
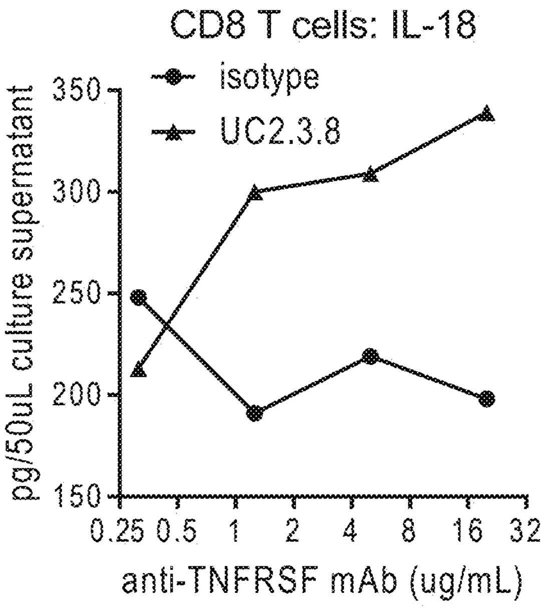
Figure 22F:
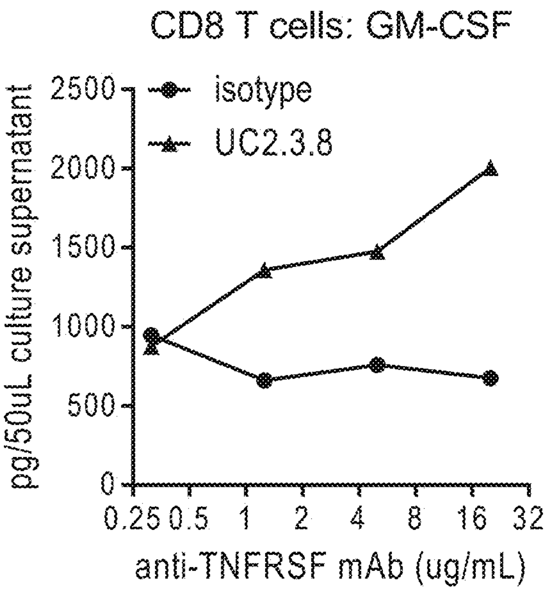
Figure 23A:
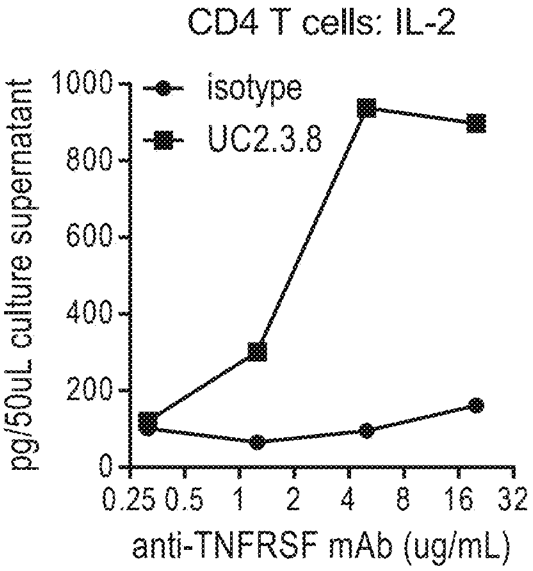
FIGS. 23A-23F are graphs showing the effects of antibody UC2.3.8 on cytokine production by CD4+ T cells, as assessed by the Luminex platform
Figure 23B:
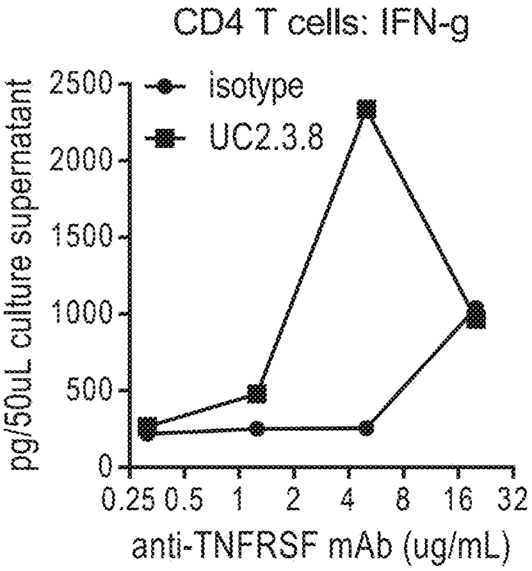
Figure 23C:
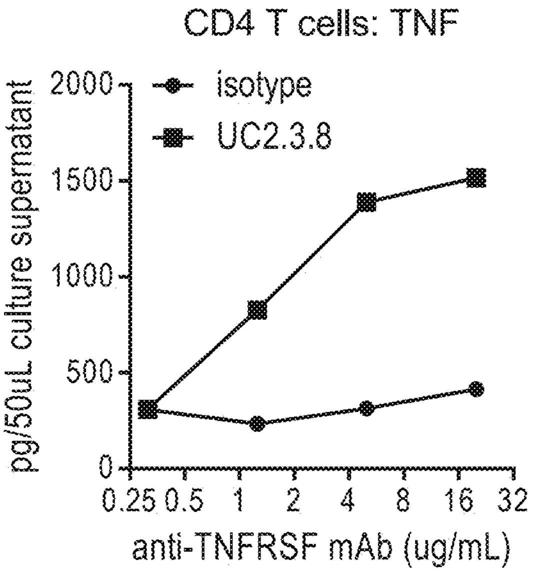
Figure 23D:
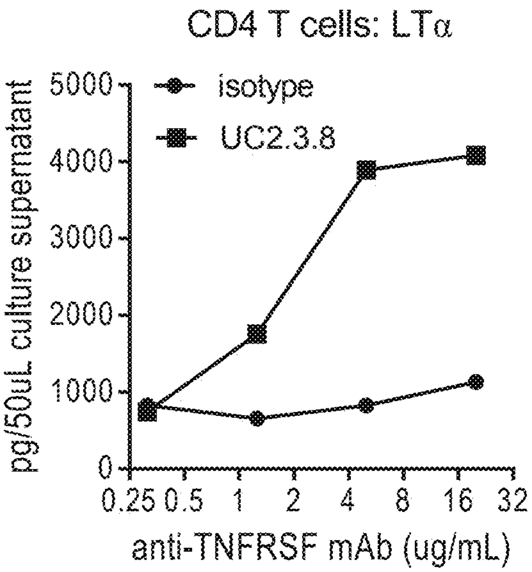
Figure 23E:
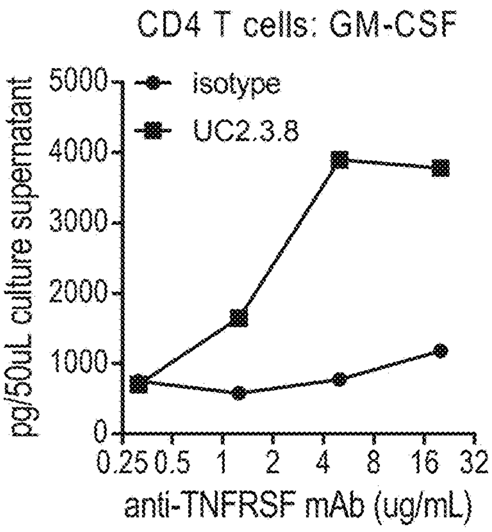
Figure 23F:
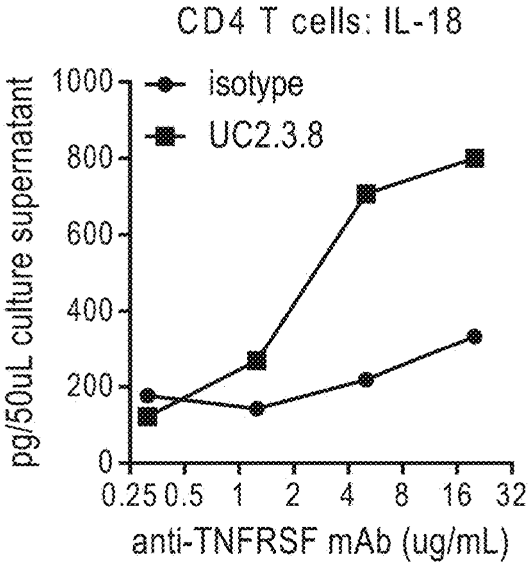

UC2.3.8 induced of NF-kB activity with an EC50 of 1.0 μg/ml and was found to be more active than UC2.3 (EC50=4 μg/ml), comparator A (EC50=9.7 μg/ml), comparator B (EC50=16.6 g/ml) and comparator C (EC50=44 μg/ml) (FIG. 21E).

Overall, UC2.3.8 was superior to the lower affinity version UC2.3 and comparator prior art antibodies A, B, and C.

Example 11. Cytokine Production by Human Anti-TNFR2 Antibody

Following in vitro stimulation of isolated human naïve CD8 T cells and CD4 T cells using the same conditions described in Example 10, supernatants were collected and assayed for cytokines using the Luminex platform (ThermoFisher Invitrogen: Thl/Th2 Cytokine 18-Plex Human ProcartaPlex Panel 1C, 18 analytes). Data are from a single donor and are representative of 4 individual donors for FIGS. 22A-22F) and 2 individual donors for FIGS. 23A-23F).

As shown in FIGS. 22A-22F and FIGS. 23A-23F, UC2.3.8 induced the production of IL-2, IFN-γ, TNF, LTα, IL-18, and GM-CSF in both CD4 T cells and CD8 T cells.

Example 12. Anti-Tumor Activity of Anti-Human TNFR2 Antibody in Patient-Derived Xenograft Model in Humanized Mice To test the activity of anti-human TNFR2 antibody in a tumor model, 3-week-old NSG-SGM3 female mice (Jackson Laboratories) were irradiated with 140 cGy and then injected i.v. with $2\times10^4$ human cord blood $CD34^+$ stem cells from mixed donors (AllCells) the same day. After resting for 12 weeks to allow hematopoietic stem cell engraftment and reconstitution with a human immune system, peripheral blood was screened for human immune cell engraftment by staining with flow antibodies for anti-human CD45 and anti-mouse CD45. Mice were considered humanized when ≥25% of total $CD45^+$ cells were of human origin. Humanized mice were injected s.c. with $5\times10^6$ cells of the patient-derived xenograft cell line LG1306 (Jackson Laboratories). When the average tumor size was ~75 $mm^3$, mice were equally distributed into 3 treatment groups and injected with 0.3 mg i.p. of human isotype IgG1 (BioXCell), nivolumab (anti-PD-1, IgG1) alone, or nivolumab plus UC2.3.8 (IgG1) in combination for a total of 5 injections every 7 days. Tumor volumes were measured every 2-3 days.

Figure 24:
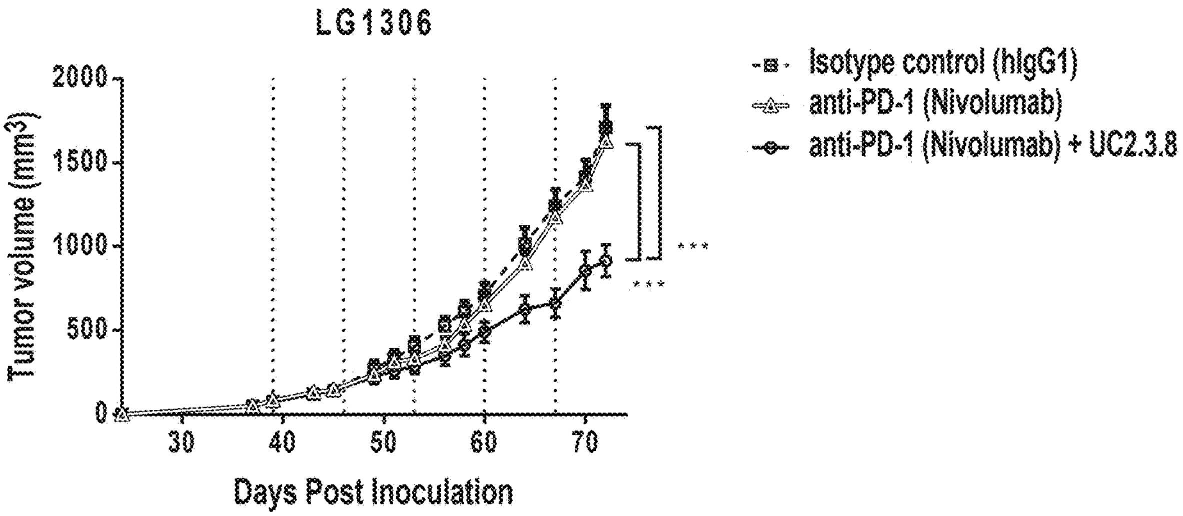
FIG. 24 is a graph showing anti-tumor activity of anti-human TNFR2 antibody UC2.3.8 in a patient-derived xenograph model in humanized mice. Shown are tumor growth kinetics with mean and standard error of mean (N=9 animals per arm). Statistical significance was assessed at the end of study at day 72 using ANOVA and Tukey's honestly significant difference procedure for multiple comparison correction.
Figure 25A:
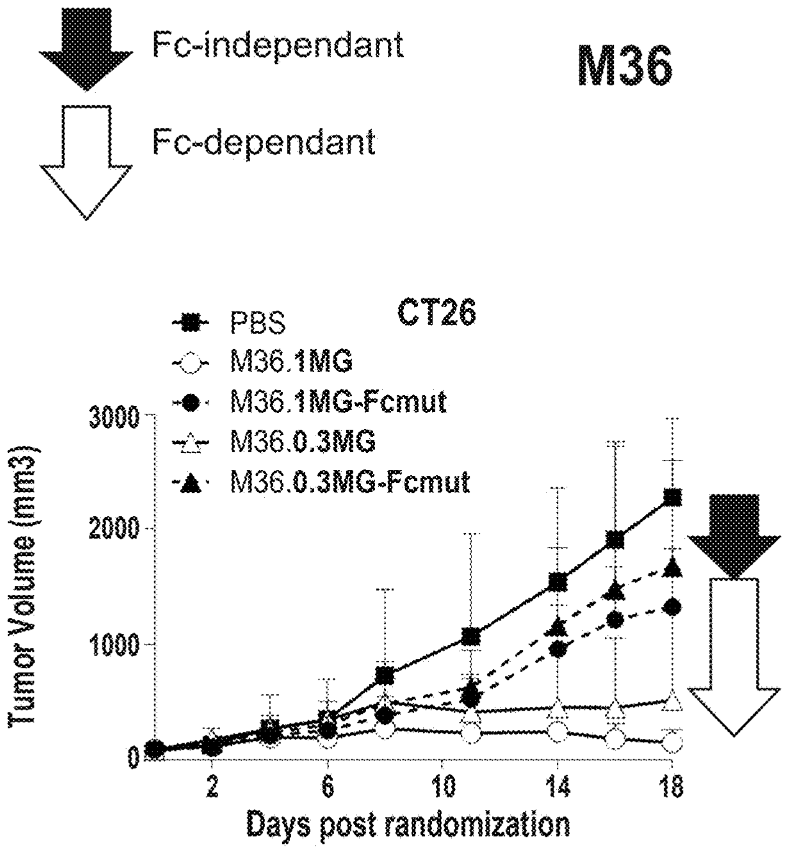
FIG. 25A is a graph showing the effects of 1 mg or 0.3 mg M36, with or without mutations that affect effector function, on tumor growth in the CT26 mouse model.
Figure 25B:
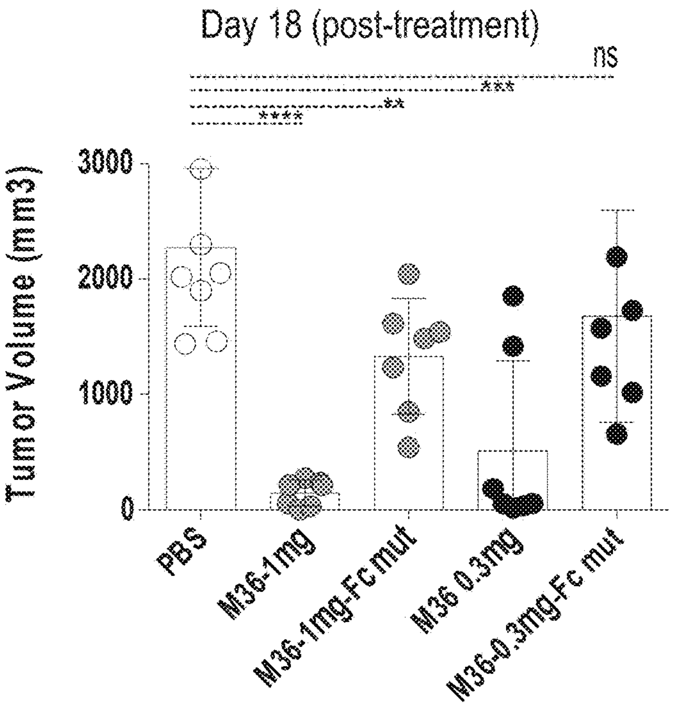
FIG. 25B shows a histogram representation of tumor size at day 18 post-randomization.
Figure 25C:
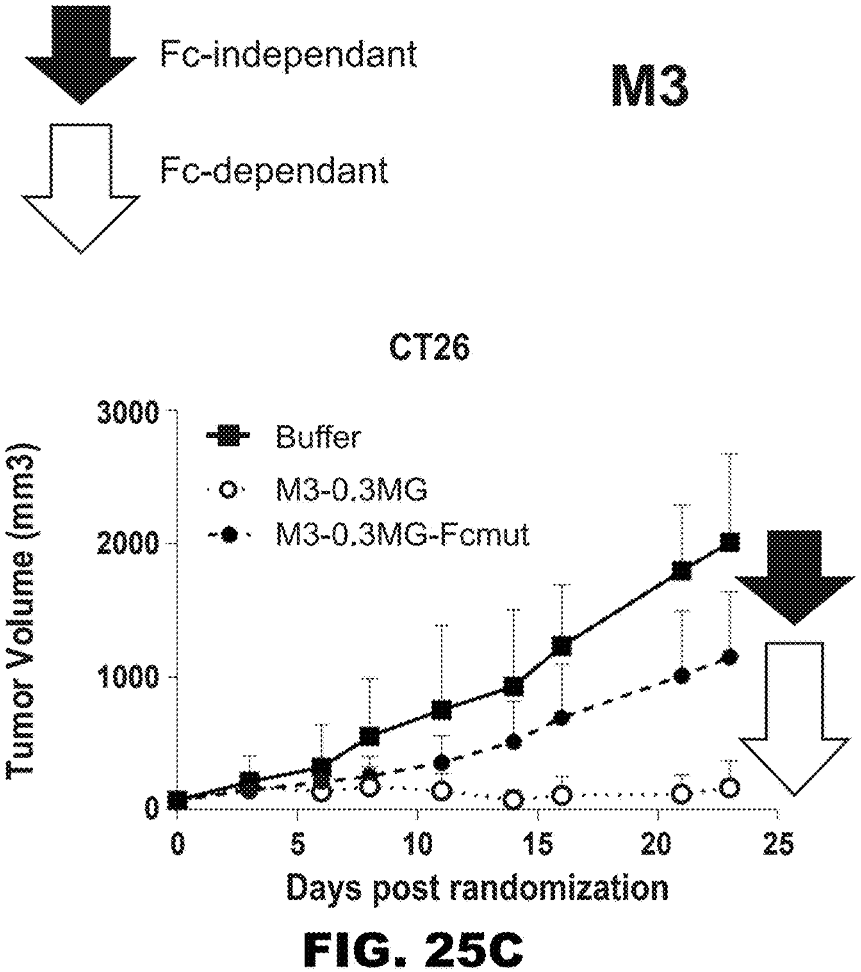
FIG. 25C is a graph showing the effects of 0.3 mg M3, with or without mutations that affect effector function, on tumor growth in the CT26 mouse model.
Figure 25D:
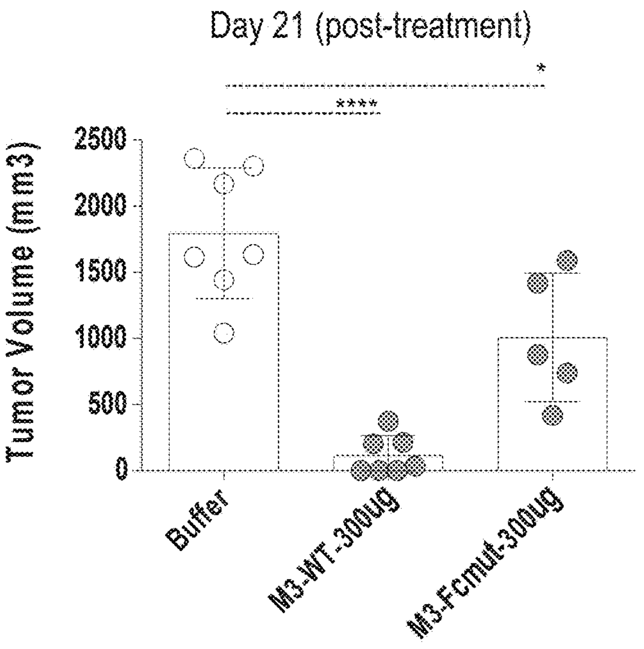
FIG. 25D shows a histogram representation of tumor size at day 18 post-randomization. CT26 cells (5×10E5) were inoculated subcutaneously in 6-week-old female Balb/c mice (7 mice/group).
Figure 25E:
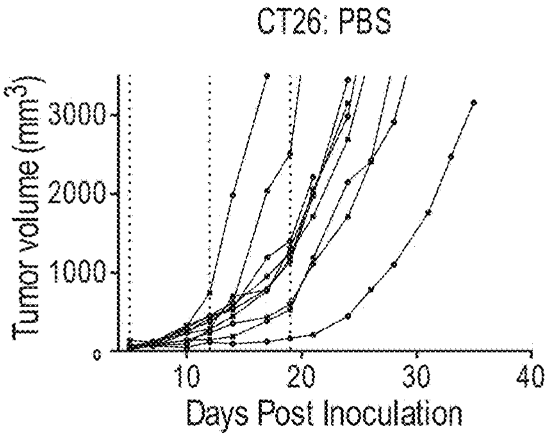
FIGS. 25E-25J are graphs showing the effects of 3×0.3 mg Y9, with or without mutations that affect effector function, on tumor growth in a CT26 (FIGS. 25E-25G) or Wehi164 (FIGS. 25H-25J) mouse model).
Figure 25F:
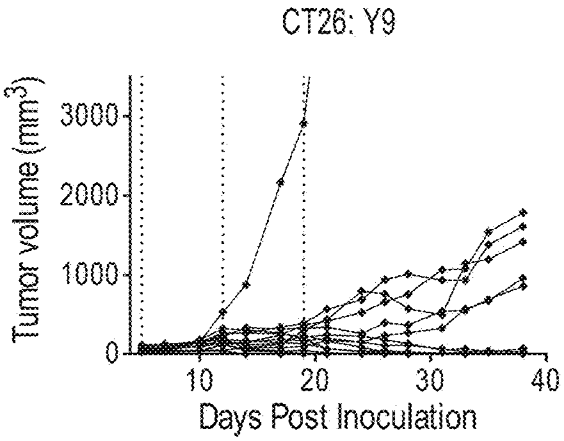
Figure 25G:
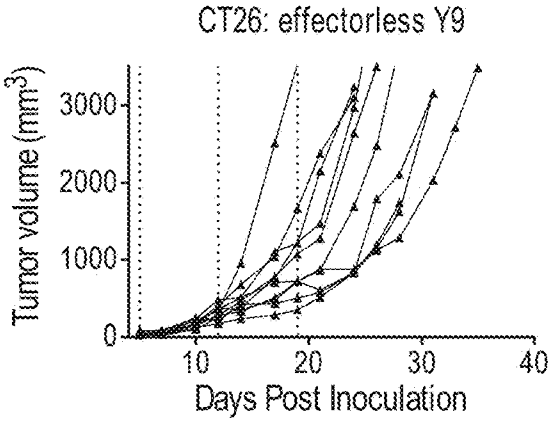
Figure 25H:
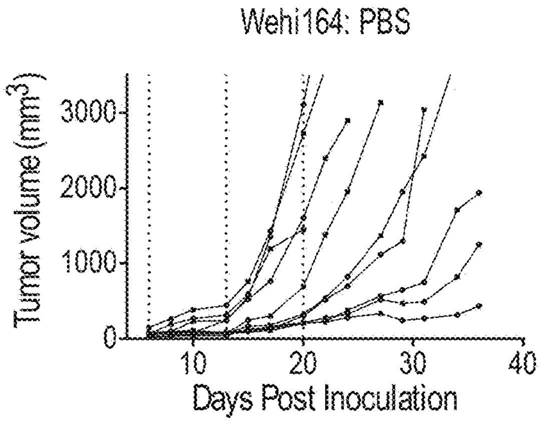
Figure 25I:
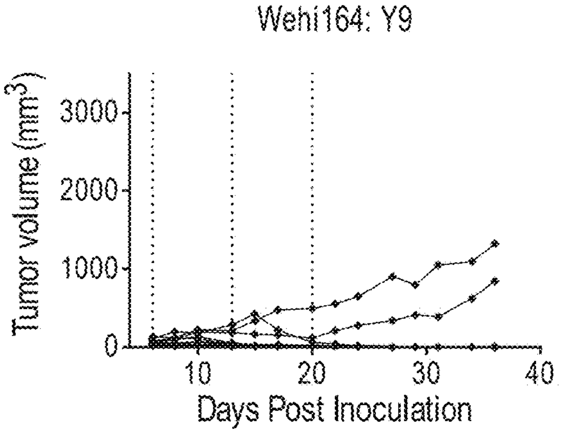
Figure 25J:
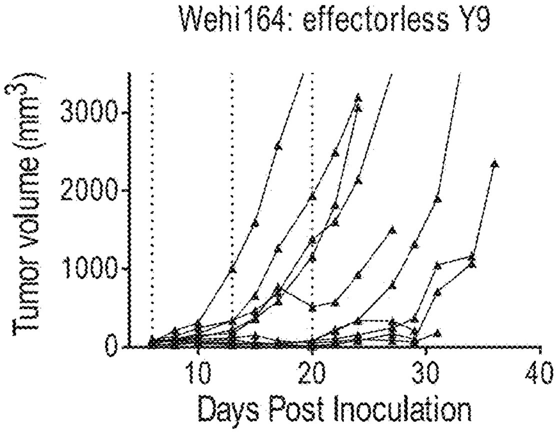

As shown in FIG. 24, statistically significant differences (ANOVA, Tukey's honestly significant difference procedure) in tumor volume were observed between isotype control and nivolumab plus UC2.3.8 arms, as well as between nivolumab and nivolumab plus UC2.3.8 arms.

Example 13. Therapeutic Efficacy of Anti-Mouse TNFR2 Antibodies in a Syngeneic Tumor Model This Example shows the effects of anti-tumor effects of anti-mouse TNFR2 antibodies in a syngeneic tumor model, as well as the impact of Fc effector function on the anti-tumor effects.

Antibody Y9 is an anti-mouse TNFR2 antibody which completely blocks binding of mouse TNFα to mouse TNFR2 and binds within the A1 module of CRD1 region of mouse TNFR2. Antibody M3 is a non-ligand competitor and binds an epitope within the B2 module of CRD1 and A1 module of CRD2 in mouse TNFR2. M36 is a partial ligand-competitor.

CT26 tumors were established in mice and antibodies M3 and M36 (wild type or Fc-mutated) were administered to the mice. The Fc mutants harbor two single amino acid substitutions D265A and N297G, which abrogate Fc-mediated effector functions. CT26 cells (5×10E5) were inoculated subcutaneously in 6-week-old female Balb/c mice (7 mice/group). The indicated antibodies were injected i.p. in mice harboring tumors with an average size of 80-90 $mm^3$. Antibody M36 (wild type or Fc-mutated) was tested at two different dose-regimen (i) 1000 μg on days 0, 2, 4, 6, and 8 or (ii) 300 μg on days 0, 2, 4, 6, and 8. Antibody M3 was administered at 300 μg on days 0, 2, 4, 6, and 8. As shown in FIGS. 25A-25D, Fc-mediated effector function was required to reach maximum anti-cancer therapeutic efficacy of the anti-mouse TNFR2 antibodies in the CT26 mouse model.

Additionally, similar results were observed with Y9. CT26 and Wehi164 tumors were established in mice, and Y9 or Fc-mutated (D265A and N297A) Y9 were injected i.p. in mice harboring tumors with an average size of 60-90 $mm^3$ in three doses of 0.3 mg once per week (n=15 per group). As shown in FIGS. 25E-25J, the antitumor effect of Y9 was severely abrogated by the Fc mutation.

Antibodies Y9, M3 and M36 target distinct epitopes on mouse TNFR2. Additionally, M3 is a non-ligand competitor and M36 is a partial ligand-competitor. Importantly, maximal anti-cancer therapeutic efficacy was achieved independent of the epitope targeted and ligand-competition property.

Example 14. Therapeutic Efficacy of Anti-Mouse TNFR2 Antibodies Targeting Distinct Epitopes in Syngeneic Tumor Models This Example demonstrates the therapeutic efficacy of several candidate anti-mouse TNFR2 antibodies that target distinct epitopes on mouse TNFR2.

Figure 26A:
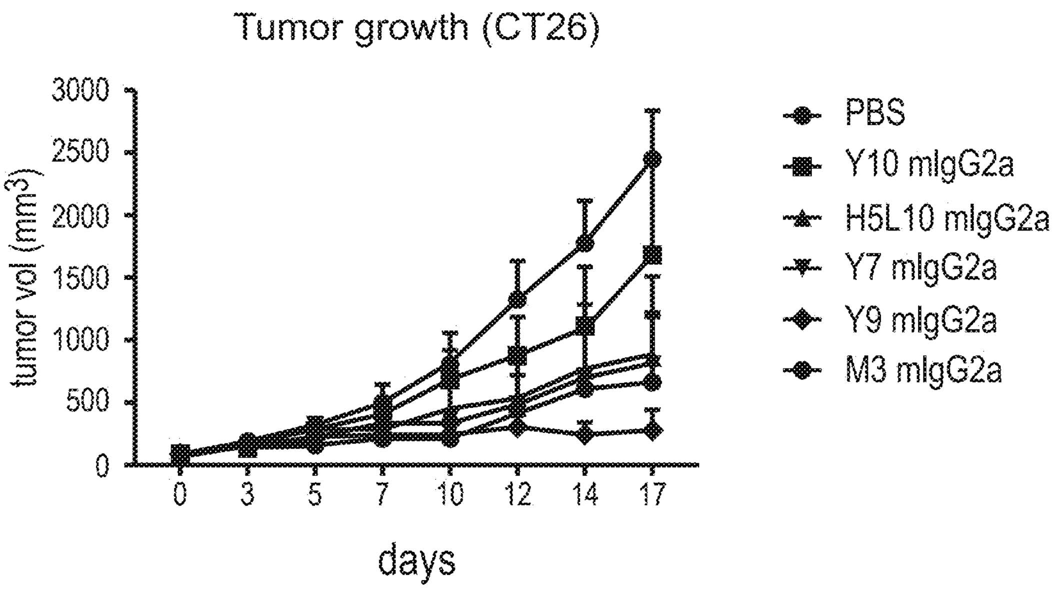
FIG. 26A is a graph showing the effects of the indicated anti-mouse TNFR2 antibodies on tumor growth in the CT26 mouse model.
Figure 26B:
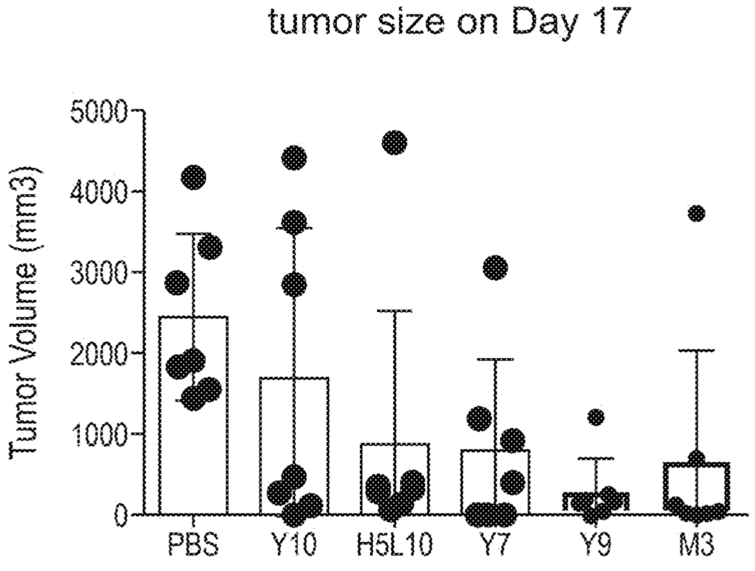
FIG. 26B shows a histogram representation of tumor size at day 18 post-randomization.

CT26 tumors were established in mice as described in Example 7, and the indicated antibodies were administered at 1 mg on day 0. All antibodies tested were equally potent at saturating doses (not shown), but at sub-optimal doses, antibodies Y9 and M3 showed the best anti-tumor effects in vivo (FIGS. 26A and 26B), with Y9 being superior.

In a separate experiment, EMT6 tumors were established in mice as described in Example 7, and the indicated antibodies were administered in a single dose at 1 mg (FIGS.

Figure 27A:
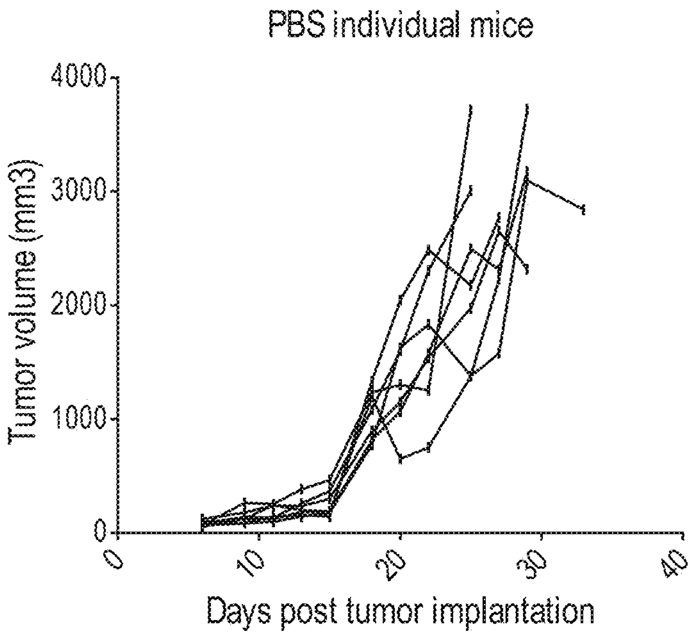
FIGS. 27A-27I are graphs showing the effects of 1 mg (FIGS. 27A-27F) or 0.3 mg (FIGS. 27G-27I) of the indicated antibodies on tumor growth in the EMT6 mouse model.
Figure 27B:
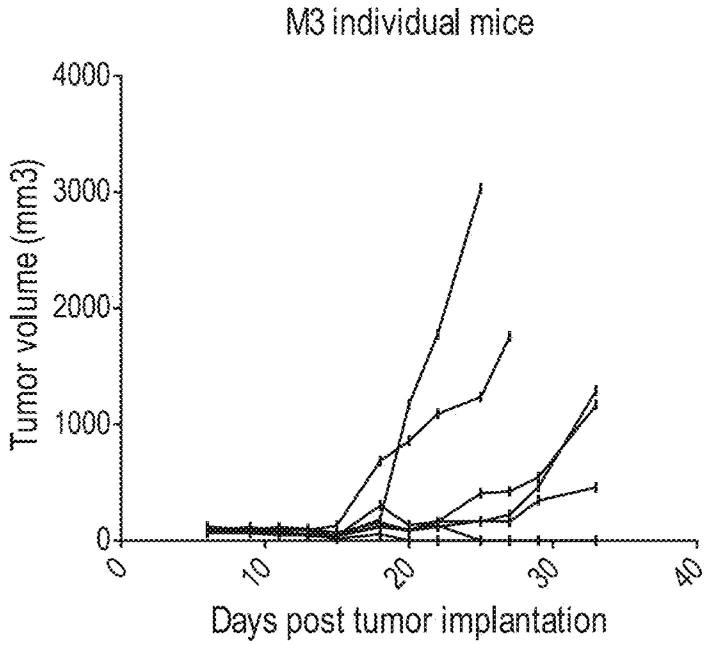
Figure 27C:
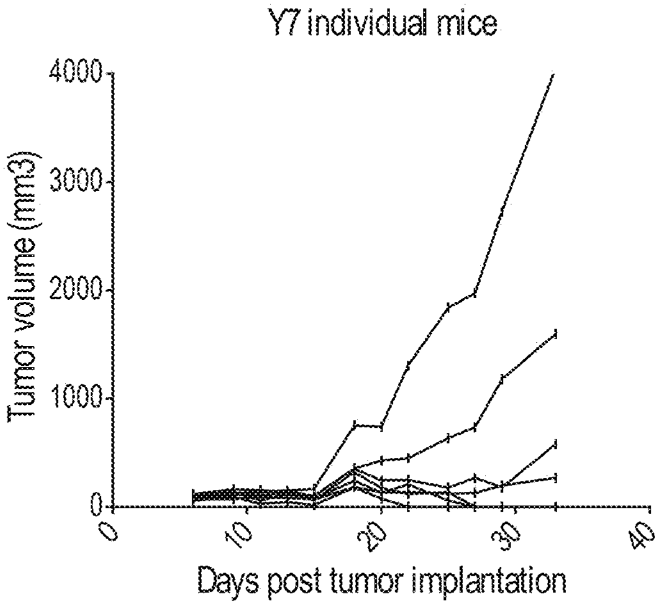
Figure 27D:
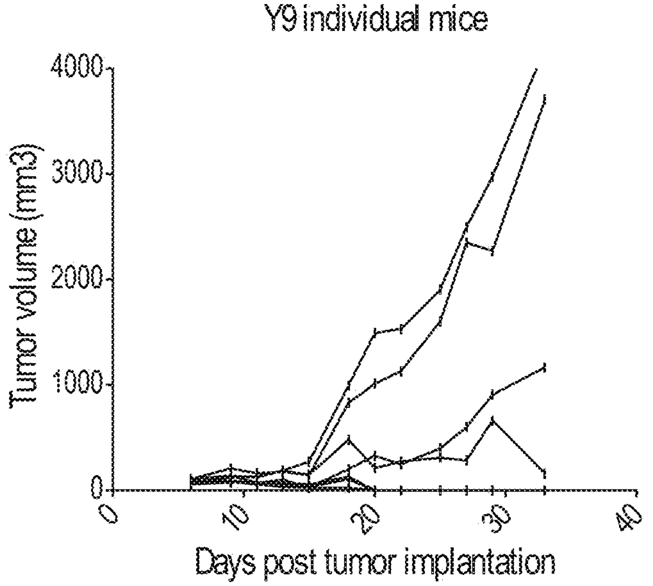
Figure 27E:
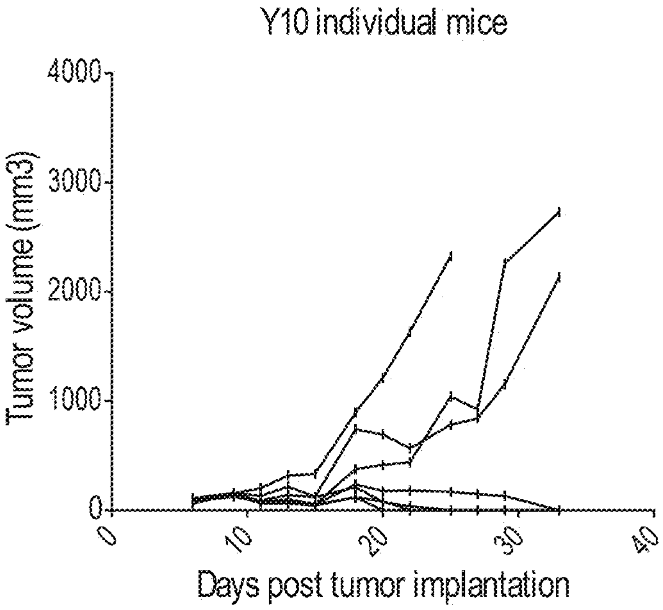
Figure 27F:
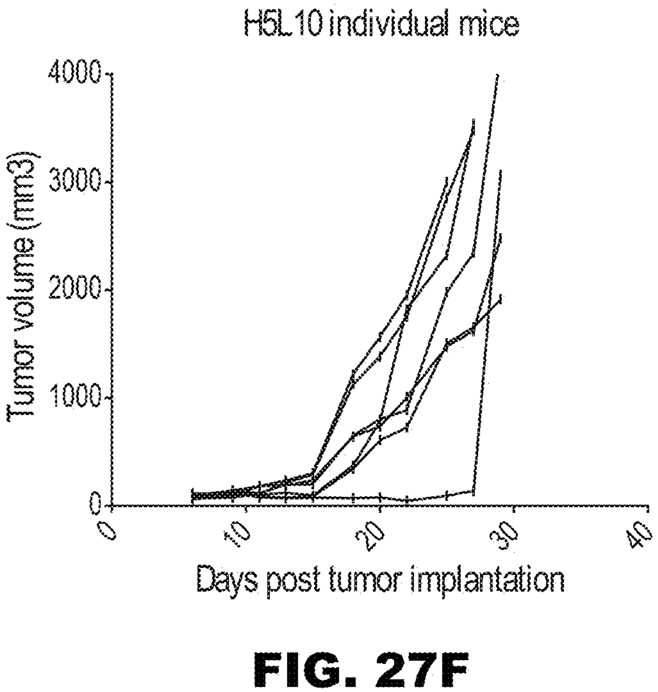
Figure 27G:
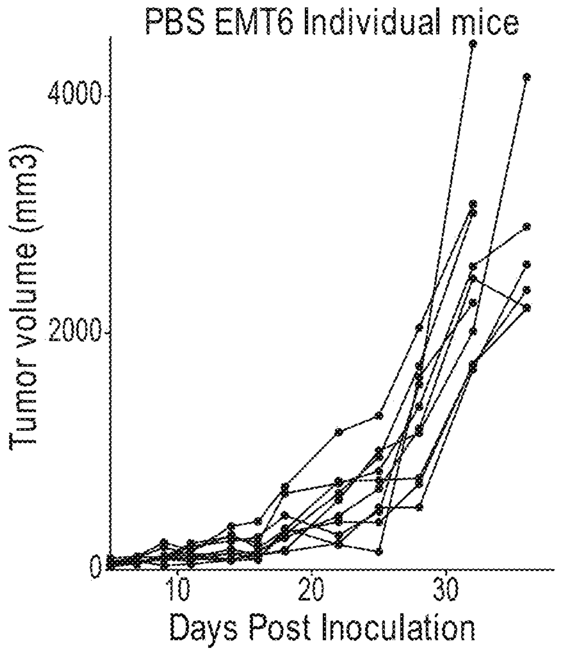
Figure 27H:
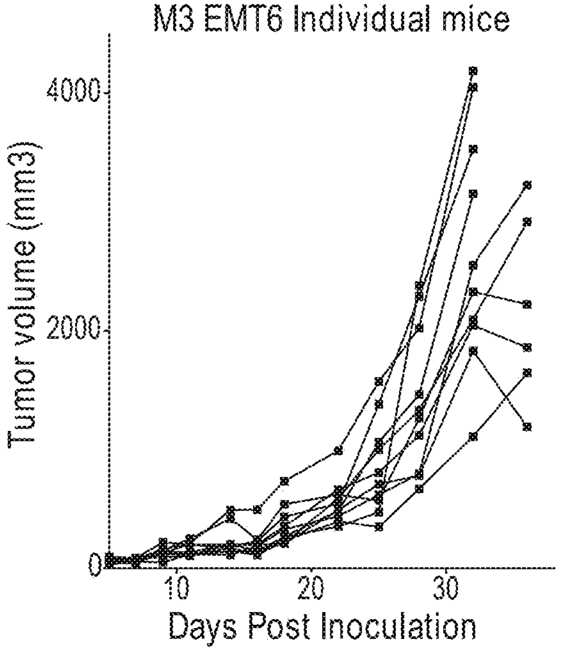
Figure 27I:
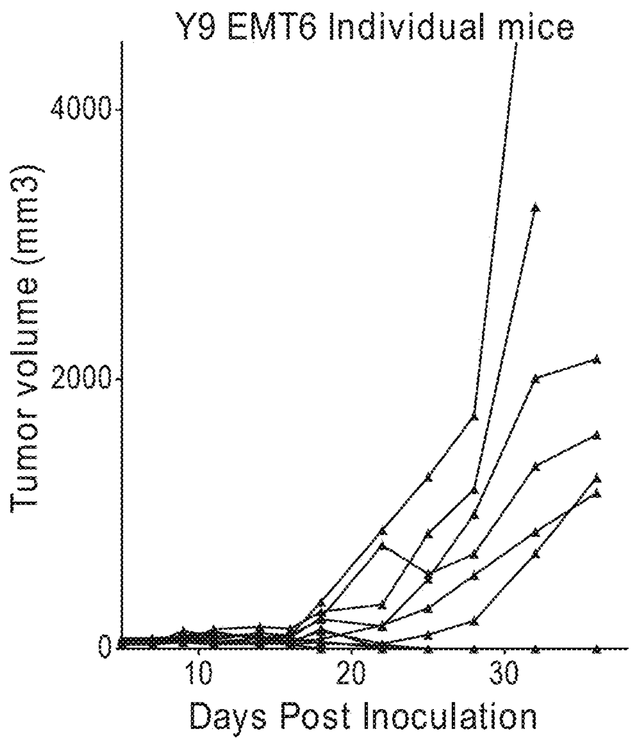

27A-27F) or 0.3 mg (FIGS. 27G-27I). Antibodies Y9 and M3 showed the best anti-tumor effects in vivo, with Y9 again being superior, particularly at the lower dose level.

Example 15. Therapeutic Efficacy of Antibody Y9 in Anti-PD-1 Sensitive and Resistant Syngeneic Mouse Models This example compares the efficacy of antibody Y9 and an anti-PD-1 antibody in syngeneic mouse models that are sensitive or resistant to anti-PD-1 therapy.

Figure 28A:
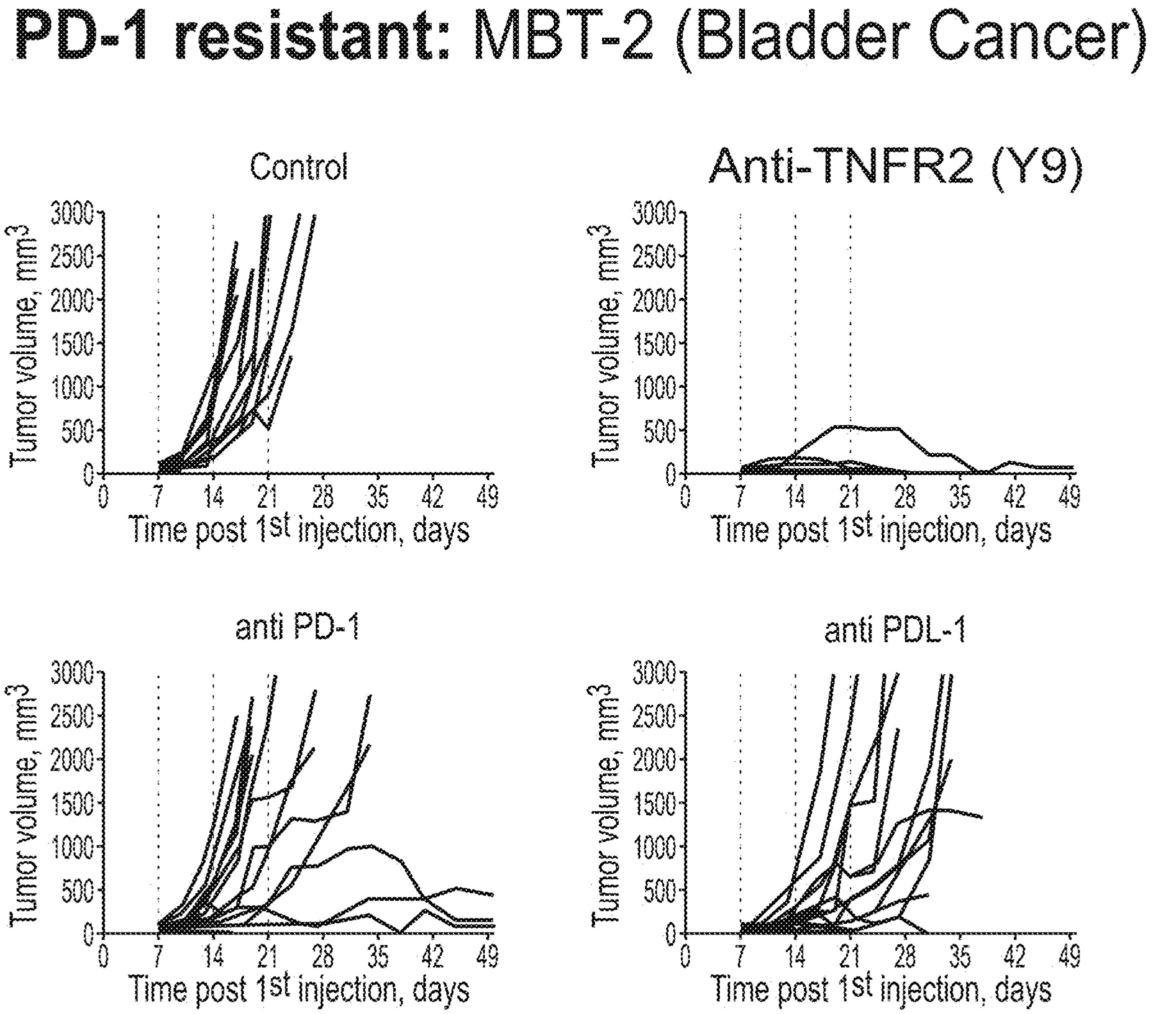
FIGS. 28A and 28B are graphs showing the anti-tumor response of antibody Y9 and an anti-PD-1 antibody on anti-PD-1 resistant (MBT-2) and anti-PD-1 sensitive (Sa1/N) tumor models.
Figure 28B:
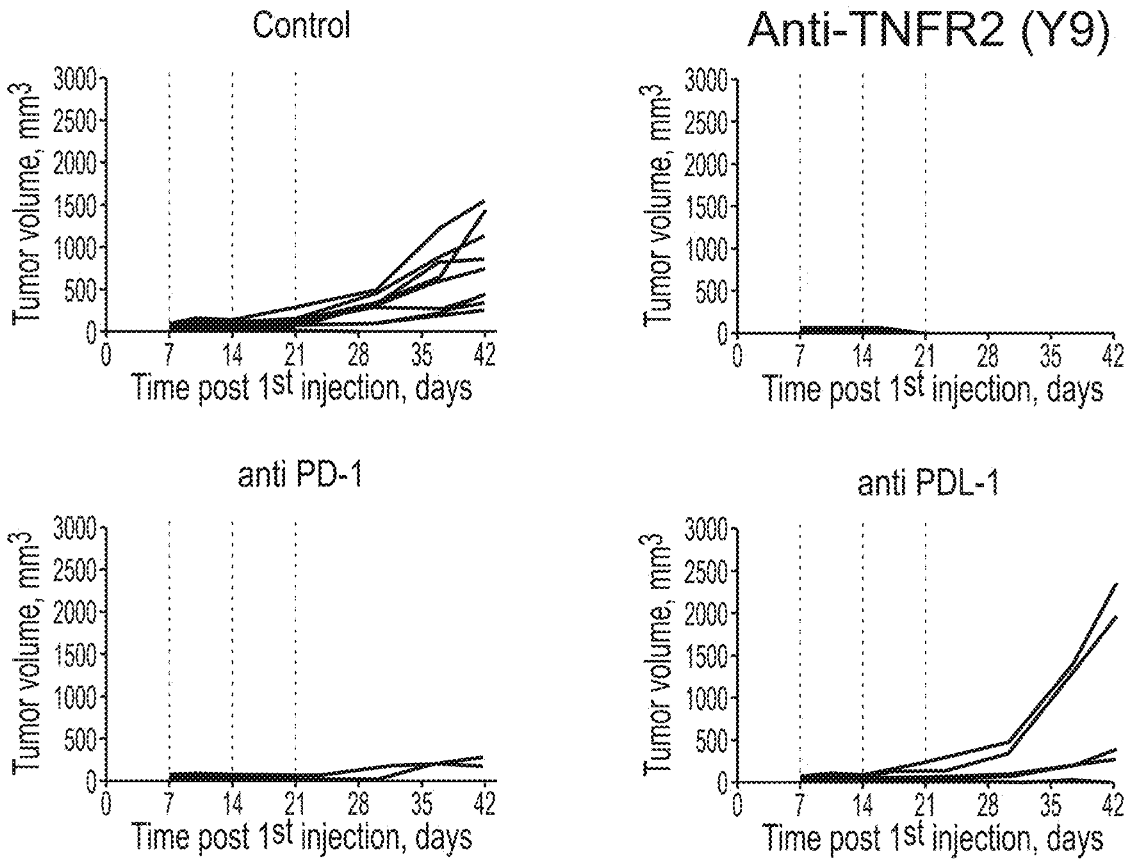

To evaluate the activity of antibody Y9 relative to an anti-PD-1 antibody, a murine version of the hamster anti-mouse PD-1 antibody (J43 clone; Agata et al. Int Immunol. 1996; 8:765-72) was generated by replacing the hamster Fc with a murine IgG2a Fc having D265A and N297A substitutions. Both antibodies were tested in anti-PD-1 sensitive (SaI/N) and resistant (MBT-2) syngeneic mouse models. 6- to 8-week-old female mice were housed in a pathogen-free environment under controlled conditions. Tumors were established by subcutaneous injection of $1\times10^6$ MBT-2 (C3H bladder) or $5\times10^6$ SaI/N (NCI 1/JCR fibrosarcoma) cells in 200 μL PBS into the right flank (10-15 mice/group). Tumor growth was monitored using calipers, and volumes were calculated according to the formula: π/6×(length×width×width). When tumors reached an average size of 50-100 $mm^3$, 300 μg of antibody was injected i.p. as indicated once weekly for three weeks in a total volume of 200 μL. In both Sa1/N (anti-PD-1 sensitive) and MBT-2 (anti-PD-1 resistant) models, anti-TNFR2 (Y9) treatment alone led to complete tumor regression in all treated animals. However, treatment of the MBT-2 bladder model with the anti-PD-1 mAb resulted in only limited activity (FIG. 28).

Example 16. Therapeutic Efficacy of Combination Therapy with Antibody Y9 and an Anti-PD-1 or Anti-PD-L1 Antibody in Syngeneic Mouse Models This example describes combination therapy with antibody Y9 and an anti-PD-1 or anti-PD-L1 antibody in various syngeneic mouse models.

Figure 29:
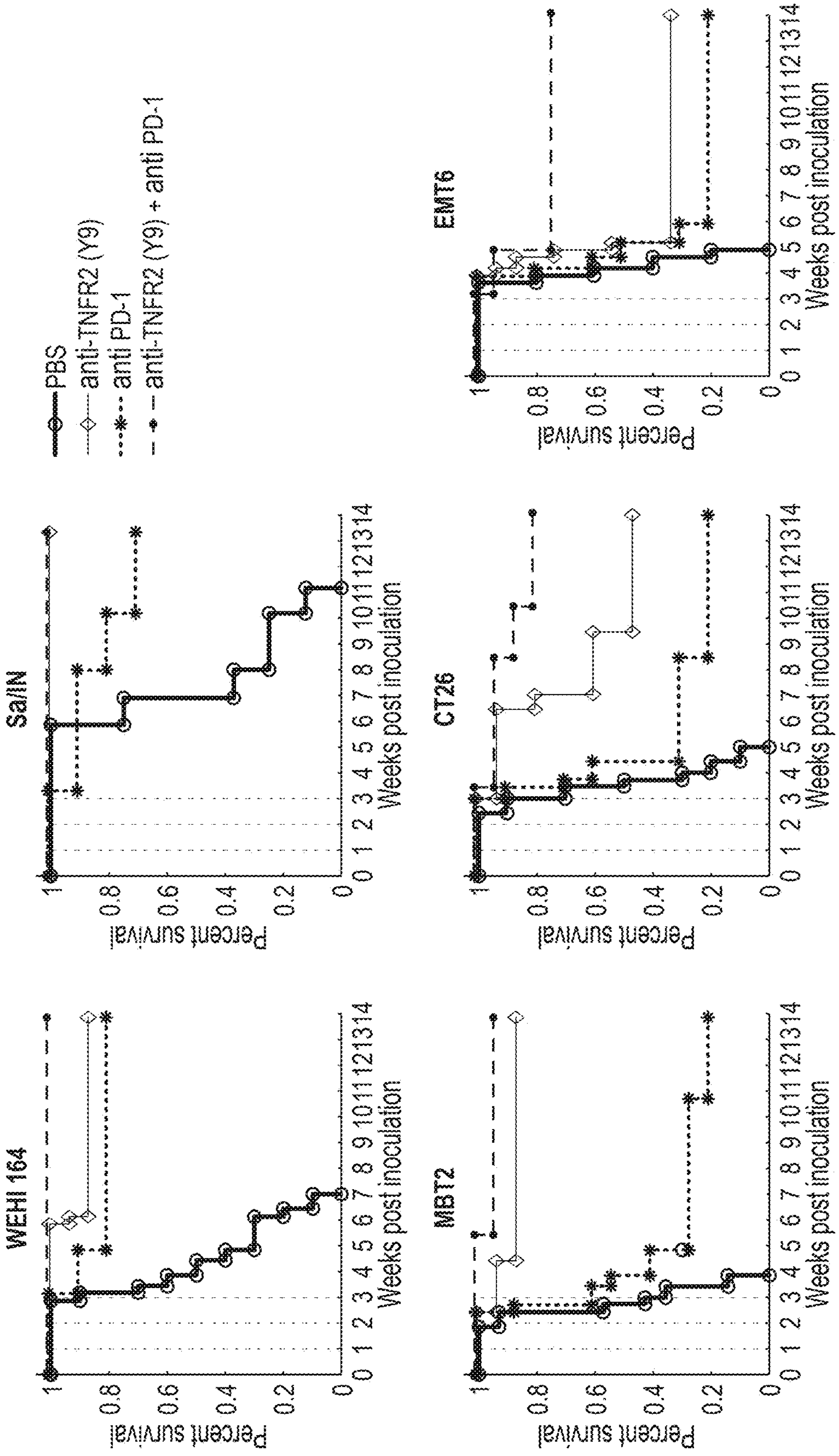
FIG. 29 shows a series of graphs on the anti-tumor activity of antibody Y9 alone, anti-PD-1 antibody alone, and the combination of Y9 and the anti-PD-1 antibody in various syngeneic models (WEHI164, Sa1/N, MBT2, CT26, and EMT6).

To evaluate whether treatment with murine surrogate anti-TNFR2 antibody (Y9) would synergize with anti-PD-1 or anti-PD-L1 antibody treatment, a murine version of J43 was generated as described in Example 12. A murine version of the PD-L1 antibody, MPDL3280a (Powles et al., Nature 2014; 515:558-62), was also generated by replacing the human Fc with a murine IgG2a Fc with D265A and N297A substitutions. The antibody combinations were tested for activity in syngeneic mouse models. 6- to 8-week-old female mice were housed in a pathogen-free environment under controlled conditions. Tumors were established by subcutaneous injection of $3\times10^5$ CT26 (Balb/C colon), EMT6 (Balb/C breast), or Wehi164 (Balb/C fibrosarcoma) cells, $1\times10^6$ MBT-2 (C3H bladder) cells, or $5\times10^6$ SaI/N (NCI 1/JCR fibrosarcoma) cells in 200 μL PBS into the right flank (7-15 mice/group). Tumor growth was monitored using calipers, and volumes were calculated according to the formula: π/6×(length×width×width). When tumors reached an average size of 50-100 $mm^3$, 300 μg of antibody was injected i.p. as indicated once weekly for three weeks in a total volume of 200 μL. In WEHI164, SaI/N, and MBT2 models, long-term survival was driven by anti-TNFR2 (Y9) treatment alone, whereas in the CT26 and EMT6 models, the combination of anti-TNFR2 (Y9) and anti-PD-1 treatment showed the greatest long-term survival (FIG. 29). Similar results were obtained for anti-PD-L1 treatment, alone and in combination with Y9 (data not shown).

Example 17. Safety Profile of Antibody Y9 in Comparison with that of an Anti-CTLA4 Antibody This Example describes various safety/toxicity parameters of antibody Y9 in comparison with an anti-CTLA4 antibody.

Figure 30:
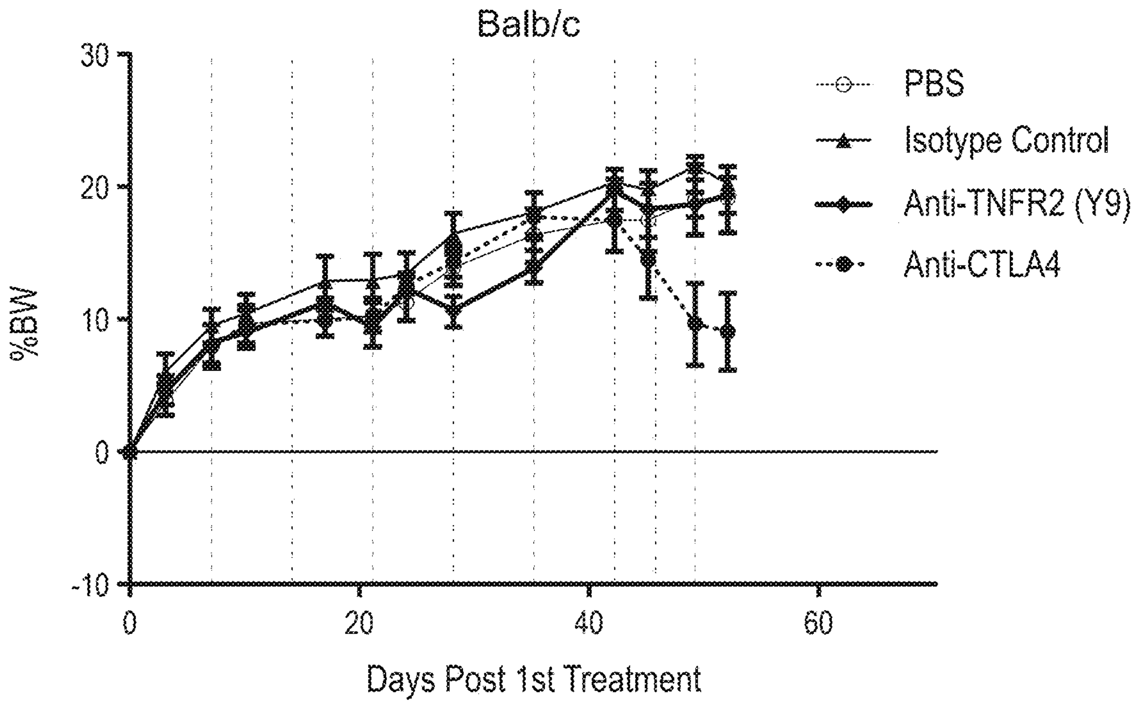
FIG. 30 is a graph showing the effects of antibody Y9 and an anti-CTLA4 antibody on body weight of healthy mice.
Figure 31:
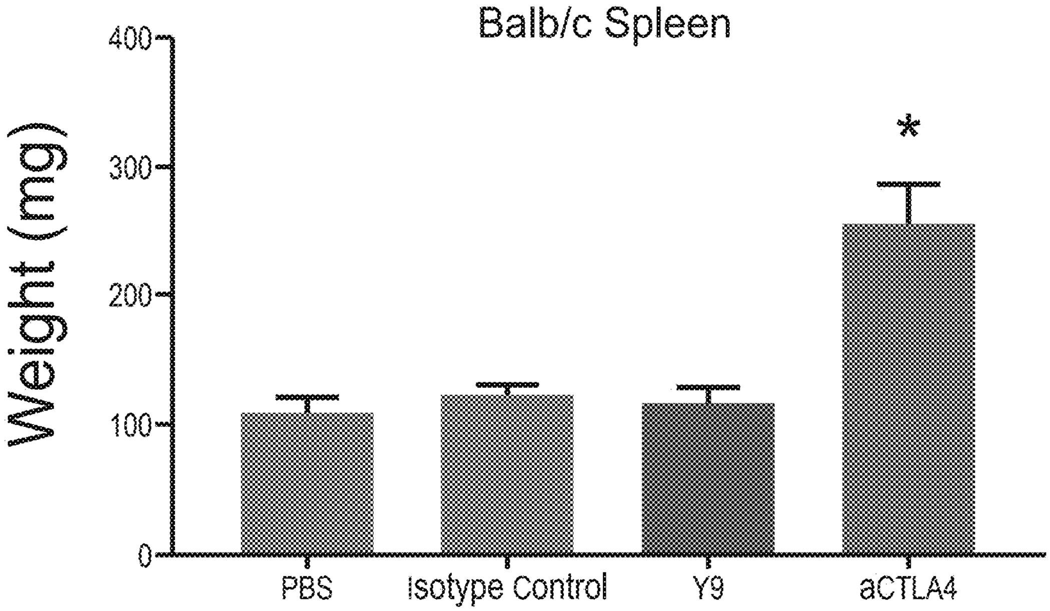
FIG. 31 is a graph showing the effects of antibody Y9 and an anti-CTLA4 antibody on spleen weight of healthy mice.

To compare the toxicity profile of antibody Y9 with an anti-CTLA4 antibody, a recombinant version of the mouse anti-mouse CTLA-4 antibody, 9D9 clone (Quezada et al. 2006), with a mouse IgG2a Fc was generated (same isotype as antibody Y9). A long-term exposure study using the antibodies was performed in twenty 6- to 8-week-old Balb/c female mice. Mice were housed in a pathogen-free environment under controlled conditions. For a total of 8 weeks, mice were injected i.p. with 1 mg of antibody (PBS, mouse IgG2a isotype control, anti-TNFR2 (Y9), or anti-CTLA4, n=5 per group) once per week in a total volume of 200 μl. Mouse weight was measured twice per week, and physical well-being of the mice were tracked throughout the study. Saphenous blood from all groups was collected once per week, following the treatment schedule, and one pre-treatment bleed was performed to serve as a baseline control. All mice were sacrificed 48 hours following the final ($8^{th}$) weekly treatment, whereby spleens were harvested and weighed, and blood was collected via cardiac puncture. As shown in FIG. 30, no difference in weight was detected across groups for the first 6 weeks of treatment, but after the $7^{th}$ dose of antibody, the anti-CTLA4 group lost weight rapidly, while all other groups had no weight change. Splenomegaly was observed in mice treated with anti-CTLA4 antibody, which was reflected in the significant increase of spleen weight in the anti-CTLA4 group, when compared to Y9 or the control groups (FIG. 31).

Figure 32A:
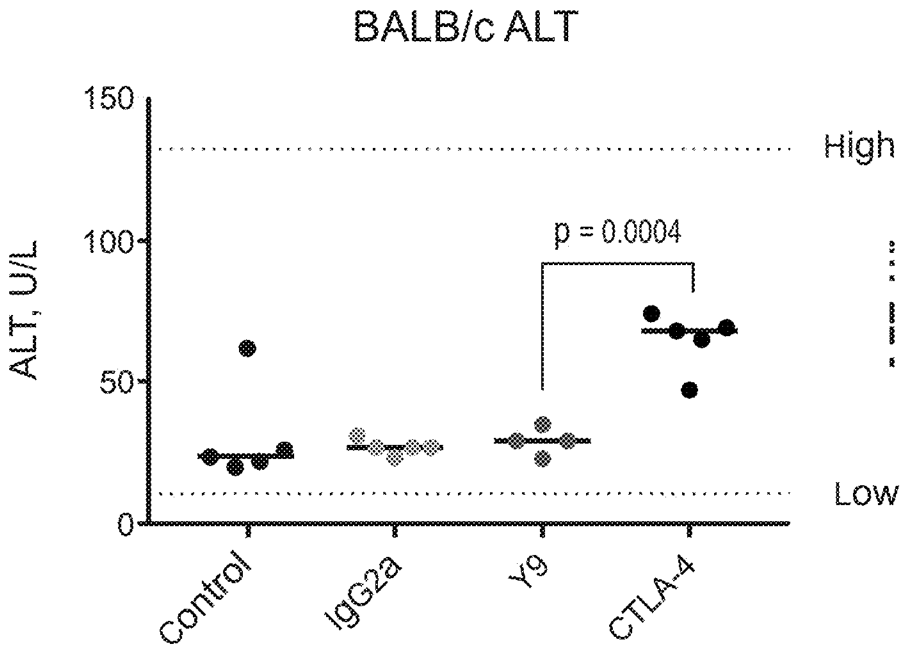
FIGS. 32A and 32B are graphs showing the effects of antibody Y9 and an anti-CTLA4 antibody on levels of alanine aminotransferase (ALT.
Figure 32B:
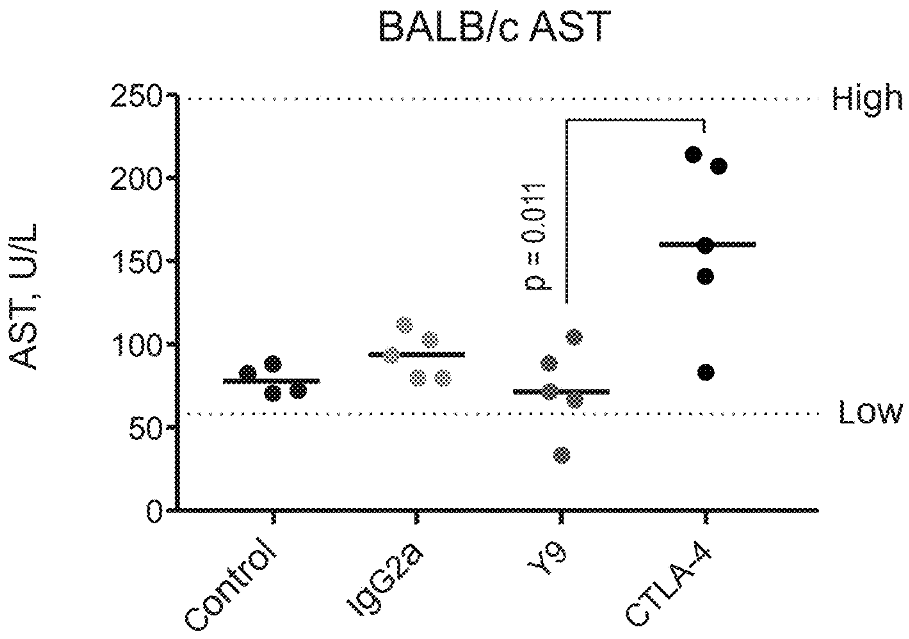

Levels of liver enzymes in the blood were evaluated using Catalyst Dx Chemistry Analyzer (IDEXX, Westbrook, ME). Briefly, blood samples were collected by cardiac puncture and transferred into lithium heparin whole blood separators (IDEXX, #98-14323-00). Blood levels of ALT (alanine aminotransferase) and AST (aspartate aminotransferase) were analyzed using NSAID 6 CLIP (IDEXX, #98-11007-01). Significant increases in blood ALT (FIG. 32A) and AST (FIG. 32B) were observed in the anti-CTLA4 group, although all groups were within the normal range.

Figures 33A, 33B, 33C, 33D:
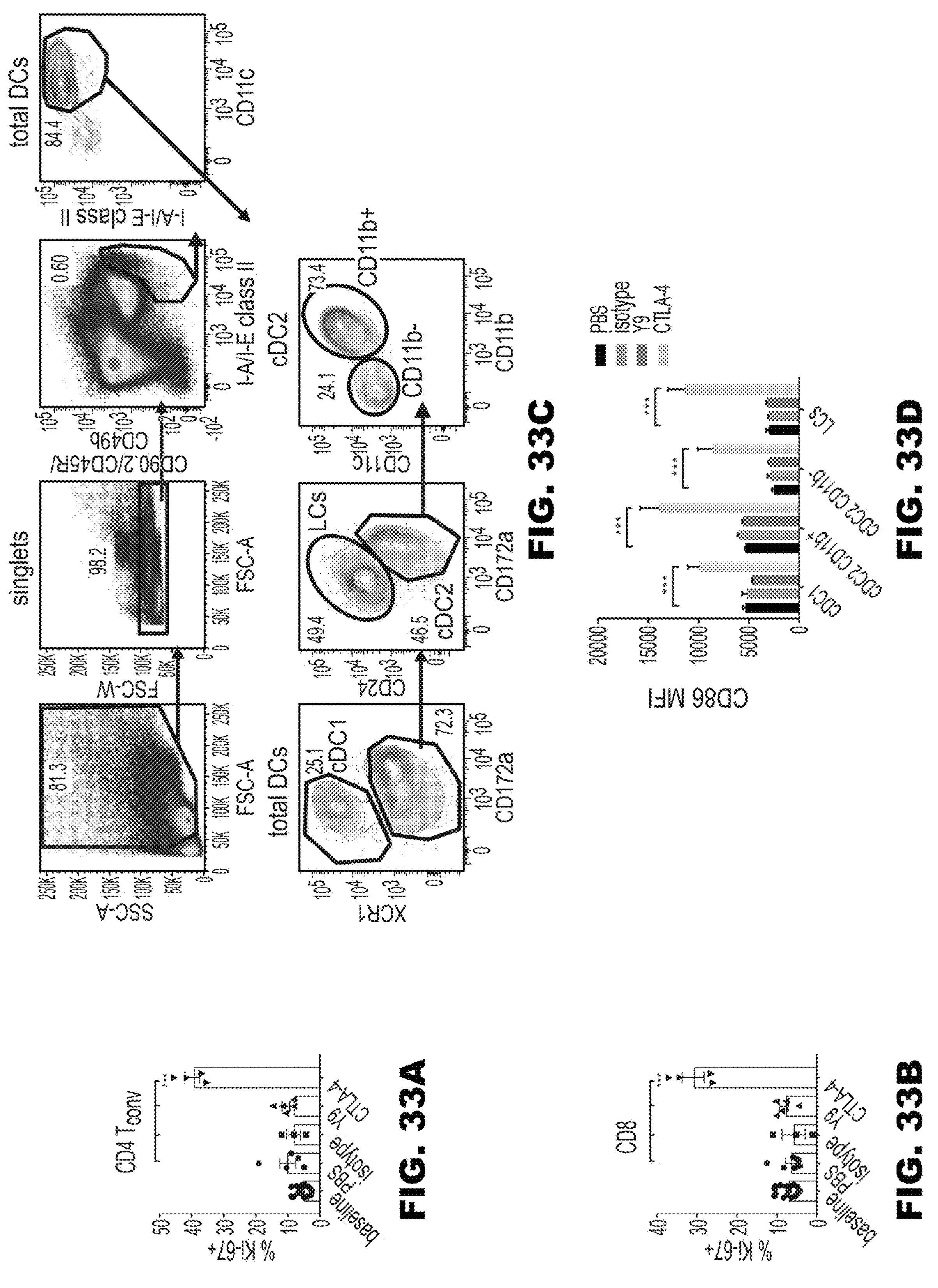
FIGS. 33A-33D show the effects of antibody Y9 and an anti-CTLA4 antibody on immune cell phenotypes of peripheral blood lymphocytes and dendritic cells isolated from skin-draining lymph nodes.

To profile the effect of treatment on immune cell phenotype, peripheral blood lymphocytes and dendritic cells from skin-draining lymph nodes 48 hrs after the final treatment were analyzed by flow cytometry (FIGS. 33A-33D). To prepare blood for flow cytometry, red blood cells were lysed using ACK lysing buffer (Lonza) and washed in flow cytometry buffer (PBS with 1% FCS and 0.02% sodium azide). For DC analysis, skin-draining lymph nodes were digested using the Spleen Dissociation Kit (Miltenyi Biotec) following the manufacturer's instructions. Single cell suspensions were first stained with Fc-Block and live/dead stain in PBS for 10 min at 4° C. Cells were then stained for extracellular markers for 30 min at 4° C. To identify CD4 Tregs, cells were fixed and permeabilized using the Foxp3 Staining Kit (BioLegend) following manufacturer's instructions and stained intracellularly for Ki-67, Foxp3, and CTLA-4. Expression of Ki-67, which is expressed at all stages of the cell cycle except GO, was used to assess T cell proliferation. In mice treated with anti-CTLA-4 antibody, the frequency of CD4 and CD8 T cells proliferating substantially increased relative to isotype controls (FIGS. 33A and 33B). In contract, mice treated with Y9 showed no increase in T cell proliferation, indicating that, unlike the anti-CTLA-4 antibody, Y9 does not cause spontaneous activation and proliferation of peripheral T cells. Consistent with this, Y9 did not upregulate CD86 (B7.2) expression, a co-stimulatory molecule important for dendritic cell activation of T cells, whereas the anti-CTLA-4 antibody did (FIG. 33D). Taken together, these data indicate that administration of anti-TNFR2 antibody Y9 does not lead to spontaneous immune cell activation in healthy mice.

Example 18. Comparison of Therapeutic Efficacy of Antibody Y9 in Different Engineered Mouse Models and Between Different Antibody Isotype Variants Fcγ receptor engagement of the murine surrogate anti-TNFR2 antibody Y9 is important for its activity in vivo. Fcγ receptor engagement can indicate: 1) contribution of effector functions of the antibody such as antibody dependent cellular cytotoxicity (ADCC) or antibody dependent cellular phagocytosis (ADCP) via activating Fcγ receptors mFcγRI, mFcγRIII, or mFcγRIV; or 2) enhanced agonism via clustering of the antibody on Fcγ receptor-expression cell types (Nimmerjahn et al., Trends in Immunology 2015; 36:325-36). For the latter, the inhibitory Fcγ receptor mFcγRII is considered to be the most important to facilitate agonism (see, e.g., Dahan et al., Cancer Cell 2016; 29:820-31).

Figure 34:
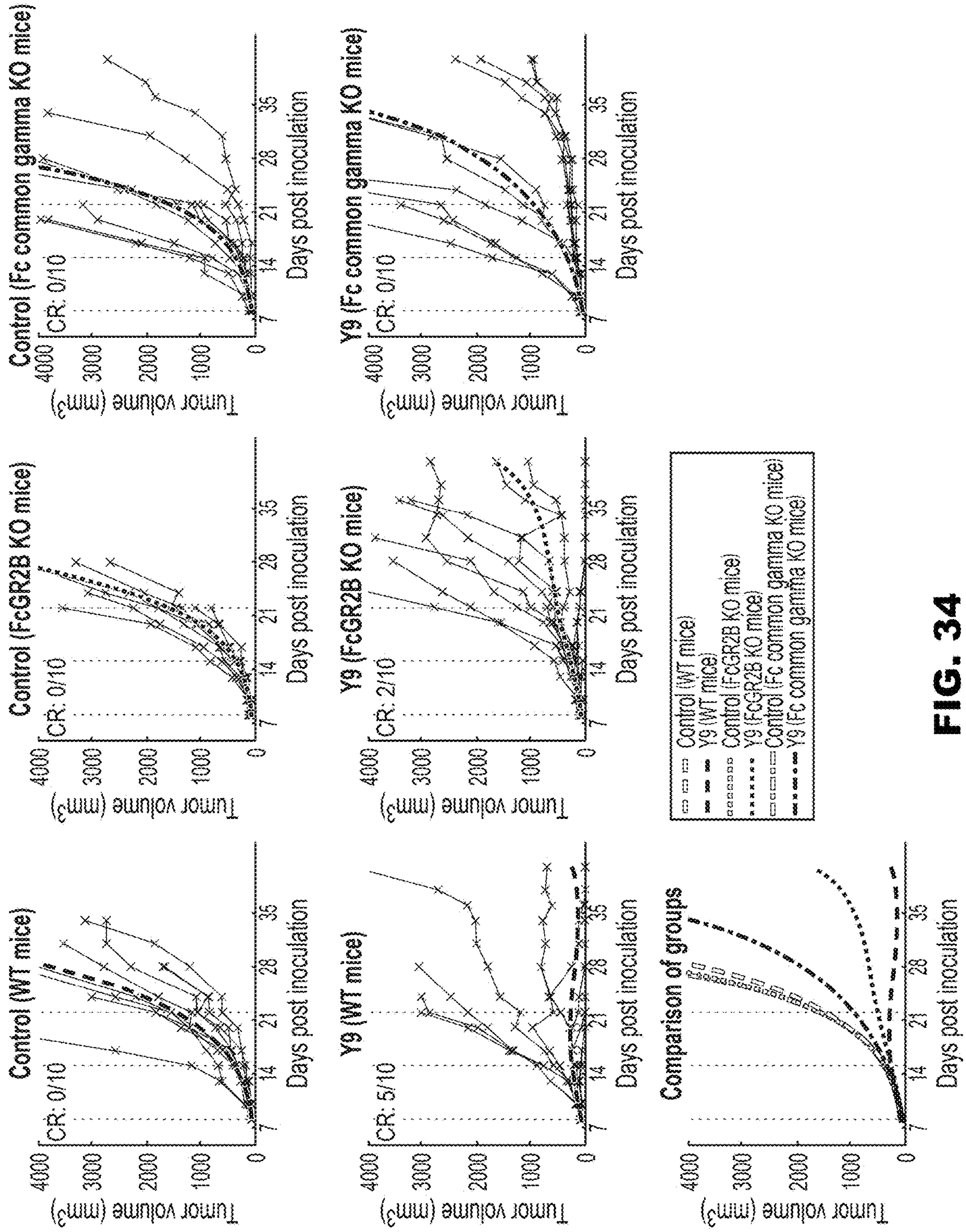
FIG. 34 shows a series of graphs on the anti-tumor activity of antibody Y9 in wild-type mice, FcGR2BKO mice, and Fc common gamma KO mice in the CT26 syngeneic mouse tumor model.

To evaluate which Fcγ receptors are most important for the efficacy of Y9, syngeneic mouse models that are wild-type for the Fcγ receptors ("WT", Balb/C), lack mFcγRII ("FcGR2B KO"; Fcεr2b—Model 579, Taconic), or lack the common Fc-gamma chain ("Fc common gamma KO"; Fcer1g—Model 584, Taconic) were used. Fc common gamma KO mice are deficient in expression of mFcγRI, mFcγRIII, or mFcγRIV. 6- to 8-week-old female mice were housed in a pathogen-free environment under controlled conditions. Tumors were established by subcutaneous injection of $3\times10^5$ CT26 (colon) cells in 200 μL PBS into the right flank (10 mice/group). Tumor growth was monitored using calipers, and volumes were calculated according to the formula: π/6×(length×width×width). When tumors reached an average size of 50-100 $mm^3$, 300 ug of Y9 antibody or PBS as control was injected i.p. as indicated once weekly for three weeks in a total volume of 200 μL. As shown in FIG. 34, Y9 activity was reduced both in FcGR2B KO and Fc common gamma KO mice. This data suggests that both enhanced agonistic activity by clustering by Fcγ receptors as well as ADCC or ADCP potentially contribute to the activity of Y9 in vivo.

Figure 35:
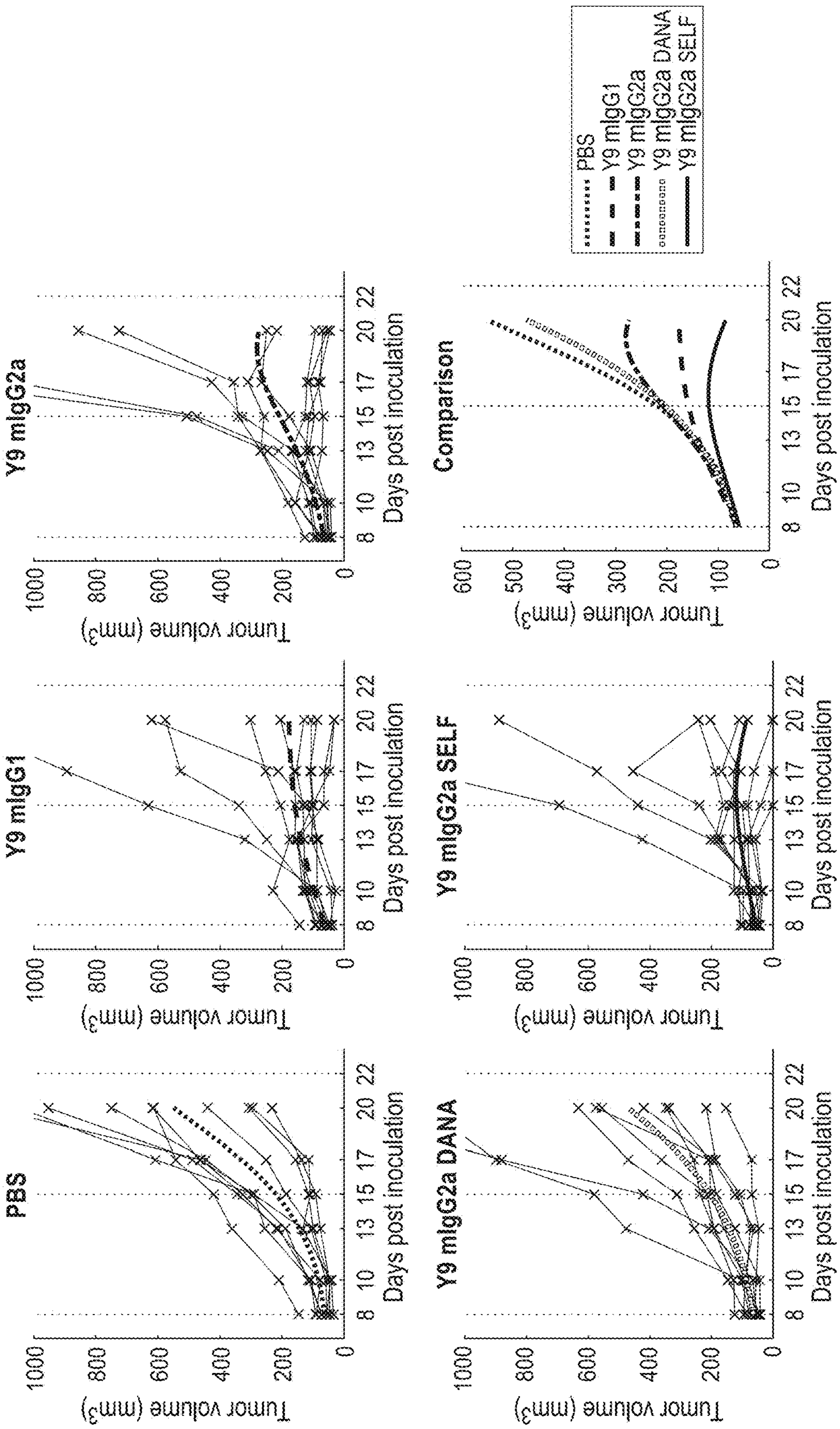
FIG. 35 shows a series of graphs on the anti-tumor activity of antibody Y9 having different antibody isotypes and variant Fc regions in the CT26 syngeneic mouse tumor model.

To evaluate which antibody isotype confers the highest activity via engagement of Fcγ receptors, variants of Y9 were created using differ Fc isotypes and mutated isotypes: 1) murine IgG2a which has high affinity for mFcγRI, mFcγRIII, and mFcγRIV; 2) murine IgG1 which has intermediate affinity for mFcγRII and mFcγRIII; murine IgG2a with D265A and N297A mutations (DANA) which does not bind any mFcγRs; and murine IgG2a with S267E and L328F mutations (SELF) which does has increase affinity for mFcγRII. The activity of the different variants was compared in the CT26 (colon) syngeneic mouse model. 6- to 8-week-old female mice were housed in a pathogen-free environment under controlled conditions. Generation of the CT26 model and conditions for administration of Y9 variants were as described above. As shown in FIG. 35, the SELF variant had highest activity, followed by the mIgG1 isotype, then the mIgG2a isotype. The DANA variant lacked efficacy. This data suggests that enhanced agonistic activity by clustering is the major contributor to Fcγ receptor-mediated activity.

Example 19. Co-Stimulatory Activity of Antibody Y9 and Effects on Proliferation and Functionality of CD8+ T Cells In Vitro This example describes the direct effects of Y9-mediated cross-linking of CD8+ T cells on co-stimulatory activity, proliferation, and functionality of CD8+ T cells.

Figure 36:
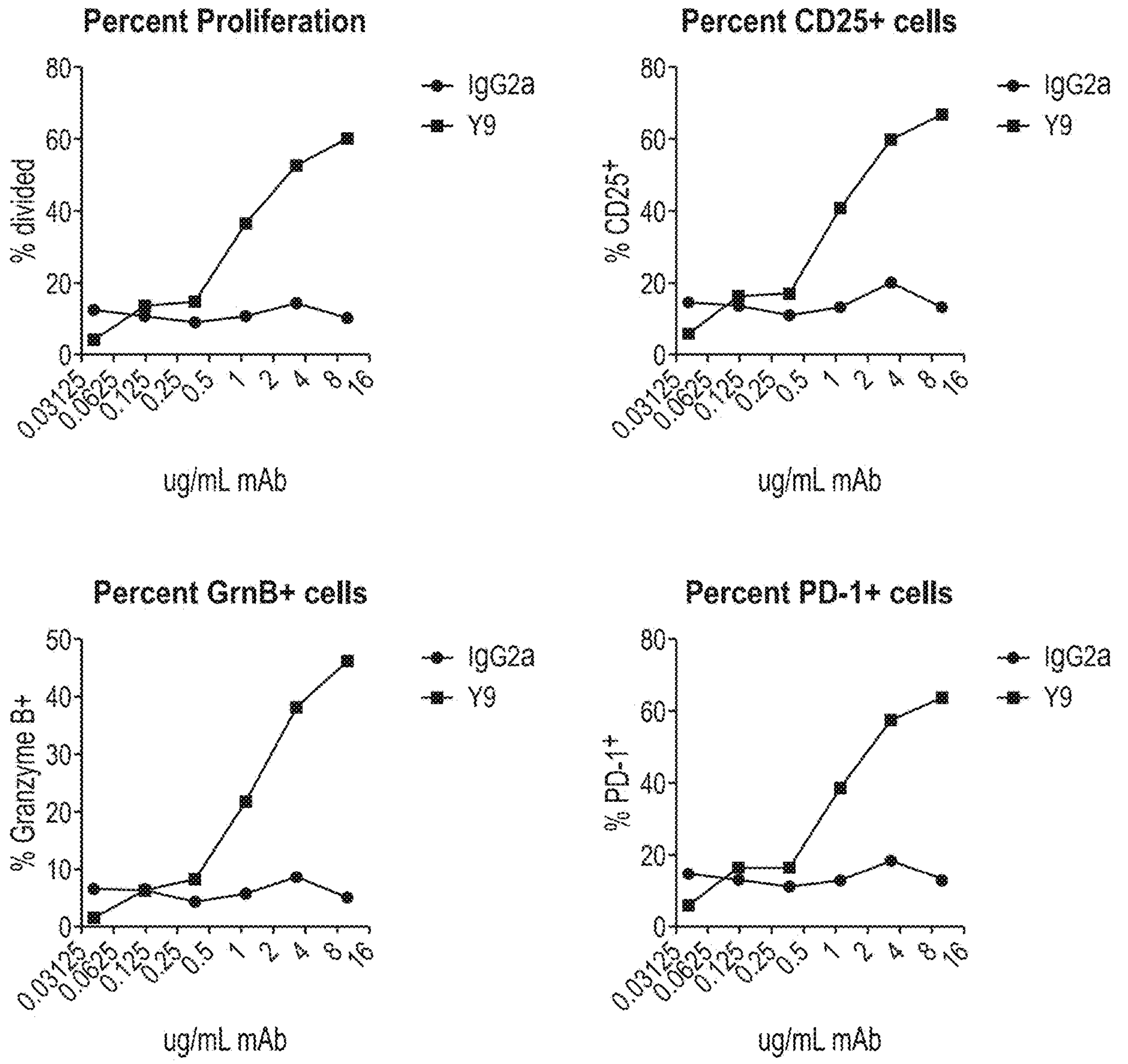
FIG. 36 shows a series of graphs showing the effects of antibody Y9 on various aspects of CD8+ T cells, including proliferation, percent CD25+ cells, percent GrnB+ cells, and percent PD-1+ cells.

Murine CD8+ T cells were stimulated in vitro with anti-CD3/CD28 in the presence of titrated concentrations of Y9. 96-well flat bottom plates were incubated overnight at 4° C. with titrated amounts of functional-grade anti-CD3 (clone 17A2; ThermoFisher Scientific) and Y9 suspended in PBS. Total CD8+ T cells were purified via negative selection (CD8+ T Cell Isolation Kit, mouse; Miltenyi Biotec) from spleens and skin-draining lymph nodes of a BALB/c mouse. CD8 T cells were then labelled with 5 μM CellTrace Violet (Invitrogen). Prior to adding cells, antibody was aspirated from the 96-well plate, wells were blocked for 10 min at room temperature with RPMI containing 10% FCS, and then aspirated again. $4\times10^4$ CD8+ T cells were added per well along with 1 μg/mL soluble anti-CD28 (clone 37.51) and incubated at 37° C. for 72 h. Cells were then stained for activation markers and intracellular granzyme B and analyzed by flow cytometry. As shown in FIG. 36, Y9 exhibited co-stimulatory activity, and increased the proliferation and functionality of CD8+ T cells in vitro. Data shown used 1.67 μg/mL plate-bound anti-CD3, 1 μg/mL anti-CD28, and titrated concentrations of Y9. Proliferation was defined as cells undergoing at least 1 round of division indicated by 2-fold dilution of CellTrace Violet mean fluorescence intensity.

Example 20. Epitope Mapping of Antibody Y9

This Example describes the fine epitope mapping of antibody Y9 using yeast surface display.

Domain level mapping identified the epitope of Y9 antibody to the CRD1 region of mouse TNFR2. A fine epitope mapping strategy was used to further define the epitope with amino acid resolution (Levy et al., JMB 2007; 365:196-210). A total of fifteen TNFR2 mutants, each containing a single amino acid substitution at surface exposed positions, were displayed on the surface of yeast. To assess the contribution of each position to Y9 binding, substitutions at each position were made to either alanine or aspartate (Table 3).

TABLE 3

TNFR2 mutant panel

| Substitution | Y9 Binding[A] | Corresp. Human Residue |
|---|---|---|
| G37D | +++ | G37 |
| E39A | +++ | T39 |
| I42A | +++ | L42 |
| R49A | − | Q48 |
| K50A | +++ | T49 |
| Q52A | +++ | Q51 |
| K57A | +++ | K56 |
| H66A | +++ | V65 |
| F67A | +++ | F66 |
| N69A | − | T68 |

TABLE 3-continued

| TNFR2 mutant panel | | |
|---|---|---|
| Substitution | Y9 Binding[A] | Corresp. Human Residue |
| K70A | +++ | K69 |
| V87A | +++ | L86 |
| Q90A | +++ | W89 |
| F91A | ++ | V90 |
| R92A | +++ | P91 |

Figure 37:
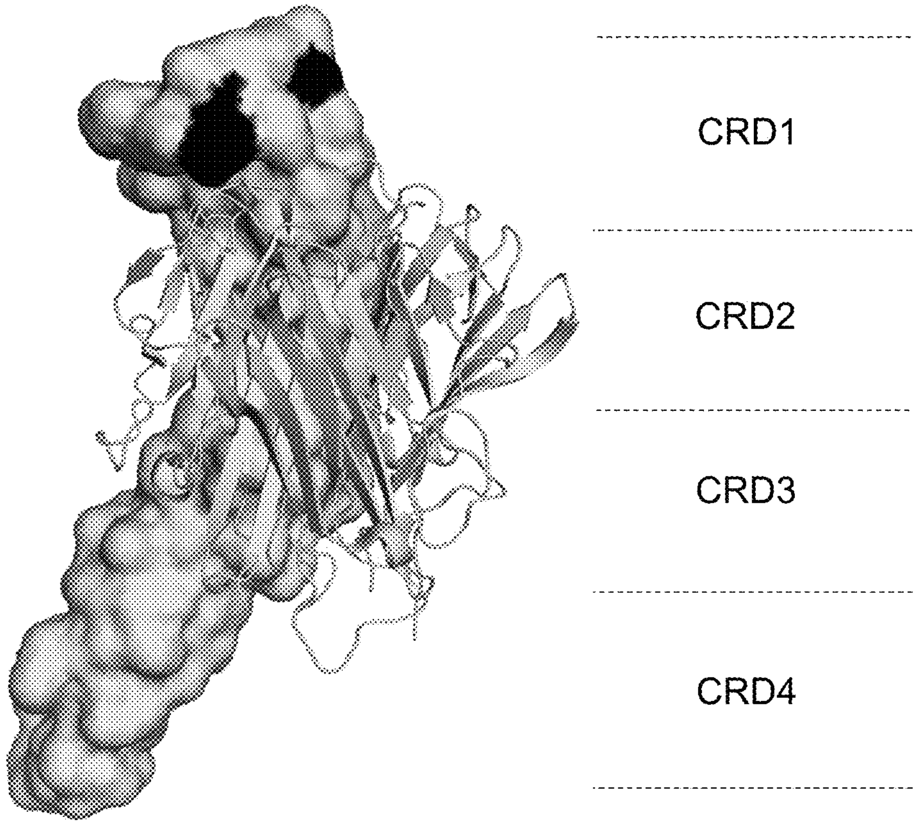
FIG. 37 is a homology model of mouse TNFR2 (space-filling model) bound to mouse TNF (ribbon model). Amino acid positions at which Y9 binding was significantly disrupted by mutations are mapped (-, black).
Figure 38A:
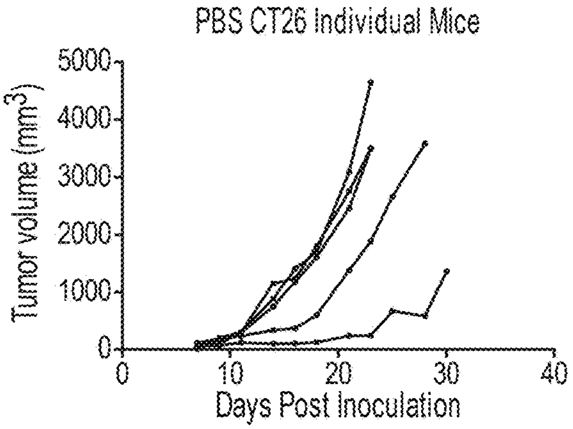
FIGS. 38A-38D are a series of graphs demonstrating the antitumor response of a single dose of PBS anti-TNFR2 antibody (1 mg, 0.3 mg, and 0.1 mg) in a syngeneic tumor model with colorectal CT26 cancer cells.
Figure 38B:
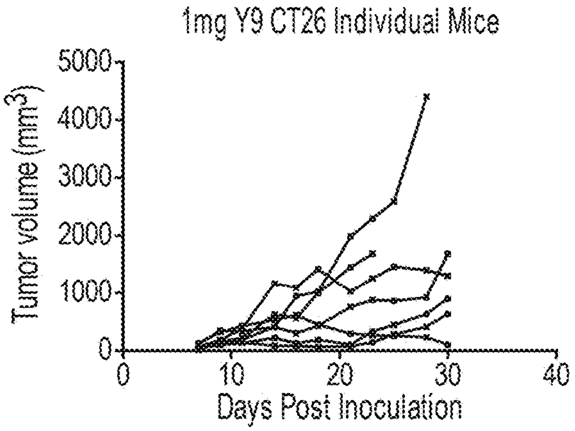
Figure 38C:
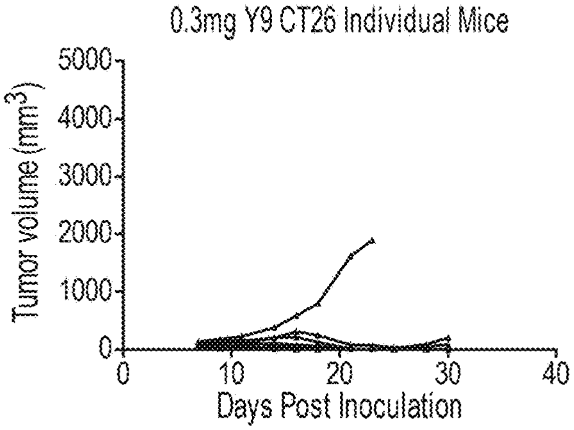
Figure 38D:
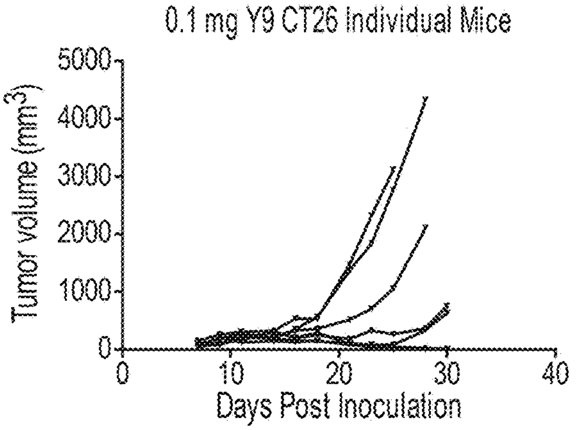
Figure 39A:
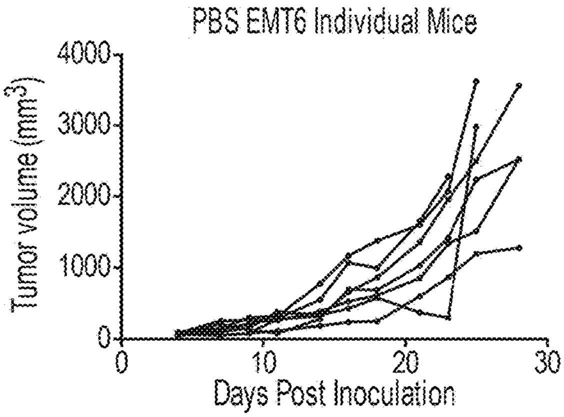
FIGS. 39A-39D are a series of graphs demonstrating the antitumor response of a single dose of PBS or anti-TNFR2 antibody (1 mg, 0.3 mg, and 0.1 mg) in a syngeneic tumor model with EMT6 breast cancer cells.
Figure 39B:
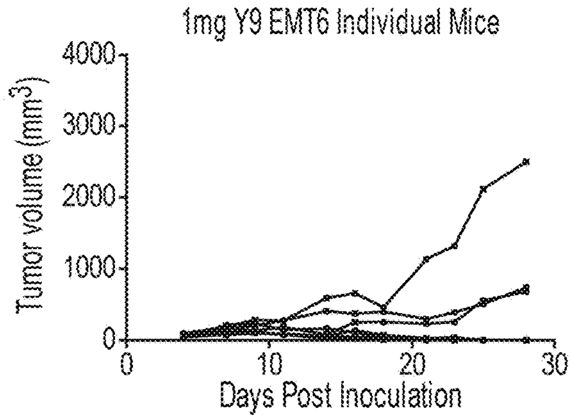
Figure 39C:
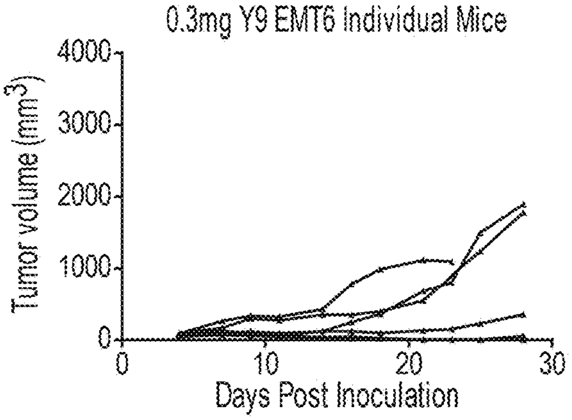
Figure 39D:
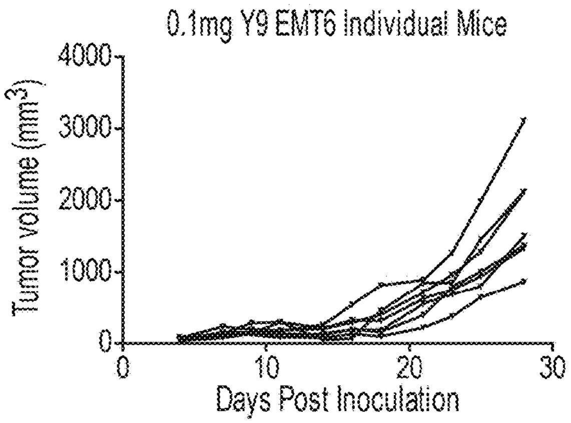
Figure 40A:
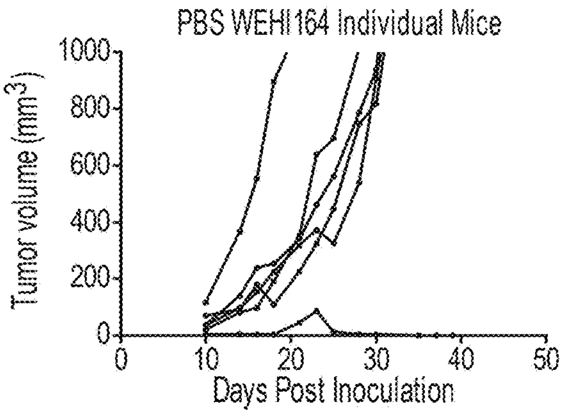
FIGS. 40A-40D are a series of graphs demonstrating the antitumor response of a single dose of PBS or anti-TNFR2 antibody (1 mg, 0.3 mg, and 0.1 mg) in a syngeneic tumor model with Wehi64 fibrosarcoma cells.
Figure 40B:
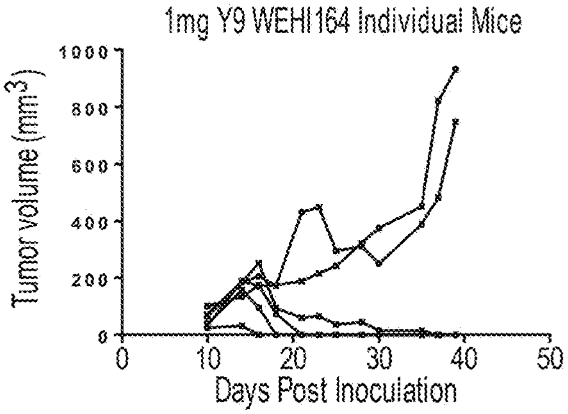
Figure 40C:
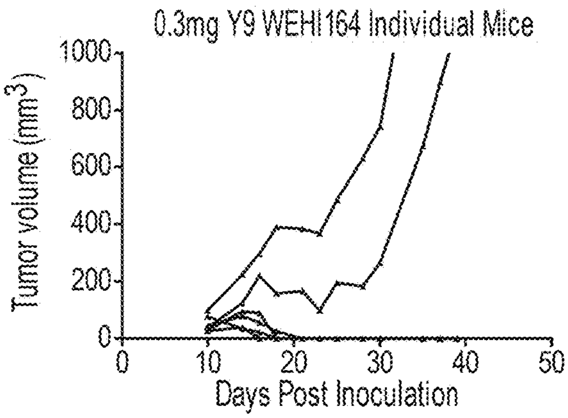
Figure 40D:
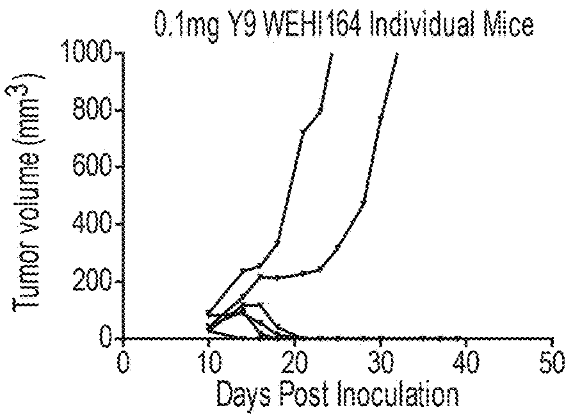
Figure 41A:
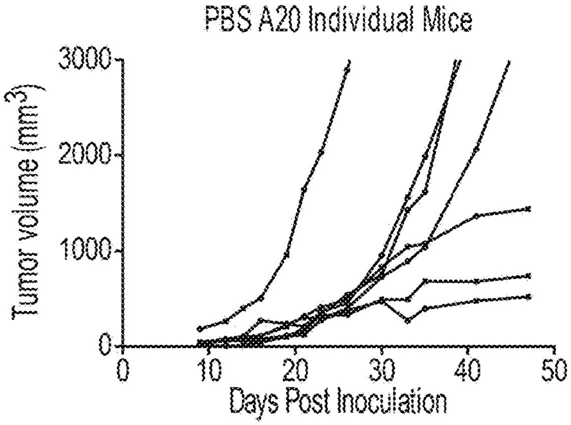
FIGS. 41A-41D are a series of graphs demonstrating the antitumor response of a single dose of PBS or anti-TNFR2 antibody (1 mg, 0.3 mg, and 0.1 mg) in a syngeneic tumor model with A20 B cell lymphoma cells.
Figure 41B:
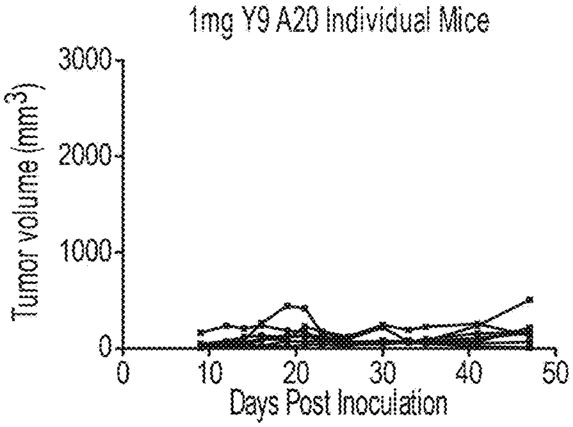
Figure 41C:
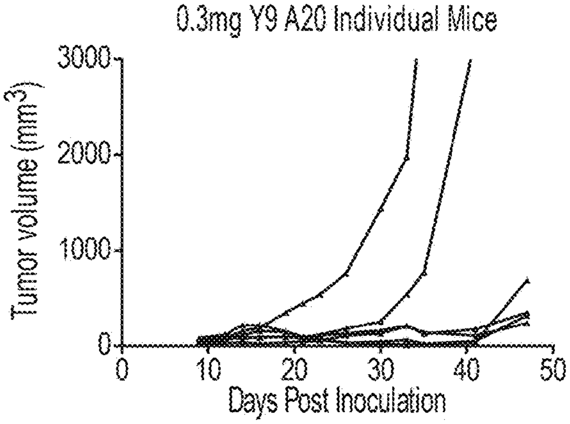
Figure 41D:
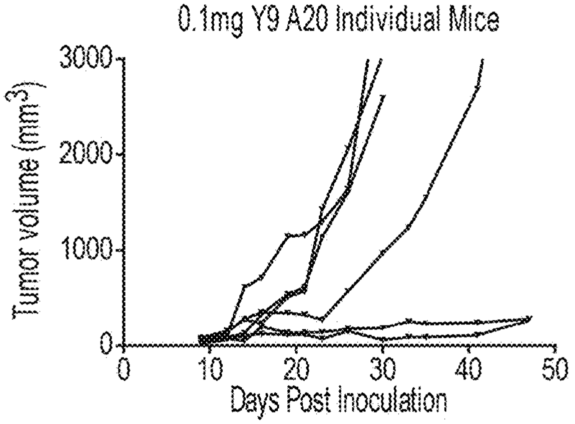

[A]+++, no reduction in Y9 binding;
++, 0-50% reduction;
+, 50-90% reduction;
−, > 90% reduction Binding isotherms to Y9 (400 nMA) were determined for all fifteen mutants and the wild-type sequence (Table 3). The positions at which Y9 binding was significantly disrupted (−) were mapped onto the homology model of mouse TNFR2 (FIG. 37). The proximity of R49 to the receptor/ligand interface is consistent with the observation that Y9 can compete with ligand for binding to TNFR2.

Example 21. Anti-Tumor Effects of a Single Dose of Anti-Mouse TNFR2 Antibody in Syngeneic Tumor Models This example demonstrates the antitumor response of a single dose of anti-TNFR2 antibody in multiple syngeneic tumor models. 6-8 week-old female Balb/C mice were housed in a pathogen-free environment under controlled conditions. Tumors were established by subcutaneous injection of $3\times10^5$ CT26 (colon), EMT6 (breast), Wehi64 (fibrosarcoma), or A20 (B cell lymphoma) cells in 200 μL PBS into the right flank (6-7 mice/group). Tumor growth was monitored using calipers, and volumes were calculated according to the formula: $\pi/6\times(\text{length}\times\text{width}\times\text{width})$. When the tumors reached an average size of 50-70 $mm^3$, Y9 antibody was injected i.p. as a single dose (0.1 mg, 0.3 mg, or 1 mg) in a total volume of 200 μL. Significant antitumor activity was seen with only one dose of antibody in all four models (Table 4, FIGS. 38A-38D, 39A-39D, and 40A-40D, and 41A-41D).

TABLE 4

Anti-tumor effects of single dose of anti-mouse TNFR2 antibody

| | PBS | | 0.1 mg Y9 | | 0.3 mg Y9 | | 1 mg Y9 | |
|---|---|---|---|---|---|---|---|---|
| Model | PR | CR | PR | CR | PR | CR | PR | CR |
| CT26 | 1/7 | 0/7 | 3/7 | 1/7 | 2/7 | 4/7 | 5/7 | 0/7 |
| EMT6 | 0/7 | 0/7 | 0/7 | 0/7 | 4/7 | 3/7 | 2/7 | 4/7 |
| Wehi64 | 0/6 | 1/6 | 0/6 | 4/6 | 1/6 | 4/6 | 2/6 | 4/6 |
| A20 | 2/7 | 0/7 | 2/6 | 0/6 | 3/6 | 0/6 | 7/7 | 0/7 |

PBS: phosphate buffered saline, PR: partial response, CR: complete response

Figure 42:
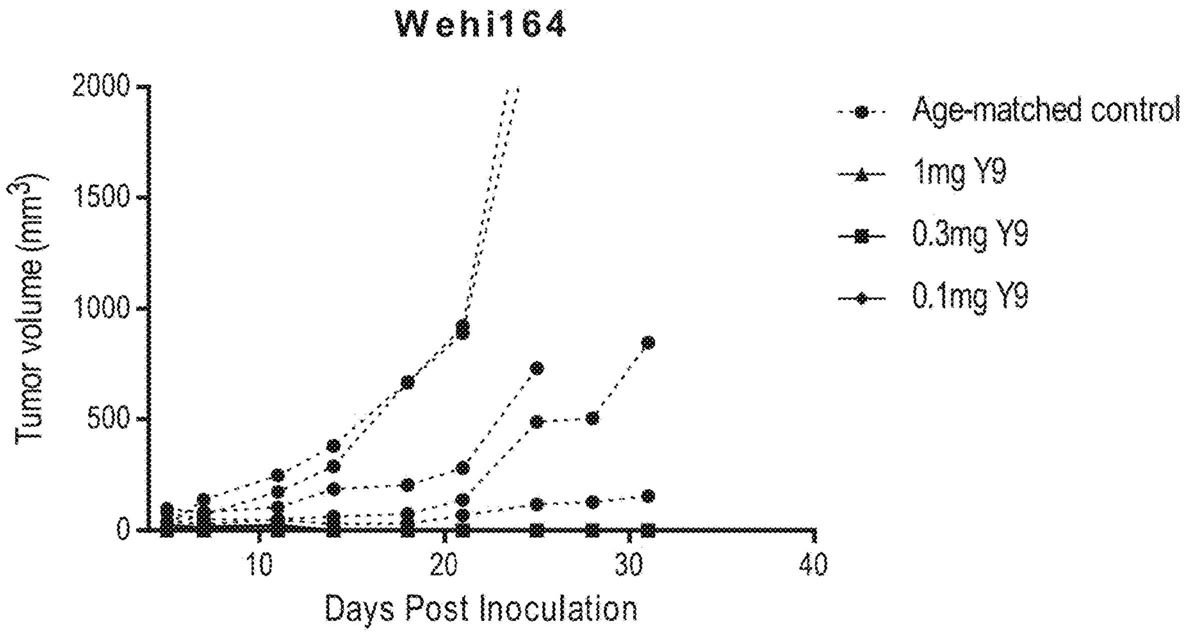
FIG. 42 is a graph demonstrating sustained antitumor response of a single dose of anti-TNFR2 antibody (1 mg, 0.3 mg, and 0.1 mg) in a syngeneic tumor model with Wehi64 fibrosarcoma cells vs. untreated age-matched controls.

The eleven Wehi64 complete responders were subjected to rechallenge to determine whether a lasting antitumor response was elicited. At day 214 after the initial inoculation, the CR mice and age-matched control mice (5) were rechallenged by subcutaneous injection of $3\times10^5$ Wehi64 cells in 200 μL PBS into the left flank, opposite the initial inoculation. Tumor size was monitored as described above. Mice originally administered any of 0.1, 0.3, or 1 mg Y9 experienced no tumor growth, whereas the age-matched controls all had tumor growth (FIG. 42).

This example shows that a single dose of anti-TNFR2 antibodies demonstrate antitumor effects in multiple syngeneic tumor models and that the effects may be retained after tumor clearance.

Example 22. Effects of Anti-TNFR2 Antibodies on Surface CTLA4 Expression

This example describes the effects of an anti-mouse TNFR2 antibody on CTLA4 expression on T cells.

Figure 43A:
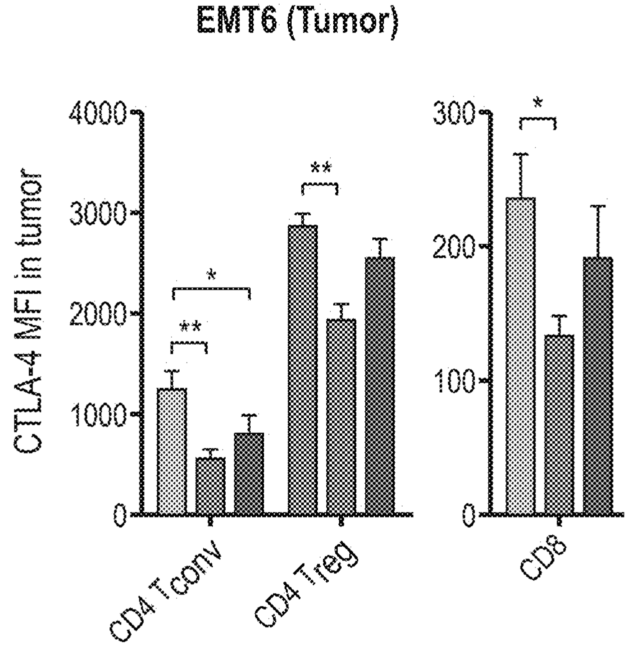
FIGS. 43A and 43B are graphs showing the effects of antibody Y9 and Y9 DANA on CTLA4 expression in CD4+ conventional T cells, Tregs, and CD8+ T cells in tumors and tumor draining lymph node of a EMT-6 syngeneic model.
Figure 43B:
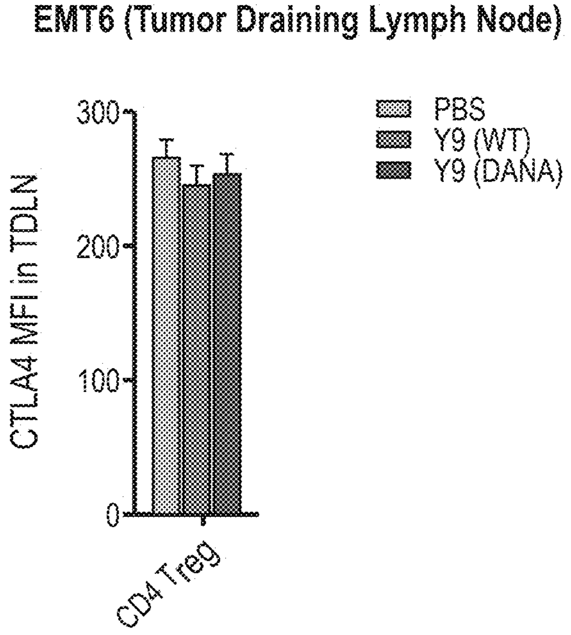

C57BL/6 mice were subcutaneously injected with $3\times10^5$ EMT-6 cells. When tumors reached an average size of 200-300 $mm^3$, mice were treated with PBS or 300 μg Y9 or Y9-DANA (i.e., Y9 with an Fc region having D265A and N297A substitutions). Tumors were harvested 36 hours later, digested using the Tumor Dissociation Kit, mouse (Miltenyi Biotec) following the manufacturer's instructions, and stained for T cell lineage markers and CTLA-4 (clone UC10-4B9, BioLegend). As shown in FIGS. 43A and 43B, Y9 treatment (and to a lesser extent, Y9 DANA treatment) significantly reduced the surface expression of CTLA4 in CD4+ conventional T cells, Tregs, and CD8+ T cells in tumors, whereas no change was observed in the tumor draining lymph node.

Example 23. Effects of Anti-TNFR2 Antibodies on GITR, GARP, and PD-1 Expression in Tumors This example describes the effects of anti-mouse TNFR2 antibodies on GITR, GARP, and PD-1 expression in tumors.

C57BL/6 mice were subcutaneously injected with $3\times10^5$ EMT-6 cells. When tumors reached an average size of 200-300 $mm^3$, mice were treated with PBS or 300 μg Y9 or Y9-DANA. Tumors were harvested 36 hours later, digested using the Tumor Dissociation Kit, mouse (Miltenyi Biotec) following the manufacturer's instructions, and stained for T cell lineage markers, GITR (clone DTA-1, BioLegend), GARP (clone FO 11-5, BioLegend), LAP (TW7-16B4, BioLegend), and PD-1 (RMP1-30, BioLegend). There was a significant decrease in the surface expression of GITR with Y9 treatment, and to a lesser extent, with Y9 DANA (FIG. 44A). Y9, but not Y9 DANA, caused a coordinated decrease in GARP expression, which serves as a docking station for latent TGF-b, as well as LAP (latency-associated peptide) which is associated with TGF-b (FIG. 44B). Similar to GITR, Y9 caused decreased frequencies of PD-1+ effector T cells as well as a notable decrease in the per cell expression on CD8 T cells (shown as median fluorescence intensity) (FIG. 44C).

Example 24. Effects of Anti-TNFR2 Antibodies on TNFR2 Expression

This example describes the effects of anti-mouse TNFR2 antibodies on TNFR2 expression in tumors.

C57BL/6 mice were subcutaneously injected with $3\times10^5$ cells for CT26, MC38 and WEHI-164 syngeneic tumor models. When tumors reached an average size of 200-300 $mm^3$, mice were treated with PBS or 300 μg Y9 or Y9-DANA. Tumors were harvested 36 hours (CT26) or 24 hours (MC38 and WEHI-164) later, digested using the Tumor Dissociation Kit, mouse (Miltenyi Biotec) following the manufacturer's instructions, and stained for T cell lineage markers and TNFR2 (clone TR75-89, BioLegend). As shown in FIGS. 45A-45C, a significant decrease was observed in the surface expression of TNFR2 with Y9 treatment, and to a lesser extent, with Y9 DANA treatment.

TABLE 5

SEQUENCE TABLE

| SEQ ID | Description | Sequence |
|---|---|---|
| 1 | Human TNFR2 (leader sequence is underlined) | MAPVAVWAALAVGLELWAAAHALPAQVAFTPYAPEPGSTCRLREYYDQ<br>TAQMCCSKCSPGQHAKVFCTKTSDTVCDSCEDSTYTQLWNWVPECLSC<br>GSRCSSDQVETQACTREQNRICTCRPGWYCALSKQEGCRLCAPLRKCR<br>PGFGVARPGTETSDVVCKPCAPGTFSNTTSSTDICRPHQICNVVAIPG<br>NASMDAVCTSTSPTRSMAPGAVHLPQPVSTRSQHTQPTPEPSTAPSTS<br>FLLPMGPSPPAEGSTGDFALPVGLIVGVTALGLLIIGVVNCVIMTQVK<br>KKPLCLQREAKVPHLPADKARGTQGPEQQHLLITAPSSSSSSLESSAS<br>ALDRRAPTRNQPQAPGVEASGAGEARASTGSSDSSPGGHGTQVNVTCI<br>VNVCSSSDHSSQCSSQASSTMGDTDSSPSESPKDEQVPFSKEECAFRS<br>QLETPETLLGSTEEKPLPLGVPDAGMKPS |
| 2 | Human TNFR2 (extracellular domain) | LPAQVAFTPYAPEPGSTCRLREYYDQTAQMCCSKCSPGQHAKVFCTKT<br>SDTVCDSCEDSTYTQLWNWVPECLSCGSRCSSDQVETQACTREQNRIC<br>TCRPGWYCALSKQEGCRLCAPLRKCRPGFGVARPGTETSDVVCKPCAP<br>GTFSNTTSSTDICRPHQICNVVAIPGNASMDAVCTSTSPTRSMAPGAV<br>HLPQPVSTRSQHTQPTPEPSTAPSTSFLLPMGPSPPAEGSTGD |
| 3 | Human IgG1 heavy chain | ASTKGPSVFPLAPSSKSTSGGTAALGCLVKDYFPEPVTVSWNSGALTSGVHTF<br>PAVLQSSGLYSLSSVVTVPSSSLGTQTYICNVNHKPSNTKVDKKVEPKSCDKT<br>HTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALP<br>APIEKTISKAKGQPREPQVYTLPPSREEMTKNQVSLTCLVKGFYPSDIAVEWE<br>SNGQPENNYKTTPPVLDSDGSFFLYSKLTVDKSRWQQGNVFSCSVMHEALHNH<br>YTQKSLSLSPG |
| 4 | Mouse TNFR2 (leader sequence is underlined) | MAPAALWVALVFELQLWATGHTVPAQVVLTPYKPEPGYECQISQEYYD<br>RKAQMCCAKCPPGQYVKHFCNKTSDTVCADCEASMYTQVWNQFRTCLS<br>CSSSCTTDQVEIRACTKQQNRVCACEAGRYCALKTHSGSCRQCMRLSK<br>CGPGFGVASSRAPNGNVLCKACAPGTFSDTTSSTDVCRPHRICSILAI<br>PGNASTDAVCAPESPTLSAIPRTLYVSQPEPTRSQPLDQEPGPSQTPS<br>ILTSLGSTPIIEQSTKGGISLPIGLIVGVTSLGLLMLGLVNCIILVQR<br>KKKPSCLQRDAKVPHVPDEKSQDAVGLEQQHLLTTAPSSSSSSLESSA<br>SAGDRRAPPGGHPQARVMAEAQGFQEARASSRISDSSHGSHGTHVNVT<br>CIVNVCSSSDHSSQCSSQASATVGDPDAKPSASPKDEQVPFSQEECPS<br>QSPCETTETLQSHEKPLPLGVPDMGMKPSQAGWFDQIAVKVA |
| 5 | Mouse TNFR2 (extracellular domain) | VPAQVVLTPYKPEPGYECQISQEYYDRKAQMCCAKCPPGQYVKHFCNK<br>TSDTVCADCEASMYTQVWNQFRTCLSCSSSCTTDQVEIRACTKQQNRV<br>CACEAGRYCALKTHSGSCRQCMRLSKCGPGFGVASSRAPNGNVLCKAC<br>APGTFSDTTSSTDVCRPHRICSILAIPGNASTDAVCAPESPTLSAIPR<br>TLYVSQPEPTRSQPLDQEPGPSQTPSILTSLGSTPIIEQSTKGG |
| 6 | UC2 (S4-2 1D10) scFv | QVQLLESGGGLVQPGGSLRLSCAASGFTFSTYAMSWVRQAPGKGLEWVSIISD<br>GGDATFYADSVKGRFTISRDNSKNTLYLQMNSLRAEDTAVYYCARDGTSAAAF<br>DSWGQGTLVTVSSASSGGSTSGSGKPGSGEGSSGSARDIQMTQSPSSLSASVG<br>DRVTITCQASQDITNFLNWYQQKPGKAPKLLIYDASTLQTGVPSRFSGSGSGT<br>DFTFTISSLQPEDIATYYCQQSDSYPITFGQGTKVEIKR |
| 7 | UC2 VHCDR1 (Chothia) | GFTFSTY |
| 8 | UC2 VHCDR2 (Chothia) | SDGGDA |
| 9 | UC2 VHCDR3 (Chothia) | DGTSAAAFDS |
| 10 | UC2 VLCDR1 (Chothia) | QASQDITNFLN |
| 11 | UC2 VLCDR2 (Chothia) | DASTLQT |
| 12 | UC2 VLCDR3 (Chothia) | QQSDSYPIT |
| 13 | UC2 VHCDR1 (Kabat) | TYAMS |
| 14 | UC2 VHCDR2 (Kabat) | IISDGGDATFYADSVKG |
| 15 | UC2 VHCDR3 (Kabat) | DGTSAAAFDS |

TABLE 5-continued

SEQUENCE TABLE

| SEQ ID | Description | Sequence |
|---|---|---|
| 16 | UC2 VLCDR1 (Kabat) | QASQDITNFLN |
| 17 | UC2 VLCDR2 (Kabat) | DASTLQT |
| 18 | UC2 VLCDR3 (Kabat) | QQSDSYPIT |
| 19 | UC2 VHCDR1 (IMGT) | GFTFSTYA |
| 20 | UC2 VHCDR2 (IMGT) | ISDGGDAT |
| 21 | UC2 VHCDR3 (IMGT) | ARDGTSAAAFDS |
| 22 | UC2 VLCDR1 (IMGT) | QDITNF |
| 23 | UC2 VLCDR2 (IMGT) | DAS |
| 24 | UC2 VLCDR3 (IMGT) | QQSDSYPIT |
| 25 | UC2 VH | QVQLLESGGGLVQPGGSLRLSCAASGFTFSTYAMSWVRQAPGKGLEWVSIISD GGDATFYADSVKGRFTISRDNSKNTLYLQMNSLRAEDTAVYYCARDGTSAAAF DSWGQGTLVTVSS |
| 26 | UC2 VL | DIQMTQSPSSLSASVGDRVTITCQASQDITNFLNWYQQKPGKAPKLLIYDAST LQTGVPSRFSGSGSGTDFTFTISSLQPEDIATYYCQQSDSYPITFGQGTKVEI K |
| 27 | UC2-IgG1 heavy chain | QVQLLESGGGLVQPGGSLRLSCAASGFTFSTYAMSWVRQAPGKGLEWVSIISD GGDATFYADSVKGRFTISRDNSKNTLYLQMNSLRAEDTAVYYCARDGTSAAAF DSWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPG |
| 28 | UC2-IgG1 light chain | DIQMTQSPSSLSASVGDRVTITCQASQDITNFLNWYQQKPGKAPKLLIYDAST LQTGVPSRFSGSGSGTDFTFTISSLQPEDIATYYCQQSDSYPITFGQGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| 29 | UC2.3 (S4-2 1D10-1G9) scFv | QVQLLESGGGLVQPGGSLRLSCAASGFTFSTYAMSWIRQAPGKGLEWVSIISD GGDATVYADSVKGRFTISRDNSKNTLYLQMNSLRAEDTAVYYCARDGTSAAAF DSWGQGTLVTVSSASSGGSTSGSGKPGSGEGSSGSARDIQMTQSPSSLSASVG DRVTITCQASQDITNFLNWYQQKPGKAPKLLIYDASTLQTGVPSRFSGSGSGT DFTFTISSLQPEDIATYYCQQSDSYPITFGQGTKVEIKR |
| 30 | UC2.3 VHCDR1 (Chothia) | GFTFSTY |
| 31 | UC2.3 VHCDR2 (Chothia) | SDGGDA |
| 32 | UC2.3 VHCDR3 (Chothia) | DGTSAAAFDS |
| 33 | UC2.3 VLCDR1 (Chothia) | QASQDITNFLN |
| 34 | UC2.3 VLCDR2 (Chothia) | DASTLQT |
| 35 | UC2.3 VLCDR3 (Chothia) | QQSDSYPIT |

TABLE 5-continued

| SEQUENCE TABLE | | |
|---|---|---|
| SEQ ID | Description | Sequence |
| 36 | UC2.3 VHCDR1 (Kabat) | TYAMS |
| 37 | UC2.3 VHCDR2 (Kabat) | IISDGGDATVYADSVKG |
| 38 | UC2.3 VHCDR3 (Kabat) | DGTSAAAFD |
| 39 | UC2.3 VLCDR1 (Kabat) | QASQDITNFLN |
| 40 | UC2.3 VLCDR2 (Kabat) | DASTLQT |
| 41 | UC2.3 VLCDR3 (Kabat) | QQSDSYPIT |
| 42 | UC2.3 VHCDR1 (IMGT) | GFTFSTYA |
| 43 | UC2.3 VHCDR2 (IMGT) | ISDGGDAT |
| 44 | UC2.3 VHCDR3 (IMGT) | ARDGTSAAAFDS |
| 45 | UC2.3 VLCDR1 (IMGT) | QDITNF |
| 46 | UC2.3 VLCDR2 (IMGT) | DAS |
| 47 | UC2.3 VLCDR3 (IMGT) | QQSDSYPIT |
| 48 | UC2.3 VH | QVQLLESGGGLVQPGGSLRLSCAASGFTFSTYAMSWIRQAPGKGLEWVSIISD GGDATVYADSVKGRFTISRDNSKNTLYLQMNSLRAEDTAVYYCARDGTSAAAF DSWGQGTLVTVSS |
| 49 | UC2.3 VL | DIQMTQSPSSLSASVGDRVTITCQASQDITNFLNWYQQKPGKAPKLLIYDAST LQTGVPSRFSGSGSGTDFTFTISSLQPEDIATYYCQQSDSYPITFGQGTKVEI K |
| 50 | UC2.3-IgG1 heavy chain | QVQLLESGGGLVQPGGSLRLSCAASGFTFSTYAMSWIRQAPGKGLEWVSIISD GGDATVYADSVKGRFTISRDNSKNTLYLQMNSLRAEDTAVYYCARDGTSAAAF DSWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPG |
| 51 | UC2.3-IgG1 light chain | DIQMTQSPSSLSASVGDRVTITCQASQDITNFLNWYQQKPGKAPKLLIYDAST LQTGVPSRFSGSGSGTDFTFTISSLQPEDIATYYCQQSDSYPITFGQGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| 52 | UC2.3.3 (S4-2 1D10-1G9-1F10) scFv | QVQLLESGGGLVQPGGSLRLSCAASGFTFSTYAMSWIRQAPGKGLEWVSIISD GGDATVYADSVKGRFTISRDNNRNTLYLQMNSLRAEDTAVYYCARDGTSAAAF DSWGQGTLVTVSSASSGGSTSGSGKPGSGEGSSGSARDIQMTQSPSSLSASVG DRVTITCQASQDITNFLNWYQQKPGKAPKLLIYDASTLQTGVPSRFSGSGSGT DFTFTISSLQPEDIATYYCQQSDSYPITFGQGTKVEIKR |
| 53 | UC2.3.3 VHCDR1 (Chothia) | GFTFSTY |
| 54 | UC2.3.3 VHCDR2 (Chothia) | SDGGDA |
| 55 | UC2.3.3 VHCDR3 (Chothia) | DGTSAAAFDS |

TABLE 5-continued

SEQUENCE TABLE

| SEQ ID | Description | Sequence |
|---|---|---|
| 56 | UC2.3.3 VLCDR1 (Chothia) | QASQDITNFLN |
| 57 | UC2.3.3 VLCDR2 (Chothia) | DASTLQT |
| 58 | UC2.3.3 VLCDR3 (Chothia) | QQSDSYPIT |
| 59 | UC2.3.3 VHCDR1 (Kabat) | TYAMS |
| 60 | UC2.3.3 VHCDR2 (Kabat) | IISDGGDATVYADSVKG |
| 61 | UC2.3.3 VHCDR3 (Kabat) | DGTSAAAFDS |
| 62 | UC2.3.3 VLCDR1 (Kabat) | QASQDITNFLN |
| 63 | UC2.3.3 VLCDR2 (Kabat) | DASTLQT |
| 64 | UC2.3.3 VLCDR3 (Kabat) | QQSDSYPIT |
| 65 | UC2.3.3 VHCDR1 (IMGT) | GFTFSTYA |
| 66 | UC2.3.3 VHCDR2 (IMGT) | ISDGGDAT |
| 67 | UC2.3.3 VHCDR3 (IMGT) | ARDGTSAAAFDS |
| 68 | UC2.3.3 VLCDR1 (IMGT) | QDITNF |
| 69 | UC2.3.3 VLCDR2 (IMGT) | DAS |
| 70 | UC2.3.3 VLCDR3 (IMGT) | QQSDSYPIT |
| 71 | UC2.3.3 VH | QVQLLESGGGLVQPGGSLRLSCAASGFTFSTYAMSWIRQAPGKGLEWVSIISD GGDATVYADSVKGRFTISRDNNRNTLYLQMNSLRAEDTAVYYCARDGTSAAAF DSWGQGTLVTVSS |
| 72 | UC2.3.3 VL | DIQMTQSPSSLSASVGDRVTITCQASQDITNFLNWYQQKPGKAPKLLIYDAST LQTGVPSRFSGSGSGTDFTFTISSLQPEDIATYYCQQSDSYPITFGQGTKVEI K |
| 73 | UC2.3.3-IgG1 heavy chain | QVQLLESGGGLVQPGGSLRLSCAASGFTFSTYAMSWIRQAPGKGLEWVSIISD GGDATVYADSVKGRFTISRDNNRNTLYLQMNSLRAEDTAVYYCARDGTSAAAF DSWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPG |
| 74 | UC2.3.3-IgG1 light chain | DIQMTQSPSSLSASVGDRVTITCQASQDITNFLNWYQQKPGKAPKLLIYDAST LQTGVPSRFSGSGSGTDFTFTISSLQPEDIATYYCQQSDSYPITFGQGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| 75 | UC2.3.7 scFv | QVQLLESGGGLVQPGGSLRLSCAASGFTFSTYAMSWVRQAPGKGLEWVSIISD GGDATFYADSVKGRFTISRDNSKNTLYLQMNSLRAEDTAVYYCARDGTSAAAF DSWGQGTLVTVSSASSGGSTSGSGKPGSGEGSSGSARDIQMTQSPSSLSASVG DRVTITCQASQDITNFLNWYQQKPGKAPKLLIYDASRRRTGVPSRFSGSGSGT DFTFTISSLQPEDIATYYCQQSDSYPITFGQGTKVEIKR |

TABLE 5-continued

SEQUENCE TABLE

| SEQ ID | Description | Sequence |
|---|---|---|
| 76 | UC2.3.7 VHCDR1 (Chothia) | GFTFSTY |
| 77 | UC2.3.7 VHCDR2 (Chothia) | SDGGDA |
| 78 | UC2.3.7 VHCDR3 (Chothia) | DGTSAAAFDS |
| 79 | UC2.3.7 VLCDR1 (Chothia) | QASQDITNFLN |
| 80 | UC2.3.7 VLCDR2 (Chothia) | DASRRRT |
| 81 | UC2.3.7 VLCDR3 (Chothia) | QQSDSYPIT |
| 82 | UC2.3.7 VHCDR1 (Kabat) | TYAMS |
| 83 | UC2.3.7 VHCDR2 (Kabat) | IISDGGDATFYADSVKG |
| 84 | UC2.3.7 VHCDR3 (Kabat) | DGTSAAAFDS |
| 85 | UC2.3.7 VLCDR1 (Kabat) | QASQDITNFLN |
| 86 | UC2.3.7 VLCDR2 (Kabat) | DASRRRT |
| 87 | UC2.3.7 VLCDR3 (Kabat) | QQSDSYPIT |
| 88 | UC2.3.7 VHCDR1 (IMGT) | GFTFSTYA |
| 89 | UC2.3.7 VHCDR2 (IMGT) | ISDGGDAT |
| 90 | UC2.3.7 VHCDR3 (IMGT) | ARDGTSAAAFDS |
| 91 | UC2.3.7 VLCDR1 (IMGT) | QDITNF |
| 92 | UC2.3.7 VLCDR2 (IMGT) | DAS |
| 93 | UC2.3.7 VLCDR3 (IMGT) | QQSDSYPIT |
| 94 | UC2.3.7 VH | QVQLLESGGGLVQPGGSLRLSCAASGFTFSTYAMSWVRQAPGKGLEWVSIISD GGDATFYADSVKGRFTISRDNSKNTLYLQMNSLRAEDTAVYYCARDGTSAAAF DSWGQGTLVTVSS |
| 95 | UC2.3.7 VL | DIQMTQSPSSLSASVGDRVTITCQASQDITNFLNWYQQKPGKAPKLLIYDASR RRTGVPSRFSGSGSGTDFTFTISSLQPEDIATYYCQQSDSYPITFGQGTKVEI K |
| 96 | UC2.3.7-IgG1 heavy chain | QVQLLESGGGLVQPGGSLRLSCAASGFTFSTYAMSWIRQAPGKGLEWVSIISD GGDATVYADSVKGRFTISRDNSKNTLYLQMNSLRAEDTAVYYCARDGTSAAAF DSWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPG |

TABLE 5-continued

SEQUENCE TABLE

| SEQ ID | Description | Sequence |
|---|---|---|
| 97 | UC2.3.7-IgG1 light chain | DIQMTQSPSSLSASVGDRVTITCQASQDITNFLNWYQQKPGKAPKLLIYDASR RRAGVPSRFSGSGSGTDFTFTISSLQPEDIATYYCQQSDSYPITFGQGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| 98 | UC2.3.8 scFv | QVQLLESGGGLVQPGGSLRLSCAASGFTFSTYAMSWIRQAPGKGLEWVSIISD GGDATVYADSVKGRFTISRDNNRNTLYLQMNSLRAEDTAVYYCARDGTSAAAF DSWGQGTLVTVSSASSGGSTSGSGKPGSGEGSSGSARDIQMTQSPSSLSASVG DRVTITCQASQDITNFLNWYQQKPGKAPKLLIYDASRRRAGVPSRFSGSGSGT DFTFTISSLQPEDIATYYCQQSDSYPITFGQGTKVEIKR |
| 99 | UC2.3.8 VHCDR1 (Chothia) | GFTFSTY |
| 100 | UC2.3.8 VHCDR2 (Chothia) | SDGGDA |
| 101 | UC2.3.8 VHCDR3 (Chothia) | DGTSAAAFDS |
| 102 | UC2.3.8 VLCDR1 (Chothia) | QASQDITNFLN |
| 103 | UC2.3.8 VLCDR2 (Chothia) | DASRRRT |
| 104 | UC2.3.8 VLCDR3 (Chothia) | QQSDSYPIT |
| 105 | UC2.3.8 VHCDR1 (Kabat) | TYAMS |
| 106 | UC2.3.8 VHCDR2 (Kabat) | IISDGGDATVYADSVKG |
| 107 | UC2.3.8 VHCDR3 (Kabat) | DGTSAAAFDS |
| 108 | UC2.3.8 VLCDR1 (Kabat) | QASQDITNFLN |
| 109 | UC2.3.8 VLCDR2 (Kabat) | DASRRRT |
| 110 | UC2.3.8 VLCDR3 (Kabat) | QQSDSYPIT |
| 111 | UC2.3.8 VHCDR1 (IMGT) | GFTFSTYA |
| 112 | UC2.3.8 VHCDR2 (IMGT) | ISDGGDAT |
| 113 | UC2.3.8 VHCDR3 (IMGT) | ARDGTSAAAFDS |
| 114 | UC2.3.8 VLCDR1 (IMGT) | QDITNF |
| 115 | UC2.3.8 VLCDR2 (IMGT) | DAS |
| 116 | UC2.3.8 VLCDR3 (IMGT) | QQSDSYPIT |
| 117 | UC2.3.8 VH | QVQLLESGGGLVQPGGSLRLSCAASGFTFSTYAMSWIRQAPGKGLEWVSIISD GGDATVYADSVKGRFTISRDNNRNTLYLQMNSLRAEDTAVYYCARDGTSAAAF DSWGQGTLVTVSS |
| 118 | UC2.3.8VL | DIQMTQSPSSLSASVGDRVTITCQASQDITNFLNWYQQKPGKAPKLLIYDASR RRAGVPSRFSGSGSGTDFTFTISSLQPEDIATYYCQQSDSYPITFGQGTKVEI K |

TABLE 5-continued

SEQUENCE TABLE

| SEQ ID | Description | Sequence |
|---|---|---|
| 119 | UC2.3.8-IgG1 heavy chain | QVQLLESGGGLVQPGGSLRLSCAASGFTFSTYAMSWIRQAPGKGLEWVSIISD GGDATVYADSVKGRFTISRDNNRNTLYLQMNSLRAEDTAVYYCARDGTSAAAF DSWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPG |
| 120 | UC2.3.8-IgG1 light chain | DIQMTQSPSSLSASVGDRVTITCQASQDITNFLNWYQQKPGKAPKLLIYDASR RRAGVPSRFSGSGSGTDFTFTISSLQPEDIATYYCQQSDSYPITFGQGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| 121 | UC2.3.9(S4-2 1D10-1G9-1F12) scFv | QVQLLESGGGLVQPGGSLRLSCAASGFTFSTYAMSWIRQAPGKGLEWVSIISD GGDATVYADSVKGRFTISRDNNRNTLYLQMNSLRAEDTAVYYCARDGTSAAAF DSWGQGTLVTVSSASSGGSTSGSGKPGSGEGSSGSARDIQMTQSPSSLSASVG DRVTITCHASQDITNFLNWYQQKPGKAPKLLIYDASTLQTGVPSRFSGSGSGT DFTFTISSLQPEDIATYYCQQSDSYPITFGQGTKVEIKR |
| 122 | UC2.3.9 VHCDR1 (Chothia) | GFTFSTY |
| 123 | UC2.3.9 VHCDR2 (Chothia) | SDGGDA |
| 124 | UC2.3.9 VHCDR3 (Chothia) | DGTSAAAFDS |
| 125 | UC2.3.9 VLCDR1 (Chothia) | HASQDITNFLN |
| 126 | UC2.3.9 VLCDR2 (Chothia) | DASTLQT |
| 127 | UC2.3.9 VLCDR3 (Chothia) | QQSDSYPIT |
| 128 | UC2.3.9 VHCDR1 (Kabat) | TYAMS |
| 129 | UC2.3.9 VHCDR2 (Kabat) | IISDGGDATVYADSVKG |
| 130 | UC2.3.9 VHCDR3 (Kabat) | DGTSAAAFDS |
| 131 | UC2.3.9 VLCDR1 (Kabat) | HASQDITNFLN |
| 132 | UC2.3.9 VLCDR2 (Kabat) | DASTLQT |
| 133 | UC2.3.9 VLCDR3 (Kabat) | QQSDSYPIT |
| 134 | UC2.3.9 VHCDR1 (IMGT) | GFTFSTYA |
| 135 | UC2.3.9 VHCDR2 (IMGT) | ISDGGDAT |
| 136 | UC2.3.9 VHCDR3 (IMGT) | ARDGTSAAAFDS |
| 137 | UC2.3.9 VLCDR1 (IMGT) | QDITNF |
| 138 | UC2.3.9 VLCDR2 (IMGT) | DAS |
| 139 | UC2.3.9 VLCDR3 (IMGT) | QQSDSYPIT |

TABLE 5-continued

SEQUENCE TABLE

| SEQ ID | Description | Sequence |
|---|---|---|
| 140 | UC2.3.9 VH | QVQLLESGGGLVQPGGSLRLSCAASGFTFSTYAMSWIRQAPGKGLEWVSIISD GGDATVYADSVKGRFTISRDNNRNTLYLQMNSLRAEDTAVYYCARDGTSAAAF DSWGQGTLVTVSS |
| 141 | UC2.3.9 VL | DIQMTQSPSSLSASVGDRVTITCHASQDITNFLNWYQQKPGKAPKLLIYDAST LQTGVPSRFSGSGSGTDFTFTISSLQPEDIATYYCQQSDSYPITFGQGTKVEI K |
| 142 | UC2.3.9-IgG1 heavy chain | QVQLLESGGGLVQPGGSLRLSCAASGFTFSTYAMSWIRQAPGKGLEWVSIISD GGDATVYADSVKGRFTISRDNNRNTLYLQMNSLRAEDTAVYYCARDGTSAAAF DSWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPG |
| 143 | UC2.3.9-IgG1 light chain | DIQMTQSPSSLSASVGDRVTITCHASQDITNFLNWYQQKPGKAPKLLIYDAST LQTGVPSRFSGSGSGTDFTFTISSLQPEDIATYYCQQSDSYPITFGQGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| 144 | UC2.3.10 (S4-2 1D10-1G9-1G2) scFv | QVQLLESGGGLVQPGGSLRLSYAASGFTFSTYAMSWIRQAPGKGLEWVSIISD GGDATVYADSVKGRFTISRDNSKNTLYLQMNSLRAEDTAVYYCARDRTSAAAF DSWGQGTLVTVSSASSGGSTSGSGKPGSGEGSSGSARDIQMTQSPSSLSASVG DRVTITCQASQDITNFLNWYQQKPGKAPKLLIYDASTLQTGVPSRFSGSGSGT DFTFTISSLQPEDIATYYCQQSDSYPITFGQGTKVEIKR |
| 145 | UC2.3.10 VHCDR1 (Chothia) | GFTFSTY |
| 146 | UC2.3.10 VHCDR2 (Chothia) | DGGDA |
| 147 | UC2.3.10 VHCDR3 (Chothia) | DRTSAAAFDS |
| 148 | UC2.3.10 VLCDR1 (Chothia) | QASQDITNFLN |
| 149 | UC2.3.10 VLCDR2 (Chothia) | DASTLQT |
| 150 | UC2.3.10 VLCDR3 (Chothia) | QQSDSYPIT |
| 151 | UC2.3.10 VHCDR1 (Kabat) | TYAMS |
| 152 | UC2.3.10 VHCDR2 (Kabat) | IISDGGDATVYADSVKG |
| 153 | UC2.3.10 VHCDR3 (Kabat) | DRTSAAAFDS |
| 154 | UC2.3.10 VLCDR1 (Kabat) | QASQDITNFLN |
| 155 | UC2.3.10 VLCDR2 (Kabat) | DASTLQT |
| 156 | UC2.3.10 VLCDR3 (Kabat) | QQSDSYPIT |
| 157 | UC2.3.10 VHCDR1 (IMGT) | GFTFSTYA |
| 158 | UC2.3.10 VHCDR2 (IMGT) | ISDGGDAT |

TABLE 5-continued

SEQUENCE TABLE

| SEQ ID | Description | Sequence |
|---|---|---|
| 159 | UC2.3.10 VHCDR3 (IMGT) | ARDRTSAAAFDS |
| 160 | UC2.3.10 VLCDR1 (IMGT) | QDITNF |
| 161 | UC2.3.10 VLCDR2 (IMGT) | DAS |
| 162 | UC2.3.10 VLCDR3 (IMGT) | QQSDSYPIT |
| 163 | UC2.3.10 VH | QVQLLESGGGLVQPGGSLRLSYAASGFTFSTYAMSWIRQAPGKGLEWVSIISD GGDATVYADSVKGRFTISRDNSKNTLYLQMNSLRAEDTAVYYCARDRTSAAAF DSWGQGTLVTVSS |
| 164 | UC2.3.10 VL | DIQMTQSPSSLSASVGDRVTITCQASQDITNFLNWYQQKPGKAPKLLIYDAST LQTGVPSRFSGSGSGTDFTFTISSLQPEDIATYYCQQSDSYPITFGQGTKVEI K |
| 165 | UC2.3.10-IgG1 heavy chain | QVQLLESGGGLVQPGGSLRLSYAASGFTFSTYAMSWIRQAPGKGLEWVSIISD GGDATVYADSVKGRFTISRDNSKNTLYLQMNSLRAEDTAVYYCARDRTSAAAF DSWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPG |
| 166 | UC2.3.10-IgG1 light chain | DIQMTQSPSSLSASVGDRVTITCQASQDITNFLNWYQQKPGKAPKLLIYDAST LQTGVPSRFSGSGSGTDFTFTISSLQPEDIATYYCQQSDSYPITFGQGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| 167 | UC2.3.11 (S4-2 1D10-1G9-1G3) scFv | QVQLLESGGGLVQPGGSLRLSCAVSGFTFSTYAMSWIRQAPGKGLEWVSIISD GGDATVYADSVKGRFTISRDNSKNTLYLQMNSLRAEDTAVYYWARDGTSAAAF DSWGQGTLVTVSSANSGGSTSGSGKPGSGEGSSGSARDIQMTQSPSSLSASVG DRVTITCQASQDITNFLNWYQQKPGKAPKLLIYDASTLQTGVPSRFSGSGSGT DFTFTISSLQPEDIATYYCQQSDSYPITFGQGTKVEIKR |
| 168 | UC2.3.11 VHCDR1 (Chothia) | GFTFSTY |
| 169 | UC2.3.11 VHCDR2 (Chothia) | SDGGDA |
| 170 | UC2.3.11 VHCDR3 (Chothia) | DGTSAAAFDS |
| 171 | UC2.3.11 VLCDR1 (Chothia) | QASQDITNFLN |
| 172 | UC2.3.11 VLCDR2 (Chothia) | DASTLQT |
| 173 | UC2.3.11 VLCDR3 (Chothia) | QQSDSYPIT |
| 174 | UC2.3.11 VHCDR1 (Kabat) | TYAMS |
| 175 | UC2.3.11 VHCDR2 (Kabat) | ISDGGDATVYADSVKG |
| 176 | UC2.3.11 VHCDR3 (Kabat) | DGTSAAAFDS |
| 177 | UC2.3.11 VLCDR1 (Kabat) | QASQDITNFLN |

TABLE 5-continued

SEQUENCE TABLE

| SEQ ID | Description | Sequence |
|---|---|---|
| 178 | UC2.3.11 VLCDR2 (Kabat) | DASTLQT |
| 179 | UC2.3.11 VLCDR3 (Kabat) | QQSDSYPIT |
| 180 | UC2.3.11 VHCDR1 (IMGT) | GFTFSTYA |
| 181 | UC2.3.11 VHCDR2 (IMGT) | ISDGGDAT |
| 182 | UC2.3.11 VHCDR3 (IMGT) | ARDGTSAAAFDS |
| 183 | UC2.3.11 VLCDR1 (IMGT) | QDITNF |
| 184 | UC2.3.11 VLCDR2 (IMGT) | DAS |
| 185 | UC2.3.11 VLCDR3 (IMGT) | QQSDSYPIT |
| 186 | UC2.3.11 VH | QVQLLESGGGLVQPGGSLRLSCAVSGFTFSTYAMSWIRQAPGKGLEWVSIISD GGDATVYADSVKGRFTISRDNSKNTLYLQMNSLRAEDTAVYYWARDGTSAAAF DSWGQGTLVTVSS |
| 187 | UC2.3.11 VL | DIQMTQSPSSLSASVGDRVTITCQASQDITNFLNWYQQKPGKAPKLLIYDAST LQTGVPSRFSGSGSGTDFTFTISSLQPEDIATYYCQQSDSYPITFGQGTKVEI K |
| 188 | UC2.3.11-IgG1 heavy chain | QVQLLESGGGLVQPGGSLRLSCAVSGFTFSTYAMSWIRQAPGKGLEWVSIISD GGDATVYADSVKGRFTISRDNSKNTLYLQMNSLRAEDTAVYYWARDGTSAAAF DSWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPG |
| 189 | UC2.3.11-IgG1 light chain | DIQMTQSPSSLSASVGDRVTITCQASQDITNFLNWYQQKPGKAPKLLIYDAST LQTGVPSRFSGSGSGTDFTFTISSLQPEDIATYYCQQSDSYPITFGQGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| 190 | UC2.3.12 (S4-2 1D10-1G9-1H1) scFv | QVQLLESGGGLVQPGDSLRLSCAASGFTFSTYAMSWIRQAPGKGLEWVSIISD GGDATVYADSVKGRFTISRDNNRNTLYLQMNSLRAEDTAVYYCARDGTSAAAF DSWGQGTLVTVSSASSGGSTSGSGKPGSGEGSSGSARDIQMTQSPSSLSASVG DRVTITCQASQDITNFLNWYQQKPGKAPKLLIYDASTLQTGVPSRFSGSGSGT NFTFTISSLQPEDIATYYCQQSDSYPITFGQGTKVEIKR |
| 191 | UC2.3.12 VHCDR1 (Chothia) | GFTFSTY |
| 192 | UC2.3.12 VHCDR2 (Chothia) | SDGGDA |
| 193 | UC2.3.12 VHCDR3 (Chothia) | DGTSAAAFDS |
| 194 | UC2.3.12 VLCDR1 (Chothia) | QASQDITNFLN |
| 195 | UC2.3.12 VLCDR2 (Chothia) | DASTLQT |
| 196 | UC2.3.12 VLCDR3 (Chothia) | QQSDSYPIT |

TABLE 5-continued

SEQUENCE TABLE

| SEQ ID | Description | Sequence |
|---|---|---|
| 197 | UC2.3.12 VHCDR1 (Kabat) | TYAMS |
| 198 | UC2.3.12 VHCDR2 (Kabat) | IISDGGDATVYADSVKG |
| 199 | UC2.3.12 VHCDR3 (Kabat) | DGTSAAAFDS |
| 200 | UC2.3.12 VLCDR1 (Kabat) | QASQDITNFLN |
| 201 | UC2.3.12 VLCDR2 (Kabat) | DASTLQT |
| 202 | UC2.3.12 VLCDR3 (Kabat) | QQSDSYPIT |
| 203 | UC2.3.12 VHCDR1 (IMGT) | GFTFSTYA |
| 204 | UC2.3.12 VHCDR2 (IMGT) | ISDGGDAT |
| 205 | UC2.3.12 VHCDR3 (IMGT) | ARDGTSAAAFDS |
| 206 | UC2.3.12 VLCDR1 (IMGT) | QDITNF |
| 207 | UC2.3.12 VLCDR2 (IMGT) | DAS |
| 208 | UC2.3.12 VLCDR3 (IMGT) | QQSDSYPIT |
| 209 | UC2.3.12 VH | QVQLLESGGGLVQPGDSLRLSCAASGFTFSTYAMSWIRQAPGKGLEWVSIISD GGDATVYADSVKGRFTISRDNNRNTLYLQMNSLRAEDTAVYYCARDGTSAAAF DSWGQGTLVTVSS |
| 210 | UC2.3.12 VL | DIQMTQSPSSLSASVGDRVTITCQASQDITNFLNWYQQKPGKAPKLLIYDAST LQTGVPSRFSGSGSGTNFTFTISSLQPEDIATYYCQQSDSYPITFGQGTKVEI K |
| 211 | UC2.3.12-IgG1 heavy chain | QVQLLESGGGLVQPGDSLRLSCAASGFTFSTYAMSWIRQAPGKGLEWVSIISD GGDATVYADSVKGRFTISRDNNRNTLYLQMNSLRAEDTAVYYCARDGTSAAAF DSWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPG |
| 212 | UC2.3.12-IgG1 light chain | DIQMTQSPSSLSASVGDRVTITCQASQDITNFLNWYQQKPGKAPKLLIYDAST LQTGVPSRFSGSGSGTNFTFTISSLQPEDIATYYCQQSDSYPITFGQGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| 213 | UC2.3.13 (S4-2 1D10-1G9-1G11) scFv | QVQLLESVGGLVQPGGSLRLSCAVSGFTFSTYAMSWIRQAPGKGLEWVSIISD GGDVTVYADSVKGRFTISRDNSKNTLYLQMNSLRAEDTAVYYCARDRTSAAAF DSWGQGTLVSDSSASSGGSTSGSGKPGSGEGSSGSSRDIQMTQSPSSLSASVG DRVTITCQASQDITNFLNWYQQKPGKAPKLLIYDASTLQTGVPSRFSGSGSGT DFNFTISSLQPEDIATYYCQQSDSYPITFGQGTKVEIKR |
| 214 | UC2.3.13 VHCDR1 (Chothia) | GFTFSTY |
| 215 | UC2.3.13 VHCDR2 (Chothia) | SDGGDV |

TABLE 5-continued

SEQUENCE TABLE

| SEQ ID | Description | Sequence |
|---|---|---|
| 216 | UC2.3.13 VHCDR3 (Chothia) | DRTSAAAFDS |
| 217 | UC2.3.13 VLCDR1 (Chothia) | QASQDITNFLN |
| 218 | UC2.3.13 VLCDR2 (Chothia) | DASTLQT |
| 219 | UC2.3.13 VLCDR3 (Chothia) | QQSDSYPIT |
| 220 | UC2.3.13 VHCDR1 (Kabat) | TYAMS |
| 221 | UC2.3.13 VHCDR2 (Kabat) | IISDGGDVTVYADSVKG |
| 222 | UC2.3.13 VHCDR3 (Kabat) | DRTSAAAFDS |
| 223 | UC2.3.13 VLCDR1 (Kabat) | QASQDITNFLN |
| 224 | UC2.3.13 VLCDR2 (Kabat) | DASTLQT |
| 225 | UC2.3.13 VLCDR3 (Kabat) | QQSDSYPIT |
| 226 | UC2.3.13 VHCDR1 (IMGT) | GFTFSTYA |
| 227 | UC2.3.13 VHCDR2 (IMGT) | ISDGGDVT |
| 228 | UC2.3.13 VHCDR3 (IMGT) | ARDRTSAAAFDS |
| 229 | UC2.3.13 VLCDR1 (IMGT) | QDITNF |
| 230 | UC2.3.13 VLCDR2 (IMGT) | DAS |
| 231 | UC2.3.13 VLCDR3 (IMGT) | QQSDSYPIT |
| 232 | UC2.3.13 VH | QVQLLESVGGLVQPGGSLRLSCAVSGFTFSTYAMSWIRQAPGKGLEWVSIISD GGDVTVYADSVKGRFTISRDNSKNTLYLQMNSLRAEDTAVYYCARDRTSAAAF DSWGQGTLVSDSS |
| 233 | UC2.3.13 VL | DIQMTQSPSSLSASVGDRVTITCQASQDITNFLNWYQQKPGKAPKLLIYDAST LQTGVPSRFSGSGSGTDFNFTISSLQPEDIATYYCQQSDSYPITFGQGTKVEI K |
| 234 | UC2.3.13-IgG1 heavy chain | QVQLLESVGGLVQPGGSLRLSCAVSGFTFSTYAMSWIRQAPGKGLEWVSIISD GGDVTVYADSVKGRFTISRDNSKNTLYLQMNSLRAEDTAVYYCARDRTSAAAF DSWGQGTLVSDSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPG |
| 235 | UC2.3.13-IgG1 light chain | DIQMTQSPSSLSASVGDRVTITCQASQDITNFLNWYQQKPGKAPKLLIYDAST LQTGVPSRFSGSGSGTDFNFTISSLQPEDIATYYCQQSDSYPITFGQGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |

TABLE 5-continued

SEQUENCE TABLE

| SEQ ID | Description | Sequence |
|---|---|---|
| 236 | UC2.3.14 (S4-2 1D10-1G9-1H11) scFv | QVQLLESGGGLVQPGGSLRLSYAASGFTFSTYAMSWIRQAPRKGLEWVSIISD GGDATVYADSVKGRFTISRDNSKNTLYLQMNSLRAEDTAVYYCARDRTSAAAF DSWGQGTLVTVSSASSGGSTSGSGKPGSGEGSSGSARDIQMTQSPSSLSASVG DRVTITCQASQDITNFLNWYQQKPGKAPKLLIYDASTLQTGVPSRFSGSGSGT DFTFTISSLQPEDIATYYCQQSDSYPITFGQGTKVEIKR |
| 237 | UC2.3.14 VHCDR1 (Chothia) | GFTFSTY |
| 238 | UC2.3.14 VHCDR2 (Chothia) | SDGGDA |
| 239 | UC2.3.14 VHCDR3 (Chothia) | DRTSAAAFDS |
| 240 | UC2.3.14 VLCDR1 (Chothia) | QASQDITNFLN |
| 241 | UC2.3.14 VLCDR2 (Chothia) | DASTLQT |
| 242 | UC2.3.14 VLCDR3 (Chothia) | QQSDSYPIT |
| 243 | UC2.3.14 VHCDR1 (Kabat) | TYAMS |
| 244 | UC2.3.14 VHCDR2 (Kabat) | IISDGGDATVYADSVKG |
| 245 | UC2.3.14 VHCDR3 (Kabat) | DRTSAAAFDS |
| 246 | UC2.3.14 VLCDR1 (Kabat) | QASQDITNFLN |
| 247 | UC2.3.14 VLCDR2 (Kabat) | DASTLQT |
| 248 | UC2.3.14 VLCDR3 (Kabat) | QQSDSYPIT |
| 249 | UC2.3.14 VHCDR1 (IMGT) | GFTFSTYA |
| 250 | UC2.3.14 VHCDR2 (IMGT) | ISDGGDAT |
| 251 | UC2.3.14 VHCDR3 (IMGT) | ARDRTSAAAFDS |
| 252 | UC2.3.14 VLCDR1 (IMGT) | QDITNF |
| 253 | UC2.3.14 VLCDR2 (IMGT) | DAS |
| 254 | UC2.3.14 VLCDR3 (IMGT) | QQSDSYPIT |
| 255 | UC2.3.14 VH | QVQLLESGGGLVQPGGSLRLSYAASGFTFSTYAMSWIRQAPRKGLEWVSIISD GGDATVYADSVKGRFTISRDNSKNTLYLQMNSLRAEDTAVYYCARDRTSAAAF DSWGQGTLVTVSS |
| 256 | UC2.3.14 VL | DIQMTQSPSSLSASVGDRVTITCQASQDITNFLNWYQQKPGKAPKLLIYDAST LQTGVPSRFSGSGSGTDFTFTISSLQPEDIATYYCQQSDSYPITFGQGTKVEI K |
| 257 | UC2.3.14-IgG1 heavy chain | QVQLLESGGGLVQPGGSLRLSYAASGFTFSTYAMSWIRQAPRKGLEWVSIISD GGDATVYADSVKGRFTISRDNSKNTLYLQMNSLRAEDTAVYYCARDRTSAAAF DSWGQGTLVTVSSASTKGPSVFPLAPSSKSTSGGTAALGCLVKDYFPEPVTVS |

TABLE 5-continued

SEQUENCE TABLE

| SEQ ID | Description | Sequence |
|---|---|---|
| | | WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPG |
| 258 | UC2.3.14-IgG1 light chain | DIQMTQSPSSLSASVGDRVTITCQASQDITNFLNWYQQKPGKAPKLLIYDAST LQTGVPSRFSGSGSGTDFTFTISSLQPEDIATYYCQQSDSYPITFGQGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| 259 | UC2.3.15 (S4-2 1D10-1G9-1H12) scFv | QVQLLESGGGLVQPGGSLRLSCAVSGFTFSTYAMSWIRQAPGKGLEWVSIISD GGDATVYADSVKGRFTISRDNSKNTLYLQMNSLRAEDTAVYYWARDGTSAAAF DSWGQGTLVTVSSANSGGSTSGSGKPGSGEGSSGSARDIQMTQSPSSLSASVG DRVTITCQASQDITNFLNWYQQKPGKAPKLLIYDASTLQTGVPSRFSGSGSGT DFTFTISSLQPEDIATYYCQQSDSYPITFGQGTKVEIKR |
| 260 | UC2.3.15 VHCDR1 (Chothia) | GFTFSTY |
| 261 | UC2.3.15 VHCDR2 (Chothia) | SDGGDA |
| 262 | UC2.3.15 VHCDR3 (Chothia) | DGTSAAAFDS |
| 263 | UC2.3.15 VLCDR1 (Chothia) | QASQDITNFLN |
| 264 | UC2.3.15 VLCDR2 (Chothia) | DASTLQT |
| 265 | UC2.3.15 VLCDR3 (Chothia) | QQSDSYPIT |
| 266 | UC2.3.15 VHCDR1 (Kabat) | TYAMS |
| 267 | UC2.3.15 VHCDR2 (Kabat) | IISDGGDATVYADSVKG |
| 268 | UC2.3.15 VHCDR3 (Kabat) | DGTSAAAFDS |
| 269 | UC2.3.15 VLCDR1 (Kabat) | QASQDITNFLN |
| 270 | UC2.3.15 VLCDR2 (Kabat) | DASTLQT |
| 271 | UC2.3.15 VLCDR3 (Kabat) | QQSDSYPIT |
| 272 | UC2.3.15 VHCDR1 (IMGT) | GFTFSTYA |
| 273 | UC2.3.15 VHCDR2 (IMGT) | ISDGGDAT |
| 274 | UC2.3.15 VHCDR3 (IMGT) | ARDGTSAAAFDS |
| 275 | UC2.3.15 VLCDR1 (IMGT) | QDITNF |
| 276 | UC2.3.15 VLCDR2 (IMGT) | DAS |
| 277 | UC2.3.15 VLCDR3 (IMGT) | QQSDSYPIT |

TABLE 5-continued

SEQUENCE TABLE

| SEQ ID | Description | Sequence |
|---|---|---|
| 278 | UC2.3.15 VH | QVQLLESGGGLVQPGGSLRLSCAVSGFTFSTYAMSWIRQAPGKGLEWVSIISD GGDATVYADSVKGRFTISRDNSKNTLYLQMNSLRAEDTAVYYWARDGTSAAAF DSWGQGTLVTVSS |
| 279 | UC2.3.15 VL | DIQMTQSPSSLSASVGDRVTITCQASQDITNFLNWYQQKPGKAPKLLIYDAST LQTGVPSRFSGSGSGTDFTFTISSLQPEDIATYYCQQSDSYPITFGQGTKVEI K |
| 280 | UC2.3.15-IgG1 heavy chain | QVQLLESGGGLVQPGGSLRLSCAVSGFTFSTYAMSWIRQAPGKGLEWVSIISD GGDATVYADSVKGRFTISRDNSKNTLYLQMNSLRAEDTAVYYWARDGTSAAAF DSWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPG |
| 281 | UC2.3.15-IgG1 light chain | DIQMTQSPSSLSASVGDRVTITCQASQDITNFLNWYQQKPGKAPKLLIYDAST LQTGVPSRFSGSGSGTDFTFTISSLQPEDIATYYCQQSDSYPITFGQGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| 282 | UC1 (S4-2 1B5) scFv | QVQLLESGGGLVQPGGSLRLSCAASGFSFTSYAMTWVRQAPGKGLEWVSGISG GGAATFYADSVKGRFTISRDNSKNTLYLQMNSLRAEDTAVYYCARQSQYVGGF DYWGQGTLVTVSSASSGGSTSGSGKPGSGEGSSGSARQSVLTQPPSVSGAPGQ RVTISCTGSSSNIGAGYGVHWYQQLPGTAPKLLIYGNTNRPSGVPDRFSGFKS GTSASLAITGLQAEDEADYYCQSYDSSLSGWVFGGGTKLTVLG |
| 283 | UC1 VHCDR1 (Chothia) | GFSFTSY |
| 284 | UC1 VHCDR2 (Chothia) | SGGGAA |
| 285 | UC1 VHCDR3 (Chothia) | QSQYVGGFDY |
| 286 | UC1 VLCDR1 (Chothia) | TGSSSNIGAGYGVH |
| 287 | UC1 VLCDR2 (Chothia) | GNTNRPS |
| 288 | UC1 VLCDR3 (Chothia) | QSYDSSLSGWV |
| 289 | UC1 VHCDR1 (Kabat) | SYAMT |
| 290 | UC1 VHCDR2 (Kabat) | GISGGGAATFYADSVKG |
| 291 | UC1 VHCDR3 (Kabat) | QSQYVGGFDY |
| 292 | UC1 VLCDR1 (Kabat) | TGSSSNIGAGYGVH |
| 293 | UC1 VLCDR2 (Kabat) | GNTNRPS |
| 294 | UC1 VLCDR3 (Kabat) | QSYDSSLSGWV |
| 295 | UC1 VHCDR1 (IMGT) | GFSFTSYA |
| 296 | UC1 VHCDR2 (IMGT) | ISGGGAAT |
| 297 | UC1 VHCDR3 (IMGT) | ARQSQYVGGFDY |

TABLE 5-continued

SEQUENCE TABLE

| SEQ ID | Description | Sequence |
| --- | --- | --- |
| 298 | UC1 VLCDR1 (IMGT) | SSNIGAGYG |
| 299 | UC1 VLCDR2 (IMGT) | GNT |
| 300 | UC1 VLCDR3 (IMGT) | QSYDSSLSGWV |
| 301 | UC1 VH | QVQLLESGGGLVQPGGSLRLSCAASGFSFTSYAMTWVRQAPGKGLEWVSGISGGGAATFYADSVKGRFTISRDNSKNTLYLQMNSLRAEDTAVYYCARQSQYVGGFDYWGQGTLVTVSS |
| 302 | UC1 VL | QSVLTQPPSVSGAPGQRVTISCTGSSSNIGAGYGVHWYQQLPGTAPKLLIYGNTNRPSGVPDRFSGFKSGTSASLAITGLQAEDEADYYCQSYDSSLSGWVFGGGTKLTVL |
| 303 | UC1.1 (S4-2 1B5-1D9) scFv | QVQLLESGGGLVQPGGSLRLSCAASGFSFTSYAMTWVRQAPGKGLEWVSGISGGGAATFYADSVKGRFTISRDNSKNTLYLQMNSLRAEDTAVYYCARQSQYVGGFDYWGQGTLVTVSSASSGGSTSGSGKPGSGEGSSGSARQSVLTQPPSVSGAPGQRVTISCTGSSSNIGAGYGVHWYQQLPGTAPKLLIHGNTNRPSGVPDRFSGFKSGTSASLAITGLQAEDEADYYCQSYDSSLSGWVFGGGTKLTVLG |
| 304 | UC1.1 VHCDR1 (Chothia) | GFSFTSY |
| 305 | UC1.1 VHCDR2 (Chothia) | SGGGAA |
| 306 | UC1.1 VHCDR3 (Chothia) | QSQYVGGFDY |
| 307 | UC1.1 VLCDR1 (Chothia) | TGSSSNIGAGYGVH |
| 308 | UC1.1 VLCDR2 (Chothia) | GNTNRPS |
| 309 | UC1.1 VLCDR3 (Chothia) | QSYDSSLSGWV |
| 310 | UC1.1 VHCDR1 (Kabat) | SYAMT |
| 311 | UC1.1 VHCDR2 (Kabat) | GISGGGAATFYADSVKG |
| 312 | UC1.1 VHCDR3 (Kabat) | QSQYVGGFDY |
| 313 | UC1.1 VLCDR1 (Kabat) | TGSSSNIGAGYGVH |
| 314 | UC1.1 VLCDR2 (Kabat) | GNTNRPS |
| 315 | UC1.1 VLCDR3 (Kabat) | QSYDSSLSGWV |
| 316 | UC1.1 VHCDR1 (IMGT) | GFSFTSYA |
| 317 | UC1.1 VHCDR2 (IMGT) | ISGGGAAT |
| 318 | UC1.1 VHCDR3 (IMGT) | ARQSQYVGGFDY |
| 319 | UC1.1 VLCDR1 (IMGT) | SSNIGAGYG |
| 320 | UC1.1 VLCDR2 (IMGT) | GNT |

TABLE 5-continued

SEQUENCE TABLE

| SEQ ID | Description | Sequence |
|---|---|---|
| 321 | UC1.1 VLCDR3 (IMGT) | QSYDSSLSGWV |
| 322 | UC1.1 VH | QVQLLESGGGLVQPGGSLRLSCAASGFSFTSYAMTWVRQAPGKGLEWVSGISGGGAATFYADSVKGRFTISRDNSKNTLYLQMNSLRAEDTAVYYCARQSQYVGGFDYWGQGTLVTVSS |
| 323 | UC1.1 VL | QSVLTQPPSVSGAPGQRVTISCTGSSSNIGAGYGVHWYQQLPGTAPKLLIHGNTNRPSGVPDRFSGFKSGTSASLAITGLQAEDEADYYCQSYDSSLSGWVFGGGTKLTVL |
| 324 | UC1.2 (S4-2 IB5-1A5) scFv | QVQLLESGGGLVQPGGSLRLSCAASGFSFTSYAMTWVRQAPGKGLEWVSGISGGGAATFYADSVKGRFTI SRDNSKNTLYLQMNSLRAEDTAVYYCARQSQYVGGFDYWGQGTLVTVSSASSGGSTSGSGKPDSGEGSSGSARQSVLTQPPSVSGAPGQRVTISCTGSSSNFGAGYGVHWYQQLPGTAPKLLIHGNTNRPSGVPDRFSGFKSGTSASLAITGLQAEDEADYYCQSYDSSLSGWVFGGGTKLTVLG |
| 325 | UC1.2 VHCDR1 (Chothia) | GFSFTSY |
| 326 | UC1.2 VHCDR2 (Chothia) | SGGGAA |
| 327 | UC1.2 VHCDR3 (Chothia) | QSQYVGGFDY |
| 328 | UC1.2 VLCDR1 (Chothia) | TGSSSNFGAGYGVH |
| 329 | UC1.2 VLCDR2 (Chothia) | GNTNRPS |
| 330 | UC1.2 VLCDR3 (Chothia) | QSYDSSLSGWV |
| 331 | UC1.2 VHCDR1 (Kabat) | SYAMT |
| 332 | UC1.2 VHCDR2 (Kabat) | GISGGGAATFYADSVKG |
| 333 | UC1.2 VHCDR3 (Kabat) | QSQYVGGFDY |
| 334 | UC1.2 VLCDR1 (Kabat) | TGSSSNFGAGYGVH |
| 335 | UC1.2 VLCDR2 (Kabat) | GNTNRPS |
| 336 | UC1.2 VLCDR3 (Kabat) | QSYDSSLSGWV |
| 337 | UC1.2 VHCDR1 (IMGT) | GFSFTSYA |
| 338 | UC1.2 VHCDR2 (IMGT) | ISGGGAAT |
| 339 | UC1.2 VHCDR3 (IMGT) | ARQSQYVGGFDY |
| 340 | UC1.2 VLCDR1 (IMGT) | SSNFGAGYG |
| 341 | UC1.2 VLCDR2 (IMGT) | GNT |
| 342 | UC1.2 VLCDR3 (IMGT) | QSYDSSLSGWV |
| 343 | UC1.2 VH | QVQLLESGGGLVQPGGSLRLSCAASGFSFTSYAMTWVRQAPGKGLEWVSGISGGGAATFYADSVKGRFTISRDNSKNTLYLQMNSLRAEDTAVYYCARQSQYVGGFDYWGQGTLVTVSS |

TABLE 5-continued

SEQUENCE TABLE

| SEQ ID | Description | Sequence |
|---|---|---|
| 344 | UC1.2 VL | QSVLTQPPSVSGAPGQRVTISCTGSSSNFGAGYGVHWYQQLPGTAPKLLIHGNTNRPSGVPDRFSGFKSGTSASLAITGLQAEDEADYYCQSYDSSLSGWVFGGGTKLTVL |
| 345 | UC1.3 (S4-2 1B5-1B3) scFv | QVQLLESGGGLVQPGGSLRLSCAASGFSFTSYAMTWVRQAPGKGLEWVSGISGDGAATFYADSVKGRFTISRDNSKNTLYLQMNSLRAEDTAVYYCARQSQYVGGFDYWGQGTLVTVSSASSGGSTSGSGKPDSGEGSSGSARQSVLTQPPSVSGAPGQRVTISCTGSSSNFGAGYGVHWYQQLPGTAPKLLIHGNTNRPSGVPDRFSGFKSGTSASLAITGLQAEDEADYYCQSYDSSLSGWVFGGGTKLTVLG |
| 346 | UC1.3 VHCDR1 (Chothia) | GFSFTSY |
| 347 | UC1.3 VHCDR2 (Chothia) | SGDGAA |
| 348 | UC1.3 VHCDR3 (Chothia) | QSQYVGGFDY |
| 349 | UC1.3 VLCDR1 (Chothia) | TGSSSNFGAGYGVH |
| 350 | UC1.3 VLCDR2 (Chothia) | GNTNRPS |
| 351 | UC1.3 VLCDR3 (Chothia) | QSYDSSLSGWV |
| 352 | UC1.3 VHCDR1 (Kabat) | SYAMT |
| 353 | UC1.3 VHCDR2 (Kabat) | GISGDGAATFYADSVKG |
| 354 | UC1.3 VHCDR3 (Kabat) | QSQYVGGFDY |
| 355 | UC1.3 VLCDR1 (Kabat) | TGSSSNFGAGYGVH |
| 356 | UC1.3 VLCDR2 (Kabat) | GNTNRPS |
| 357 | UC1.3 VLCDR3 (Kabat) | QSYDSSLSGWV |
| 358 | UC1.3 VHCDR1 (IMGT) | GFSFTSYA |
| 359 | UC1.3 VHCDR2 (IMGT) | ISGDGAAT |
| 360 | UC1.3 VHCDR3 (IMGT) | ARQSQYVGGFDY |
| 361 | UC1.3 VLCDR1 (IMGT) | SSNFGAGYG |
| 362 | UC1.3 VLCDR2 (IMGT) | GNT |
| 363 | UC1.3 VLCDR3 (IMGT) | QSYDSSLSGWV |
| 364 | UC1.3 VH | QVQLLESGGGLVQPGGSLRLSCAASGFSFTSYAMTWVRQAPGKGLEWVSGISGDGAATFYADSVKGRFTISRDNSKNTLYLQMNSLRAEDTAVYYCARQSQYVGGFDYWGQGTLVTVSS |
| 365 | UC1.3 VL | QSVLTQPPSVSGAPGQRVTISCTGSSSNFGAGYGVHWYQQLPGTAPKLLIHGNTNRPSGVPDRFSGFKSGTSASLAITGLQAEDEADYYCQSYDSSLSGWVFGGGTKLTVL |

TABLE 5-continued

SEQUENCE TABLE

| SEQ ID | Description | Sequence |
|---|---|---|
| 366 | UC3 (S4-2 1E5) scFv | QVQLLESGGGLVQPGGSLRLSCAASGFSFSSYAMSWVRQAPGKGLEWVSGISA GGGETFYADSVKGRFTISRDNSKNTLYLQMNSLRAEDTAVYYCARVHPISYGF DIWGQGTLVTVSSASSGGSTSGSGKPGSGEGSSGSARDIQMTQSPSSLSASVG DRVTITCQASQDIKKYLNWYQQKPGKAPKLLIYDASTLQTGVPSRFSGSGSGT DFTFTISSLQPEDIATYYCQQSDNTPVTFGQGTKVEIKR |
| 367 | UC3 VHCDR1 (Chothia) | GFSFSSY |
| 368 | UC3 VHCDR2 (Chothia) | SAGGGE |
| 369 | UC3 VHCDR3 (Chothia) | VHPISYGFDI |
| 370 | UC3 VLCDR1 (Chothia) | QASQDIKKYLN |
| 371 | UC3 VLCDR2 (Chothia) | DASTLQT |
| 372 | UC3 VLCDR3 (Chothia) | QQSDNTPVT |
| 373 | UC3 VHCDR1 (Kabat) | SYAMS |
| 374 | UC3 VHCDR2 (Kabat) | GISAGGGETFYADSVKG |
| 375 | UC3 VHCDR3 (Kabat) | VHPISYGFDI |
| 376 | UC3 VLCDR1 (Kabat) | QASQDIKKYLN |
| 377 | UC3 VLCDR2 (Kabat) | DASTLQT |
| 378 | UC3 VLCDR3 (Kabat) | QQSDNTPVT |
| 379 | UC3 VHCDR1 (IMGT) | GFSFSSYA |
| 380 | UC3 VHCDR2 (IMGT) | ISAGGGET |
| 381 | UC3 VHCDR3 (IMGT) | ARVHPISYGFDI |
| 382 | UC3 VLCDR1 (IMGT) | QDIKKY |
| 383 | UC3 VLCDR2 (IMGT) | DAS |
| 384 | UC3 VLCDR3 (IMGT) | QQSDNTPVT |
| 385 | UC3 VH | QVQLLESGGGLVQPGGSLRLSCAASGFSFSSYAMSWVRQAPGKGLEWVSGISA GGGETFYADSVKGRFTISRDNSKNTLYLQMNSLRAEDTAVYYCARVHPISYGF DIWGQGTLVTVSS |
| 386 | UC3 VL | DIQMTQSPSSLSASVGDRVTITCQASQDIKKYLNWYQQKPGKAPKLLIYDAST LQTGVPSRFSGSGSGTDFTFTISSLQPEDIATYYCQQSDNTPVTFGQGTKVEI K |
| 387 | UC4 (7-2E8) scFv | QVQLVESGGGVVQPGRSLRLSCAASGFTFSSYAIHWVRQAPGKGLEWVAVISS DGGYKNYADSVKGRFTISRDNSKNTLYLQMDSLRAEDTAVYYCAKDRQIGDLG QGTLVTVSSGGGGSGGGGSGGGGSDVVMTQSPSFLSASVGDRVTITCRASHGI SNYLAWYQQKPGKAPKLLIYAASTLQSGVPSRFSGSGSGTEFTLTISSLQPDD FATYYCQQYNTYRTFGQGTKVEIKR |

TABLE 5-continued

SEQUENCE TABLE

| SEQ ID | Description | Sequence |
|---|---|---|
| 388 | UC4 VHCDR1 (Chothia) | GFTFSSY |
| 389 | UC4 VHCDR2 (Chothia) | SSDGGY |
| 390 | UC4 VHCDR3 (Chothia) | DRQIGD |
| 391 | UC4 VLCDR1 (Chothia) | RASHGISNYLA |
| 392 | UC4 VLCDR2 (Chothia) | AASTLQS |
| 393 | UC4 VLCDR3 (Chothia) | QQYNTYRT |
| 394 | UC4 VHCDR1 (Kabat) | SYAIH |
| 395 | UC4 VHCDR2 (Kabat) | VISSDGGYKNYADSVKG |
| 396 | UC4 VHCDR3 (Kabat) | DRQIGD |
| 397 | UC4 VLCDR1 (Kabat) | RASHGISNYLA |
| 398 | UC4 VLCDR2 (Kabat) | AASTLQS |
| 399 | UC4 VLCDR3 (Kabat) | QQYNTYRT |
| 400 | UC4 VHCDR1 (IMGT) | GFTFSSYA |
| 401 | UC4 VHCDR2 (IMGT) | ISSDGGYK |
| 402 | UC4 VHCDR3 (IMGT) | AKDRQIGD |
| 403 | UC4 VLCDR1 (IMGT) | HGISNY |
| 404 | UC4 VLCDR2 (IMGT) | AAS |
| 405 | UC4 VLCDR3 (IMGT) | QQYNTYRT |
| 406 | UC4 VH | QVQLVESGGGVVQPGRSLRLSCAASGFTFSSYAIHWVRQAPGKGLEWVAVISS DGGYKNYADSVKGRFTISRDNSKNTLYLQMDSLRAEDTAVYYCAKDRQIGDLG QGTLVTVSS |
| 407 | UC4 VL | DVVMTQSPSFLSASVGDRVTITCRASHGISNYLAWYQQKPGKAPKLLIYAAST LQSGVPSRFSGSGSGTEFTLTISSLQPDDFATYYCQQYNTYRTFGQGTKVEIK |
| 408 | UC5 (8-2A10) scFv | QVQLLESGGGLVQPGGSLRLSCAASGFTFNTYAMTWVRQAPGKGLEWVSAISD SGGDTFYADSVKGRFTISRDNSKNTLYLQMNSLRAEDTAVYYCARDGTYAARF DYWGQGTLVTVSSASSGGSTSGSGKPGSGEGSSGSARDIQMTQSPSSLSASVG DRVTITCQASQDISNYLNWYQQKPGKAPKLLIYDASTLETGVPSRFSGSGSGT DFTFTISSLQPEDIATYYCQQSDSFPITFGQGTKVEIKR |
| 409 | UC5 VHCDR1 (Chothia) | GFTFNTY |
| 410 | UC5 VHCDR2 (Chothia) | SDSGGD |
| 411 | UC5 VHCDR3 (Chothia) | DGTYAARFDY |

TABLE 5-continued

SEQUENCE TABLE

| SEQ ID | Description | Sequence |
|---|---|---|
| 412 | UC5 VLCDR1 (Chothia) | QASQDISNYLN |
| 413 | UC5 VLCDR2 (Chothia) | DASTLET |
| 414 | UC5 VLCDR3 (Chothia) | QQSDSFPIT |
| 415 | UC5 VHCDR1 (Kabat) | TYAMT |
| 416 | UC5 VHCDR2 (Kabat) | AISDSGGDTFYADSVKG |
| 417 | UC5 VHCDR3 (Kabat) | DGTYAARFDY |
| 418 | UC5 VLCDR1 (Kabat) | QASQDISNYLN |
| 419 | UC5 VLCDR2 (Kabat) | DASTLET |
| 420 | UC5 VLCDR3 (Kabat) | QQSDSFPIT |
| 421 | UC5 VHCDR1 (IMGT) | GFTFNTYA |
| 422 | UC5 VHCDR2 (IMGT) | ISDSGGDT |
| 423 | UC5 VHCDR3 (IMGT) | ARDGTYAARFDY |
| 424 | UC5 VLCDR1 (IMGT) | QDISNY |
| 425 | UC5 VLCDR2 (IMGT) | DAS |
| 426 | UC5 VLCDR3 (IMGT) | QQSDSFPIT |
| 427 | UC5 VH | QVQLLESGGGLVQPGGSLRLSCAASGFTFNTYAMTWVRQAPGKGLEWVSAISD SGGDTFYADSVKGRFTISRDNSKNTLYLQMNSLRAEDTAVYYCARDGTYAARF DYWGQGTLVTVSS |
| 428 | UC5 VL | DIQMTQSPSSLSASVGDRVTITCQASQDISNYLNWYQQKPGKAPKLLIYDAST LETGVPSRFSGSGSGTDFTFTISSLQPEDIATYYCQQSDSFPITFGQGTKVEI K |
| 429 | UC6 (9-1A6) scFv | QVQLVQSGAEVKKPGSSVKVSCKASGDSFNNFGISWVRQAPGQGLEWMGGIVP VLGIATYAQKFQGRVTITADESTSTAYMELSSLRSEDTAVYYCARGSAWYDGS FQYWGQGTLVTVSSASSGGSTSGSGKPGSGEGSSGSAREIVLTQSPGTLSLSP GERATLSCRASQSVSSTFLAWYQQKPGQAPRLLIYDASTRATGIPDRFSGSDS GTDFTLTISRLEPEDFAVYYCQQYDSWPFTFGQGTKVEIKR |
| 430 | UC6 VHCDR1 (Chothia) | GDSFNNF |
| 431 | UC6 VHCDR2 (Chothia) | VPVLGI |
| 432 | UC6 VHCDR3 (Chothia) | GSAWYDGSFQY |
| 433 | UC6 VLCDR1 (Chothia) | RASQSVSSTFLA |
| 434 | UC6 VLCDR2 (Chothia) | DASTRAT |

TABLE 5-continued

SEQUENCE TABLE

| SEQ ID | Description | Sequence |
|---|---|---|
| 435 | UC6 VLCDR3 (Chothia) | QQYDSWPFT |
| 436 | UC6 VHCDR1 (Kabat) | NFGIS |
| 437 | UC6 VHCDR2 (Kabat) | GIVPVLGIATYAQKFQG |
| 438 | UC6 VHCDR3 (Kabat) | GSAWYDGSFQY |
| 439 | UC6 VLCDR1 (Kabat) | RASQSVSSTFLA |
| 440 | UC6 VLCDR2 (Kabat) | DASTRAT |
| 441 | UC6 VLCDR3 (Kabat) | QQYDSWPFT |
| 442 | UC6 VHCDR1 (IMGT) | GDSFNNFG |
| 443 | UC6 VHCDR2 (IMGT) | IVPVLGIA |
| 444 | UC6 VHCDR3 (IMGT) | ARGSAWYDGSFQY |
| 445 | UC6 VLCDR1 (IMGT) | QSVSSTF |
| 446 | UC6 VLCDR2 (IMGT) | DAS |
| 447 | UC6 VLCDR3 (IMGT) | QQYDSWPFT |
| 448 | UC6 VH | QVQLVQSGAEVKKPGSSVKVSCKASGDSFNNFGISWVRQAPGQGLEWMGGIVP VLGIATYAQKFQGRVTITADESTSTAYMELSSLRSEDTAVYYCARGSAWYDGS FQYWGQGTLVTVSS |
| 449 | UC6VL | EIVLTQSPGTLSLSPGERATLSCRASQSVSSTFLAWYQQKPGQAPRLLIYDAS TRATGIPDRFSGSDSGTDFTLTISRLEPEDFAVYYCQQYDSWPFTFGQGTKVE IK |
| 450 | UC7 (9-1B5) scFv | QVQLVQSGAEVKKPGSSVKVSCKASGDTFSSYGVSWVRQAPGQGLEWMGRIVP VFGIANYAQKFQGRVTITADESTSTAYMELSSLRSEDTAVYYCARQSPYVTYS SYYFDYWGQGTLVTVSSASSGGSTSGSGKPGSGEGSSGSAREIVLTQSPGTLS LSPGERATLSCRASQSVSNNFLAWYQQKPGQAPRLLIYDASTRATGIPDRFSG SGSGTDFTLTISRLEPEDFAVYYCQQYGSWPITFGQGTKVEIKR |
| 451 | UC7 VHCDR1 (Chothia) | GDTFSSY |
| 452 | UC7 VHCDR2 (Chothia) | VPVFGI |
| 453 | UC7 VHCDR3 (Chothia) | QSPYVTYSSYYFDY |
| 454 | UC7 VLCDR1 (Chothia) | RASQSVSNNFLA |
| 455 | UC7 VLCDR2 (Chothia) | DASTRAT |
| 456 | UC7 VLCDR3 (Chothia) | QQYGSWPIT |
| 457 | UC7 VHCDR1 (Kabat) | SYGVS |

TABLE 5-continued

| SEQUENCE TABLE | | |
|---|---|---|
| SEQ ID | Description | Sequence |
| 458 | UC7 VHCDR2 (Kabat) | RIVPVFGIANYAQKFQG |
| 459 | UC7 VHCDR3 (Kabat) | QSPYVTYSSYYFDY |
| 460 | UC7 VLCDR1 (Kabat) | RASQSVSNNFLA |
| 461 | UC7 VLCDR2 (Kabat) | DASTRAT |
| 462 | UC7 VLCDR3 (Kabat) | QQYGSWPIT |
| 463 | UC7 VHCDR1 (IMGT) | GDTFSSYG |
| 464 | UC7 VHCDR2 (IMGT) | IVPVFGIA |
| 465 | UC7 VHCDR3 (IMGT) | ARQSPYVTYSSYYFDY |
| 466 | UC7 VLCDR1 (IMGT) | QSVSNNF |
| 467 | UC7 VLCDR2 (IMGT) | DAS |
| 468 | UC7 VLCDR3 (IMGT) | QQYGSWPIT |
| 469 | UC7 VH | QVQLVQSGAEVKKPGSSVKVSCKASGDTFSSYGVSWVRQAPGQGLEWMGRIVP VFGIANYAQKFQGRVTITADESTSTAYMELSSLRSEDTAVYYCARQSPYVTYS SYYFDYWGQGTLVTVSS |
| 470 | UC7 VL | EIVLTQSPGTLSLSPGERATLSCRASQSVSNNFLAWYQQKPGQAPRLLIYDAS TRATGIPDRFSGSGSGTDFTLTISRLEPEDFAVYYCQQYGSWPITFGQGTKVE IK |
| 471 | UC 8 (9-2A4) scFv | QVQLVQSGAEVKKPGSSVKVSCKASGDTFSNYGFSWVRQAPGQGLEWMGGIVP VFGIATYAQKFQGRVTITADESTSTAYMELSSLRSEDTAVYYCARDYSYYPDD PRYFEYWGQGTLVTVSSASSGGSTSGSGKPGSGEGSSGSAREIVLTQSPGTLS LSPGERATLSCRASQSVSSTFLAWYQQKPGQAPRLLIYAASSRATGIPDRFSG SGSGTDFTLTISRLEPEDFAVYYCQQYGSWPLTFGQGTKVEIKR |
| 472 | UC8 VHCDR1 (Chothia) | GDTFSNY |
| 473 | UC8 VHCDR2 (Chothia) | VPVFGI |
| 474 | UC8 VHCDR3 (Chothia) | DYSYYPDDPRYFEY |
| 475 | UC8 VLCDR1 (Chothia) | RASQSVSSTFLA |
| 476 | UC8 VLCDR2 (Chothia) | AASSRAT |
| 477 | UC8 VLCDR3 (Chothia) | QQYGSWPLT |
| 478 | UC8 VHCDR1 (Kabat) | NYGFS |
| 479 | UC8 VHCDR2 (Kabat) | GIVPVFGIATYAQKFQG |
| 480 | UC8 VHCDR3 (Kabat) | DYSYYPDDPRYFEY |

TABLE 5-continued

SEQUENCE TABLE

| SEQ ID | Description | Sequence |
|---|---|---|
| 481 | UC8 VLCDR1 (Kabat) | RASQSVSSTFLA |
| 482 | UC8 VLCDR2 (Kabat) | AASSRAT |
| 483 | UC8 VLCDR3 (Kabat) | QQYGSWPLT |
| 484 | UC8 VHCDR1 (IMGT) | GDTFSNYG |
| 485 | UC8 VHCDR2 (IMGT) | IVPVFGIA |
| 486 | UC8 VHCDR3 (IMGT) | ARDYSYYPDDPRYFEY |
| 487 | UC8 VLCDR1 (IMGT) | QSVSSTF |
| 488 | UC8 VLCDR2 (IMGT) | AAS |
| 489 | UC8 VLCDR3 (IMGT) | QQYGSWPLT |
| 490 | UC8 VH | QVQLVQSGAEVKKPGSSVKVSCKASGDTFSNYGFSWVRQAPGQGLEWMGGIVP VFGIATYAQKFQGRVTITADESTSTAYMELSSLRSEDTAVYYCARDYSYYPDD PRYFEYWGQGTLVTVSS |
| 491 | UC8 VL | EIVLTQSPGTLSLSPGERATLSCRASQSVSSTFLAWYQQKPGQAPRLLIYAAS SRATGIPDRFSGSGSGTDFTLTISRLEPEDFAVYYCQQYGSWPLTFGQGTKVE IK |

EQUIVALENTS

Those skilled in the art will recognize, or be able to ascertain using no more than routine experimentation, many equivalents of the specific embodiments disclosed herein. Such equivalents are intended to be encompassed by the following claims.

We claim:

1. An isolated antibody which binds to human TNFR2 comprising heavy and light chain CDRs of the heavy and light chain variable region pairs of SEQ ID NOs: 117 and 118, respectively.

2. The isolated antibody of claim 1, comprising:

heavy chain CDR1, CDR2, and CDR3 sequences comprising SEQ ID NOs: 105-107, respectively; and light chain CDR1, CDR2, and CDR3 sequences comprising SEQ ID NOs: 108-110, respectively.

3. The isolated antibody of claim 1, wherein the heavy chain variable region comprises the amino acid sequence set forth in SEQ ID NO: 117, or an amino acid sequence which is at least 80%, 85%, 90%, 95%, 96%, 97%, 98%, or 99% identical to the amino acid sequence set forth in SEQ ID NO: 117.

4. The isolated antibody of claim 1, wherein the light chain variable region comprises the amino acid sequence set forth in SEQ ID NO: 118, or an amino acid sequence which is at least 80%, 85%, 90%, 95%, 96%, 97%, 98%, or 99% identical to the amino acid sequence set forth in SEQ ID NO: 118.

5. The isolated antibody of claim 1, wherein the heavy chain variable region comprises the amino acid sequence set forth in SEQ ID NO: 117, or an amino acid sequence which is at least 80%, 85%, 90%, 95%, 96%, 97%, 98%, or 99% identical to the amino acid sequence set forth in SEQ ID NO: 117, and the light chain variable region comprises the amino acid sequence set forth in SEQ ID NO: 118, or an amino acid sequence which is at least 80%, 85%, 90%, 95%, 96%, 97%, 98%, or 99% identical to the amino acid sequence set forth in SEQ ID NO: 118.

6. The isolated antibody of claim 1, wherein the antibody is selected from the group consisting of an IgG1, an IgG2, an IgG3, and an IgG4, or variant thereof, optionally wherein the antibody comprises a variant Fc region.

7. A bispecific antibody comprising the antigen binding region of the antibody of claim 1, and a second different antigen binding region.

8. An immunoconjugate comprising the antibody of claim 1, linked to an agent.

9. A composition comprising the antibody of claim 1, and a carrier.

10. A method of increasing T cell proliferation in a subject comprising administering an effective amount of the antibody of claim 1 to the subject to achieve increased T cell proliferation.

11. A method of treating a cancer that expresses TNFR2 in a subject in need thereof, the method comprising administering to the subject a therapeutically effective amount of the antibody of claim 1.

12. The method of claim 11, wherein the cancer is selected from the group consisting of: non-small cell lung cancer, breast cancer, ovarian cancer, and colorectal cancer.

13. The method of claim 11, further comprising administering one or more additional therapeutic agents.

14. The method of claim 13, wherein the one or more additional therapeutic agents are selected from the group consisting of: immunomodulatory drug, a cytotoxic drug, a targeted therapeutic, and cancer vaccine.

15. A method of treating an autoimmune disease comprising administering to a subject in need thereof a therapeutically effective amount of the antibody of claim 1.

16. The method of claim 15, wherein the autoimmune disease is selected from the group consisting of graft-versus-host disease, rheumatoid arthritis, Crohn's disease, multiple sclerosis, colitis, psoriasis, autoimmune uveitis, pemphigus, epidermolysis bullosa, and type 1 diabetes.

* * * * *

SEQUENCE LISTING

<160> NUMBER OF SEQ ID NOS: 493

<210> SEQ ID NO 1
<211> LENGTH: 461
<212> TYPE: PRT
<213> ORGANISM: Homo sapiens
<220> FEATURE:
<221> NAME/KEY: misc_feature
<223> OTHER INFORMATION: Human TNFR2

<400> SEQUENCE: 1

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60
```

Val Phe Cys Thr Lys Thr Ser Asp Thr Val Cys Asp Ser Cys Glu Asp
65 70 75 80

Ser Thr Tyr Thr Gln Leu Trp Asn Trp Val Pro Glu Cys Leu Ser Cys
85 90 95

Gly Ser Arg Cys Ser Ser Asp Gln Val Glu Thr Gln Ala Cys Thr Arg
100 105 110

Glu Gln Asn Arg Ile Cys Thr Cys Arg Pro Gly Trp Tyr Cys Ala Leu
115 120 125

Ser Lys Gln Glu Gly Cys Arg Leu Cys Ala Pro Leu Arg Lys Cys Arg
130 135 140

Pro Gly Phe Gly Val Ala Arg Pro Gly Thr Glu Thr Ser Asp Val Val
145 150 155 160

Cys Lys Pro Cys Ala Pro Gly Thr Phe Ser Asn Thr Thr Ser Ser Thr
165 170 175

Asp Ile Cys Arg Pro His Gln Ile Cys Asn Val Val Ala Ile Pro Gly
180 185 190

Asn Ala Ser Met Asp Ala Val Cys Thr Ser Thr Ser Pro Thr Arg Ser
195 200 205

Met Ala Pro Gly Ala Val His Leu Pro Gln Pro Val Ser Thr Arg Ser
210 215 220

Gln His Thr Gln Pro Thr Pro Glu Pro Ser Thr Ala Pro Ser Thr Ser
225 230 235 240

Phe Leu Leu Pro Met Gly Pro Ser Pro Pro Ala Glu Gly Ser Thr Gly
245 250 255

Asp Phe Ala Leu Pro Val Gly Leu Ile Val Gly Val Thr Ala Leu Gly
260 265 270

Leu Leu Ile Ile Gly Val Val Asn Cys Val Ile Met Thr Gln Val Lys
275 280 285

Lys Lys Pro Leu Cys Leu Gln Arg Glu Ala Lys Val Pro His Leu Pro
290 295 300

Ala Asp Lys Ala Arg Gly Thr Gln Gly Pro Glu Gln Gln His Leu Leu
305 310 315 320

Ile Thr Ala Pro Ser Ser Ser Ser Ser Ser Leu Glu Ser Ser Ala Ser
325 330 335

Ala Leu Asp Arg Arg Ala Pro Thr Arg Asn Gln Pro Gln Ala Pro Gly
340 345 350

Val Glu Ala Ser Gly Ala Gly Glu Ala Arg Ala Ser Thr Gly Ser Ser
355 360 365

Asp Ser Ser Pro Gly Gly His Gly Thr Gln Val Asn Val Thr Cys Ile
370 375 380

Val Asn Val Cys Ser Ser Ser Asp His Ser Ser Gln Cys Ser Ser Gln
385 390 395 400

Ala Ser Ser Thr Met Gly Asp Thr Asp Ser Ser Pro Ser Glu Ser Pro
405 410 415

Lys Asp Glu Gln Val Pro Phe Ser Lys Glu Glu Cys Ala Phe Arg Ser
420 425 430

Gln Leu Glu Thr Pro Glu Thr Leu Leu Gly Ser Thr Glu Glu Lys Pro
435 440 445

Leu Pro Leu Gly Val Pro Asp Ala Gly Met Lys Pro Ser
450 455 460

<210> SEQ ID NO 2
<211> LENGTH: 235
<212> TYPE: PRT

<213> ORGANISM: Homo sapiens
<220> FEATURE:
<221> NAME/KEY: misc_feature
<223> OTHER INFORMATION: Human TNFR2 (extracellular domain)

<400> SEQUENCE: 2

Leu Pro Ala Gln Val Ala Phe Thr Pro Tyr Ala Pro Glu Pro Gly Ser
1 5 10 15

Thr Cys Arg Leu Arg Glu Tyr Tyr Asp Gln Thr Ala Gln Met Cys Cys
20 25 30

Ser Lys Cys Ser Pro Gly Gln His Ala Lys Val Phe Cys Thr Lys Thr
35 40 45

Ser Asp Thr Val Cys Asp Ser Cys Glu Asp Ser Thr Tyr Thr Gln Leu
50 55 60

Trp Asn Trp Val Pro Glu Cys Leu Ser Cys Gly Ser Arg Cys Ser Ser
65 70 75 80

Asp Gln Val Glu Thr Gln Ala Cys Thr Arg Glu Gln Asn Arg Ile Cys
85 90 95

Thr Cys Arg Pro Gly Trp Tyr Cys Ala Leu Ser Lys Gln Glu Gly Cys
100 105 110

Arg Leu Cys Ala Pro Leu Arg Lys Cys Arg Pro Gly Phe Gly Val Ala
115 120 125

Arg Pro Gly Thr Glu Thr Ser Asp Val Val Cys Lys Pro Cys Ala Pro
130 135 140

Gly Thr Phe Ser Asn Thr Thr Ser Ser Thr Asp Ile Cys Arg Pro His
145 150 155 160

Gln Ile Cys Asn Val Val Ala Ile Pro Gly Asn Ala Ser Met Asp Ala
165 170 175

Val Cys Thr Ser Thr Ser Pro Thr Arg Ser Met Ala Pro Gly Ala Val
180 185 190

His Leu Pro Gln Pro Val Ser Thr Arg Ser Gln His Thr Gln Pro Thr
195 200 205

Pro Glu Pro Ser Thr Ala Pro Ser Thr Ser Phe Leu Leu Pro Met Gly
210 215 220

Pro Ser Pro Pro Ala Glu Gly Ser Thr Gly Asp
225 230 235

<210> SEQ ID NO 3
<211> LENGTH: 329
<212> TYPE: PRT
<213> ORGANISM: Homo sapiens
<220> FEATURE:
<221> NAME/KEY: misc_feature
<223> OTHER INFORMATION: Human IgG1 heavy chain

<400> SEQUENCE: 3

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys

```
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 4
<211> LENGTH: 474
<212> TYPE: PRT
<213> ORGANISM: Mus musculus
<220> FEATURE:
<221> NAME/KEY: misc_feature
<223> OTHER INFORMATION: Mouse TNFR2

<400> SEQUENCE: 4

Met Ala Pro Ala Ala Leu Trp Val Ala Leu Val Phe Glu Leu Gln Leu
1               5                   10                  15

Trp Ala Thr Gly His Thr Val Pro Ala Gln Val Val Leu Thr Pro Tyr
            20                  25                  30

Lys Pro Glu Pro Gly Tyr Glu Cys Gln Ile Ser Gln Glu Tyr Tyr Asp
        35                  40                  45

Arg Lys Ala Gln Met Cys Cys Ala Lys Cys Pro Pro Gly Gln Tyr Val
    50                  55                  60

Lys His Phe Cys Asn Lys Thr Ser Asp Thr Val Cys Ala Asp Cys Glu
65                  70                  75                  80

Ala Ser Met Tyr Thr Gln Val Trp Asn Gln Phe Arg Thr Cys Leu Ser
                85                  90                  95

Cys Ser Ser Ser Cys Thr Thr Asp Gln Val Glu Ile Arg Ala Cys Thr
            100                 105                 110
```

```
Lys Gln Gln Asn Arg Val Cys Ala Cys Glu Ala Gly Arg Tyr Cys Ala
        115                 120                 125

Leu Lys Thr His Ser Gly Ser Cys Arg Gln Cys Met Arg Leu Ser Lys
    130                 135                 140

Cys Gly Pro Gly Phe Gly Val Ala Ser Ser Arg Ala Pro Asn Gly Asn
145                 150                 155                 160

Val Leu Cys Lys Ala Cys Ala Pro Gly Thr Phe Ser Asp Thr Thr Ser
                165                 170                 175

Ser Thr Asp Val Cys Arg Pro His Arg Ile Cys Ser Ile Leu Ala Ile
            180                 185                 190

Pro Gly Asn Ala Ser Thr Asp Ala Val Cys Ala Pro Glu Ser Pro Thr
        195                 200                 205

Leu Ser Ala Ile Pro Arg Thr Leu Tyr Val Ser Gln Pro Glu Pro Thr
    210                 215                 220

Arg Ser Gln Pro Leu Asp Gln Glu Pro Gly Pro Ser Gln Thr Pro Ser
225                 230                 235                 240

Ile Leu Thr Ser Leu Gly Ser Thr Pro Ile Ile Glu Gln Ser Thr Lys
                245                 250                 255

Gly Gly Ile Ser Leu Pro Ile Gly Leu Ile Val Gly Val Thr Ser Leu
            260                 265                 270

Gly Leu Leu Met Leu Gly Leu Val Asn Cys Ile Ile Leu Val Gln Arg
        275                 280                 285

Lys Lys Lys Pro Ser Cys Leu Gln Arg Asp Ala Lys Val Pro His Val
    290                 295                 300

Pro Asp Glu Lys Ser Gln Asp Ala Val Gly Leu Glu Gln Gln His Leu
305                 310                 315                 320

Leu Thr Thr Ala Pro Ser Ser Ser Ser Ser Ser Leu Glu Ser Ser Ala
                325                 330                 335

Ser Ala Gly Asp Arg Arg Ala Pro Pro Gly Gly His Pro Gln Ala Arg
            340                 345                 350

Val Met Ala Glu Ala Gln Gly Phe Gln Glu Ala Arg Ala Ser Ser Arg
        355                 360                 365

Ile Ser Asp Ser Ser His Gly Ser His Gly Thr His Val Asn Val Thr
    370                 375                 380

Cys Ile Val Asn Val Cys Ser Ser Ser Asp His Ser Ser Gln Cys Ser
385                 390                 395                 400

Ser Gln Ala Ser Ala Thr Val Gly Asp Pro Asp Ala Lys Pro Ser Ala
                405                 410                 415

Ser Pro Lys Asp Glu Gln Val Pro Phe Ser Gln Glu Glu Cys Pro Ser
            420                 425                 430

Gln Ser Pro Cys Glu Thr Thr Glu Thr Leu Gln Ser His Glu Lys Pro
        435                 440                 445

Leu Pro Leu Gly Val Pro Asp Met Gly Met Lys Pro Ser Gln Ala Gly
    450                 455                 460

Trp Phe Asp Gln Ile Ala Val Lys Val Ala
465                 470
```

<210> SEQ ID NO 5
<211> LENGTH: 236
<212> TYPE: PRT
<213> ORGANISM: Mus musculus
<220> FEATURE:
<221> NAME/KEY: misc_feature
<223> OTHER INFORMATION: Mouse TNFR2 (extracellular domain)

<400> SEQUENCE: 5

```
Val Pro Ala Gln Val Val Leu Thr Pro Tyr Lys Pro Glu Pro Gly Tyr
1               5                   10                  15

Glu Cys Gln Ile Ser Gln Glu Tyr Tyr Asp Arg Lys Ala Gln Met Cys
            20                  25                  30

Cys Ala Lys Cys Pro Pro Gly Gln Tyr Val Lys His Phe Cys Asn Lys
        35                  40                  45

Thr Ser Asp Thr Val Cys Ala Asp Cys Glu Ala Ser Met Tyr Thr Gln
    50                  55                  60

Val Trp Asn Gln Phe Arg Thr Cys Leu Ser Cys Ser Ser Ser Cys Thr
65                  70                  75                  80

Thr Asp Gln Val Glu Ile Arg Ala Cys Thr Lys Gln Gln Asn Arg Val
                85                  90                  95

Cys Ala Cys Glu Ala Gly Arg Tyr Cys Ala Leu Lys Thr His Ser Gly
            100                 105                 110

Ser Cys Arg Gln Cys Met Arg Leu Ser Lys Cys Gly Pro Gly Phe Gly
        115                 120                 125

Val Ala Ser Ser Arg Ala Pro Asn Gly Asn Val Leu Cys Lys Ala Cys
    130                 135                 140

Ala Pro Gly Thr Phe Ser Asp Thr Thr Ser Ser Thr Asp Val Cys Arg
145                 150                 155                 160

Pro His Arg Ile Cys Ser Ile Leu Ala Ile Pro Gly Asn Ala Ser Thr
                165                 170                 175

Asp Ala Val Cys Ala Pro Glu Ser Pro Thr Leu Ser Ala Ile Pro Arg
            180                 185                 190

Thr Leu Tyr Val Ser Gln Pro Glu Pro Thr Arg Ser Gln Pro Leu Asp
        195                 200                 205

Gln Glu Pro Gly Pro Ser Gln Thr Pro Ser Ile Leu Thr Ser Leu Gly
    210                 215                 220

Ser Thr Pro Ile Ile Glu Gln Ser Thr Lys Gly Gly
225                 230                 235
```

<210> SEQ ID NO 6
<211> LENGTH: 251
<212> TYPE: PRT
<213> ORGANISM: Artificial Sequence
<220> FEATURE:
<223> OTHER INFORMATION: Synthetic: UC2 (S4-2 1D10) scFv

<400> SEQUENCE: 6

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ile Ile Ser Asp Gly Gly Asp Ala Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Ser Ser Gly Gly Ser Thr Ser Gly
        115                 120                 125
```

```
Ser Gly Lys Pro Gly Ser Gly Glu Gly Ser Ser Gly Ser Ala Arg Asp
    130                 135                 140

Ile Gln Met Thr Gln Ser Pro Ser Ser Leu Ser Ala Ser Val Gly Asp
145                 150                 155                 160

Arg Val Thr Ile Thr Cys Gln Ala Ser Gln Asp Ile Thr Asn Phe Leu
                165                 170                 175

Asn Trp Tyr Gln Gln Lys Pro Gly Lys Ala Pro Lys Leu Leu Ile Tyr
            180                 185                 190

Asp Ala Ser Thr Leu Gln Thr Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Gln Gln Ser Asp Ser Tyr Pro Ile Thr
225                 230                 235                 240

Phe Gly Gln Gly Thr Lys Val Glu Ile Lys Arg
                245                 250


<210> SEQ ID NO 7
<211> LENGTH: 7
<212> TYPE: PRT
<213> ORGANISM: Artificial Sequence
<220> FEATURE:
<223> OTHER INFORMATION: Synthetic: UC2 VHCDR1 (Chothia)

<400> SEQUENCE: 7

Gly Phe Thr Phe Ser Thr Tyr
1               5


<210> SEQ ID NO 8
<211> LENGTH: 6
<212> TYPE: PRT
<213> ORGANISM: Artificial Sequence
<220> FEATURE:
<223> OTHER INFORMATION: Synthetic: UC2 VHCDR2 (Chothia)

<400> SEQUENCE: 8

Ser Asp Gly Gly Asp Ala
1               5


<210> SEQ ID NO 9
<211> LENGTH: 10
<212> TYPE: PRT
<213> ORGANISM: Artificial Sequence
<220> FEATURE:
<223> OTHER INFORMATION: Synthetic: UC2 VHCDR3 (Chothia)

<400> SEQUENCE: 9

Asp Gly Thr Ser Ala Ala Ala Phe Asp Ser
1               5                   10


<210> SEQ ID NO 10
<211> LENGTH: 11
<212> TYPE: PRT
<213> ORGANISM: Artificial Sequence
<220> FEATURE:
<223> OTHER INFORMATION: Synthetic: UC2 VLCDR1 (Chothia)

<400> SEQUENCE: 10

Gln Ala Ser Gln Asp Ile Thr Asn Phe Leu Asn
1               5                   10


<210> SEQ ID NO 11
```

<211> LENGTH: 7
<212> TYPE: PRT
<213> ORGANISM: Artificial Sequence
<220> FEATURE:
<223> OTHER INFORMATION: Synthetic: UC2 VLCDR2 (Chothia)

<400> SEQUENCE: 11

Asp Ala Ser Thr Leu Gln Thr
1 5

<210> SEQ ID NO 12
<211> LENGTH: 9
<212> TYPE: PRT
<213> ORGANISM: Artificial Sequence
<220> FEATURE:
<223> OTHER INFORMATION: Synthetic: UC2 VLCDR3 (Chothia)

<400> SEQUENCE: 12

Gln Gln Ser Asp Ser Tyr Pro Ile Thr
1 5

<210> SEQ ID NO 13
<211> LENGTH: 5
<212> TYPE: PRT
<213> ORGANISM: Artificial Sequence
<220> FEATURE:
<223> OTHER INFORMATION: Synthetic: UC2 VHCDR1 (Kabat)

<400> SEQUENCE: 13

Thr Tyr Ala Met Ser
1 5

<210> SEQ ID NO 14
<211> LENGTH: 17
<212> TYPE: PRT
<213> ORGANISM: Artificial Sequence
<220> FEATURE:
<223> OTHER INFORMATION: Synthetic: UC2 VHCDR2 (Kabat)

<400> SEQUENCE: 14

Ile Ile Ser Asp Gly Gly Asp Ala Thr Phe Tyr Ala Asp Ser Val Lys
1 5 10 15

Gly

<210> SEQ ID NO 15
<211> LENGTH: 10
<212> TYPE: PRT
<213> ORGANISM: Artificial Sequence
<220> FEATURE:
<223> OTHER INFORMATION: Synthetic: UC2 VHCDR3 (Kabat)

<400> SEQUENCE: 15

Asp Gly Thr Ser Ala Ala Ala Phe Asp Ser
1 5 10

<210> SEQ ID NO 16
<211> LENGTH: 11
<212> TYPE: PRT
<213> ORGANISM: Artificial Sequence
<220> FEATURE:
<223> OTHER INFORMATION: Synthetic: UC2 VLCDR1 (Kabat)

<400> SEQUENCE: 16

Gln Ala Ser Gln Asp Ile Thr Asn Phe Leu Asn
1 5 10

<210> SEQ ID NO 17
<211> LENGTH: 7
<212> TYPE: PRT
<213> ORGANISM: Artificial Sequence
<220> FEATURE:
<223> OTHER INFORMATION: Synthetic: UC2 VLCDR2 (Kabat)

<400> SEQUENCE: 17

Asp Ala Ser Thr Leu Gln Thr
1 5

<210> SEQ ID NO 18
<211> LENGTH: 9
<212> TYPE: PRT
<213> ORGANISM: Artificial Sequence
<220> FEATURE:
<223> OTHER INFORMATION: Synthetic: UC2 VLCDR3 (Kabat)

<400> SEQUENCE: 18

Gln Gln Ser Asp Ser Tyr Pro Ile Thr
1 5

<210> SEQ ID NO 19
<211> LENGTH: 8
<212> TYPE: PRT
<213> ORGANISM: Artificial Sequence
<220> FEATURE:
<223> OTHER INFORMATION: Synthetic: UC2 VHCDR1 (IMGT)

<400> SEQUENCE: 19

Gly Phe Thr Phe Ser Thr Tyr Ala
1 5

<210> SEQ ID NO 20
<211> LENGTH: 8
<212> TYPE: PRT
<213> ORGANISM: Artificial Sequence
<220> FEATURE:
<223> OTHER INFORMATION: Synthetic: UC2 VHCDR2 (IMGT)

<400> SEQUENCE: 20

Ile Ser Asp Gly Gly Asp Ala Thr
1 5

<210> SEQ ID NO 21
<211> LENGTH: 12
<212> TYPE: PRT
<213> ORGANISM: Artificial Sequence
<220> FEATURE:
<223> OTHER INFORMATION: Synthetic: UC2 VHCDR3 (IMGT)

<400> SEQUENCE: 21

Ala Arg Asp Gly Thr Ser Ala Ala Ala Phe Asp Ser
1 5 10

<210> SEQ ID NO 22
<211> LENGTH: 6
<212> TYPE: PRT
<213> ORGANISM: Artificial Sequence
<220> FEATURE:
<223> OTHER INFORMATION: Synthetic: UC2 VLCDR1 (IMGT)

<400> SEQUENCE: 22

Gln Asp Ile Thr Asn Phe
1 5

<210> SEQ ID NO 23

<211> LENGTH: 3
<212> TYPE: PRT
<213> ORGANISM: Artificial Sequence
<220> FEATURE:
<223> OTHER INFORMATION: Synthetic: UC2 VLCDR2 (IMGT)

<400> SEQUENCE: 23

Asp Ala Ser
1

<210> SEQ ID NO 24
<211> LENGTH: 9
<212> TYPE: PRT
<213> ORGANISM: Artificial Sequence
<220> FEATURE:
<223> OTHER INFORMATION: Synthetic: UC2 VLCDR3 (IMGT)

<400> SEQUENCE: 24

Gln Gln Ser Asp Ser Tyr Pro Ile Thr
1               5

<210> SEQ ID NO 25
<211> LENGTH: 119
<212> TYPE: PRT
<213> ORGANISM: Artificial Sequence
<220> FEATURE:
<223> OTHER INFORMATION: Synthetic: UC2 VH

<400> SEQUENCE: 25

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ile Ile Ser Asp Gly Gly Asp Ala Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser
        115

<210> SEQ ID NO 26
<211> LENGTH: 107
<212> TYPE: PRT
<213> ORGANISM: Artificial Sequence
<220> FEATURE:
<223> OTHER INFORMATION: Synthetic: UC2 VL

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Thr Gly Val Pro Ser Arg Phe Ser Gly
    50                  55                  60

```
Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Ser Tyr Pro Ile
                85                  90                  95

Thr Phe Gly Gln Gly Thr Lys Val Glu Ile Lys
            100                 105


<210> SEQ ID NO 27
<211> LENGTH: 448
<212> TYPE: PRT
<213> ORGANISM: Artificial Sequence
<220> FEATURE:
<223> OTHER INFORMATION: Synthetic: UC2-IgG1 heavy chain

<400> SEQUENCE: 27

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ile Ile Ser Asp Gly Gly Asp Ala Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 28
<211> LENGTH: 214
<212> TYPE: PRT
<213> ORGANISM: Artificial Sequence
<220> FEATURE:
<223> OTHER INFORMATION: Synthetic: UC2-IgG1 light chain

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Ser Tyr Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 29
```

<211> LENGTH: 251
<212> TYPE: PRT
<213> ORGANISM: Artificial Sequence
<220> FEATURE:
<223> OTHER INFORMATION: Synthetic: UC2.3 (S4-2 1D10-1G9) scFv

<400> SEQUENCE: 29

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Ser Ser Gly Gly Ser Thr Ser Gly
        115                 120                 125

Ser Gly Lys Pro Gly Ser Gly Glu Gly Ser Ser Gly Ser Ala Arg Asp
    130                 135                 140

Ile Gln Met Thr Gln Ser Pro Ser Ser Leu Ser Ala Ser Val Gly Asp
145                 150                 155                 160

Arg Val Thr Ile Thr Cys Gln Ala Ser Gln Asp Ile Thr Asn Phe Leu
                165                 170                 175

Asn Trp Tyr Gln Gln Lys Pro Gly Lys Ala Pro Lys Leu Leu Ile Tyr
            180                 185                 190

Asp Ala Ser Thr Leu Gln Thr Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Gln Gln Ser Asp Ser Tyr Pro Ile Thr
225                 230                 235                 240

Phe Gly Gln Gly Thr Lys Val Glu Ile Lys Arg
                245                 250
```

<210> SEQ ID NO 30
<211> LENGTH: 7
<212> TYPE: PRT
<213> ORGANISM: Artificial Sequence
<220> FEATURE:
<223> OTHER INFORMATION: Synthetic: UC2.3 VHCDR1 (Chothia)

<400> SEQUENCE: 30

```
Gly Phe Thr Phe Ser Thr Tyr
1               5
```

<210> SEQ ID NO 31
<211> LENGTH: 6
<212> TYPE: PRT
<213> ORGANISM: Artificial Sequence
<220> FEATURE:
<223> OTHER INFORMATION: Synthetic: UC2.3 VHCDR2 (Chothia)

<400> SEQUENCE: 31

Ser Asp Gly Gly Asp Ala
1 5

<210> SEQ ID NO 32
<211> LENGTH: 10
<212> TYPE: PRT
<213> ORGANISM: Artificial Sequence
<220> FEATURE:
<223> OTHER INFORMATION: Synthetic: UC2.3 VHCDR3 (Chothia)

<400> SEQUENCE: 32

Asp Gly Thr Ser Ala Ala Ala Phe Asp Ser
1 5 10

<210> SEQ ID NO 33
<211> LENGTH: 11
<212> TYPE: PRT
<213> ORGANISM: Artificial Sequence
<220> FEATURE:
<223> OTHER INFORMATION: Synthetic: UC2.3 VLCDR1 (Chothia)

<400> SEQUENCE: 33

Gln Ala Ser Gln Asp Ile Thr Asn Phe Leu Asn
1 5 10

<210> SEQ ID NO 34
<211> LENGTH: 7
<212> TYPE: PRT
<213> ORGANISM: Artificial Sequence
<220> FEATURE:
<223> OTHER INFORMATION: Synthetic: UC2.3 VLCDR2 (Chothia)

<400> SEQUENCE: 34

Asp Ala Ser Thr Leu Gln Thr
1 5

<210> SEQ ID NO 35
<211> LENGTH: 9
<212> TYPE: PRT
<213> ORGANISM: Artificial Sequence
<220> FEATURE:
<223> OTHER INFORMATION: Synthetic: UC2.3 VLCDR3 (Chothia)

<400> SEQUENCE: 35

Gln Gln Ser Asp Ser Tyr Pro Ile Thr
1 5

<210> SEQ ID NO 36
<211> LENGTH: 5
<212> TYPE: PRT
<213> ORGANISM: Artificial Sequence
<220> FEATURE:
<223> OTHER INFORMATION: Synthetic: UC2.3 VHCDR1 (Kabat)

<400> SEQUENCE: 36

Thr Tyr Ala Met Ser
1 5

<210> SEQ ID NO 37
<211> LENGTH: 17
<212> TYPE: PRT
<213> ORGANISM: Artificial Sequence
<220> FEATURE:
<223> OTHER INFORMATION: Synthetic: UC2.3 VHCDR2 (Kabat)

<400> SEQUENCE: 37

Ile Ile Ser Asp Gly Gly Asp Ala Thr Val Tyr Ala Asp Ser Val Lys 1 5 10 15

Gly

<210> SEQ ID NO 38
<211> LENGTH: 10
<212> TYPE: PRT
<213> ORGANISM: Artificial Sequence
<220> FEATURE:
<223> OTHER INFORMATION: Synthetic: UC2.3 VHCDR3 (Kabat)

<400> SEQUENCE: 38

Asp Gly Thr Ser Ala Ala Ala Phe Asp Ser
1 5 10

<210> SEQ ID NO 39
<211> LENGTH: 11
<212> TYPE: PRT
<213> ORGANISM: Artificial Sequence
<220> FEATURE:
<223> OTHER INFORMATION: Synthetic: UC2.3 VLCDR1 (Kabat)

<400> SEQUENCE: 39

Gln Ala Ser Gln Asp Ile Thr Asn Phe Leu Asn
1 5 10

<210> SEQ ID NO 40
<211> LENGTH: 7
<212> TYPE: PRT
<213> ORGANISM: Artificial Sequence
<220> FEATURE:
<223> OTHER INFORMATION: Synthetic: UC2.3 VLCDR2 (Kabat)

<400> SEQUENCE: 40

Asp Ala Ser Thr Leu Gln Thr
1 5

<210> SEQ ID NO 41
<211> LENGTH: 9
<212> TYPE: PRT
<213> ORGANISM: Artificial Sequence
<220> FEATURE:
<223> OTHER INFORMATION: Synthetic: UC2.3 VLCDR3 (Kabat)

<400> SEQUENCE: 41

Gln Gln Ser Asp Ser Tyr Pro Ile Thr
1 5

<210> SEQ ID NO 42
<211> LENGTH: 8
<212> TYPE: PRT
<213> ORGANISM: Artificial Sequence
<220> FEATURE:
<223> OTHER INFORMATION: Synthetic: UC2.3 VHCDR1 (IMGT)

<400> SEQUENCE: 42

Gly Phe Thr Phe Ser Thr Tyr Ala
1 5

<210> SEQ ID NO 43
<211> LENGTH: 8
<212> TYPE: PRT
<213> ORGANISM: Artificial Sequence
<220> FEATURE:
<223> OTHER INFORMATION: Synthetic: UC2.3 VHCDR2 (IMGT)

<400> SEQUENCE: 43

```
Ile Ser Asp Gly Gly Asp Ala Thr
1               5


<210> SEQ ID NO 44
<211> LENGTH: 12
<212> TYPE: PRT
<213> ORGANISM: Artificial Sequence
<220> FEATURE:
<223> OTHER INFORMATION: Synthetic: UC2.3 VHCDR3 (IMGT)

<400> SEQUENCE: 44

Ala Arg Asp Gly Thr Ser Ala Ala Ala Phe Asp Ser
1               5                   10


<210> SEQ ID NO 45
<211> LENGTH: 6
<212> TYPE: PRT
<213> ORGANISM: Artificial Sequence
<220> FEATURE:
<223> OTHER INFORMATION: Synthetic: UC2.3 VLCDR1 (IMGT)

<400> SEQUENCE: 45

Gln Asp Ile Thr Asn Phe
1               5


<210> SEQ ID NO 46
<211> LENGTH: 3
<212> TYPE: PRT
<213> ORGANISM: Artificial Sequence
<220> FEATURE:
<223> OTHER INFORMATION: Synthetic: UC2.3 VLCDR2 (IMGT)

<400> SEQUENCE: 46

Asp Ala Ser
1


<210> SEQ ID NO 47
<211> LENGTH: 9
<212> TYPE: PRT
<213> ORGANISM: Artificial Sequence
<220> FEATURE:
<223> OTHER INFORMATION: Synthetic: UC2.3 VLCDR3 (IMGT)

<400> SEQUENCE: 47

Gln Gln Ser Asp Ser Tyr Pro Ile Thr
1               5


<210> SEQ ID NO 48
<211> LENGTH: 119
<212> TYPE: PRT
<213> ORGANISM: Artificial Sequence
<220> FEATURE:
<223> OTHER INFORMATION: Synthetic: UC2.3 VH

<400> SEQUENCE: 48

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser
        115


<210> SEQ ID NO 49
<211> LENGTH: 107
<212> TYPE: PRT
<213> ORGANISM: Artificial Sequence
<220> FEATURE:
<223> OTHER INFORMATION: Synthetic: UC2.3 VL

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Ser Tyr Pro Ile
                85                  90                  95

Thr Phe Gly Gln Gly Thr Lys Val Glu Ile Lys
            100                 105


<210> SEQ ID NO 50
<211> LENGTH: 448
<212> TYPE: PRT
<213> ORGANISM: Artificial Sequence
<220> FEATURE:
<223> OTHER INFORMATION: Synthetic: UC2.3-IgG1 heavy chain

<400> SEQUENCE: 50

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

<210> SEQ ID NO 51
<211> LENGTH: 214
<212> TYPE: PRT
<213> ORGANISM: Artificial Sequence
<220> FEATURE:
<223> OTHER INFORMATION: Synthetic: UC2.3-IgG1 light chain

<400> SEQUENCE: 51

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Asp Ala Ser Thr Leu Gln Thr Gly Val Pro Ser Arg Phe Ser Gly
50 55 60

Ser Gly Ser Gly Thr Asp Phe Thr Phe Thr Ile Ser Ser Leu Gln Pro

```
65                  70                  75                  80

Glu Asp Ile Ala Thr Tyr Tyr Cys Gln Gln Ser Asp Ser Tyr Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 52
<211> LENGTH: 251
<212> TYPE: PRT
<213> ORGANISM: Artificial Sequence
<220> FEATURE:
<223> OTHER INFORMATION: Synthetic: UC2.3.3 (S4-2 1D10-1G9-1F10) scFv

<400> SEQUENCE: 52

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Asn Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Ser Ser Gly Gly Ser Thr Ser Gly
        115                 120                 125

Ser Gly Lys Pro Gly Ser Gly Glu Gly Ser Ser Gly Ser Ala Arg Asp
    130                 135                 140

Ile Gln Met Thr Gln Ser Pro Ser Ser Leu Ser Ala Ser Val Gly Asp
145                 150                 155                 160

Arg Val Thr Ile Thr Cys Gln Ala Ser Gln Asp Ile Thr Asn Phe Leu
                165                 170                 175

Asn Trp Tyr Gln Gln Lys Pro Gly Lys Ala Pro Lys Leu Leu Ile Tyr
            180                 185                 190

Asp Ala Ser Thr Leu Gln Thr Gly Val Pro Ser Arg Phe Ser Gly Ser
        195                 200                 205

Gly Ser Gly Thr Asp Phe Thr Phe Thr Ile Ser Ser Leu Gln Pro Glu
```

```
    210                 215                 220

Asp Ile Ala Thr Tyr Tyr Cys Gln Gln Ser Asp Ser Tyr Pro Ile Thr
225                 230                 235                 240

Phe Gly Gln Gly Thr Lys Val Glu Ile Lys Arg
                245                 250


<210> SEQ ID NO 53
<211> LENGTH: 7
<212> TYPE: PRT
<213> ORGANISM: Artificial Sequence
<220> FEATURE:
<223> OTHER INFORMATION: Synthetic: UC2.3.3 VHCDR1 (Chothia)

<400> SEQUENCE: 53

Gly Phe Thr Phe Ser Thr Tyr
1               5


<210> SEQ ID NO 54
<211> LENGTH: 6
<212> TYPE: PRT
<213> ORGANISM: Artificial Sequence
<220> FEATURE:
<223> OTHER INFORMATION: Synthetic: UC2.3.3 VHCDR2 (Chothia)

<400> SEQUENCE: 54

Ser Asp Gly Gly Asp Ala
1               5


<210> SEQ ID NO 55
<211> LENGTH: 10
<212> TYPE: PRT
<213> ORGANISM: Artificial Sequence
<220> FEATURE:
<223> OTHER INFORMATION: Synthetic: UC2.3.3 VHCDR3 (Chothia)

<400> SEQUENCE: 55

Asp Gly Thr Ser Ala Ala Ala Phe Asp Ser
1               5                   10


<210> SEQ ID NO 56
<211> LENGTH: 11
<212> TYPE: PRT
<213> ORGANISM: Artificial Sequence
<220> FEATURE:
<223> OTHER INFORMATION: Synthetic: UC2.3.3 VLCDR1 (Chothia)

<400> SEQUENCE: 56

Gln Ala Ser Gln Asp Ile Thr Asn Phe Leu Asn
1               5                   10


<210> SEQ ID NO 57
<211> LENGTH: 7
<212> TYPE: PRT
<213> ORGANISM: Artificial Sequence
<220> FEATURE:
<223> OTHER INFORMATION: Synthetic: UC2.3.3 VLCDR2 (Chothia)

<400> SEQUENCE: 57

Asp Ala Ser Thr Leu Gln Thr
1               5


<210> SEQ ID NO 58
<211> LENGTH: 9
<212> TYPE: PRT
<213> ORGANISM: Artificial Sequence
<220> FEATURE:
```

<223> OTHER INFORMATION: Synthetic: UC2.3.3 VLCDR3 (Chothia)

<400> SEQUENCE: 58

Gln Gln Ser Asp Ser Tyr Pro Ile Thr
1 5

<210> SEQ ID NO 59
<211> LENGTH: 5
<212> TYPE: PRT
<213> ORGANISM: Artificial Sequence
<220> FEATURE:
<223> OTHER INFORMATION: Synthetic: UC2.3.3 VHCDR1 (Kabat)

<400> SEQUENCE: 59

Thr Tyr Ala Met Ser
1 5

<210> SEQ ID NO 60
<211> LENGTH: 17
<212> TYPE: PRT
<213> ORGANISM: Artificial Sequence
<220> FEATURE:
<223> OTHER INFORMATION: Synthetic: UC2.3.3 VHCDR2 (Kabat)

<400> SEQUENCE: 60

Ile Ile Ser Asp Gly Gly Asp Ala Thr Val Tyr Ala Asp Ser Val Lys
1 5 10 15

Gly

<210> SEQ ID NO 61
<211> LENGTH: 10
<212> TYPE: PRT
<213> ORGANISM: Artificial Sequence
<220> FEATURE:
<223> OTHER INFORMATION: Synthetic: UC2.3.3 VHCDR3 (Kabat)

<400> SEQUENCE: 61

Asp Gly Thr Ser Ala Ala Ala Phe Asp Ser
1 5 10

<210> SEQ ID NO 62
<211> LENGTH: 11
<212> TYPE: PRT
<213> ORGANISM: Artificial Sequence
<220> FEATURE:
<223> OTHER INFORMATION: Synthetic: UC2.3.3 VLCDR1 (Kabat)

<400> SEQUENCE: 62

Gln Ala Ser Gln Asp Ile Thr Asn Phe Leu Asn
1 5 10

<210> SEQ ID NO 63
<211> LENGTH: 7
<212> TYPE: PRT
<213> ORGANISM: Artificial Sequence
<220> FEATURE:
<223> OTHER INFORMATION: Synthetic: UC2.3.3 VLCDR2 (Kabat)

<400> SEQUENCE: 63

Asp Ala Ser Thr Leu Gln Thr
1 5

<210> SEQ ID NO 64
<211> LENGTH: 9
<212> TYPE: PRT
<213> ORGANISM: Artificial Sequence
<220> FEATURE:
<223> OTHER INFORMATION: Synthetic: UC2.3.3 VLCDR3 (Kabat)

<400> SEQUENCE: 64

Gln Gln Ser Asp Ser Tyr Pro Ile Thr
1 5

<210> SEQ ID NO 65
<211> LENGTH: 8
<212> TYPE: PRT
<213> ORGANISM: Artificial Sequence
<220> FEATURE:
<223> OTHER INFORMATION: Synthetic: UC2.3.3 VHCDR1 (IMGT)

<400> SEQUENCE: 65

Gly Phe Thr Phe Ser Thr Tyr Ala
1 5

<210> SEQ ID NO 66
<211> LENGTH: 8
<212> TYPE: PRT
<213> ORGANISM: Artificial Sequence
<220> FEATURE:
<223> OTHER INFORMATION: Synthetic: UC2.3.3 VHCDR2 (IMGT)

<400> SEQUENCE: 66

Ile Ser Asp Gly Gly Asp Ala Thr
1 5

<210> SEQ ID NO 67
<211> LENGTH: 12
<212> TYPE: PRT
<213> ORGANISM: Artificial Sequence
<220> FEATURE:
<223> OTHER INFORMATION: Synthetic: UC2.3.3 VHCDR3 (IMGT)

<400> SEQUENCE: 67

Ala Arg Asp Gly Thr Ser Ala Ala Ala Phe Asp Ser
1 5 10

<210> SEQ ID NO 68
<211> LENGTH: 6
<212> TYPE: PRT
<213> ORGANISM: Artificial Sequence
<220> FEATURE:
<223> OTHER INFORMATION: Synthetic: UC2.3.3 VLCDR1 (IMGT)

<400> SEQUENCE: 68

Gln Asp Ile Thr Asn Phe
1 5

<210> SEQ ID NO 69
<211> LENGTH: 3
<212> TYPE: PRT
<213> ORGANISM: Artificial Sequence
<220> FEATURE:
<223> OTHER INFORMATION: Synthetic: UC2.3.3 VLCDR2 (IMGT)

<400> SEQUENCE: 69

Asp Ala Ser
1

<210> SEQ ID NO 70
<211> LENGTH: 9
<212> TYPE: PRT
<213> ORGANISM: Artificial Sequence
<220> FEATURE:

<223> OTHER INFORMATION: Synthetic: UC2.3.3 VLCDR3 (IMGT)

<400> SEQUENCE: 70

Gln Gln Ser Asp Ser Tyr Pro Ile Thr
1 5

<210> SEQ ID NO 71
<211> LENGTH: 119
<212> TYPE: PRT
<213> ORGANISM: Artificial Sequence
<220> FEATURE:
<223> OTHER INFORMATION: Synthetic: UC2.3.3 VH

<400> SEQUENCE: 71

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Ala Met Ser Trp Ile Arg Gln Ala Pro Gly Lys Gly Leu Glu Trp Val
35 40 45

Ser Ile Ile Ser Asp Gly Gly Asp Ala Thr Val Tyr Ala Asp Ser Val
50 55 60

Lys Gly Arg Phe Thr Ile Ser Arg Asp Asn Asn Arg Asn Thr Leu Tyr
65 70 75 80

Leu Gln Met Asn Ser Leu Arg Ala Glu Asp Thr Ala Val Tyr Tyr Cys
85 90 95

Ala Arg Asp Gly Thr Ser Ala Ala Ala Phe Asp Ser Trp Gly Gln Gly
100 105 110

Thr Leu Val Thr Val Ser Ser
115

<210> SEQ ID NO 72
<211> LENGTH: 107
<212> TYPE: PRT
<213> ORGANISM: Artificial Sequence
<220> FEATURE:
<223> OTHER INFORMATION: Synthetic: UC2.3.3 VL

<400> SEQUENCE: 72

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Asp Ala Ser Thr Leu Gln Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Ser Asp Ser Tyr Pro Ile
85 90 95

Thr Phe Gly Gln Gly Thr Lys Val Glu Ile Lys
100 105

<210> SEQ ID NO 73
<211> LENGTH: 448
<212> TYPE: PRT
<213> ORGANISM: Artificial Sequence
<220> FEATURE:
<223> OTHER INFORMATION: Synthetic: UC2.3.3-IgG1 heavy chain

<400> SEQUENCE: 73

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Ala Met Ser Trp Ile Arg Gln Ala Pro Gly Lys Gly Leu Glu Trp Val
35 40 45

Ser Ile Ile Ser Asp Gly Gly Asp Ala Thr Val Tyr Ala Asp Ser Val
50 55 60

Lys Gly Arg Phe Thr Ile Ser Arg Asp Asn Asn Arg Asn Thr Leu Tyr
65 70 75 80

Leu Gln Met Asn Ser Leu Arg Ala Glu Asp Thr Ala Val Tyr Tyr Cys
85 90 95

Ala Arg Asp Gly Thr Ser Ala Ala Ala Phe Asp Ser Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys 405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

<210> SEQ ID NO 74
<211> LENGTH: 214
<212> TYPE: PRT
<213> ORGANISM: Artificial Sequence
<220> FEATURE:
<223> OTHER INFORMATION: Synthetic: UC2.3.3-IgG1 light chain

<400> SEQUENCE: 74

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Asp Ala Ser Thr Leu Gln Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Ser Asp Ser Tyr Pro Ile
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 75
<211> LENGTH: 251
<212> TYPE: PRT
<213> ORGANISM: Artificial Sequence
<220> FEATURE:
<223> OTHER INFORMATION: Synthetic: UC2.3.7 scFv

<400> SEQUENCE: 75

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Ala Met Ser Trp Val Arg Gln Ala Pro Gly Lys Gly Leu Glu Trp Val
35 40 45

```
Ser Ile Ile Ser Asp Gly Gly Asp Ala Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Ser Ser Gly Gly Ser Thr Ser Gly
        115                 120                 125

Ser Gly Lys Pro Gly Ser Gly Glu Gly Ser Ser Gly Ser Ala Arg Asp
    130                 135                 140

Ile Gln Met Thr Gln Ser Pro Ser Ser Leu Ser Ala Ser Val Gly Asp
145                 150                 155                 160

Arg Val Thr Ile Thr Cys Gln Ala Ser Gln Asp Ile Thr Asn Phe Leu
                165                 170                 175

Asn Trp Tyr Gln Gln Lys Pro Gly Lys Ala Pro Lys Leu Leu Ile Tyr
            180                 185                 190

Asp Ala Ser Arg Arg Arg Thr Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Gln Gln Ser Asp Ser Tyr Pro Ile Thr
225                 230                 235                 240

Phe Gly Gln Gly Thr Lys Val Glu Ile Lys Arg
                245                 250
```

<210> SEQ ID NO 76
<211> LENGTH: 7
<212> TYPE: PRT
<213> ORGANISM: Artificial Sequence
<220> FEATURE:
<223> OTHER INFORMATION: Synthetic: UC2.3.7 VHCDR1 (Chothia)

<400> SEQUENCE: 76

```
Gly Phe Thr Phe Ser Thr Tyr
1               5
```

<210> SEQ ID NO 77
<211> LENGTH: 6
<212> TYPE: PRT
<213> ORGANISM: Artificial Sequence
<220> FEATURE:
<223> OTHER INFORMATION: Synthetic: UC2.3.7 VHCDR2 (Chothia)

<400> SEQUENCE: 77

```
Ser Asp Gly Gly Asp Ala
1               5
```

<210> SEQ ID NO 78
<211> LENGTH: 10
<212> TYPE: PRT
<213> ORGANISM: Artificial Sequence
<220> FEATURE:
<223> OTHER INFORMATION: Synthetic: UC2.3.7 VHCDR3 (Chothia)

<400> SEQUENCE: 78

```
Asp Gly Thr Ser Ala Ala Ala Phe Asp Ser
1               5                   10
```

<210> SEQ ID NO 79
<211> LENGTH: 11
<212> TYPE: PRT
<213> ORGANISM: Artificial Sequence
<220> FEATURE:
<223> OTHER INFORMATION: Synthetic: UC2.3.7 VLCDR1 (Chothia)

<400> SEQUENCE: 79

Gln Ala Ser Gln Asp Ile Thr Asn Phe Leu Asn
1 5 10

<210> SEQ ID NO 80
<211> LENGTH: 7
<212> TYPE: PRT
<213> ORGANISM: Artificial Sequence
<220> FEATURE:
<223> OTHER INFORMATION: Synthetic: UC2.3.7 VLCDR2 (Chothia)

<400> SEQUENCE: 80

Asp Ala Ser Arg Arg Arg Thr
1 5

<210> SEQ ID NO 81
<211> LENGTH: 9
<212> TYPE: PRT
<213> ORGANISM: Artificial Sequence
<220> FEATURE:
<223> OTHER INFORMATION: Synthetic: UC2.3.7 VLCDR3 (Chothia)

<400> SEQUENCE: 81

Gln Gln Ser Asp Ser Tyr Pro Ile Thr
1 5

<210> SEQ ID NO 82
<211> LENGTH: 5
<212> TYPE: PRT
<213> ORGANISM: Artificial Sequence
<220> FEATURE:
<223> OTHER INFORMATION: Synthetic: UC2.3.7 VHCDR1 (Kabat)

<400> SEQUENCE: 82

Thr Tyr Ala Met Ser
1 5

<210> SEQ ID NO 83
<211> LENGTH: 17
<212> TYPE: PRT
<213> ORGANISM: Artificial Sequence
<220> FEATURE:
<223> OTHER INFORMATION: Synthetic: UC2.3.7 VHCDR2 (Kabat)

<400> SEQUENCE: 83

Ile Ile Ser Asp Gly Gly Asp Ala Thr Phe Tyr Ala Asp Ser Val Lys
1 5 10 15

Gly

<210> SEQ ID NO 84
<211> LENGTH: 10
<212> TYPE: PRT
<213> ORGANISM: Artificial Sequence
<220> FEATURE:
<223> OTHER INFORMATION: Synthetic: UC2.3.7 VHCDR3 (Kabat)

<400> SEQUENCE: 84

Asp Gly Thr Ser Ala Ala Ala Phe Asp Ser
1 5 10

<210> SEQ ID NO 85
<211> LENGTH: 11
<212> TYPE: PRT
<213> ORGANISM: Artificial Sequence
<220> FEATURE:
<223> OTHER INFORMATION: Synthetic: UC2.3.7 VLCDR1 (Kabat)

<400> SEQUENCE: 85

Gln Ala Ser Gln Asp Ile Thr Asn Phe Leu Asn
1 5 10

<210> SEQ ID NO 86
<211> LENGTH: 7
<212> TYPE: PRT
<213> ORGANISM: Artificial Sequence
<220> FEATURE:
<223> OTHER INFORMATION: Synthetic: UC2.3.7 VLCDR2 (Kabat)

<400> SEQUENCE: 86

Asp Ala Ser Arg Arg Arg Thr
1 5

<210> SEQ ID NO 87
<211> LENGTH: 9
<212> TYPE: PRT
<213> ORGANISM: Artificial Sequence
<220> FEATURE:
<223> OTHER INFORMATION: Synthetic: UC2.3.7 VLCDR3 (Kabat)

<400> SEQUENCE: 87

Gln Gln Ser Asp Ser Tyr Pro Ile Thr
1 5

<210> SEQ ID NO 88
<211> LENGTH: 8
<212> TYPE: PRT
<213> ORGANISM: Artificial Sequence
<220> FEATURE:
<223> OTHER INFORMATION: Synthetic: UC2.3.7 VHCDR1 (IMGT)

<400> SEQUENCE: 88

Gly Phe Thr Phe Ser Thr Tyr Ala
1 5

<210> SEQ ID NO 89
<211> LENGTH: 8
<212> TYPE: PRT
<213> ORGANISM: Artificial Sequence
<220> FEATURE:
<223> OTHER INFORMATION: Synthetic: UC2.3.7 VHCDR2 (IMGT)

<400> SEQUENCE: 89

Ile Ser Asp Gly Gly Asp Ala Thr
1 5

<210> SEQ ID NO 90
<211> LENGTH: 12
<212> TYPE: PRT
<213> ORGANISM: Artificial Sequence
<220> FEATURE:
<223> OTHER INFORMATION: Synthetic: UC2.3.7 VHCDR3 (IMGT)

<400> SEQUENCE: 90

Ala Arg Asp Gly Thr Ser Ala Ala Ala Phe Asp Ser
1 5 10

<210> SEQ ID NO 91
<211> LENGTH: 6
<212> TYPE: PRT
<213> ORGANISM: Artificial Sequence
<220> FEATURE:
<223> OTHER INFORMATION: Synthetic: UC2.3.7 VLCDR1 (IMGT)

<400> SEQUENCE: 91

Gln Asp Ile Thr Asn Phe
1               5

<210> SEQ ID NO 92
<211> LENGTH: 3
<212> TYPE: PRT
<213> ORGANISM: Artificial Sequence
<220> FEATURE:
<223> OTHER INFORMATION: Synthetic: UC2.3.7 VLCDR2 (IMGT)

<400> SEQUENCE: 92

Asp Ala Ser
1

<210> SEQ ID NO 93
<211> LENGTH: 9
<212> TYPE: PRT
<213> ORGANISM: Artificial Sequence
<220> FEATURE:
<223> OTHER INFORMATION: Synthetic: UC2.3.7 VLCDR3 (IMGT)

<400> SEQUENCE: 93

Gln Gln Ser Asp Ser Tyr Pro Ile Thr
1               5

<210> SEQ ID NO 94
<211> LENGTH: 119
<212> TYPE: PRT
<213> ORGANISM: Artificial Sequence
<220> FEATURE:
<223> OTHER INFORMATION: Synthetic: UC2.3.7 VH

<400> SEQUENCE: 94

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ile Ile Ser Asp Gly Gly Asp Ala Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser
        115

<210> SEQ ID NO 95
<211> LENGTH: 107
<212> TYPE: PRT
<213> ORGANISM: Artificial Sequence
<220> FEATURE:
<223> OTHER INFORMATION: Synthetic: UC2.3.7 VL

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
            20                  25                  30

Leu Asn Trp Tyr Gln Gln Lys Pro Gly Lys Ala Pro Lys Leu Leu Ile
        35                  40                  45

Tyr Asp Ala Ser Arg Arg Arg Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Ser Tyr Pro Ile
                85                  90                  95

Thr Phe Gly Gln Gly Thr Lys Val Glu Ile Lys
            100                 105

<210> SEQ ID NO 96
<211> LENGTH: 448
<212> TYPE: PRT
<213> ORGANISM: Artificial Sequence
<220> FEATURE:
<223> OTHER INFORMATION: Synthetic: UC2.3.7-IgG1 heavy chain

<400> SEQUENCE: 96

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

<210> SEQ ID NO 97
<211> LENGTH: 214
<212> TYPE: PRT
<213> ORGANISM: Artificial Sequence
<220> FEATURE:
<223> OTHER INFORMATION: Synthetic: UC2.3.7-IgG1 light chain

<400> SEQUENCE: 97

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Asp Ala Ser Arg Arg Arg Ala Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Ser Asp Ser Tyr Pro Ile
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 98
<211> LENGTH: 251
<212> TYPE: PRT
<213> ORGANISM: Artificial Sequence
<220> FEATURE:
<223> OTHER INFORMATION: Synthetic: UC2.3.8 scFv

<400> SEQUENCE: 98

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Asn Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Ser Ser Gly Gly Ser Thr Ser Gly
        115                 120                 125

Ser Gly Lys Pro Gly Ser Gly Glu Gly Ser Ser Gly Ser Ala Arg Asp
    130                 135                 140

Ile Gln Met Thr Gln Ser Pro Ser Ser Leu Ser Ala Ser Val Gly Asp
145                 150                 155                 160

Arg Val Thr Ile Thr Cys Gln Ala Ser Gln Asp Ile Thr Asn Phe Leu
                165                 170                 175

Asn Trp Tyr Gln Gln Lys Pro Gly Lys Ala Pro Lys Leu Leu Ile Tyr
            180                 185                 190

Asp Ala Ser Arg Arg Arg Ala Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Gln Gln Ser Asp Ser Tyr Pro Ile Thr
225                 230                 235                 240

Phe Gly Gln Gly Thr Lys Val Glu Ile Lys Arg
                245                 250


<210> SEQ ID NO 99
<211> LENGTH: 7
<212> TYPE: PRT
<213> ORGANISM: Artificial Sequence
<220> FEATURE:
<223> OTHER INFORMATION: Synthetic: UC2.3.8 VHCDR1 (Chothia)

<400> SEQUENCE: 99
```

Gly Phe Thr Phe Ser Thr Tyr
1 5

<210> SEQ ID NO 100
<211> LENGTH: 6
<212> TYPE: PRT
<213> ORGANISM: Artificial Sequence
<220> FEATURE:
<223> OTHER INFORMATION: Synthetic: UC2.3.8 VHCDR2 (Chothia)

<400> SEQUENCE: 100

Ser Asp Gly Gly Asp Ala
1 5

<210> SEQ ID NO 101
<211> LENGTH: 10
<212> TYPE: PRT
<213> ORGANISM: Artificial Sequence
<220> FEATURE:
<223> OTHER INFORMATION: Synthetic: UC2.3.8 VHCDR3 (Chothia)

<400> SEQUENCE: 101

Asp Gly Thr Ser Ala Ala Ala Phe Asp Ser
1 5 10

<210> SEQ ID NO 102
<211> LENGTH: 11
<212> TYPE: PRT
<213> ORGANISM: Artificial Sequence
<220> FEATURE:
<223> OTHER INFORMATION: Synthetic: UC2.3.8 VLCDR1 (Chothia)

<400> SEQUENCE: 102

Gln Ala Ser Gln Asp Ile Thr Asn Phe Leu Asn
1 5 10

<210> SEQ ID NO 103
<211> LENGTH: 7
<212> TYPE: PRT
<213> ORGANISM: Artificial Sequence
<220> FEATURE:
<223> OTHER INFORMATION: Synthetic: UC2.3.8 VLCDR2 (Chothia)

<400> SEQUENCE: 103

Asp Ala Ser Arg Arg Arg Thr
1 5

<210> SEQ ID NO 104
<211> LENGTH: 9
<212> TYPE: PRT
<213> ORGANISM: Artificial Sequence
<220> FEATURE:
<223> OTHER INFORMATION: Synthetic: UC2.3.8 VLCDR3 (Chothia)

<400> SEQUENCE: 104

Gln Gln Ser Asp Ser Tyr Pro Ile Thr
1 5

<210> SEQ ID NO 105
<211> LENGTH: 5
<212> TYPE: PRT
<213> ORGANISM: Artificial Sequence
<220> FEATURE:
<223> OTHER INFORMATION: Synthetic: UC2.3.8 VHCDR1 (Kabat)

<400> SEQUENCE: 105

Thr Tyr Ala Met Ser
1 5

<210> SEQ ID NO 106
<211> LENGTH: 17
<212> TYPE: PRT
<213> ORGANISM: Artificial Sequence
<220> FEATURE:
<223> OTHER INFORMATION: Synthetic: UC2.3.8 VHCDR2 (Kabat)

<400> SEQUENCE: 106

Ile Ile Ser Asp Gly Gly Asp Ala Thr Val Tyr Ala Asp Ser Val Lys
1 5 10 15

Gly

<210> SEQ ID NO 107
<211> LENGTH: 10
<212> TYPE: PRT
<213> ORGANISM: Artificial Sequence
<220> FEATURE:
<223> OTHER INFORMATION: Synthetic: UC2.3.8 VHCDR3 (Kabat)

<400> SEQUENCE: 107

Asp Gly Thr Ser Ala Ala Ala Phe Asp Ser
1 5 10

<210> SEQ ID NO 108
<211> LENGTH: 11
<212> TYPE: PRT
<213> ORGANISM: Artificial Sequence
<220> FEATURE:
<223> OTHER INFORMATION: Synthetic: UC2.3.8 VLCDR1 (Kabat)

<400> SEQUENCE: 108

Gln Ala Ser Gln Asp Ile Thr Asn Phe Leu Asn
1 5 10

<210> SEQ ID NO 109
<211> LENGTH: 7
<212> TYPE: PRT
<213> ORGANISM: Artificial Sequence
<220> FEATURE:
<223> OTHER INFORMATION: Synthetic: UC2.3.8 VLCDR2 (Kabat)

<400> SEQUENCE: 109

Asp Ala Ser Arg Arg Arg Thr
1 5

<210> SEQ ID NO 110
<211> LENGTH: 9
<212> TYPE: PRT
<213> ORGANISM: Artificial Sequence
<220> FEATURE:
<223> OTHER INFORMATION: Synthetic: UC2.3.8 VLCDR3 (Kabat)

<400> SEQUENCE: 110

Gln Gln Ser Asp Ser Tyr Pro Ile Thr
1 5

<210> SEQ ID NO 111
<211> LENGTH: 8
<212> TYPE: PRT
<213> ORGANISM: Artificial Sequence
<220> FEATURE:
<223> OTHER INFORMATION: Synthetic: UC2.3.8 VHCDR1 (IMGT)

<400> SEQUENCE: 111

Gly Phe Thr Phe Ser Thr Tyr Ala
1 5

<210> SEQ ID NO 112
<211> LENGTH: 8
<212> TYPE: PRT
<213> ORGANISM: Artificial Sequence
<220> FEATURE:
<223> OTHER INFORMATION: Synthetic: UC2.3.8 VHCDR2 (IMGT)

<400> SEQUENCE: 112

Ile Ser Asp Gly Gly Asp Ala Thr
1 5

<210> SEQ ID NO 113
<211> LENGTH: 12
<212> TYPE: PRT
<213> ORGANISM: Artificial Sequence
<220> FEATURE:
<223> OTHER INFORMATION: Synthetic: UC2.3.8 VHCDR3 (IMGT)

<400> SEQUENCE: 113

Ala Arg Asp Gly Thr Ser Ala Ala Ala Phe Asp Ser
1 5 10

<210> SEQ ID NO 114
<211> LENGTH: 6
<212> TYPE: PRT
<213> ORGANISM: Artificial Sequence
<220> FEATURE:
<223> OTHER INFORMATION: Synthetic: UC2.3.8 VLCDR1 (IMGT)

<400> SEQUENCE: 114

Gln Asp Ile Thr Asn Phe
1 5

<210> SEQ ID NO 115
<211> LENGTH: 3
<212> TYPE: PRT
<213> ORGANISM: Artificial Sequence
<220> FEATURE:
<223> OTHER INFORMATION: Synthetic: UC2.3.8 VLCDR2 (IMGT)

<400> SEQUENCE: 115

Asp Ala Ser
1

<210> SEQ ID NO 116
<211> LENGTH: 9
<212> TYPE: PRT
<213> ORGANISM: Artificial Sequence
<220> FEATURE:
<223> OTHER INFORMATION: Synthetic: UC2.3.8 VLCDR3 (IMGT)

<400> SEQUENCE: 116

Gln Gln Ser Asp Ser Tyr Pro Ile Thr
1 5

<210> SEQ ID NO 117
<211> LENGTH: 119
<212> TYPE: PRT
<213> ORGANISM: Artificial Sequence
<220> FEATURE:
<223> OTHER INFORMATION: Synthetic: UC2.3.8 VH

<400> SEQUENCE: 117

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Asn Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser
        115


<210> SEQ ID NO 118
<211> LENGTH: 107
<212> TYPE: PRT
<213> ORGANISM: Artificial Sequence
<220> FEATURE:
<223> OTHER INFORMATION: Synthetic: UC2.3.8VL

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
            20                  25                  30

Leu Asn Trp Tyr Gln Gln Lys Pro Gly Lys Ala Pro Lys Leu Leu Ile
        35                  40                  45

Tyr Asp Ala Ser Arg Arg Arg Ala Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Ser Tyr Pro Ile
                85                  90                  95

Thr Phe Gly Gln Gly Thr Lys Val Glu Ile Lys
            100                 105


<210> SEQ ID NO 119
<211> LENGTH: 448
<212> TYPE: PRT
<213> ORGANISM: Artificial Sequence
<220> FEATURE:
<223> OTHER INFORMATION: Synthetic: UC2.3.8-IgG1 heavy chain

<400> SEQUENCE: 119

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Asn Arg Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 120
<211> LENGTH: 214
<212> TYPE: PRT
<213> ORGANISM: Artificial Sequence
<220> FEATURE:
<223> OTHER INFORMATION: Synthetic: UC2.3.8-IgG1 light chain

<400> SEQUENCE: 120

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
            20                  25                  30

Leu Asn Trp Tyr Gln Gln Lys Pro Gly Lys Ala Pro Lys Leu Leu Ile
        35                  40                  45

Tyr Asp Ala Ser Arg Arg Arg Ala Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Ser Tyr Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 121
<211> LENGTH: 251
<212> TYPE: PRT
<213> ORGANISM: Artificial Sequence
<220> FEATURE:
<223> OTHER INFORMATION: Synthetic: UC2.3.9 (S4-2 1D10-1G9-1F12) scFv

<400> SEQUENCE: 121

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Asn Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Ser Ser Gly Gly Ser Thr Ser Gly
        115                 120                 125

Ser Gly Lys Pro Gly Ser Gly Glu Gly Ser Ser Gly Ser Ala Arg Asp
    130                 135                 140
```

```
Ile Gln Met Thr Gln Ser Pro Ser Ser Leu Ser Ala Ser Val Gly Asp
145                 150                 155                 160

Arg Val Thr Ile Thr Cys His Ala Ser Gln Asp Ile Thr Asn Phe Leu
                165                 170                 175

Asn Trp Tyr Gln Gln Lys Pro Gly Lys Ala Pro Lys Leu Leu Ile Tyr
            180                 185                 190

Asp Ala Ser Thr Leu Gln Thr Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Gln Gln Ser Asp Ser Tyr Pro Ile Thr
225                 230                 235                 240

Phe Gly Gln Gly Thr Lys Val Glu Ile Lys Arg
                245                 250


<210> SEQ ID NO 122
<211> LENGTH: 7
<212> TYPE: PRT
<213> ORGANISM: Artificial Sequence
<220> FEATURE:
<223> OTHER INFORMATION: Synthetic: UC2.3.9 VHCDR1 (Chothia)

<400> SEQUENCE: 122

Gly Phe Thr Phe Ser Thr Tyr
1               5


<210> SEQ ID NO 123
<211> LENGTH: 6
<212> TYPE: PRT
<213> ORGANISM: Artificial Sequence
<220> FEATURE:
<223> OTHER INFORMATION: Synthetic: UC2.3.9 VHCDR2 (Chothia)

<400> SEQUENCE: 123

Ser Asp Gly Gly Asp Ala
1               5


<210> SEQ ID NO 124
<211> LENGTH: 10
<212> TYPE: PRT
<213> ORGANISM: Artificial Sequence
<220> FEATURE:
<223> OTHER INFORMATION: Synthetic: UC2.3.9 VHCDR3 (Chothia)

<400> SEQUENCE: 124

Asp Gly Thr Ser Ala Ala Ala Phe Asp Ser
1               5                   10


<210> SEQ ID NO 125
<211> LENGTH: 11
<212> TYPE: PRT
<213> ORGANISM: Artificial Sequence
<220> FEATURE:
<223> OTHER INFORMATION: Synthetic: UC2.3.9 VLCDR1 (Chothia)

<400> SEQUENCE: 125

His Ala Ser Gln Asp Ile Thr Asn Phe Leu Asn
1               5                   10


<210> SEQ ID NO 126
<211> LENGTH: 7
<212> TYPE: PRT
<213> ORGANISM: Artificial Sequence
```

```
<220> FEATURE:
<223> OTHER INFORMATION: Synthetic: UC2.3.9 VLCDR2 (Chothia)

<400> SEQUENCE: 126

Asp Ala Ser Thr Leu Gln Thr
1               5


<210> SEQ ID NO 127
<211> LENGTH: 9
<212> TYPE: PRT
<213> ORGANISM: Artificial Sequence
<220> FEATURE:
<223> OTHER INFORMATION: Synthetic: UC2.3.9 VLCDR3 (Chothia)

<400> SEQUENCE: 127

Gln Gln Ser Asp Ser Tyr Pro Ile Thr
1               5


<210> SEQ ID NO 128
<211> LENGTH: 5
<212> TYPE: PRT
<213> ORGANISM: Artificial Sequence
<220> FEATURE:
<223> OTHER INFORMATION: Synthetic: UC2.3.9 VHCDR1 (Kabat)

<400> SEQUENCE: 128

Thr Tyr Ala Met Ser
1               5


<210> SEQ ID NO 129
<211> LENGTH: 17
<212> TYPE: PRT
<213> ORGANISM: Artificial Sequence
<220> FEATURE:
<223> OTHER INFORMATION: Synthetic: UC2.3.9 VHCDR2 (Kabat)

<400> SEQUENCE: 129

Ile Ile Ser Asp Gly Gly Asp Ala Thr Val Tyr Ala Asp Ser Val Lys
1               5                   10                  15

Gly


<210> SEQ ID NO 130
<211> LENGTH: 10
<212> TYPE: PRT
<213> ORGANISM: Artificial Sequence
<220> FEATURE:
<223> OTHER INFORMATION: Synthetic: UC2.3.9 VHCDR3 (Kabat)

<400> SEQUENCE: 130

Asp Gly Thr Ser Ala Ala Ala Phe Asp Ser
1               5                   10


<210> SEQ ID NO 131
<211> LENGTH: 11
<212> TYPE: PRT
<213> ORGANISM: Artificial Sequence
<220> FEATURE:
<223> OTHER INFORMATION: Synthetic: UC2.3.9 VLCDR1 (Kabat)

<400> SEQUENCE: 131

His Ala Ser Gln Asp Ile Thr Asn Phe Leu Asn
1               5                   10


<210> SEQ ID NO 132
<211> LENGTH: 7
<212> TYPE: PRT
```

<213> ORGANISM: Artificial Sequence
<220> FEATURE:
<223> OTHER INFORMATION: Synthetic: UC2.3.9 VLCDR2 (Kabat)

<400> SEQUENCE: 132

Asp Ala Ser Thr Leu Gln Thr
1 5

<210> SEQ ID NO 133
<211> LENGTH: 9
<212> TYPE: PRT
<213> ORGANISM: Artificial Sequence
<220> FEATURE:
<223> OTHER INFORMATION: Synthetic: UC2.3.9 VLCDR3 (Kabat)

<400> SEQUENCE: 133

Gln Gln Ser Asp Ser Tyr Pro Ile Thr
1 5

<210> SEQ ID NO 134
<211> LENGTH: 8
<212> TYPE: PRT
<213> ORGANISM: Artificial Sequence
<220> FEATURE:
<223> OTHER INFORMATION: Synthetic: UC2.3.9 VHCDR1 (IMGT)

<400> SEQUENCE: 134

Gly Phe Thr Phe Ser Thr Tyr Ala
1 5

<210> SEQ ID NO 135
<211> LENGTH: 8
<212> TYPE: PRT
<213> ORGANISM: Artificial Sequence
<220> FEATURE:
<223> OTHER INFORMATION: Synthetic: UC2.3.9 VHCDR2 (IMGT)

<400> SEQUENCE: 135

Ile Ser Asp Gly Gly Asp Ala Thr
1 5

<210> SEQ ID NO 136
<211> LENGTH: 12
<212> TYPE: PRT
<213> ORGANISM: Artificial Sequence
<220> FEATURE:
<223> OTHER INFORMATION: Synthetic: UC2.3.9 VHCDR3 (IMGT)

<400> SEQUENCE: 136

Ala Arg Asp Gly Thr Ser Ala Ala Ala Phe Asp Ser
1 5 10

<210> SEQ ID NO 137
<211> LENGTH: 6
<212> TYPE: PRT
<213> ORGANISM: Artificial Sequence
<220> FEATURE:
<223> OTHER INFORMATION: Synthetic: UC2.3.9 VLCDR1 (IMGT)

<400> SEQUENCE: 137

Gln Asp Ile Thr Asn Phe
1 5

<210> SEQ ID NO 138
<211> LENGTH: 3
<212> TYPE: PRT
<213> ORGANISM: Artificial Sequence
<220> FEATURE:
<223> OTHER INFORMATION: Synthetic: UC2.3.9 VLCDR2 (IMGT)

<400> SEQUENCE: 138

Asp Ala Ser
1

<210> SEQ ID NO 139
<211> LENGTH: 9
<212> TYPE: PRT
<213> ORGANISM: Artificial Sequence
<220> FEATURE:
<223> OTHER INFORMATION: Synthetic: UC2.3.9 VLCDR3 (IMGT)

<400> SEQUENCE: 139

Gln Gln Ser Asp Ser Tyr Pro Ile Thr
1 5

<210> SEQ ID NO 140
<211> LENGTH: 119
<212> TYPE: PRT
<213> ORGANISM: Artificial Sequence
<220> FEATURE:
<223> OTHER INFORMATION: Synthetic: UC2.3.9 VH

<400> SEQUENCE: 140

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Ala Met Ser Trp Ile Arg Gln Ala Pro Gly Lys Gly Leu Glu Trp Val
35 40 45

Ser Ile Ile Ser Asp Gly Gly Asp Ala Thr Val Tyr Ala Asp Ser Val
50 55 60

Lys Gly Arg Phe Thr Ile Ser Arg Asp Asn Asn Arg Asn Thr Leu Tyr
65 70 75 80

Leu Gln Met Asn Ser Leu Arg Ala Glu Asp Thr Ala Val Tyr Tyr Cys
85 90 95

Ala Arg Asp Gly Thr Ser Ala Ala Ala Phe Asp Ser Trp Gly Gln Gly
100 105 110

Thr Leu Val Thr Val Ser Ser
115

<210> SEQ ID NO 141
<211> LENGTH: 107
<212> TYPE: PRT
<213> ORGANISM: Artificial Sequence
<220> FEATURE:
<223> OTHER INFORMATION: Synthetic: UC2.3.9 VL

<400> SEQUENCE: 141

Asp Ile Gln Met Thr Gln Ser Pro Ser Ser Leu Ser Ala Ser Val Gly
1 5 10 15

Asp Arg Val Thr Ile Thr Cys His Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Asp Ala Ser Thr Leu Gln Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

```
Glu Asp Ile Ala Thr Tyr Tyr Cys Gln Gln Ser Asp Ser Tyr Pro Ile
                85                  90                  95

Thr Phe Gly Gln Gly Thr Lys Val Glu Ile Lys
            100                 105


<210> SEQ ID NO 142
<211> LENGTH: 448
<212> TYPE: PRT
<213> ORGANISM: Artificial Sequence
<220> FEATURE:
<223> OTHER INFORMATION: Synthetic: UC2.3.9-IgG1 heavy chain

<400> SEQUENCE: 142

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Asn Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

<210> SEQ ID NO 143
<211> LENGTH: 214
<212> TYPE: PRT
<213> ORGANISM: Artificial Sequence
<220> FEATURE:
<223> OTHER INFORMATION: Synthetic: UC2.3.9-IgG1 light chain

<400> SEQUENCE: 143

Asp Ile Gln Met Thr Gln Ser Pro Ser Ser Leu Ser Ala Ser Val Gly
1 5 10 15

Asp Arg Val Thr Ile Thr Cys His Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Asp Ala Ser Thr Leu Gln Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Ser Asp Ser Tyr Pro Ile
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 144
<211> LENGTH: 251
<212> TYPE: PRT
<213> ORGANISM: Artificial Sequence
<220> FEATURE:
<223> OTHER INFORMATION: Synthetic: UC2.3.10 (S4-2 1D10-1G9-1G2) scFv

<400> SEQUENCE: 144

```
Gln Val Gln Leu Leu Glu Ser Gly Gly Gly Leu Val Gln Pro Gly Gly
1               5                   10                  15

Ser Leu Arg Leu Ser Tyr Ala Ala Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Thr Ser Ala Ala Ala Phe Asp Ser Trp Gly Gln Gly
            100                 105                 110

Thr Leu Val Thr Val Ser Ser Ala Ser Ser Gly Gly Ser Thr Ser Gly
        115                 120                 125

Ser Gly Lys Pro Gly Ser Gly Glu Gly Ser Ser Gly Ser Ala Arg Asp
    130                 135                 140

Ile Gln Met Thr Gln Ser Pro Ser Ser Leu Ser Ala Ser Val Gly Asp
145                 150                 155                 160

Arg Val Thr Ile Thr Cys Gln Ala Ser Gln Asp Ile Thr Asn Phe Leu
                165                 170                 175

Asn Trp Tyr Gln Gln Lys Pro Gly Lys Ala Pro Lys Leu Leu Ile Tyr
            180                 185                 190

Asp Ala Ser Thr Leu Gln Thr Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Gln Gln Ser Asp Ser Tyr Pro Ile Thr
225                 230                 235                 240

Phe Gly Gln Gly Thr Lys Val Glu Ile Lys Arg
                245                 250
```

<210> SEQ ID NO 145
<211> LENGTH: 7
<212> TYPE: PRT
<213> ORGANISM: Artificial Sequence
<220> FEATURE:
<223> OTHER INFORMATION: Synthetic: UC2.3.10 VHCDR1 (Chothia)

<400> SEQUENCE: 145

```
Gly Phe Thr Phe Ser Thr Tyr
1               5
```

<210> SEQ ID NO 146
<211> LENGTH: 5
<212> TYPE: PRT
<213> ORGANISM: Artificial Sequence
<220> FEATURE:
<223> OTHER INFORMATION: Synthetic: UC2.3.10 VHCDR2 (Chothia)

<400> SEQUENCE: 146

```
Asp Gly Gly Asp Ala
1               5
```

<210> SEQ ID NO 147
<211> LENGTH: 10
<212> TYPE: PRT
<213> ORGANISM: Artificial Sequence
<220> FEATURE:
<223> OTHER INFORMATION: Synthetic: UC2.3.10 VHCDR3 (Chothia)

<400> SEQUENCE: 147

Asp Arg Thr Ser Ala Ala Ala Phe Asp Ser
1 5 10

<210> SEQ ID NO 148
<211> LENGTH: 11
<212> TYPE: PRT
<213> ORGANISM: Artificial Sequence
<220> FEATURE:
<223> OTHER INFORMATION: Synthetic: UC2.3.10 VLCDR1 (Chothia)

<400> SEQUENCE: 148

Gln Ala Ser Gln Asp Ile Thr Asn Phe Leu Asn
1 5 10

<210> SEQ ID NO 149
<211> LENGTH: 7
<212> TYPE: PRT
<213> ORGANISM: Artificial Sequence
<220> FEATURE:
<223> OTHER INFORMATION: Synthetic: UC2.3.10 VLCDR2 (Chothia)

<400> SEQUENCE: 149

Asp Ala Ser Thr Leu Gln Thr
1 5

<210> SEQ ID NO 150
<211> LENGTH: 9
<212> TYPE: PRT
<213> ORGANISM: Artificial Sequence
<220> FEATURE:
<223> OTHER INFORMATION: Synthetic: UC2.3.10 VLCDR3 (Chothia)

<400> SEQUENCE: 150

Gln Gln Ser Asp Ser Tyr Pro Ile Thr
1 5

<210> SEQ ID NO 151
<211> LENGTH: 5
<212> TYPE: PRT
<213> ORGANISM: Artificial Sequence
<220> FEATURE:
<223> OTHER INFORMATION: Synthetic: UC2.3.10 VHCDR1 (Kabat)

<400> SEQUENCE: 151

Thr Tyr Ala Met Ser
1 5

<210> SEQ ID NO 152
<211> LENGTH: 17
<212> TYPE: PRT
<213> ORGANISM: Artificial Sequence
<220> FEATURE:
<223> OTHER INFORMATION: Synthetic: UC2.3.10 VHCDR2 (Kabat)

<400> SEQUENCE: 152

Ile Ile Ser Asp Gly Gly Asp Ala Thr Val Tyr Ala Asp Ser Val Lys
1 5 10 15

Gly

```
<210> SEQ ID NO 153
<211> LENGTH: 10
<212> TYPE: PRT
<213> ORGANISM: Artificial Sequence
<220> FEATURE:
<223> OTHER INFORMATION: Synthetic: UC2.3.10 VHCDR3 (Kabat)

<400> SEQUENCE: 153

Asp Arg Thr Ser Ala Ala Ala Phe Asp Ser
1               5                   10


<210> SEQ ID NO 154
<211> LENGTH: 11
<212> TYPE: PRT
<213> ORGANISM: Artificial Sequence
<220> FEATURE:
<223> OTHER INFORMATION: Synthetic: UC2.3.10 VLCDR1 (Kabat)

<400> SEQUENCE: 154

Gln Ala Ser Gln Asp Ile Thr Asn Phe Leu Asn
1               5                   10


<210> SEQ ID NO 155
<211> LENGTH: 7
<212> TYPE: PRT
<213> ORGANISM: Artificial Sequence
<220> FEATURE:
<223> OTHER INFORMATION: Synthetic: UC2.3.10 VLCDR2 (Kabat)

<400> SEQUENCE: 155

Asp Ala Ser Thr Leu Gln Thr
1               5


<210> SEQ ID NO 156
<211> LENGTH: 9
<212> TYPE: PRT
<213> ORGANISM: Artificial Sequence
<220> FEATURE:
<223> OTHER INFORMATION: Synthetic: UC2.3.10 VLCDR3 (Kabat)

<400> SEQUENCE: 156

Gln Gln Ser Asp Ser Tyr Pro Ile Thr
1               5


<210> SEQ ID NO 157
<211> LENGTH: 8
<212> TYPE: PRT
<213> ORGANISM: Artificial Sequence
<220> FEATURE:
<223> OTHER INFORMATION: Synthetic: UC2.3.10 VHCDR1 (IMGT)

<400> SEQUENCE: 157

Gly Phe Thr Phe Ser Thr Tyr Ala
1               5


<210> SEQ ID NO 158
<211> LENGTH: 8
<212> TYPE: PRT
<213> ORGANISM: Artificial Sequence
<220> FEATURE:
<223> OTHER INFORMATION: Synthetic: UC2.3.10 VHCDR2 (IMGT)

<400> SEQUENCE: 158

Ile Ser Asp Gly Gly Asp Ala Thr
1               5
```

<210> SEQ ID NO 159
<211> LENGTH: 12
<212> TYPE: PRT
<213> ORGANISM: Artificial Sequence
<220> FEATURE:
<223> OTHER INFORMATION: Synthetic: UC2.3.10 VHCDR3 (IMGT)

<400> SEQUENCE: 159

Ala Arg Asp Arg Thr Ser Ala Ala Ala Phe Asp Ser
1 5 10

<210> SEQ ID NO 160
<211> LENGTH: 6
<212> TYPE: PRT
<213> ORGANISM: Artificial Sequence
<220> FEATURE:
<223> OTHER INFORMATION: Synthetic: UC2.3.10 VLCDR1 (IMGT)

<400> SEQUENCE: 160

Gln Asp Ile Thr Asn Phe
1 5

<210> SEQ ID NO 161
<211> LENGTH: 3
<212> TYPE: PRT
<213> ORGANISM: Artificial Sequence
<220> FEATURE:
<223> OTHER INFORMATION: Synthetic: UC2.3.10 VLCDR2 (IMGT)

<400> SEQUENCE: 161

Asp Ala Ser
1

<210> SEQ ID NO 162
<211> LENGTH: 9
<212> TYPE: PRT
<213> ORGANISM: Artificial Sequence
<220> FEATURE:
<223> OTHER INFORMATION: Synthetic: UC2.3.10 VLCDR3 (IMGT)

<400> SEQUENCE: 162

Gln Gln Ser Asp Ser Tyr Pro Ile Thr
1 5

<210> SEQ ID NO 163
<211> LENGTH: 119
<212> TYPE: PRT
<213> ORGANISM: Artificial Sequence
<220> FEATURE:
<223> OTHER INFORMATION: Synthetic: UC2.3.10 VH

<400> SEQUENCE: 163

Gln Val Gln Leu Leu Glu Ser Gly Gly Gly Leu Val Gln Pro Gly Gly
1 5 10 15

Ser Leu Arg Leu Ser Tyr Ala Ala Ser Gly Phe Thr Phe Ser Thr Tyr
20 25 30

Ala Met Ser Trp Ile Arg Gln Ala Pro Gly Lys Gly Leu Glu Trp Val
35 40 45

Ser Ile Ile Ser Asp Gly Gly Asp Ala Thr Val Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Arg Thr Ser Ala Ala Ala Phe Asp Ser Trp Gly Gln Gly
100 105 110

Thr Leu Val Thr Val Ser Ser
115

<210> SEQ ID NO 164
<211> LENGTH: 107
<212> TYPE: PRT
<213> ORGANISM: Artificial Sequence
<220> FEATURE:
<223> OTHER INFORMATION: Synthetic: UC2.3.10 VL

<400> SEQUENCE: 164

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Asp Ala Ser Thr Leu Gln Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Ser Asp Ser Tyr Pro Ile
85 90 95

Thr Phe Gly Gln Gly Thr Lys Val Glu Ile Lys
100 105

<210> SEQ ID NO 165
<211> LENGTH: 448
<212> TYPE: PRT
<213> ORGANISM: Artificial Sequence
<220> FEATURE:
<223> OTHER INFORMATION: Synthetic: UC2.3.10-IgG1 heavy chain

<400> SEQUENCE: 165

Gln Val Gln Leu Leu Glu Ser Gly Gly Gly Leu Val Gln Pro Gly Gly
1 5 10 15

Ser Leu Arg Leu Ser Tyr Ala Ala Ser Gly Phe Thr Phe Ser Thr Tyr
20 25 30

Ala Met Ser Trp Ile Arg Gln Ala Pro Gly Lys Gly Leu Glu Trp Val
35 40 45

Ser Ile Ile Ser Asp Gly Gly Asp Ala Thr Val Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Arg Thr Ser Ala Ala Ala Phe Asp Ser Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu

```
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 166
<211> LENGTH: 214
<212> TYPE: PRT
<213> ORGANISM: Artificial Sequence
<220> FEATURE:
<223> OTHER INFORMATION: Synthetic: UC2.3.10-IgG1  light chain

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Ser Tyr Pro Ile
```

```
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 167
<211> LENGTH: 251
<212> TYPE: PRT
<213> ORGANISM: Artificial Sequence
<220> FEATURE:
<223> OTHER INFORMATION: Synthetic: UC2.3.11 (S4-2 1D10-1G9-1G3) scFv

<400> SEQUENCE: 167

Gln Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Trp
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Asn Ser Gly Gly Ser Thr Ser Gly
        115                 120                 125

Ser Gly Lys Pro Gly Ser Gly Glu Gly Ser Ser Gly Ser Ala Arg Asp
    130                 135                 140

Ile Gln Met Thr Gln Ser Pro Ser Ser Leu Ser Ala Ser Val Gly Asp
145                 150                 155                 160

Arg Val Thr Ile Thr Cys Gln Ala Ser Gln Asp Ile Thr Asn Phe Leu
                165                 170                 175

Asn Trp Tyr Gln Gln Lys Pro Gly Lys Ala Pro Lys Leu Leu Ile Tyr
            180                 185                 190

Asp Ala Ser Thr Leu Gln Thr Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Gln Gln Ser Asp Ser Tyr Pro Ile Thr
```

```
225                 230                 235                 240

Phe Gly Gln Gly Thr Lys Val Glu Ile Lys Arg
                245                 250


<210> SEQ ID NO 168
<211> LENGTH: 7
<212> TYPE: PRT
<213> ORGANISM: Artificial Sequence
<220> FEATURE:
<223> OTHER INFORMATION: Synthetic: UC2.3.11 VHCDR1 (Chothia)

<400> SEQUENCE: 168

Gly Phe Thr Phe Ser Thr Tyr
1               5


<210> SEQ ID NO 169
<211> LENGTH: 6
<212> TYPE: PRT
<213> ORGANISM: Artificial Sequence
<220> FEATURE:
<223> OTHER INFORMATION: Synthetic: UC2.3.11 VHCDR2 (Chothia)

<400> SEQUENCE: 169

Ser Asp Gly Gly Asp Ala
1               5


<210> SEQ ID NO 170
<211> LENGTH: 10
<212> TYPE: PRT
<213> ORGANISM: Artificial Sequence
<220> FEATURE:
<223> OTHER INFORMATION: Synthetic: UC2.3.11 VHCDR3 (Chothia)

<400> SEQUENCE: 170

Asp Gly Thr Ser Ala Ala Ala Phe Asp Ser
1               5                   10


<210> SEQ ID NO 171
<211> LENGTH: 11
<212> TYPE: PRT
<213> ORGANISM: Artificial Sequence
<220> FEATURE:
<223> OTHER INFORMATION: Synthetic: UC2.3.11 VLCDR1 (Chothia)

<400> SEQUENCE: 171

Gln Ala Ser Gln Asp Ile Thr Asn Phe Leu Asn
1               5                   10


<210> SEQ ID NO 172
<211> LENGTH: 7
<212> TYPE: PRT
<213> ORGANISM: Artificial Sequence
<220> FEATURE:
<223> OTHER INFORMATION: Synthetic: UC2.3.11 VLCDR2 (Chothia)

<400> SEQUENCE: 172

Asp Ala Ser Thr Leu Gln Thr
1               5


<210> SEQ ID NO 173
<211> LENGTH: 9
<212> TYPE: PRT
<213> ORGANISM: Artificial Sequence
<220> FEATURE:
<223> OTHER INFORMATION: Synthetic: UC2.3.11 VLCDR3 (Chothia)

<400> SEQUENCE: 173
```

Gln Gln Ser Asp Ser Tyr Pro Ile Thr
1 5

<210> SEQ ID NO 174
<211> LENGTH: 5
<212> TYPE: PRT
<213> ORGANISM: Artificial Sequence
<220> FEATURE:
<223> OTHER INFORMATION: Synthetic: UC2.3.11 VHCDR1 (Kabat)

<400> SEQUENCE: 174

Thr Tyr Ala Met Ser
1 5

<210> SEQ ID NO 175
<211> LENGTH: 16
<212> TYPE: PRT
<213> ORGANISM: Artificial Sequence
<220> FEATURE:
<223> OTHER INFORMATION: Synthetic: UC2.3.11 VHCDR2 (Kabat)

<400> SEQUENCE: 175

Ile Ser Asp Gly Gly Asp Ala Thr Val Tyr Ala Asp Ser Val Lys Gly
1 5 10 15

<210> SEQ ID NO 176
<211> LENGTH: 10
<212> TYPE: PRT
<213> ORGANISM: Artificial Sequence
<220> FEATURE:
<223> OTHER INFORMATION: Synthetic: UC2.3.11 VHCDR3 (Kabat)

<400> SEQUENCE: 176

Asp Gly Thr Ser Ala Ala Ala Phe Asp Ser
1 5 10

<210> SEQ ID NO 177
<211> LENGTH: 11
<212> TYPE: PRT
<213> ORGANISM: Artificial Sequence
<220> FEATURE:
<223> OTHER INFORMATION: Synthetic: UC2.3.11 VLCDR1 (Kabat)

<400> SEQUENCE: 177

Gln Ala Ser Gln Asp Ile Thr Asn Phe Leu Asn
1 5 10

<210> SEQ ID NO 178
<211> LENGTH: 7
<212> TYPE: PRT
<213> ORGANISM: Artificial Sequence
<220> FEATURE:
<223> OTHER INFORMATION: Synthetic: UC2.3.11 VLCDR2 (Kabat)

<400> SEQUENCE: 178

Asp Ala Ser Thr Leu Gln Thr
1 5

<210> SEQ ID NO 179
<211> LENGTH: 9
<212> TYPE: PRT
<213> ORGANISM: Artificial Sequence
<220> FEATURE:
<223> OTHER INFORMATION: Synthetic: UC2.3.11 VLCDR3 (Kabat)

<400> SEQUENCE: 179

Gln Gln Ser Asp Ser Tyr Pro Ile Thr
1 5

<210> SEQ ID NO 180
<211> LENGTH: 8
<212> TYPE: PRT
<213> ORGANISM: Artificial Sequence
<220> FEATURE:
<223> OTHER INFORMATION: Synthetic: UC2.3.11 VHCDR1 (IMGT)

<400> SEQUENCE: 180

Gly Phe Thr Phe Ser Thr Tyr Ala
1 5

<210> SEQ ID NO 181
<211> LENGTH: 8
<212> TYPE: PRT
<213> ORGANISM: Artificial Sequence
<220> FEATURE:
<223> OTHER INFORMATION: Synthetic: UC2.3.11 VHCDR2 (IMGT)

<400> SEQUENCE: 181

Ile Ser Asp Gly Gly Asp Ala Thr
1 5

<210> SEQ ID NO 182
<211> LENGTH: 12
<212> TYPE: PRT
<213> ORGANISM: Artificial Sequence
<220> FEATURE:
<223> OTHER INFORMATION: Synthetic: UC2.3.11 VHCDR3 (IMGT)

<400> SEQUENCE: 182

Ala Arg Asp Gly Thr Ser Ala Ala Ala Phe Asp Ser
1 5 10

<210> SEQ ID NO 183
<211> LENGTH: 6
<212> TYPE: PRT
<213> ORGANISM: Artificial Sequence
<220> FEATURE:
<223> OTHER INFORMATION: Synthetic: UC2.3.11 VLCDR1 (IMGT)

<400> SEQUENCE: 183

Gln Asp Ile Thr Asn Phe
1 5

<210> SEQ ID NO 184
<211> LENGTH: 3
<212> TYPE: PRT
<213> ORGANISM: Artificial Sequence
<220> FEATURE:
<223> OTHER INFORMATION: Synthetic: UC2.3.11 VLCDR2 (IMGT)

<400> SEQUENCE: 184

Asp Ala Ser
1

<210> SEQ ID NO 185
<211> LENGTH: 9
<212> TYPE: PRT
<213> ORGANISM: Artificial Sequence
<220> FEATURE:
<223> OTHER INFORMATION: Synthetic: UC2.3.11 VLCDR3 (IMGT)

<400> SEQUENCE: 185

Gln Gln Ser Asp Ser Tyr Pro Ile Thr 1 5

<210> SEQ ID NO 186
<211> LENGTH: 119
<212> TYPE: PRT
<213> ORGANISM: Artificial Sequence
<220> FEATURE:
<223> OTHER INFORMATION: Synthetic: UC2.3.11 VH

<400> SEQUENCE: 186

Gln Val Gln Leu Leu Glu Ser Gly Gly Gly Leu Val Gln Pro Gly Gly
1 5 10 15

Ser Leu Arg Leu Ser Cys Ala Val Ser Gly Phe Thr Phe Ser Thr Tyr
20 25 30

Ala Met Ser Trp Ile Arg Gln Ala Pro Gly Lys Gly Leu Glu Trp Val
35 40 45

Ser Ile Ile Ser Asp Gly Gly Asp Ala Thr Val Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Trp
85 90 95

Ala Arg Asp Gly Thr Ser Ala Ala Ala Phe Asp Ser Trp Gly Gln Gly
100 105 110

Thr Leu Val Thr Val Ser Ser
115

<210> SEQ ID NO 187
<211> LENGTH: 107
<212> TYPE: PRT
<213> ORGANISM: Artificial Sequence
<220> FEATURE:
<223> OTHER INFORMATION: Synthetic: UC2.3.11 VL

<400> SEQUENCE: 187

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Asp Ala Ser Thr Leu Gln Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Ser Asp Ser Tyr Pro Ile
85 90 95

Thr Phe Gly Gln Gly Thr Lys Val Glu Ile Lys
100 105

<210> SEQ ID NO 188
<211> LENGTH: 448
<212> TYPE: PRT
<213> ORGANISM: Artificial Sequence
<220> FEATURE:
<223> OTHER INFORMATION: Synthetic: UC2.3.11-IgG1 heavy chain

<400> SEQUENCE: 188

Gln Val Gln Leu Leu Glu Ser Gly Gly Gly Leu Val Gln Pro Gly Gly
1 5 10 15

```
Ser Leu Arg Leu Ser Cys Ala Val Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Trp
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

Ala Leu His Asn His Tyr Thr Gln Lys Ser Leu Ser Leu Ser Pro Gly
435 440 445

<210> SEQ ID NO 189
<211> LENGTH: 214
<212> TYPE: PRT
<213> ORGANISM: Artificial Sequence
<220> FEATURE:
<223> OTHER INFORMATION: Synthetic: UC2.3.11-IgG1 light chain

<400> SEQUENCE: 189

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Asp Ala Ser Thr Leu Gln Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Ser Asp Ser Tyr Pro Ile
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 190
<211> LENGTH: 251
<212> TYPE: PRT
<213> ORGANISM: Artificial Sequence
<220> FEATURE:
<223> OTHER INFORMATION: Synthetic: UC2.3.12 (S4-2 1D10-1G9-1H1) scFv

<400> SEQUENCE: 190

Gln Val Gln Leu Leu Glu Ser Gly Gly Gly Leu Val Gln Pro Gly Asp
1 5 10 15

Ser Leu Arg Leu Ser Cys Ala Ala Ser Gly Phe Thr Phe Ser Thr Tyr
20 25 30

Ala Met Ser Trp Ile Arg Gln Ala Pro Gly Lys Gly Leu Glu Trp Val
35 40 45

Ser Ile Ile Ser Asp Gly Gly Asp Ala Thr Val Tyr Ala Asp Ser Val
50 55 60

Lys Gly Arg Phe Thr Ile Ser Arg Asp Asn Asn Arg Asn Thr Leu Tyr
65 70 75 80

```
Leu Gln Met Asn Ser Leu Arg Ala Glu Asp Thr Ala Val Tyr Tyr Cys
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Ser Ser Gly Gly Ser Thr Ser Gly
        115                 120                 125

Ser Gly Lys Pro Gly Ser Gly Glu Gly Ser Ser Gly Ser Ala Arg Asp
    130                 135                 140

Ile Gln Met Thr Gln Ser Pro Ser Ser Leu Ser Ala Ser Val Gly Asp
145                 150                 155                 160

Arg Val Thr Ile Thr Cys Gln Ala Ser Gln Asp Ile Thr Asn Phe Leu
                165                 170                 175

Asn Trp Tyr Gln Gln Lys Pro Gly Lys Ala Pro Lys Leu Leu Ile Tyr
            180                 185                 190

Asp Ala Ser Thr Leu Gln Thr Gly Val Pro Ser Arg Phe Ser Gly Ser
        195                 200                 205

Gly Ser Gly Thr Asn Phe Thr Phe Thr Ile Ser Ser Leu Gln Pro Glu
    210                 215                 220

Asp Ile Ala Thr Tyr Tyr Cys Gln Gln Ser Asp Ser Tyr Pro Ile Thr
225                 230                 235                 240

Phe Gly Gln Gly Thr Lys Val Glu Ile Lys Arg
                245                 250


<210> SEQ ID NO 191
<211> LENGTH: 7
<212> TYPE: PRT
<213> ORGANISM: Artificial Sequence
<220> FEATURE:
<223> OTHER INFORMATION: Synthetic: UC2.3.12 VHCDR1 (Chothia)

<400> SEQUENCE: 191

Gly Phe Thr Phe Ser Thr Tyr
1               5


<210> SEQ ID NO 192
<211> LENGTH: 6
<212> TYPE: PRT
<213> ORGANISM: Artificial Sequence
<220> FEATURE:
<223> OTHER INFORMATION: Synthetic: UC2.3.12 VHCDR2 (Chothia)

<400> SEQUENCE: 192

Ser Asp Gly Gly Asp Ala
1               5


<210> SEQ ID NO 193
<211> LENGTH: 10
<212> TYPE: PRT
<213> ORGANISM: Artificial Sequence
<220> FEATURE:
<223> OTHER INFORMATION: Synthetic: UC2.3.12 VHCDR3 (Chothia)

<400> SEQUENCE: 193

Asp Gly Thr Ser Ala Ala Ala Phe Asp Ser
1               5                   10


<210> SEQ ID NO 194
<211> LENGTH: 11
<212> TYPE: PRT
<213> ORGANISM: Artificial Sequence
<220> FEATURE:
```

<223> OTHER INFORMATION: Synthetic: UC2.3.12 VLCDR1 (Chothia)

<400> SEQUENCE: 194

Gln Ala Ser Gln Asp Ile Thr Asn Phe Leu Asn
1 5 10

<210> SEQ ID NO 195
<211> LENGTH: 7
<212> TYPE: PRT
<213> ORGANISM: Artificial Sequence
<220> FEATURE:
<223> OTHER INFORMATION: Synthetic: UC2.3.12 VLCDR2 (Chothia)

<400> SEQUENCE: 195

Asp Ala Ser Thr Leu Gln Thr
1 5

<210> SEQ ID NO 196
<211> LENGTH: 9
<212> TYPE: PRT
<213> ORGANISM: Artificial Sequence
<220> FEATURE:
<223> OTHER INFORMATION: Synthetic: UC2.3.12 VLCDR3 (Chothia)

<400> SEQUENCE: 196

Gln Gln Ser Asp Ser Tyr Pro Ile Thr
1 5

<210> SEQ ID NO 197
<211> LENGTH: 5
<212> TYPE: PRT
<213> ORGANISM: Artificial Sequence
<220> FEATURE:
<223> OTHER INFORMATION: Synthetic: UC2.3.12 VHCDR1 (Kabat)

<400> SEQUENCE: 197

Thr Tyr Ala Met Ser
1 5

<210> SEQ ID NO 198
<211> LENGTH: 17
<212> TYPE: PRT
<213> ORGANISM: Artificial Sequence
<220> FEATURE:
<223> OTHER INFORMATION: Synthetic: UC2.3.12 VHCDR2 (Kabat)

<400> SEQUENCE: 198

Ile Ile Ser Asp Gly Gly Asp Ala Thr Val Tyr Ala Asp Ser Val Lys
1 5 10 15

Gly

<210> SEQ ID NO 199
<211> LENGTH: 10
<212> TYPE: PRT
<213> ORGANISM: Artificial Sequence
<220> FEATURE:
<223> OTHER INFORMATION: Synthetic: UC2.3.12 VHCDR3 (Kabat)

<400> SEQUENCE: 199

Asp Gly Thr Ser Ala Ala Ala Phe Asp Ser
1 5 10

<210> SEQ ID NO 200
<211> LENGTH: 11
<212> TYPE: PRT
<213> ORGANISM: Artificial Sequence
<220> FEATURE:
<223> OTHER INFORMATION: Synthetic: UC2.3.12 VLCDR1 (Kabat)

<400> SEQUENCE: 200

Gln Ala Ser Gln Asp Ile Thr Asn Phe Leu Asn
1 5 10

<210> SEQ ID NO 201
<211> LENGTH: 7
<212> TYPE: PRT
<213> ORGANISM: Artificial Sequence
<220> FEATURE:
<223> OTHER INFORMATION: Synthetic: UC2.3.12 VLCDR2 (Kabat)

<400> SEQUENCE: 201

Asp Ala Ser Thr Leu Gln Thr
1 5

<210> SEQ ID NO 202
<211> LENGTH: 9
<212> TYPE: PRT
<213> ORGANISM: Artificial Sequence
<220> FEATURE:
<223> OTHER INFORMATION: Synthetic: UC2.3.12 VLCDR3 (Kabat)

<400> SEQUENCE: 202

Gln Gln Ser Asp Ser Tyr Pro Ile Thr
1 5

<210> SEQ ID NO 203
<211> LENGTH: 8
<212> TYPE: PRT
<213> ORGANISM: Artificial Sequence
<220> FEATURE:
<223> OTHER INFORMATION: Synthetic: UC2.3.12 VHCDR1 (IMGT)

<400> SEQUENCE: 203

Gly Phe Thr Phe Ser Thr Tyr Ala
1 5

<210> SEQ ID NO 204
<211> LENGTH: 8
<212> TYPE: PRT
<213> ORGANISM: Artificial Sequence
<220> FEATURE:
<223> OTHER INFORMATION: Synthetic: UC2.3.12 VHCDR2 (IMGT)

<400> SEQUENCE: 204

Ile Ser Asp Gly Gly Asp Ala Thr
1 5

<210> SEQ ID NO 205
<211> LENGTH: 12
<212> TYPE: PRT
<213> ORGANISM: Artificial Sequence
<220> FEATURE:
<223> OTHER INFORMATION: Synthetic: UC2.3.12 VHCDR3 (IMGT)

<400> SEQUENCE: 205

Ala Arg Asp Gly Thr Ser Ala Ala Ala Phe Asp Ser
1 5 10

<210> SEQ ID NO 206
<211> LENGTH: 6
<212> TYPE: PRT
<213> ORGANISM: Artificial Sequence
<220> FEATURE:

<223> OTHER INFORMATION: Synthetic: UC2.3.12 VLCDR1 (IMGT)

<400> SEQUENCE: 206

Gln Asp Ile Thr Asn Phe
1 5

<210> SEQ ID NO 207
<211> LENGTH: 3
<212> TYPE: PRT
<213> ORGANISM: Artificial Sequence
<220> FEATURE:
<223> OTHER INFORMATION: Synthetic: UC2.3.12 VLCDR2 (IMGT)

<400> SEQUENCE: 207

Asp Ala Ser
1

<210> SEQ ID NO 208
<211> LENGTH: 9
<212> TYPE: PRT
<213> ORGANISM: Artificial Sequence
<220> FEATURE:
<223> OTHER INFORMATION: Synthetic: UC2.3.12 VLCDR3 (IMGT)

<400> SEQUENCE: 208

Gln Gln Ser Asp Ser Tyr Pro Ile Thr
1 5

<210> SEQ ID NO 209
<211> LENGTH: 119
<212> TYPE: PRT
<213> ORGANISM: Artificial Sequence
<220> FEATURE:
<223> OTHER INFORMATION: Synthetic: UC2.3.12 VH

<400> SEQUENCE: 209

Gln Val Gln Leu Leu Glu Ser Gly Gly Gly Leu Val Gln Pro Gly Asp
1 5 10 15

Ser Leu Arg Leu Ser Cys Ala Ala Ser Gly Phe Thr Phe Ser Thr Tyr
20 25 30

Ala Met Ser Trp Ile Arg Gln Ala Pro Gly Lys Gly Leu Glu Trp Val
35 40 45

Ser Ile Ile Ser Asp Gly Gly Asp Ala Thr Val Tyr Ala Asp Ser Val
50 55 60

Lys Gly Arg Phe Thr Ile Ser Arg Asp Asn Asn Arg Asn Thr Leu Tyr
65 70 75 80

Leu Gln Met Asn Ser Leu Arg Ala Glu Asp Thr Ala Val Tyr Tyr Cys
85 90 95

Ala Arg Asp Gly Thr Ser Ala Ala Ala Phe Asp Ser Trp Gly Gln Gly
100 105 110

Thr Leu Val Thr Val Ser Ser
115

<210> SEQ ID NO 210
<211> LENGTH: 107
<212> TYPE: PRT
<213> ORGANISM: Artificial Sequence
<220> FEATURE:
<223> OTHER INFORMATION: Synthetic: UC2.3.12 VL

<400> SEQUENCE: 210

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Asp Ala Ser Thr Leu Gln Thr Gly Val Pro Ser Arg Phe Ser Gly
50 55 60

Ser Gly Ser Gly Thr Asn Phe Thr Phe Thr Ile Ser Ser Leu Gln Pro
65 70 75 80

Glu Asp Ile Ala Thr Tyr Tyr Cys Gln Gln Ser Asp Ser Tyr Pro Ile
85 90 95

Thr Phe Gly Gln Gly Thr Lys Val Glu Ile Lys
100 105

<210> SEQ ID NO 211
<211> LENGTH: 448
<212> TYPE: PRT
<213> ORGANISM: Artificial Sequence
<220> FEATURE:
<223> OTHER INFORMATION: Synthetic: UC2.3.12-IgG1 heavy chain

<400> SEQUENCE: 211

Gln Val Gln Leu Leu Glu Ser Gly Gly Gly Leu Val Gln Pro Gly Asp
1 5 10 15

Ser Leu Arg Leu Ser Cys Ala Ala Ser Gly Phe Thr Phe Ser Thr Tyr
20 25 30

Ala Met Ser Trp Ile Arg Gln Ala Pro Gly Lys Gly Leu Glu Trp Val
35 40 45

Ser Ile Ile Ser Asp Gly Gly Asp Ala Thr Val Tyr Ala Asp Ser Val
50 55 60

Lys Gly Arg Phe Thr Ile Ser Arg Asp Asn Asn Arg Asn Thr Leu Tyr
65 70 75 80

Leu Gln Met Asn Ser Leu Arg Ala Glu Asp Thr Ala Val Tyr Tyr Cys
85 90 95

Ala Arg Asp Gly Thr Ser Ala Ala Ala Phe Asp Ser Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

<210> SEQ ID NO 212
<211> LENGTH: 214
<212> TYPE: PRT
<213> ORGANISM: Artificial Sequence
<220> FEATURE:
<223> OTHER INFORMATION: Synthetic: UC2.3.12-IgG1 light chain

<400> SEQUENCE: 212

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Asp Ala Ser Thr Leu Gln Thr Gly Val Pro Ser Arg Phe Ser Gly
50 55 60

Ser Gly Ser Gly Thr Asn Phe Thr Phe Thr Ile Ser Ser Leu Gln Pro
65 70 75 80

Glu Asp Ile Ala Thr Tyr Tyr Cys Gln Gln Ser Asp Ser Tyr Pro Ile
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

```
Ala Cys Glu Val Thr His Gln Gly Leu Ser Ser Pro Val Thr Lys Ser
        195                 200                 205

Phe Asn Arg Gly Glu Cys
    210


<210> SEQ ID NO 213
<211> LENGTH: 251
<212> TYPE: PRT
<213> ORGANISM: Artificial Sequence
<220> FEATURE:
<223> OTHER INFORMATION: Synthetic: UC2.3.13 (S4-2 1D10-1G9-1G11) scFv

<400> SEQUENCE: 213

Gln Val Gln Leu Leu Glu Ser Val Gly Gly Leu Val Gln Pro Gly Gly
1               5                   10                  15

Ser Leu Arg Leu Ser Cys Ala Val Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Val Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Thr Ser Ala Ala Ala Phe Asp Ser Trp Gly Gln Gly
            100                 105                 110

Thr Leu Val Ser Asp Ser Ser Ala Ser Ser Gly Gly Ser Thr Ser Gly
        115                 120                 125

Ser Gly Lys Pro Gly Ser Gly Glu Gly Ser Ser Gly Ser Ser Arg Asp
    130                 135                 140

Ile Gln Met Thr Gln Ser Pro Ser Ser Leu Ser Ala Ser Val Gly Asp
145                 150                 155                 160

Arg Val Thr Ile Thr Cys Gln Ala Ser Gln Asp Ile Thr Asn Phe Leu
                165                 170                 175

Asn Trp Tyr Gln Gln Lys Pro Gly Lys Ala Pro Lys Leu Leu Ile Tyr
            180                 185                 190

Asp Ala Ser Thr Leu Gln Thr Gly Val Pro Ser Arg Phe Ser Gly Ser
        195                 200                 205

Gly Ser Gly Thr Asp Phe Asn Phe Thr Ile Ser Ser Leu Gln Pro Glu
    210                 215                 220

Asp Ile Ala Thr Tyr Tyr Cys Gln Gln Ser Asp Ser Tyr Pro Ile Thr
225                 230                 235                 240

Phe Gly Gln Gly Thr Lys Val Glu Ile Lys Arg
                245                 250


<210> SEQ ID NO 214
<211> LENGTH: 7
<212> TYPE: PRT
<213> ORGANISM: Artificial Sequence
<220> FEATURE:
<223> OTHER INFORMATION: Synthetic: UC2.3.13 VHCDR1 (Chothia)

<400> SEQUENCE: 214

Gly Phe Thr Phe Ser Thr Tyr
1               5
```

<210> SEQ ID NO 215
<211> LENGTH: 6
<212> TYPE: PRT
<213> ORGANISM: Artificial Sequence
<220> FEATURE:
<223> OTHER INFORMATION: Synthetic: UC2.3.13 VHCDR2 (Chothia)

<400> SEQUENCE: 215

Ser Asp Gly Gly Asp Val
1               5

<210> SEQ ID NO 216
<211> LENGTH: 10
<212> TYPE: PRT
<213> ORGANISM: Artificial Sequence
<220> FEATURE:
<223> OTHER INFORMATION: Synthetic: UC2.3.13 VHCDR3 (Chothia)

<400> SEQUENCE: 216

Asp Arg Thr Ser Ala Ala Ala Phe Asp Ser
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Synthetic: UC2.3.13 VLCDR1 (Chothia)

<400> SEQUENCE: 217

Gln Ala Ser Gln Asp Ile Thr Asn Phe Leu Asn
1               5                   10

<210> SEQ ID NO 218
<211> LENGTH: 7
<212> TYPE: PRT
<213> ORGANISM: Artificial Sequence
<220> FEATURE:
<223> OTHER INFORMATION: Synthetic: UC2.3.13 VLCDR2 (Chothia)

<400> SEQUENCE: 218

Asp Ala Ser Thr Leu Gln Thr
1               5

<210> SEQ ID NO 219
<211> LENGTH: 9
<212> TYPE: PRT
<213> ORGANISM: Artificial Sequence
<220> FEATURE:
<223> OTHER INFORMATION: Synthetic: UC2.3.13 VLCDR3 (Chothia)

<400> SEQUENCE: 219

Gln Gln Ser Asp Ser Tyr Pro Ile Thr
1               5

<210> SEQ ID NO 220
<211> LENGTH: 5
<212> TYPE: PRT
<213> ORGANISM: Artificial Sequence
<220> FEATURE:
<223> OTHER INFORMATION: Synthetic: UC2.3.13 VHCDR1 (Kabat)

<400> SEQUENCE: 220

Thr Tyr Ala Met Ser
1               5

<210> SEQ ID NO 221

<211> LENGTH: 17
<212> TYPE: PRT
<213> ORGANISM: Artificial Sequence
<220> FEATURE:
<223> OTHER INFORMATION: Synthetic: UC2.3.13 VHCDR2 (Kabat)

<400> SEQUENCE: 221

Ile Ile Ser Asp Gly Gly Asp Val Thr Val Tyr Ala Asp Ser Val Lys
1 5 10 15

Gly

<210> SEQ ID NO 222
<211> LENGTH: 10
<212> TYPE: PRT
<213> ORGANISM: Artificial Sequence
<220> FEATURE:
<223> OTHER INFORMATION: Synthetic: UC2.3.13 VHCDR3 (Kabat)

<400> SEQUENCE: 222

Asp Arg Thr Ser Ala Ala Ala Phe Asp Ser
1 5 10

<210> SEQ ID NO 223
<211> LENGTH: 11
<212> TYPE: PRT
<213> ORGANISM: Artificial Sequence
<220> FEATURE:
<223> OTHER INFORMATION: Synthetic: UC2.3.13 VLCDR1 (Kabat)

<400> SEQUENCE: 223

Gln Ala Ser Gln Asp Ile Thr Asn Phe Leu Asn
1 5 10

<210> SEQ ID NO 224
<211> LENGTH: 7
<212> TYPE: PRT
<213> ORGANISM: Artificial Sequence
<220> FEATURE:
<223> OTHER INFORMATION: Synthetic: UC2.3.13 VLCDR2 (Kabat)

<400> SEQUENCE: 224

Asp Ala Ser Thr Leu Gln Thr
1 5

<210> SEQ ID NO 225
<211> LENGTH: 9
<212> TYPE: PRT
<213> ORGANISM: Artificial Sequence
<220> FEATURE:
<223> OTHER INFORMATION: Synthetic: UC2.3.13 VLCDR3 (Kabat)

<400> SEQUENCE: 225

Gln Gln Ser Asp Ser Tyr Pro Ile Thr
1 5

<210> SEQ ID NO 226
<211> LENGTH: 8
<212> TYPE: PRT
<213> ORGANISM: Artificial Sequence
<220> FEATURE:
<223> OTHER INFORMATION: Synthetic: UC2.3.13 VHCDR1 (IMGT)

<400> SEQUENCE: 226

Gly Phe Thr Phe Ser Thr Tyr Ala
1 5

<210> SEQ ID NO 227
<211> LENGTH: 8
<212> TYPE: PRT
<213> ORGANISM: Artificial Sequence
<220> FEATURE:
<223> OTHER INFORMATION: Synthetic: UC2.3.13 VHCDR2 (IMGT)

<400> SEQUENCE: 227

Ile Ser Asp Gly Gly Asp Val Thr
1 5

<210> SEQ ID NO 228
<211> LENGTH: 12
<212> TYPE: PRT
<213> ORGANISM: Artificial Sequence
<220> FEATURE:
<223> OTHER INFORMATION: Synthetic: UC2.3.13 VHCDR3 (IMGT)

<400> SEQUENCE: 228

Ala Arg Asp Arg Thr Ser Ala Ala Ala Phe Asp Ser
1 5 10

<210> SEQ ID NO 229
<211> LENGTH: 6
<212> TYPE: PRT
<213> ORGANISM: Artificial Sequence
<220> FEATURE:
<223> OTHER INFORMATION: Synthetic: UC2.3.13 VLCDR1 (IMGT)

<400> SEQUENCE: 229

Gln Asp Ile Thr Asn Phe
1 5

<210> SEQ ID NO 230
<211> LENGTH: 3
<212> TYPE: PRT
<213> ORGANISM: Artificial Sequence
<220> FEATURE:
<223> OTHER INFORMATION: Synthetic: UC2.3.13 VLCDR2 (IMGT)

<400> SEQUENCE: 230

Asp Ala Ser
1

<210> SEQ ID NO 231
<211> LENGTH: 9
<212> TYPE: PRT
<213> ORGANISM: Artificial Sequence
<220> FEATURE:
<223> OTHER INFORMATION: Synthetic: UC2.3.13 VLCDR3 (IMGT)

<400> SEQUENCE: 231

Gln Gln Ser Asp Ser Tyr Pro Ile Thr
1 5

<210> SEQ ID NO 232
<211> LENGTH: 119
<212> TYPE: PRT
<213> ORGANISM: Artificial Sequence
<220> FEATURE:
<223> OTHER INFORMATION: Synthetic: UC2.3.13 VH

<400> SEQUENCE: 232

Gln Val Gln Leu Leu Glu Ser Val Gly Gly Leu Val Gln Pro Gly Gly
1 5 10 15

Ser Leu Arg Leu Ser Cys Ala Val Ser Gly Phe Thr Phe Ser Thr Tyr
20 25 30

```
Ala Met Ser Trp Ile Arg Gln Ala Pro Gly Lys Gly Leu Glu Trp Val
        35                  40                  45

Ser Ile Ile Ser Asp Gly Gly Asp Val Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Thr Ser Ala Ala Ala Phe Asp Ser Trp Gly Gln Gly
            100                 105                 110

Thr Leu Val Ser Asp Ser Ser
        115


<210> SEQ ID NO 233
<211> LENGTH: 107
<212> TYPE: PRT
<213> ORGANISM: Artificial Sequence
<220> FEATURE:
<223> OTHER INFORMATION: Synthetic: UC2.3.13 VL

<400> SEQUENCE: 233

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Thr Gly Val Pro Ser Arg Phe Ser Gly
    50                  55                  60

Ser Gly Ser Gly Thr Asp Phe Asn Phe Thr Ile Ser Ser Leu Gln Pro
65                  70                  75                  80

Glu Asp Ile Ala Thr Tyr Tyr Cys Gln Gln Ser Asp Ser Tyr Pro Ile
                85                  90                  95

Thr Phe Gly Gln Gly Thr Lys Val Glu Ile Lys
            100                 105


<210> SEQ ID NO 234
<211> LENGTH: 448
<212> TYPE: PRT
<213> ORGANISM: Artificial Sequence
<220> FEATURE:
<223> OTHER INFORMATION: Synthetic: UC2.3.13-IgG1 heavy chain

<400> SEQUENCE: 234

Gln Val Gln Leu Leu Glu Ser Val Gly Gly Leu Val Gln Pro Gly Gly
1               5                   10                  15

Ser Leu Arg Leu Ser Cys Ala Val Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Val Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Thr Ser Ala Ala Ala Phe Asp Ser Trp Gly Gln Gly
```

```
            100                 105                 110

Thr Leu Val Ser Asp Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 235
<211> LENGTH: 214
<212> TYPE: PRT
<213> ORGANISM: Artificial Sequence
<220> FEATURE:
<223> OTHER INFORMATION: Synthetic: UC2.3.13-IgG1  light chain

<400> SEQUENCE: 235

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
```

```
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Thr Gly Val Pro Ser Arg Phe Ser Gly
    50                  55                  60

Ser Gly Ser Gly Thr Asp Phe Asn Phe Thr Ile Ser Ser Leu Gln Pro
65                  70                  75                  80

Glu Asp Ile Ala Thr Tyr Tyr Cys Gln Gln Ser Asp Ser Tyr Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 236
<211> LENGTH: 251
<212> TYPE: PRT
<213> ORGANISM: Artificial Sequence
<220> FEATURE:
<223> OTHER INFORMATION: Synthetic: UC2.3.14 (S4-2 1D10-1G9-1H11) scFv

<400> SEQUENCE: 236

Gln Val Gln Leu Leu Glu Ser Gly Gly Gly Leu Val Gln Pro Gly Gly
1               5                   10                  15

Ser Leu Arg Leu Ser Tyr Ala Ala Ser Gly Phe Thr Phe Ser Thr Tyr
            20                  25                  30

Ala Met Ser Trp Ile Arg Gln Ala Pro Arg Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Thr Ser Ala Ala Ala Phe Asp Ser Trp Gly Gln Gly
            100                 105                 110

Thr Leu Val Thr Val Ser Ser Ala Ser Ser Gly Gly Ser Thr Ser Gly
        115                 120                 125

Ser Gly Lys Pro Gly Ser Gly Glu Gly Ser Ser Gly Ser Ala Arg Asp
    130                 135                 140

Ile Gln Met Thr Gln Ser Pro Ser Ser Leu Ser Ala Ser Val Gly Asp
145                 150                 155                 160

Arg Val Thr Ile Thr Cys Gln Ala Ser Gln Asp Ile Thr Asn Phe Leu
```

```
                165                 170                 175

Asn Trp Tyr Gln Gln Lys Pro Gly Lys Ala Pro Lys Leu Leu Ile Tyr
            180                 185                 190

Asp Ala Ser Thr Leu Gln Thr Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Gln Gln Ser Asp Ser Tyr Pro Ile Thr
225                 230                 235                 240

Phe Gly Gln Gly Thr Lys Val Glu Ile Lys Arg
                245                 250


<210> SEQ ID NO 237
<211> LENGTH: 7
<212> TYPE: PRT
<213> ORGANISM: Artificial Sequence
<220> FEATURE:
<223> OTHER INFORMATION: Synthetic: UC2.3.14 VHCDR1 (Chothia)

<400> SEQUENCE: 237

Gly Phe Thr Phe Ser Thr Tyr
1               5


<210> SEQ ID NO 238
<211> LENGTH: 6
<212> TYPE: PRT
<213> ORGANISM: Artificial Sequence
<220> FEATURE:
<223> OTHER INFORMATION: Synthetic: UC2.3.14 VHCDR2 (Chothia)

<400> SEQUENCE: 238

Ser Asp Gly Gly Asp Ala
1               5


<210> SEQ ID NO 239
<211> LENGTH: 10
<212> TYPE: PRT
<213> ORGANISM: Artificial Sequence
<220> FEATURE:
<223> OTHER INFORMATION: Synthetic: UC2.3.14 VHCDR3 (Chothia)

<400> SEQUENCE: 239

Asp Arg Thr Ser Ala Ala Ala Phe Asp Ser
1               5                   10


<210> SEQ ID NO 240
<211> LENGTH: 11
<212> TYPE: PRT
<213> ORGANISM: Artificial Sequence
<220> FEATURE:
<223> OTHER INFORMATION: Synthetic: UC2.3.14 VLCDR1 (Chothia)

<400> SEQUENCE: 240

Gln Ala Ser Gln Asp Ile Thr Asn Phe Leu Asn
1               5                   10


<210> SEQ ID NO 241
<211> LENGTH: 7
<212> TYPE: PRT
<213> ORGANISM: Artificial Sequence
<220> FEATURE:
<223> OTHER INFORMATION: Synthetic: UC2.3.14 VLCDR2 (Chothia)

<400> SEQUENCE: 241
```

Asp Ala Ser Thr Leu Gln Thr
1 5

<210> SEQ ID NO 242
<211> LENGTH: 9
<212> TYPE: PRT
<213> ORGANISM: Artificial Sequence
<220> FEATURE:
<223> OTHER INFORMATION: Synthetic: UC2.3.14 VLCDR3 (Chothia)

<400> SEQUENCE: 242

Gln Gln Ser Asp Ser Tyr Pro Ile Thr
1 5

<210> SEQ ID NO 243
<211> LENGTH: 5
<212> TYPE: PRT
<213> ORGANISM: Artificial Sequence
<220> FEATURE:
<223> OTHER INFORMATION: Synthetic: UC2.3.14 VHCDR1 (Kabat)

<400> SEQUENCE: 243

Thr Tyr Ala Met Ser
1 5

<210> SEQ ID NO 244
<211> LENGTH: 17
<212> TYPE: PRT
<213> ORGANISM: Artificial Sequence
<220> FEATURE:
<223> OTHER INFORMATION: Synthetic: UC2.3.14 VHCDR2 (Kabat)

<400> SEQUENCE: 244

Ile Ile Ser Asp Gly Gly Asp Ala Thr Val Tyr Ala Asp Ser Val Lys
1 5 10 15

Gly

<210> SEQ ID NO 245
<211> LENGTH: 10
<212> TYPE: PRT
<213> ORGANISM: Artificial Sequence
<220> FEATURE:
<223> OTHER INFORMATION: Synthetic: UC2.3.14 VHCDR3 (Kabat)

<400> SEQUENCE: 245

Asp Arg Thr Ser Ala Ala Ala Phe Asp Ser
1 5 10

<210> SEQ ID NO 246
<211> LENGTH: 11
<212> TYPE: PRT
<213> ORGANISM: Artificial Sequence
<220> FEATURE:
<223> OTHER INFORMATION: Synthetic: UC2.3.14 VLCDR1 (Kabat)

<400> SEQUENCE: 246

Gln Ala Ser Gln Asp Ile Thr Asn Phe Leu Asn
1 5 10

<210> SEQ ID NO 247
<211> LENGTH: 7
<212> TYPE: PRT
<213> ORGANISM: Artificial Sequence
<220> FEATURE:
<223> OTHER INFORMATION: Synthetic: UC2.3.14 VLCDR2 (Kabat)

<400> SEQUENCE: 247

Asp Ala Ser Thr Leu Gln Thr
1 5

<210> SEQ ID NO 248
<211> LENGTH: 9
<212> TYPE: PRT
<213> ORGANISM: Artificial Sequence
<220> FEATURE:
<223> OTHER INFORMATION: Synthetic: UC2.3.14 VLCDR3 (Kabat)

<400> SEQUENCE: 248

Gln Gln Ser Asp Ser Tyr Pro Ile Thr
1 5

<210> SEQ ID NO 249
<211> LENGTH: 8
<212> TYPE: PRT
<213> ORGANISM: Artificial Sequence
<220> FEATURE:
<223> OTHER INFORMATION: Synthetic: UC2.3.14 VHCDR1 (IMGT)

<400> SEQUENCE: 249

Gly Phe Thr Phe Ser Thr Tyr Ala
1 5

<210> SEQ ID NO 250
<211> LENGTH: 8
<212> TYPE: PRT
<213> ORGANISM: Artificial Sequence
<220> FEATURE:
<223> OTHER INFORMATION: Synthetic: UC2.3.14 VHCDR2 (IMGT)

<400> SEQUENCE: 250

Ile Ser Asp Gly Gly Asp Ala Thr
1 5

<210> SEQ ID NO 251
<211> LENGTH: 12
<212> TYPE: PRT
<213> ORGANISM: Artificial Sequence
<220> FEATURE:
<223> OTHER INFORMATION: Synthetic: UC2.3.14 VHCDR3 (IMGT)

<400> SEQUENCE: 251

Ala Arg Asp Arg Thr Ser Ala Ala Ala Phe Asp Ser
1 5 10

<210> SEQ ID NO 252
<211> LENGTH: 6
<212> TYPE: PRT
<213> ORGANISM: Artificial Sequence
<220> FEATURE:
<223> OTHER INFORMATION: Synthetic: UC2.3.14 VLCDR1 (IMGT)

<400> SEQUENCE: 252

Gln Asp Ile Thr Asn Phe
1 5

<210> SEQ ID NO 253
<211> LENGTH: 3
<212> TYPE: PRT
<213> ORGANISM: Artificial Sequence
<220> FEATURE:
<223> OTHER INFORMATION: Synthetic: UC2.3.14 VLCDR2 (IMGT)

<400> SEQUENCE: 253

Asp Ala Ser
1

<210> SEQ ID NO 254
<211> LENGTH: 9
<212> TYPE: PRT
<213> ORGANISM: Artificial Sequence
<220> FEATURE:
<223> OTHER INFORMATION: Synthetic: UC2.3.14 VLCDR3 (IMGT)

<400> SEQUENCE: 254

Gln Gln Ser Asp Ser Tyr Pro Ile Thr
1 5

<210> SEQ ID NO 255
<211> LENGTH: 119
<212> TYPE: PRT
<213> ORGANISM: Artificial Sequence
<220> FEATURE:
<223> OTHER INFORMATION: Synthetic: UC2.3.14 VH

<400> SEQUENCE: 255

Gln Val Gln Leu Leu Glu Ser Gly Gly Gly Leu Val Gln Pro Gly Gly
1 5 10 15

Ser Leu Arg Leu Ser Tyr Ala Ala Ser Gly Phe Thr Phe Ser Thr Tyr
20 25 30

Ala Met Ser Trp Ile Arg Gln Ala Pro Arg Lys Gly Leu Glu Trp Val
35 40 45

Ser Ile Ile Ser Asp Gly Gly Asp Ala Thr Val Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Arg Thr Ser Ala Ala Ala Phe Asp Ser Trp Gly Gln Gly
100 105 110

Thr Leu Val Thr Val Ser Ser
115

<210> SEQ ID NO 256
<211> LENGTH: 107
<212> TYPE: PRT
<213> ORGANISM: Artificial Sequence
<220> FEATURE:
<223> OTHER INFORMATION: Synthetic: UC2.3.14 VL

<400> SEQUENCE: 256

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Asp Ala Ser Thr Leu Gln Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Ser Asp Ser Tyr Pro Ile
85 90 95

Thr Phe Gly Gln Gly Thr Lys Val Glu Ile Lys 100 105

<210> SEQ ID NO 257
<211> LENGTH: 448
<212> TYPE: PRT
<213> ORGANISM: Artificial Sequence
<220> FEATURE:
<223> OTHER INFORMATION: Synthetic: UC2.3.14-IgG1 heavy chain

<400> SEQUENCE: 257

Gln Val Gln Leu Leu Glu Ser Gly Gly Gly Leu Val Gln Pro Gly Gly
1 5 10 15

Ser Leu Arg Leu Ser Tyr Ala Ala Ser Gly Phe Thr Phe Ser Thr Tyr
20 25 30

Ala Met Ser Trp Ile Arg Gln Ala Pro Arg Lys Gly Leu Glu Trp Val
35 40 45

Ser Ile Ile Ser Asp Gly Gly Asp Ala Thr Val Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Arg Thr Ser Ala Ala Ala Phe Asp Ser Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr

```
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 258
<211> LENGTH: 214
<212> TYPE: PRT
<213> ORGANISM: Artificial Sequence
<220> FEATURE:
<223> OTHER INFORMATION: Synthetic: UC2.3.14-IgG1  light chain

<400> SEQUENCE: 258

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Ser Tyr Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 259
<211> LENGTH: 251
<212> TYPE: PRT
<213> ORGANISM: Artificial Sequence
<220> FEATURE:
<223> OTHER INFORMATION: Synthetic: UC2.3.15 (S4-2 1D10-1G9-1H12) scFv

<400> SEQUENCE: 259
```

```
Gln Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Trp
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Asn Ser Gly Gly Ser Thr Ser Gly
        115                 120                 125

Ser Gly Lys Pro Gly Ser Gly Glu Gly Ser Ser Gly Ser Ala Arg Asp
    130                 135                 140

Ile Gln Met Thr Gln Ser Pro Ser Ser Leu Ser Ala Ser Val Gly Asp
145                 150                 155                 160

Arg Val Thr Ile Thr Cys Gln Ala Ser Gln Asp Ile Thr Asn Phe Leu
                165                 170                 175

Asn Trp Tyr Gln Gln Lys Pro Gly Lys Ala Pro Lys Leu Leu Ile Tyr
            180                 185                 190

Asp Ala Ser Thr Leu Gln Thr Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Gln Gln Ser Asp Ser Tyr Pro Ile Thr
225                 230                 235                 240

Phe Gly Gln Gly Thr Lys Val Glu Ile Lys Arg
                245                 250
```

<210> SEQ ID NO 260
<211> LENGTH: 7
<212> TYPE: PRT
<213> ORGANISM: Artificial Sequence
<220> FEATURE:
<223> OTHER INFORMATION: Synthetic: UC2.3.15 VHCDR1 (Chothia)

<400> SEQUENCE: 260

```
Gly Phe Thr Phe Ser Thr Tyr
1               5
```

<210> SEQ ID NO 261
<211> LENGTH: 6
<212> TYPE: PRT
<213> ORGANISM: Artificial Sequence
<220> FEATURE:
<223> OTHER INFORMATION: Synthetic: UC2.3.15 VHCDR2 (Chothia)

<400> SEQUENCE: 261

```
Ser Asp Gly Gly Asp Ala
1               5
```

<210> SEQ ID NO 262
<211> LENGTH: 10
<212> TYPE: PRT
<213> ORGANISM: Artificial Sequence
<220> FEATURE:
<223> OTHER INFORMATION: Synthetic: UC2.3.15 VHCDR3 (Chothia)

<400> SEQUENCE: 262

Asp Gly Thr Ser Ala Ala Ala Phe Asp Ser
1 5 10

<210> SEQ ID NO 263
<211> LENGTH: 11
<212> TYPE: PRT
<213> ORGANISM: Artificial Sequence
<220> FEATURE:
<223> OTHER INFORMATION: Synthetic: UC2.3.15 VLCDR1 (Chothia)

<400> SEQUENCE: 263

Gln Ala Ser Gln Asp Ile Thr Asn Phe Leu Asn
1 5 10

<210> SEQ ID NO 264
<211> LENGTH: 7
<212> TYPE: PRT
<213> ORGANISM: Artificial Sequence
<220> FEATURE:
<223> OTHER INFORMATION: Synthetic: UC2.3.15 VLCDR2 (Chothia)

<400> SEQUENCE: 264

Asp Ala Ser Thr Leu Gln Thr
1 5

<210> SEQ ID NO 265
<211> LENGTH: 9
<212> TYPE: PRT
<213> ORGANISM: Artificial Sequence
<220> FEATURE:
<223> OTHER INFORMATION: Synthetic: UC2.3.15 VLCDR3 (Chothia)

<400> SEQUENCE: 265

Gln Gln Ser Asp Ser Tyr Pro Ile Thr
1 5

<210> SEQ ID NO 266
<211> LENGTH: 5
<212> TYPE: PRT
<213> ORGANISM: Artificial Sequence
<220> FEATURE:
<223> OTHER INFORMATION: Synthetic: UC2.3.15 VHCDR1 (Kabat)

<400> SEQUENCE: 266

Thr Tyr Ala Met Ser
1 5

<210> SEQ ID NO 267
<211> LENGTH: 17
<212> TYPE: PRT
<213> ORGANISM: Artificial Sequence
<220> FEATURE:
<223> OTHER INFORMATION: Synthetic: UC2.3.15 VHCDR2 (Kabat)

<400> SEQUENCE: 267

Ile Ile Ser Asp Gly Gly Asp Ala Thr Val Tyr Ala Asp Ser Val Lys
1 5 10 15

Gly

<210> SEQ ID NO 268
<211> LENGTH: 10
<212> TYPE: PRT

```
<213> ORGANISM: Artificial Sequence
<220> FEATURE:
<223> OTHER INFORMATION: Synthetic: UC2.3.15 VHCDR3 (Kabat)

<400> SEQUENCE: 268

Asp Gly Thr Ser Ala Ala Ala Phe Asp Ser
1               5                   10


<210> SEQ ID NO 269
<211> LENGTH: 11
<212> TYPE: PRT
<213> ORGANISM: Artificial Sequence
<220> FEATURE:
<223> OTHER INFORMATION: Synthetic: UC2.3.15 VLCDR1 (Kabat)

<400> SEQUENCE: 269

Gln Ala Ser Gln Asp Ile Thr Asn Phe Leu Asn
1               5                   10


<210> SEQ ID NO 270
<211> LENGTH: 7
<212> TYPE: PRT
<213> ORGANISM: Artificial Sequence
<220> FEATURE:
<223> OTHER INFORMATION: Synthetic: UC2.3.15 VLCDR2 (Kabat)

<400> SEQUENCE: 270

Asp Ala Ser Thr Leu Gln Thr
1               5


<210> SEQ ID NO 271
<211> LENGTH: 9
<212> TYPE: PRT
<213> ORGANISM: Artificial Sequence
<220> FEATURE:
<223> OTHER INFORMATION: Synthetic: UC2.3.15 VLCDR3 (Kabat)

<400> SEQUENCE: 271

Gln Gln Ser Asp Ser Tyr Pro Ile Thr
1               5


<210> SEQ ID NO 272
<211> LENGTH: 8
<212> TYPE: PRT
<213> ORGANISM: Artificial Sequence
<220> FEATURE:
<223> OTHER INFORMATION: Synthetic: UC2.3.15 VHCDR1 (IMGT)

<400> SEQUENCE: 272

Gly Phe Thr Phe Ser Thr Tyr Ala
1               5


<210> SEQ ID NO 273
<211> LENGTH: 8
<212> TYPE: PRT
<213> ORGANISM: Artificial Sequence
<220> FEATURE:
<223> OTHER INFORMATION: Synthetic: UC2.3.15 VHCDR2 (IMGT)

<400> SEQUENCE: 273

Ile Ser Asp Gly Gly Asp Ala Thr
1               5


<210> SEQ ID NO 274
<211> LENGTH: 12
<212> TYPE: PRT
<213> ORGANISM: Artificial Sequence
```

<220> FEATURE:
<223> OTHER INFORMATION: Synthetic: UC2.3.15 VHCDR3 (IMGT)

<400> SEQUENCE: 274

Ala Arg Asp Gly Thr Ser Ala Ala Ala Phe Asp Ser
1               5                   10

<210> SEQ ID NO 275
<211> LENGTH: 6
<212> TYPE: PRT
<213> ORGANISM: Artificial Sequence
<220> FEATURE:
<223> OTHER INFORMATION: Synthetic: UC2.3.15 VLCDR1 (IMGT)

<400> SEQUENCE: 275

Gln Asp Ile Thr Asn Phe
1               5

<210> SEQ ID NO 276
<211> LENGTH: 3
<212> TYPE: PRT
<213> ORGANISM: Artificial Sequence
<220> FEATURE:
<223> OTHER INFORMATION: Synthetic: UC2.3.15 VLCDR2 (IMGT)

<400> SEQUENCE: 276

Asp Ala Ser
1

<210> SEQ ID NO 277
<211> LENGTH: 9
<212> TYPE: PRT
<213> ORGANISM: Artificial Sequence
<220> FEATURE:
<223> OTHER INFORMATION: Synthetic: UC2.3.15 VLCDR3 (IMGT)

<400> SEQUENCE: 277

Gln Gln Ser Asp Ser Tyr Pro Ile Thr
1               5

<210> SEQ ID NO 278
<211> LENGTH: 119
<212> TYPE: PRT
<213> ORGANISM: Artificial Sequence
<220> FEATURE:
<223> OTHER INFORMATION: Synthetic: UC2.3.15 VH

<400> SEQUENCE: 278

Gln Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Trp
                85                  90                  95

Ala Arg Asp Gly Thr Ser Ala Ala Ala Phe Asp Ser Trp Gly Gln Gly
            100                 105                 110

Thr Leu Val Thr Val Ser Ser

115

<210> SEQ ID NO 279
<211> LENGTH: 107
<212> TYPE: PRT
<213> ORGANISM: Artificial Sequence
<220> FEATURE:
<223> OTHER INFORMATION: Synthetic: UC2.3.15 VL

<400> SEQUENCE: 279

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Ser Tyr Pro Ile
                85                  90                  95

Thr Phe Gly Gln Gly Thr Lys Val Glu Ile Lys
            100                 105

<210> SEQ ID NO 280
<211> LENGTH: 448
<212> TYPE: PRT
<213> ORGANISM: Artificial Sequence
<220> FEATURE:
<223> OTHER INFORMATION: Synthetic: UC2.3.15-IgG1 heavy chain

<400> SEQUENCE: 280

Gln Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Ser Thr Tyr
            20                  25                  30

Ala Met Ser Trp Ile Arg Gln Ala Pro Gly Lys Gly Leu Glu Trp Val
        35                  40                  45

Ser Ile Ile Ser Asp Gly Gly Asp Ala Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Trp
                85                  90                  95

Ala Arg Asp Gly Thr Ser Ala Ala Ala Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 281
<211> LENGTH: 214
<212> TYPE: PRT
<213> ORGANISM: Artificial Sequence
<220> FEATURE:
<223> OTHER INFORMATION: Synthetic: UC2.3.15-IgG1 light chain

<400> SEQUENCE: 281

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Ser Tyr Pro Ile
                85                  90                  95

Thr Phe Gly Gln Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 282
<211> LENGTH: 255
<212> TYPE: PRT
<213> ORGANISM: Artificial Sequence
<220> FEATURE:
<223> OTHER INFORMATION: Synthetic: UC1 (S4-2 1B5) scFv

<400> SEQUENCE: 282

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Thr Ser Tyr
            20                  25                  30

Ala Met Thr Trp Val Arg Gln Ala Pro Gly Lys Gly Leu Glu Trp Val
        35                  40                  45

Ser Gly Ile Ser Gly Gly Gly Ala Ala Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Ser Gln Tyr Val Gly Gly Phe Asp Tyr Trp Gly Gln Gly
            100                 105                 110

Thr Leu Val Thr Val Ser Ser Ala Ser Ser Gly Gly Ser Thr Ser Gly
        115                 120                 125

Ser Gly Lys Pro Gly Ser Gly Glu Gly Ser Ser Gly Ser Ala Arg Gln
    130                 135                 140

Ser Val Leu Thr Gln Pro Pro Ser Val Ser Gly Ala Pro Gly Gln Arg
145                 150                 155                 160

Val Thr Ile Ser Cys Thr Gly Ser Ser Ser Asn Ile Gly Ala Gly Tyr
                165                 170                 175

Gly Val His Trp Tyr Gln Gln Leu Pro Gly Thr Ala Pro Lys Leu Leu
            180                 185                 190

Ile Tyr Gly Asn Thr Asn Arg Pro Ser Gly Val Pro Asp Arg Phe Ser
        195                 200                 205

Gly Phe Lys Ser Gly Thr Ser Ala Ser Leu Ala Ile Thr Gly Leu Gln
    210                 215                 220

Ala Glu Asp Glu Ala Asp Tyr Tyr Cys Gln Ser Tyr Asp Ser Ser Leu
225                 230                 235                 240

Ser Gly Trp Val Phe Gly Gly Gly Thr Lys Leu Thr Val Leu Gly
                245                 250                 255
```

<210> SEQ ID NO 283
<211> LENGTH: 7
<212> TYPE: PRT
<213> ORGANISM: Artificial Sequence
<220> FEATURE:
<223> OTHER INFORMATION: Synthetic: UC1 VHCDR1 (Chothia)

<400> SEQUENCE: 283

Gly Phe Ser Phe Thr Ser Tyr
1 5

<210> SEQ ID NO 284
<211> LENGTH: 6
<212> TYPE: PRT
<213> ORGANISM: Artificial Sequence
<220> FEATURE:
<223> OTHER INFORMATION: Synthetic: UC1 VHCDR2 (Chothia)

<400> SEQUENCE: 284

Ser Gly Gly Gly Ala Ala
1 5

<210> SEQ ID NO 285
<211> LENGTH: 10
<212> TYPE: PRT
<213> ORGANISM: Artificial Sequence
<220> FEATURE:
<223> OTHER INFORMATION: Synthetic: UC1 VHCDR3 (Chothia)

<400> SEQUENCE: 285

Gln Ser Gln Tyr Val Gly Gly Phe Asp Tyr
1 5 10

<210> SEQ ID NO 286
<211> LENGTH: 14
<212> TYPE: PRT
<213> ORGANISM: Artificial Sequence
<220> FEATURE:
<223> OTHER INFORMATION: Synthetic: UC1 VLCDR1 (Chothia)

<400> SEQUENCE: 286

Thr Gly Ser Ser Ser Asn Ile Gly Ala Gly Tyr Gly Val His
1 5 10

<210> SEQ ID NO 287
<211> LENGTH: 7
<212> TYPE: PRT
<213> ORGANISM: Artificial Sequence
<220> FEATURE:
<223> OTHER INFORMATION: Synthetic: UC1 VLCDR2 (Chothia)

<400> SEQUENCE: 287

Gly Asn Thr Asn Arg Pro Ser
1 5

<210> SEQ ID NO 288
<211> LENGTH: 11
<212> TYPE: PRT
<213> ORGANISM: Artificial Sequence
<220> FEATURE:
<223> OTHER INFORMATION: Synthetic: UC1 VLCDR3 (Chothia)

<400> SEQUENCE: 288

Gln Ser Tyr Asp Ser Ser Leu Ser Gly Trp Val
1 5 10

<210> SEQ ID NO 289
<211> LENGTH: 5
<212> TYPE: PRT
<213> ORGANISM: Artificial Sequence
<220> FEATURE:
<223> OTHER INFORMATION: Synthetic: UC1 VHCDR1 (Kabat)

<400> SEQUENCE: 289

Ser Tyr Ala Met Thr
1 5

<210> SEQ ID NO 290
<211> LENGTH: 17
<212> TYPE: PRT
<213> ORGANISM: Artificial Sequence
<220> FEATURE:
<223> OTHER INFORMATION: Synthetic: UC1 VHCDR2 (Kabat)

<400> SEQUENCE: 290

Gly Ile Ser Gly Gly Gly Ala Ala Thr Phe Tyr Ala Asp Ser Val Lys
1 5 10 15

Gly

<210> SEQ ID NO 291
<211> LENGTH: 10
<212> TYPE: PRT
<213> ORGANISM: Artificial Sequence
<220> FEATURE:
<223> OTHER INFORMATION: Synthetic: UC1 VHCDR3 (Kabat)

<400> SEQUENCE: 291

Gln Ser Gln Tyr Val Gly Gly Phe Asp Tyr
1 5 10

<210> SEQ ID NO 292
<211> LENGTH: 14
<212> TYPE: PRT
<213> ORGANISM: Artificial Sequence
<220> FEATURE:
<223> OTHER INFORMATION: Synthetic: UC1 VLCDR1 (Kabat)

<400> SEQUENCE: 292

Thr Gly Ser Ser Ser Asn Ile Gly Ala Gly Tyr Gly Val His
1 5 10

<210> SEQ ID NO 293
<211> LENGTH: 7
<212> TYPE: PRT
<213> ORGANISM: Artificial Sequence
<220> FEATURE:
<223> OTHER INFORMATION: Synthetic: UC1 VLCDR2 (Kabat)

<400> SEQUENCE: 293

Gly Asn Thr Asn Arg Pro Ser
1 5

<210> SEQ ID NO 294
<211> LENGTH: 11
<212> TYPE: PRT
<213> ORGANISM: Artificial Sequence
<220> FEATURE:
<223> OTHER INFORMATION: Synthetic: UC1 VLCDR3 (Kabat)

<400> SEQUENCE: 294

Gln Ser Tyr Asp Ser Ser Leu Ser Gly Trp Val
1 5 10

<210> SEQ ID NO 295
<211> LENGTH: 8
<212> TYPE: PRT
<213> ORGANISM: Artificial Sequence
<220> FEATURE:
<223> OTHER INFORMATION: Synthetic: UC1 VHCDR1 (IMGT)

<400> SEQUENCE: 295

Gly Phe Ser Phe Thr Ser Tyr Ala
1               5

<210> SEQ ID NO 296
<211> LENGTH: 8
<212> TYPE: PRT
<213> ORGANISM: Artificial Sequence
<220> FEATURE:
<223> OTHER INFORMATION: Synthetic: UC1 VHCDR2 (IMGT)

<400> SEQUENCE: 296

Ile Ser Gly Gly Gly Ala Ala Thr
1               5

<210> SEQ ID NO 297
<211> LENGTH: 12
<212> TYPE: PRT
<213> ORGANISM: Artificial Sequence
<220> FEATURE:
<223> OTHER INFORMATION: Synthetic: UC1 VHCDR3 (IMGT)

<400> SEQUENCE: 297

Ala Arg Gln Ser Gln Tyr Val Gly Gly Phe Asp Tyr
1               5                   10

<210> SEQ ID NO 298
<211> LENGTH: 9
<212> TYPE: PRT
<213> ORGANISM: Artificial Sequence
<220> FEATURE:
<223> OTHER INFORMATION: Synthetic: UC1 VLCDR1 (IMGT)

<400> SEQUENCE: 298

Ser Ser Asn Ile Gly Ala Gly Tyr Gly
1               5

<210> SEQ ID NO 299
<211> LENGTH: 3
<212> TYPE: PRT
<213> ORGANISM: Artificial Sequence
<220> FEATURE:
<223> OTHER INFORMATION: Synthetic: UC1 VLCDR2 (IMGT)

<400> SEQUENCE: 299

Gly Asn Thr
1

<210> SEQ ID NO 300
<211> LENGTH: 11
<212> TYPE: PRT
<213> ORGANISM: Artificial Sequence
<220> FEATURE:
<223> OTHER INFORMATION: Synthetic: UC1 VLCDR3 (IMGT)

<400> SEQUENCE: 300

Gln Ser Tyr Asp Ser Ser Leu Ser Gly Trp Val
1               5                   10

```
<210> SEQ ID NO 301
<211> LENGTH: 119
<212> TYPE: PRT
<213> ORGANISM: Artificial Sequence
<220> FEATURE:
<223> OTHER INFORMATION: Synthetic: UC1 VH

<400> SEQUENCE: 301

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Thr Ser Tyr
            20                  25                  30

Ala Met Thr Trp Val Arg Gln Ala Pro Gly Lys Gly Leu Glu Trp Val
        35                  40                  45

Ser Gly Ile Ser Gly Gly Gly Ala Ala Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Ser Gln Tyr Val Gly Gly Phe Asp Tyr Trp Gly Gln Gly
            100                 105                 110

Thr Leu Val Thr Val Ser Ser
        115


<210> SEQ ID NO 302
<211> LENGTH: 111
<212> TYPE: PRT
<213> ORGANISM: Artificial Sequence
<220> FEATURE:
<223> OTHER INFORMATION: Synthetic: UC1 VL

<400> SEQUENCE: 302

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Phe Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Gly Thr Lys Leu Thr Val Leu
            100                 105                 110


<210> SEQ ID NO 303
<211> LENGTH: 255
<212> TYPE: PRT
<213> ORGANISM: Artificial Sequence
<220> FEATURE:
<223> OTHER INFORMATION: Synthetic: UC1.1 (S4-2 1B5-1D9) scFv

<400> SEQUENCE: 303

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Thr Ser Tyr
            20                  25                  30
```

```
Ala Met Thr Trp Val Arg Gln Ala Pro Gly Lys Gly Leu Glu Trp Val
        35                  40                  45

Ser Gly Ile Ser Gly Gly Gly Ala Ala Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Ser Gln Tyr Val Gly Gly Phe Asp Tyr Trp Gly Gln Gly
            100                 105                 110

Thr Leu Val Thr Val Ser Ser Ala Ser Ser Gly Gly Ser Thr Ser Gly
        115                 120                 125

Ser Gly Lys Pro Gly Ser Gly Glu Gly Ser Ser Gly Ser Ala Arg Gln
    130                 135                 140

Ser Val Leu Thr Gln Pro Pro Ser Val Ser Gly Ala Pro Gly Gln Arg
145                 150                 155                 160

Val Thr Ile Ser Cys Thr Gly Ser Ser Ser Asn Ile Gly Ala Gly Tyr
                165                 170                 175

Gly Val His Trp Tyr Gln Gln Leu Pro Gly Thr Ala Pro Lys Leu Leu
            180                 185                 190

Ile His Gly Asn Thr Asn Arg Pro Ser Gly Val Pro Asp Arg Phe Ser
        195                 200                 205

Gly Phe Lys Ser Gly Thr Ser Ala Ser Leu Ala Ile Thr Gly Leu Gln
    210                 215                 220

Ala Glu Asp Glu Ala Asp Tyr Tyr Cys Gln Ser Tyr Asp Ser Ser Leu
225                 230                 235                 240

Ser Gly Trp Val Phe Gly Gly Gly Thr Lys Leu Thr Val Leu Gly
                245                 250                 255


<210> SEQ ID NO 304
<211> LENGTH: 7
<212> TYPE: PRT
<213> ORGANISM: Artificial Sequence
<220> FEATURE:
<223> OTHER INFORMATION: Synthetic: UC1.1 VHCDR1 (Chothia)

<400> SEQUENCE: 304

Gly Phe Ser Phe Thr Ser Tyr
1               5


<210> SEQ ID NO 305
<211> LENGTH: 6
<212> TYPE: PRT
<213> ORGANISM: Artificial Sequence
<220> FEATURE:
<223> OTHER INFORMATION: Synthetic: UC1.1 VHCDR2 (Chothia)

<400> SEQUENCE: 305

Ser Gly Gly Gly Ala Ala
1               5


<210> SEQ ID NO 306
<211> LENGTH: 10
<212> TYPE: PRT
<213> ORGANISM: Artificial Sequence
<220> FEATURE:
<223> OTHER INFORMATION: Synthetic: UC1.1 VHCDR3 (Chothia)

<400> SEQUENCE: 306
```

Gln Ser Gln Tyr Val Gly Gly Phe Asp Tyr
1               5                   10

<210> SEQ ID NO 307
<211> LENGTH: 14
<212> TYPE: PRT
<213> ORGANISM: Artificial Sequence
<220> FEATURE:
<223> OTHER INFORMATION: Synthetic: UC1.1 VLCDR1 (Chothia)

<400> SEQUENCE: 307

Thr Gly Ser Ser Ser Asn Ile Gly Ala Gly Tyr Gly Val His
1               5                   10

<210> SEQ ID NO 308
<211> LENGTH: 7
<212> TYPE: PRT
<213> ORGANISM: Artificial Sequence
<220> FEATURE:
<223> OTHER INFORMATION: Synthetic: UC1.1 VLCDR2 (Chothia)

<400> SEQUENCE: 308

Gly Asn Thr Asn Arg Pro Ser
1               5

<210> SEQ ID NO 309
<211> LENGTH: 11
<212> TYPE: PRT
<213> ORGANISM: Artificial Sequence
<220> FEATURE:
<223> OTHER INFORMATION: Synthetic: UC1.1 VLCDR3 (Chothia)

<400> SEQUENCE: 309

Gln Ser Tyr Asp Ser Ser Leu Ser Gly Trp Val
1               5                   10

<210> SEQ ID NO 310
<211> LENGTH: 5
<212> TYPE: PRT
<213> ORGANISM: Artificial Sequence
<220> FEATURE:
<223> OTHER INFORMATION: Synthetic: UC1.1 VHCDR1 (Kabat)

<400> SEQUENCE: 310

Ser Tyr Ala Met Thr
1               5

<210> SEQ ID NO 311
<211> LENGTH: 17
<212> TYPE: PRT
<213> ORGANISM: Artificial Sequence
<220> FEATURE:
<223> OTHER INFORMATION: Synthetic: UC1.1 VHCDR2 (Kabat)

<400> SEQUENCE: 311

Gly Ile Ser Gly Gly Gly Ala Ala Thr Phe Tyr Ala Asp Ser Val Lys
1               5                   10                  15

Gly

<210> SEQ ID NO 312
<211> LENGTH: 10
<212> TYPE: PRT
<213> ORGANISM: Artificial Sequence
<220> FEATURE:
<223> OTHER INFORMATION: Synthetic: UC1.1 VHCDR3 (Kabat)

<400> SEQUENCE: 312

Gln Ser Gln Tyr Val Gly Gly Phe Asp Tyr
1 5 10

<210> SEQ ID NO 313
<211> LENGTH: 14
<212> TYPE: PRT
<213> ORGANISM: Artificial Sequence
<220> FEATURE:
<223> OTHER INFORMATION: Synthetic: UC1.1 VLCDR1 (Kabat)

<400> SEQUENCE: 313

Thr Gly Ser Ser Ser Asn Ile Gly Ala Gly Tyr Gly Val His
1 5 10

<210> SEQ ID NO 314
<211> LENGTH: 7
<212> TYPE: PRT
<213> ORGANISM: Artificial Sequence
<220> FEATURE:
<223> OTHER INFORMATION: Synthetic: UC1.1 VLCDR2 (Kabat)

<400> SEQUENCE: 314

Gly Asn Thr Asn Arg Pro Ser
1 5

<210> SEQ ID NO 315
<211> LENGTH: 11
<212> TYPE: PRT
<213> ORGANISM: Artificial Sequence
<220> FEATURE:
<223> OTHER INFORMATION: Synthetic: UC1.1 VLCDR3 (Kabat)

<400> SEQUENCE: 315

Gln Ser Tyr Asp Ser Ser Leu Ser Gly Trp Val
1 5 10

<210> SEQ ID NO 316
<211> LENGTH: 8
<212> TYPE: PRT
<213> ORGANISM: Artificial Sequence
<220> FEATURE:
<223> OTHER INFORMATION: Synthetic: UC1.1 VHCDR1 (IMGT)

<400> SEQUENCE: 316

Gly Phe Ser Phe Thr Ser Tyr Ala
1 5

<210> SEQ ID NO 317
<211> LENGTH: 8
<212> TYPE: PRT
<213> ORGANISM: Artificial Sequence
<220> FEATURE:
<223> OTHER INFORMATION: Synthetic: UC1.1 VHCDR2 (IMGT)

<400> SEQUENCE: 317

Ile Ser Gly Gly Gly Ala Ala Thr
1 5

<210> SEQ ID NO 318
<211> LENGTH: 12
<212> TYPE: PRT
<213> ORGANISM: Artificial Sequence
<220> FEATURE:
<223> OTHER INFORMATION: Synthetic: UC1.1 VHCDR3 (IMGT)

<400> SEQUENCE: 318

Ala Arg Gln Ser Gln Tyr Val Gly Gly Phe Asp Tyr
1               5                   10

<210> SEQ ID NO 319
<211> LENGTH: 9
<212> TYPE: PRT
<213> ORGANISM: Artificial Sequence
<220> FEATURE:
<223> OTHER INFORMATION: Synthetic: UC1.1 VLCDR1 (IMGT)

<400> SEQUENCE: 319

Ser Ser Asn Ile Gly Ala Gly Tyr Gly
1               5

<210> SEQ ID NO 320
<211> LENGTH: 3
<212> TYPE: PRT
<213> ORGANISM: Artificial Sequence
<220> FEATURE:
<223> OTHER INFORMATION: Synthetic: UC1.1 VLCDR2 (IMGT)

<400> SEQUENCE: 320

Gly Asn Thr
1

<210> SEQ ID NO 321
<211> LENGTH: 11
<212> TYPE: PRT
<213> ORGANISM: Artificial Sequence
<220> FEATURE:
<223> OTHER INFORMATION: Synthetic: UC1.1 VLCDR3 (IMGT)

<400> SEQUENCE: 321

Gln Ser Tyr Asp Ser Ser Leu Ser Gly Trp Val
1               5                   10

<210> SEQ ID NO 322
<211> LENGTH: 119
<212> TYPE: PRT
<213> ORGANISM: Artificial Sequence
<220> FEATURE:
<223> OTHER INFORMATION: Synthetic: UC1.1 VH

<400> SEQUENCE: 322

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Thr Ser Tyr
            20                  25                  30

Ala Met Thr Trp Val Arg Gln Ala Pro Gly Lys Gly Leu Glu Trp Val
        35                  40                  45

Ser Gly Ile Ser Gly Gly Gly Ala Ala Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Ser Gln Tyr Val Gly Gly Phe Asp Tyr Trp Gly Gln Gly
            100                 105                 110

Thr Leu Val Thr Val Ser Ser
        115

<210> SEQ ID NO 323
<211> LENGTH: 111

<212> TYPE: PRT
<213> ORGANISM: Artificial Sequence
<220> FEATURE:
<223> OTHER INFORMATION: Synthetic: UC1.1 VL

<400> SEQUENCE: 323

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Gly Val His Trp Tyr Gln Gln Leu Pro Gly Thr Ala Pro Lys Leu
35 40 45

Leu Ile His Gly Asn Thr Asn Arg Pro Ser Gly Val Pro Asp Arg Phe
50 55 60

Ser Gly Phe Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

Leu Ser Gly Trp Val Phe Gly Gly Gly Thr Lys Leu Thr Val Leu
100 105 110

<210> SEQ ID NO 324
<211> LENGTH: 255
<212> TYPE: PRT
<213> ORGANISM: Artificial Sequence
<220> FEATURE:
<223> OTHER INFORMATION: Synthetic: UC1.2 (S4-2 1B5-1A5) scFv

<400> SEQUENCE: 324

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Ser Phe Thr Ser Tyr
20 25 30

Ala Met Thr Trp Val Arg Gln Ala Pro Gly Lys Gly Leu Glu Trp Val
35 40 45

Ser Gly Ile Ser Gly Gly Gly Ala Ala Thr Phe Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gln Ser Gln Tyr Val Gly Gly Phe Asp Tyr Trp Gly Gln Gly
100 105 110

Thr Leu Val Thr Val Ser Ser Ala Ser Ser Gly Gly Ser Thr Ser Gly
115 120 125

Ser Gly Lys Pro Asp Ser Gly Glu Gly Ser Ser Gly Ser Ala Arg Gln
130 135 140

Ser Val Leu Thr Gln Pro Pro Ser Val Ser Gly Ala Pro Gly Gln Arg
145 150 155 160

Val Thr Ile Ser Cys Thr Gly Ser Ser Ser Asn Phe Gly Ala Gly Tyr
165 170 175

Gly Val His Trp Tyr Gln Gln Leu Pro Gly Thr Ala Pro Lys Leu Leu
180 185 190

Ile His Gly Asn Thr Asn Arg Pro Ser Gly Val Pro Asp Arg Phe Ser
195 200 205

Gly Phe Lys Ser Gly Thr Ser Ala Ser Leu Ala Ile Thr Gly Leu Gln
210 215 220

```
Ala Glu Asp Glu Ala Asp Tyr Tyr Cys Gln Ser Tyr Asp Ser Ser Leu
225                 230                 235                 240

Ser Gly Trp Val Phe Gly Gly Gly Thr Lys Leu Thr Val Leu Gly
                245                 250                 255


<210> SEQ ID NO 325
<211> LENGTH: 7
<212> TYPE: PRT
<213> ORGANISM: Artificial Sequence
<220> FEATURE:
<223> OTHER INFORMATION: Synthetic: UC1.2 VHCDR1 (Chothia)

<400> SEQUENCE: 325

Gly Phe Ser Phe Thr Ser Tyr
1               5


<210> SEQ ID NO 326
<211> LENGTH: 6
<212> TYPE: PRT
<213> ORGANISM: Artificial Sequence
<220> FEATURE:
<223> OTHER INFORMATION: Synthetic: UC1.2 VHCDR2 (Chothia)

<400> SEQUENCE: 326

Ser Gly Gly Gly Ala Ala
1               5


<210> SEQ ID NO 327
<211> LENGTH: 10
<212> TYPE: PRT
<213> ORGANISM: Artificial Sequence
<220> FEATURE:
<223> OTHER INFORMATION: Synthetic: UC1.2 VHCDR3 (Chothia)

<400> SEQUENCE: 327

Gln Ser Gln Tyr Val Gly Gly Phe Asp Tyr
1               5                   10


<210> SEQ ID NO 328
<211> LENGTH: 14
<212> TYPE: PRT
<213> ORGANISM: Artificial Sequence
<220> FEATURE:
<223> OTHER INFORMATION: Synthetic: UC1.2 VLCDR1 (Chothia)

<400> SEQUENCE: 328

Thr Gly Ser Ser Ser Asn Phe Gly Ala Gly Tyr Gly Val His
1               5                   10


<210> SEQ ID NO 329
<211> LENGTH: 7
<212> TYPE: PRT
<213> ORGANISM: Artificial Sequence
<220> FEATURE:
<223> OTHER INFORMATION: Synthetic: UC1.2 VLCDR2 (Chothia)

<400> SEQUENCE: 329

Gly Asn Thr Asn Arg Pro Ser
1               5


<210> SEQ ID NO 330
<211> LENGTH: 11
<212> TYPE: PRT
<213> ORGANISM: Artificial Sequence
<220> FEATURE:
<223> OTHER INFORMATION: Synthetic: UC1.2 VLCDR3 (Chothia)
```

<400> SEQUENCE: 330

Gln Ser Tyr Asp Ser Ser Leu Ser Gly Trp Val
1               5                   10

<210> SEQ ID NO 331
<211> LENGTH: 5
<212> TYPE: PRT
<213> ORGANISM: Artificial Sequence
<220> FEATURE:
<223> OTHER INFORMATION: Synthetic: UC1.2 VHCDR1 (Kabat)

<400> SEQUENCE: 331

Ser Tyr Ala Met Thr
1               5

<210> SEQ ID NO 332
<211> LENGTH: 17
<212> TYPE: PRT
<213> ORGANISM: Artificial Sequence
<220> FEATURE:
<223> OTHER INFORMATION: Synthetic: UC1.2 VHCDR2 (Kabat)

<400> SEQUENCE: 332

Gly Ile Ser Gly Gly Gly Ala Ala Thr Phe Tyr Ala Asp Ser Val Lys
1               5                   10                  15

Gly

<210> SEQ ID NO 333
<211> LENGTH: 10
<212> TYPE: PRT
<213> ORGANISM: Artificial Sequence
<220> FEATURE:
<223> OTHER INFORMATION: Synthetic: UC1.2 VHCDR3 (Kabat)

<400> SEQUENCE: 333

Gln Ser Gln Tyr Val Gly Gly Phe Asp Tyr
1               5                   10

<210> SEQ ID NO 334
<211> LENGTH: 14
<212> TYPE: PRT
<213> ORGANISM: Artificial Sequence
<220> FEATURE:
<223> OTHER INFORMATION: Synthetic: UC1.2 VLCDR1 (Kabat)

<400> SEQUENCE: 334

Thr Gly Ser Ser Ser Asn Phe Gly Ala Gly Tyr Gly Val His
1               5                   10

<210> SEQ ID NO 335
<211> LENGTH: 7
<212> TYPE: PRT
<213> ORGANISM: Artificial Sequence
<220> FEATURE:
<223> OTHER INFORMATION: Synthetic: UC1.2 VLCDR2 (Kabat)

<400> SEQUENCE: 335

Gly Asn Thr Asn Arg Pro Ser
1               5

<210> SEQ ID NO 336
<211> LENGTH: 11
<212> TYPE: PRT
<213> ORGANISM: Artificial Sequence
<220> FEATURE:

<223> OTHER INFORMATION: Synthetic: UC1.2 VLCDR3 (Kabat)

<400> SEQUENCE: 336

Gln Ser Tyr Asp Ser Ser Leu Ser Gly Trp Val
1 5 10

<210> SEQ ID NO 337
<211> LENGTH: 8
<212> TYPE: PRT
<213> ORGANISM: Artificial Sequence
<220> FEATURE:
<223> OTHER INFORMATION: Synthetic: UC1.2 VHCDR1 (IMGT)

<400> SEQUENCE: 337

Gly Phe Ser Phe Thr Ser Tyr Ala
1 5

<210> SEQ ID NO 338
<211> LENGTH: 8
<212> TYPE: PRT
<213> ORGANISM: Artificial Sequence
<220> FEATURE:
<223> OTHER INFORMATION: Synthetic: UC1.2 VHCDR2 (IMGT)

<400> SEQUENCE: 338

Ile Ser Gly Gly Gly Ala Ala Thr
1 5

<210> SEQ ID NO 339
<211> LENGTH: 12
<212> TYPE: PRT
<213> ORGANISM: Artificial Sequence
<220> FEATURE:
<223> OTHER INFORMATION: Synthetic: UC1.2 VHCDR3 (IMGT)

<400> SEQUENCE: 339

Ala Arg Gln Ser Gln Tyr Val Gly Gly Phe Asp Tyr
1 5 10

<210> SEQ ID NO 340
<211> LENGTH: 9
<212> TYPE: PRT
<213> ORGANISM: Artificial Sequence
<220> FEATURE:
<223> OTHER INFORMATION: Synthetic: UC1.2 VLCDR1 (IMGT)

<400> SEQUENCE: 340

Ser Ser Asn Phe Gly Ala Gly Tyr Gly
1 5

<210> SEQ ID NO 341
<211> LENGTH: 3
<212> TYPE: PRT
<213> ORGANISM: Artificial Sequence
<220> FEATURE:
<223> OTHER INFORMATION: Synthetic: UC1.2 VLCDR2 (IMGT)

<400> SEQUENCE: 341

Gly Asn Thr
1

<210> SEQ ID NO 342
<211> LENGTH: 11
<212> TYPE: PRT
<213> ORGANISM: Artificial Sequence
<220> FEATURE:
<223> OTHER INFORMATION: Synthetic: UC1.2 VLCDR3 (IMGT)

<400> SEQUENCE: 342

Gln Ser Tyr Asp Ser Ser Leu Ser Gly Trp Val
1               5                   10

<210> SEQ ID NO 343
<211> LENGTH: 119
<212> TYPE: PRT
<213> ORGANISM: Artificial Sequence
<220> FEATURE:
<223> OTHER INFORMATION: Synthetic: UC1.2 VH

<400> SEQUENCE: 343

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Thr Ser Tyr
            20                  25                  30

Ala Met Thr Trp Val Arg Gln Ala Pro Gly Lys Gly Leu Glu Trp Val
        35                  40                  45

Ser Gly Ile Ser Gly Gly Gly Ala Ala Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Ser Gln Tyr Val Gly Gly Phe Asp Tyr Trp Gly Gln Gly
            100                 105                 110

Thr Leu Val Thr Val Ser Ser
        115

<210> SEQ ID NO 344
<211> LENGTH: 111
<212> TYPE: PRT
<213> ORGANISM: Artificial Sequence
<220> FEATURE:
<223> OTHER INFORMATION: Synthetic: UC1.2 VL

<400> SEQUENCE: 344

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Phe Gly Ala Gly
            20                  25                  30

Tyr Gly Val His Trp Tyr Gln Gln Leu Pro Gly Thr Ala Pro Lys Leu
        35                  40                  45

Leu Ile His Gly Asn Thr Asn Arg Pro Ser Gly Val Pro Asp Arg Phe
    50                  55                  60

Ser Gly Phe Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Gly Thr Lys Leu Thr Val Leu
            100                 105                 110

<210> SEQ ID NO 345
<211> LENGTH: 255
<212> TYPE: PRT
<213> ORGANISM: Artificial Sequence
<220> FEATURE:
<223> OTHER INFORMATION: Synthetic: UC1.3 (S4-2 1B5-1B3) scFv

<400> SEQUENCE: 345

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Ser Phe Thr Ser Tyr
20 25 30

Ala Met Thr Trp Val Arg Gln Ala Pro Gly Lys Gly Leu Glu Trp Val
35 40 45

Ser Gly Ile Ser Gly Asp Gly Ala Ala Thr Phe Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gln Ser Gln Tyr Val Gly Gly Phe Asp Tyr Trp Gly Gln Gly
100 105 110

Thr Leu Val Thr Val Ser Ser Ala Ser Ser Gly Gly Ser Thr Ser Gly
115 120 125

Ser Gly Lys Pro Asp Ser Gly Glu Gly Ser Ser Gly Ser Ala Arg Gln
130 135 140

Ser Val Leu Thr Gln Pro Pro Ser Val Ser Gly Ala Pro Gly Gln Arg
145 150 155 160

Val Thr Ile Ser Cys Thr Gly Ser Ser Ser Asn Phe Gly Ala Gly Tyr
165 170 175

Gly Val His Trp Tyr Gln Gln Leu Pro Gly Thr Ala Pro Lys Leu Leu
180 185 190

Ile His Gly Asn Thr Asn Arg Pro Ser Gly Val Pro Asp Arg Phe Ser
195 200 205

Gly Phe Lys Ser Gly Thr Ser Ala Ser Leu Ala Ile Thr Gly Leu Gln
210 215 220

Ala Glu Asp Glu Ala Asp Tyr Tyr Cys Gln Ser Tyr Asp Ser Ser Leu
225 230 235 240

Ser Gly Trp Val Phe Gly Gly Gly Thr Lys Leu Thr Val Leu Gly
245 250 255

<210> SEQ ID NO 346
<211> LENGTH: 7
<212> TYPE: PRT
<213> ORGANISM: Artificial Sequence
<220> FEATURE:
<223> OTHER INFORMATION: Synthetic: UC1.3 VHCDR1 (Chothia)

<400> SEQUENCE: 346

Gly Phe Ser Phe Thr Ser Tyr
1 5

<210> SEQ ID NO 347
<211> LENGTH: 6
<212> TYPE: PRT
<213> ORGANISM: Artificial Sequence
<220> FEATURE:
<223> OTHER INFORMATION: Synthetic: UC1.3 VHCDR2 (Chothia)

<400> SEQUENCE: 347

Ser Gly Asp Gly Ala Ala
1 5

<210> SEQ ID NO 348
<211> LENGTH: 10

<212> TYPE: PRT
<213> ORGANISM: Artificial Sequence
<220> FEATURE:
<223> OTHER INFORMATION: Synthetic: UC1.3 VHCDR3 (Chothia)

<400> SEQUENCE: 348

Gln Ser Gln Tyr Val Gly Gly Phe Asp Tyr
1 5 10

<210> SEQ ID NO 349
<211> LENGTH: 14
<212> TYPE: PRT
<213> ORGANISM: Artificial Sequence
<220> FEATURE:
<223> OTHER INFORMATION: Synthetic: UC1.3 VLCDR1 (Chothia)

<400> SEQUENCE: 349

Thr Gly Ser Ser Ser Asn Phe Gly Ala Gly Tyr Gly Val His
1 5 10

<210> SEQ ID NO 350
<211> LENGTH: 7
<212> TYPE: PRT
<213> ORGANISM: Artificial Sequence
<220> FEATURE:
<223> OTHER INFORMATION: Synthetic: UC1.3 VLCDR2 (Chothia)

<400> SEQUENCE: 350

Gly Asn Thr Asn Arg Pro Ser
1 5

<210> SEQ ID NO 351
<211> LENGTH: 11
<212> TYPE: PRT
<213> ORGANISM: Artificial Sequence
<220> FEATURE:
<223> OTHER INFORMATION: Synthetic: UC1.3 VLCDR3 (Chothia)

<400> SEQUENCE: 351

Gln Ser Tyr Asp Ser Ser Leu Ser Gly Trp Val
1 5 10

<210> SEQ ID NO 352
<211> LENGTH: 5
<212> TYPE: PRT
<213> ORGANISM: Artificial Sequence
<220> FEATURE:
<223> OTHER INFORMATION: Synthetic: UC1.3 VHCDR1 (Kabat)

<400> SEQUENCE: 352

Ser Tyr Ala Met Thr
1 5

<210> SEQ ID NO 353
<211> LENGTH: 17
<212> TYPE: PRT
<213> ORGANISM: Artificial Sequence
<220> FEATURE:
<223> OTHER INFORMATION: Synthetic: UC1.3 VHCDR2 (Kabat)

<400> SEQUENCE: 353

Gly Ile Ser Gly Asp Gly Ala Ala Thr Phe Tyr Ala Asp Ser Val Lys
1 5 10 15

Gly

<210> SEQ ID NO 354

<211> LENGTH: 10
<212> TYPE: PRT
<213> ORGANISM: Artificial Sequence
<220> FEATURE:
<223> OTHER INFORMATION: Synthetic: UC1.3 VHCDR3 (Kabat)

<400> SEQUENCE: 354

Gln Ser Gln Tyr Val Gly Gly Phe Asp Tyr
1 5 10

<210> SEQ ID NO 355
<211> LENGTH: 14
<212> TYPE: PRT
<213> ORGANISM: Artificial Sequence
<220> FEATURE:
<223> OTHER INFORMATION: Synthetic: UC1.3 VLCDR1 (Kabat)

<400> SEQUENCE: 355

Thr Gly Ser Ser Ser Asn Phe Gly Ala Gly Tyr Gly Val His
1 5 10

<210> SEQ ID NO 356
<211> LENGTH: 7
<212> TYPE: PRT
<213> ORGANISM: Artificial Sequence
<220> FEATURE:
<223> OTHER INFORMATION: Synthetic: UC1.3 VLCDR2 (Kabat)

<400> SEQUENCE: 356

Gly Asn Thr Asn Arg Pro Ser
1 5

<210> SEQ ID NO 357
<211> LENGTH: 11
<212> TYPE: PRT
<213> ORGANISM: Artificial Sequence
<220> FEATURE:
<223> OTHER INFORMATION: Synthetic: UC1.3 VLCDR3 (Kabat)

<400> SEQUENCE: 357

Gln Ser Tyr Asp Ser Ser Leu Ser Gly Trp Val
1 5 10

<210> SEQ ID NO 358
<211> LENGTH: 8
<212> TYPE: PRT
<213> ORGANISM: Artificial Sequence
<220> FEATURE:
<223> OTHER INFORMATION: Synthetic: UC1.3 VHCDR1 (IMGT)

<400> SEQUENCE: 358

Gly Phe Ser Phe Thr Ser Tyr Ala
1 5

<210> SEQ ID NO 359
<211> LENGTH: 8
<212> TYPE: PRT
<213> ORGANISM: Artificial Sequence
<220> FEATURE:
<223> OTHER INFORMATION: Synthetic: UC1.3 VHCDR2 (IMGT)

<400> SEQUENCE: 359

Ile Ser Gly Asp Gly Ala Ala Thr
1 5

<210> SEQ ID NO 360
<211> LENGTH: 12

<212> TYPE: PRT
<213> ORGANISM: Artificial Sequence
<220> FEATURE:
<223> OTHER INFORMATION: Synthetic: UC1.3 VHCDR3 (IMGT)

<400> SEQUENCE: 360

Ala Arg Gln Ser Gln Tyr Val Gly Gly Phe Asp Tyr
1 5 10

<210> SEQ ID NO 361
<211> LENGTH: 9
<212> TYPE: PRT
<213> ORGANISM: Artificial Sequence
<220> FEATURE:
<223> OTHER INFORMATION: Synthetic: UC1.3 VLCDR1 (IMGT)

<400> SEQUENCE: 361

Ser Ser Asn Phe Gly Ala Gly Tyr Gly
1 5

<210> SEQ ID NO 362
<211> LENGTH: 3
<212> TYPE: PRT
<213> ORGANISM: Artificial Sequence
<220> FEATURE:
<223> OTHER INFORMATION: Synthetic: UC1.3 VLCDR2 (IMGT)

<400> SEQUENCE: 362

Gly Asn Thr
1

<210> SEQ ID NO 363
<211> LENGTH: 11
<212> TYPE: PRT
<213> ORGANISM: Artificial Sequence
<220> FEATURE:
<223> OTHER INFORMATION: Synthetic: UC1.3 VLCDR3 (IMGT)

<400> SEQUENCE: 363

Gln Ser Tyr Asp Ser Ser Leu Ser Gly Trp Val
1 5 10

<210> SEQ ID NO 364
<211> LENGTH: 119
<212> TYPE: PRT
<213> ORGANISM: Artificial Sequence
<220> FEATURE:
<223> OTHER INFORMATION: Synthetic: UC1.3 VH

<400> SEQUENCE: 364

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Ser Phe Thr Ser Tyr
20 25 30

Ala Met Thr Trp Val Arg Gln Ala Pro Gly Lys Gly Leu Glu Trp Val
35 40 45

Ser Gly Ile Ser Gly Asp Gly Ala Ala Thr Phe Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gln Ser Gln Tyr Val Gly Gly Phe Asp Tyr Trp Gly Gln Gly
100 105 110

```
Thr Leu Val Thr Val Ser Ser
        115


<210> SEQ ID NO 365
<211> LENGTH: 111
<212> TYPE: PRT
<213> ORGANISM: Artificial Sequence
<220> FEATURE:
<223> OTHER INFORMATION: Synthetic: UC1.3 VL

<400> SEQUENCE: 365

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Phe Gly Ala Gly
            20                  25                  30

Tyr Gly Val His Trp Tyr Gln Gln Leu Pro Gly Thr Ala Pro Lys Leu
        35                  40                  45

Leu Ile His Gly Asn Thr Asn Arg Pro Ser Gly Val Pro Asp Arg Phe
    50                  55                  60

Ser Gly Phe Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Gly Thr Lys Leu Thr Val Leu
            100                 105                 110


<210> SEQ ID NO 366
<211> LENGTH: 251
<212> TYPE: PRT
<213> ORGANISM: Artificial Sequence
<220> FEATURE:
<223> OTHER INFORMATION: Synthetic: UC3 (S4-2 1E5) scFv

<400> SEQUENCE: 366

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ala Gly Gly Gly Glu Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Pro Ile Ser Tyr Gly Phe Asp Ile Trp Gly Gln Gly
            100                 105                 110

Thr Leu Val Thr Val Ser Ser Ala Ser Ser Gly Gly Ser Thr Ser Gly
        115                 120                 125

Ser Gly Lys Pro Gly Ser Gly Glu Gly Ser Ser Gly Ser Ala Arg Asp
    130                 135                 140

Ile Gln Met Thr Gln Ser Pro Ser Ser Leu Ser Ala Ser Val Gly Asp
145                 150                 155                 160

Arg Val Thr Ile Thr Cys Gln Ala Ser Gln Asp Ile Lys Lys Tyr Leu
                165                 170                 175

Asn Trp Tyr Gln Gln Lys Pro Gly Lys Ala Pro Lys Leu Leu Ile Tyr
```

```
            180                 185                 190

Asp Ala Ser Thr Leu Gln Thr Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Gln Gln Ser Asp Asn Thr Pro Val Thr
225                 230                 235                 240

Phe Gly Gln Gly Thr Lys Val Glu Ile Lys Arg
                245                 250


<210> SEQ ID NO 367
<211> LENGTH: 7
<212> TYPE: PRT
<213> ORGANISM: Artificial Sequence
<220> FEATURE:
<223> OTHER INFORMATION: Synthetic: UC3 VHCDR1 (Chothia)

<400> SEQUENCE: 367

Gly Phe Ser Phe Ser Ser Tyr
1               5


<210> SEQ ID NO 368
<211> LENGTH: 6
<212> TYPE: PRT
<213> ORGANISM: Artificial Sequence
<220> FEATURE:
<223> OTHER INFORMATION: Synthetic: UC3 VHCDR2 (Chothia)

<400> SEQUENCE: 368

Ser Ala Gly Gly Gly Glu
1               5


<210> SEQ ID NO 369
<211> LENGTH: 10
<212> TYPE: PRT
<213> ORGANISM: Artificial Sequence
<220> FEATURE:
<223> OTHER INFORMATION: Synthetic: UC3 VHCDR3 (Chothia)

<400> SEQUENCE: 369

Val His Pro Ile Ser Tyr Gly Phe Asp Ile
1               5                   10


<210> SEQ ID NO 370
<211> LENGTH: 11
<212> TYPE: PRT
<213> ORGANISM: Artificial Sequence
<220> FEATURE:
<223> OTHER INFORMATION: Synthetic: UC3 VLCDR1 (Chothia)

<400> SEQUENCE: 370

Gln Ala Ser Gln Asp Ile Lys Lys Tyr Leu Asn
1               5                   10


<210> SEQ ID NO 371
<211> LENGTH: 7
<212> TYPE: PRT
<213> ORGANISM: Artificial Sequence
<220> FEATURE:
<223> OTHER INFORMATION: Synthetic: UC3 VLCDR2 (Chothia)

<400> SEQUENCE: 371

Asp Ala Ser Thr Leu Gln Thr
1               5
```

<210> SEQ ID NO 372
<211> LENGTH: 9
<212> TYPE: PRT
<213> ORGANISM: Artificial Sequence
<220> FEATURE:
<223> OTHER INFORMATION: Synthetic: UC3 VLCDR3 (Chothia)

<400> SEQUENCE: 372

Gln Gln Ser Asp Asn Thr Pro Val Thr
1 5

<210> SEQ ID NO 373
<211> LENGTH: 5
<212> TYPE: PRT
<213> ORGANISM: Artificial Sequence
<220> FEATURE:
<223> OTHER INFORMATION: Synthetic: UC3 VHCDR1 (Kabat)

<400> SEQUENCE: 373

Ser Tyr Ala Met Ser
1 5

<210> SEQ ID NO 374
<211> LENGTH: 17
<212> TYPE: PRT
<213> ORGANISM: Artificial Sequence
<220> FEATURE:
<223> OTHER INFORMATION: Synthetic: UC3 VHCDR2 (Kabat)

<400> SEQUENCE: 374

Gly Ile Ser Ala Gly Gly Gly Glu Thr Phe Tyr Ala Asp Ser Val Lys
1 5 10 15

Gly

<210> SEQ ID NO 375
<211> LENGTH: 10
<212> TYPE: PRT
<213> ORGANISM: Artificial Sequence
<220> FEATURE:
<223> OTHER INFORMATION: Synthetic: UC3 VHCDR3 (Kabat)

<400> SEQUENCE: 375

Val His Pro Ile Ser Tyr Gly Phe Asp Ile
1 5 10

<210> SEQ ID NO 376
<211> LENGTH: 11
<212> TYPE: PRT
<213> ORGANISM: Artificial Sequence
<220> FEATURE:
<223> OTHER INFORMATION: Synthetic: UC3 VLCDR1 (Kabat)

<400> SEQUENCE: 376

Gln Ala Ser Gln Asp Ile Lys Lys Tyr Leu Asn
1 5 10

<210> SEQ ID NO 377
<211> LENGTH: 7
<212> TYPE: PRT
<213> ORGANISM: Artificial Sequence
<220> FEATURE:
<223> OTHER INFORMATION: Synthetic: UC3 VLCDR2 (Kabat)

<400> SEQUENCE: 377

Asp Ala Ser Thr Leu Gln Thr
1 5

<210> SEQ ID NO 378
<211> LENGTH: 9
<212> TYPE: PRT
<213> ORGANISM: Artificial Sequence
<220> FEATURE:
<223> OTHER INFORMATION: Synthetic: UC3 VLCDR3 (Kabat)

<400> SEQUENCE: 378

Gln Gln Ser Asp Asn Thr Pro Val Thr
1 5

<210> SEQ ID NO 379
<211> LENGTH: 8
<212> TYPE: PRT
<213> ORGANISM: Artificial Sequence
<220> FEATURE:
<223> OTHER INFORMATION: Synthetic: UC3 VHCDR1 (IMGT)

<400> SEQUENCE: 379

Gly Phe Ser Phe Ser Ser Tyr Ala
1 5

<210> SEQ ID NO 380
<211> LENGTH: 8
<212> TYPE: PRT
<213> ORGANISM: Artificial Sequence
<220> FEATURE:
<223> OTHER INFORMATION: Synthetic: UC3 VHCDR2 (IMGT)

<400> SEQUENCE: 380

Ile Ser Ala Gly Gly Gly Glu Thr
1 5

<210> SEQ ID NO 381
<211> LENGTH: 12
<212> TYPE: PRT
<213> ORGANISM: Artificial Sequence
<220> FEATURE:
<223> OTHER INFORMATION: Synthetic: UC3 VHCDR3 (IMGT)

<400> SEQUENCE: 381

Ala Arg Val His Pro Ile Ser Tyr Gly Phe Asp Ile
1 5 10

<210> SEQ ID NO 382
<211> LENGTH: 6
<212> TYPE: PRT
<213> ORGANISM: Artificial Sequence
<220> FEATURE:
<223> OTHER INFORMATION: Synthetic: UC3 VLCDR1 (IMGT)

<400> SEQUENCE: 382

Gln Asp Ile Lys Lys Tyr
1 5

<210> SEQ ID NO 383
<211> LENGTH: 3
<212> TYPE: PRT
<213> ORGANISM: Artificial Sequence
<220> FEATURE:
<223> OTHER INFORMATION: Synthetic: UC3 VLCDR2 (IMGT)

<400> SEQUENCE: 383

Asp Ala Ser
1

<210> SEQ ID NO 384
<211> LENGTH: 9
<212> TYPE: PRT
<213> ORGANISM: Artificial Sequence
<220> FEATURE:
<223> OTHER INFORMATION: Synthetic: UC3 VLCDR3 (IMGT)

<400> SEQUENCE: 384

```
Gln Gln Ser Asp Asn Thr Pro Val Thr
1               5
```

<210> SEQ ID NO 385
<211> LENGTH: 119
<212> TYPE: PRT
<213> ORGANISM: Artificial Sequence
<220> FEATURE:
<223> OTHER INFORMATION: Synthetic: UC3 VH

<400> SEQUENCE: 385

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ala Gly Gly Gly Glu Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Pro Ile Ser Tyr Gly Phe Asp Ile Trp Gly Gln Gly
            100                 105                 110

Thr Leu Val Thr Val Ser Ser
        115
```

<210> SEQ ID NO 386
<211> LENGTH: 107
<212> TYPE: PRT
<213> ORGANISM: Artificial Sequence
<220> FEATURE:
<223> OTHER INFORMATION: Synthetic: UC3 VL

<400> SEQUENCE: 386

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Lys Lys Tyr
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Asn Thr Pro Val
                85                  90                  95

Thr Phe Gly Gln Gly Thr Lys Val Glu Ile Lys
            100                 105
```

<210> SEQ ID NO 387
<211> LENGTH: 237
<212> TYPE: PRT
<213> ORGANISM: Artificial Sequence
<220> FEATURE:
<223> OTHER INFORMATION: Synthetic: UC4 (7-2E8) scFv

<400> SEQUENCE: 387

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Ile His Trp Val Arg Gln Ala Pro Gly Lys Gly Leu Glu Trp Val
        35                  40                  45

Ala Val Ile Ser Ser Asp Gly Gly Tyr Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Lys Asp Arg Gln Ile Gly Asp Leu Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Val Val Met Thr Gln Ser Pro Ser Phe Leu Ser Ala Ser
    130                 135                 140

Val Gly Asp Arg Val Thr Ile Thr Cys Arg Ala Ser His Gly Ile Ser
145                 150                 155                 160

Asn Tyr Leu Ala Trp Tyr Gln Gln Lys Pro Gly Lys Ala Pro Lys Leu
                165                 170                 175

Leu Ile Tyr Ala Ala Ser Thr Leu Gln Ser Gly Val Pro Ser Arg Phe
            180                 185                 190

Ser Gly Ser Gly Ser Gly Thr Glu Phe Thr Leu Thr Ile Ser Ser Leu
        195                 200                 205

Gln Pro Asp Asp Phe Ala Thr Tyr Tyr Cys Gln Gln Tyr Asn Thr Tyr
    210                 215                 220

Arg Thr Phe Gly Gln Gly Thr Lys Val Glu Ile Lys Arg
225                 230                 235
```

<210> SEQ ID NO 388
<211> LENGTH: 7
<212> TYPE: PRT
<213> ORGANISM: Artificial Sequence
<220> FEATURE:
<223> OTHER INFORMATION: Synthetic: UC4 VHCDR1 (Chothia)

<400> SEQUENCE: 388

```
Gly Phe Thr Phe Ser Ser Tyr
1               5
```

<210> SEQ ID NO 389
<211> LENGTH: 6
<212> TYPE: PRT
<213> ORGANISM: Artificial Sequence
<220> FEATURE:
<223> OTHER INFORMATION: Synthetic: UC4 VHCDR2 (Chothia)

<400> SEQUENCE: 389

```
Ser Ser Asp Gly Gly Tyr
1               5
```

<210> SEQ ID NO 390
<211> LENGTH: 6
<212> TYPE: PRT
<213> ORGANISM: Artificial Sequence
<220> FEATURE:
<223> OTHER INFORMATION: Synthetic: UC4 VHCDR3 (Chothia)

<400> SEQUENCE: 390

Asp Arg Gln Ile Gly Asp
1               5

<210> SEQ ID NO 391
<211> LENGTH: 11
<212> TYPE: PRT
<213> ORGANISM: Artificial Sequence
<220> FEATURE:
<223> OTHER INFORMATION: Synthetic: UC4 VLCDR1 (Chothia)

<400> SEQUENCE: 391

Arg Ala Ser His Gly Ile Ser Asn Tyr Leu Ala
1               5                   10

<210> SEQ ID NO 392
<211> LENGTH: 7
<212> TYPE: PRT
<213> ORGANISM: Artificial Sequence
<220> FEATURE:
<223> OTHER INFORMATION: Synthetic: UC4 VLCDR2 (Chothia)

<400> SEQUENCE: 392

Ala Ala Ser Thr Leu Gln Ser
1               5

<210> SEQ ID NO 393
<211> LENGTH: 8
<212> TYPE: PRT
<213> ORGANISM: Artificial Sequence
<220> FEATURE:
<223> OTHER INFORMATION: Synthetic: UC4 VLCDR3 (Chothia)

<400> SEQUENCE: 393

Gln Gln Tyr Asn Thr Tyr Arg Thr
1               5

<210> SEQ ID NO 394
<211> LENGTH: 5
<212> TYPE: PRT
<213> ORGANISM: Artificial Sequence
<220> FEATURE:
<223> OTHER INFORMATION: Synthetic: UC4 VHCDR1 (Kabat)

<400> SEQUENCE: 394

Ser Tyr Ala Ile His
1               5

<210> SEQ ID NO 395
<211> LENGTH: 17
<212> TYPE: PRT
<213> ORGANISM: Artificial Sequence
<220> FEATURE:
<223> OTHER INFORMATION: Synthetic: UC4 VHCDR2 (Kabat)

<400> SEQUENCE: 395

Val Ile Ser Ser Asp Gly Gly Tyr Lys Asn Tyr Ala Asp Ser Val Lys
1               5                   10                  15

Gly

<210> SEQ ID NO 396
<211> LENGTH: 6
<212> TYPE: PRT
<213> ORGANISM: Artificial Sequence
<220> FEATURE:
<223> OTHER INFORMATION: Synthetic: UC4 VHCDR3 (Kabat)

<400> SEQUENCE: 396

Asp Arg Gln Ile Gly Asp
1               5

<210> SEQ ID NO 397
<211> LENGTH: 11
<212> TYPE: PRT
<213> ORGANISM: Artificial Sequence
<220> FEATURE:
<223> OTHER INFORMATION: Synthetic: UC4 VLCDR1 (Kabat)

<400> SEQUENCE: 397

Arg Ala Ser His Gly Ile Ser Asn Tyr Leu Ala
1               5                   10

<210> SEQ ID NO 398
<211> LENGTH: 7
<212> TYPE: PRT
<213> ORGANISM: Artificial Sequence
<220> FEATURE:
<223> OTHER INFORMATION: Synthetic: UC4 VLCDR2 (Kabat)

<400> SEQUENCE: 398

Ala Ala Ser Thr Leu Gln Ser
1               5

<210> SEQ ID NO 399
<211> LENGTH: 8
<212> TYPE: PRT
<213> ORGANISM: Artificial Sequence
<220> FEATURE:
<223> OTHER INFORMATION: Synthetic: UC4 VLCDR3 (Kabat)

<400> SEQUENCE: 399

Gln Gln Tyr Asn Thr Tyr Arg Thr
1               5

<210> SEQ ID NO 400
<211> LENGTH: 8
<212> TYPE: PRT
<213> ORGANISM: Artificial Sequence
<220> FEATURE:
<223> OTHER INFORMATION: Synthetic: UC4 VHCDR1 (IMGT)

<400> SEQUENCE: 400

Gly Phe Thr Phe Ser Ser Tyr Ala
1               5

<210> SEQ ID NO 401
<211> LENGTH: 8
<212> TYPE: PRT
<213> ORGANISM: Artificial Sequence
<220> FEATURE:
<223> OTHER INFORMATION: Synthetic: UC4 VHCDR2 (IMGT)

<400> SEQUENCE: 401

Ile Ser Ser Asp Gly Gly Tyr Lys
1               5

<210> SEQ ID NO 402
<211> LENGTH: 8
<212> TYPE: PRT
<213> ORGANISM: Artificial Sequence
<220> FEATURE:
<223> OTHER INFORMATION: Synthetic: UC4 VHCDR3 (IMGT)

<400> SEQUENCE: 402

Ala Lys Asp Arg Gln Ile Gly Asp
1               5

<210> SEQ ID NO 403
<211> LENGTH: 6
<212> TYPE: PRT
<213> ORGANISM: Artificial Sequence
<220> FEATURE:
<223> OTHER INFORMATION: Synthetic: UC4 VLCDR1 (IMGT)

<400> SEQUENCE: 403

His Gly Ile Ser Asn Tyr
1               5

<210> SEQ ID NO 404
<211> LENGTH: 3
<212> TYPE: PRT
<213> ORGANISM: Artificial Sequence
<220> FEATURE:
<223> OTHER INFORMATION: Synthetic: UC4 VLCDR2 (IMGT)

<400> SEQUENCE: 404

Ala Ala Ser
1

<210> SEQ ID NO 405
<211> LENGTH: 8
<212> TYPE: PRT
<213> ORGANISM: Artificial Sequence
<220> FEATURE:
<223> OTHER INFORMATION: Synthetic: UC4 VLCDR3 (IMGT)

<400> SEQUENCE: 405

Gln Gln Tyr Asn Thr Tyr Arg Thr
1               5

<210> SEQ ID NO 406
<211> LENGTH: 115
<212> TYPE: PRT
<213> ORGANISM: Artificial Sequence
<220> FEATURE:
<223> OTHER INFORMATION: Synthetic: UC4 VH

<400> SEQUENCE: 406

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Ile His Trp Val Arg Gln Ala Pro Gly Lys Gly Leu Glu Trp Val
        35                  40                  45

Ala Val Ile Ser Ser Asp Gly Gly Tyr Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys

```
                85                  90                  95

Ala Lys Asp Arg Gln Ile Gly Asp Leu Gly Gln Gly Thr Leu Val Thr
            100                 105                 110

Val Ser Ser
        115


<210> SEQ ID NO 407
<211> LENGTH: 106
<212> TYPE: PRT
<213> ORGANISM: Artificial Sequence
<220> FEATURE:
<223> OTHER INFORMATION: Synthetic: UC4 VL

<400> SEQUENCE: 407

Asp Val Val Met Thr Gln Ser Pro Ser Phe Leu Ser Ala Ser Val Gly
1               5                   10                  15

Asp Arg Val Thr Ile Thr Cys Arg Ala Ser His Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Arg Thr
                85                  90                  95

Phe Gly Gln Gly Thr Lys Val Glu Ile Lys
            100                 105


<210> SEQ ID NO 408
<211> LENGTH: 251
<212> TYPE: PRT
<213> ORGANISM: Artificial Sequence
<220> FEATURE:
<223> OTHER INFORMATION: Synthetic: UC5 (8-2A10) scFv

<400> SEQUENCE: 408

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Thr Trp Val Arg Gln Ala Pro Gly Lys Gly Leu Glu Trp Val
        35                  40                  45

Ser Ala Ile Ser Asp Ser Gly Gly Asp Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Tyr Ala Ala Arg Phe Asp Tyr Trp Gly Gln Gly
            100                 105                 110

Thr Leu Val Thr Val Ser Ser Ala Ser Ser Gly Gly Ser Thr Ser Gly
        115                 120                 125

Ser Gly Lys Pro Gly Ser Gly Glu Gly Ser Ser Gly Ser Ala Arg Asp
    130                 135                 140

Ile Gln Met Thr Gln Ser Pro Ser Ser Leu Ser Ala Ser Val Gly Asp
145                 150                 155                 160
```

Arg Val Thr Ile Thr Cys Gln Ala Ser Gln Asp Ile Ser Asn Tyr Leu
165 170 175

Asn Trp Tyr Gln Gln Lys Pro Gly Lys Ala Pro Lys Leu Leu Ile Tyr
180 185 190

Asp Ala Ser Thr Leu Glu Thr Gly Val Pro Ser Arg Phe Ser Gly Ser
195 200 205

Gly Ser Gly Thr Asp Phe Thr Phe Thr Ile Ser Ser Leu Gln Pro Glu
210 215 220

Asp Ile Ala Thr Tyr Tyr Cys Gln Gln Ser Asp Ser Phe Pro Ile Thr
225 230 235 240

Phe Gly Gln Gly Thr Lys Val Glu Ile Lys Arg
245 250

<210> SEQ ID NO 409
<211> LENGTH: 7
<212> TYPE: PRT
<213> ORGANISM: Artificial Sequence
<220> FEATURE:
<223> OTHER INFORMATION: Synthetic: UC5 VHCDR1 (Chothia)

<400> SEQUENCE: 409

Gly Phe Thr Phe Asn Thr Tyr
1 5

<210> SEQ ID NO 410
<211> LENGTH: 6
<212> TYPE: PRT
<213> ORGANISM: Artificial Sequence
<220> FEATURE:
<223> OTHER INFORMATION: Synthetic: UC5 VHCDR2 (Chothia)

<400> SEQUENCE: 410

Ser Asp Ser Gly Gly Asp
1 5

<210> SEQ ID NO 411
<211> LENGTH: 10
<212> TYPE: PRT
<213> ORGANISM: Artificial Sequence
<220> FEATURE:
<223> OTHER INFORMATION: Synthetic: UC5 VHCDR3 (Chothia)

<400> SEQUENCE: 411

Asp Gly Thr Tyr Ala Ala Arg Phe Asp Tyr
1 5 10

<210> SEQ ID NO 412
<211> LENGTH: 11
<212> TYPE: PRT
<213> ORGANISM: Artificial Sequence
<220> FEATURE:
<223> OTHER INFORMATION: Synthetic: UC5 VLCDR1 (Chothia)

<400> SEQUENCE: 412

Gln Ala Ser Gln Asp Ile Ser Asn Tyr Leu Asn
1 5 10

<210> SEQ ID NO 413
<211> LENGTH: 7
<212> TYPE: PRT
<213> ORGANISM: Artificial Sequence
<220> FEATURE:
<223> OTHER INFORMATION: Synthetic: UC5 VLCDR2 (Chothia)

<400> SEQUENCE: 413

Asp Ala Ser Thr Leu Glu Thr
1 5

<210> SEQ ID NO 414
<211> LENGTH: 9
<212> TYPE: PRT
<213> ORGANISM: Artificial Sequence
<220> FEATURE:
<223> OTHER INFORMATION: Synthetic: UC5 VLCDR3 (Chothia)

<400> SEQUENCE: 414

Gln Gln Ser Asp Ser Phe Pro Ile Thr
1 5

<210> SEQ ID NO 415
<211> LENGTH: 5
<212> TYPE: PRT
<213> ORGANISM: Artificial Sequence
<220> FEATURE:
<223> OTHER INFORMATION: Synthetic: UC5 VHCDR1 (Kabat)

<400> SEQUENCE: 415

Thr Tyr Ala Met Thr
1 5

<210> SEQ ID NO 416
<211> LENGTH: 17
<212> TYPE: PRT
<213> ORGANISM: Artificial Sequence
<220> FEATURE:
<223> OTHER INFORMATION: Synthetic: UC5 VHCDR2 (Kabat)

<400> SEQUENCE: 416

Ala Ile Ser Asp Ser Gly Gly Asp Thr Phe Tyr Ala Asp Ser Val Lys
1 5 10 15

Gly

<210> SEQ ID NO 417
<211> LENGTH: 10
<212> TYPE: PRT
<213> ORGANISM: Artificial Sequence
<220> FEATURE:
<223> OTHER INFORMATION: Synthetic: UC5 VHCDR3 (Kabat)

<400> SEQUENCE: 417

Asp Gly Thr Tyr Ala Ala Arg Phe Asp Tyr
1 5 10

<210> SEQ ID NO 418
<211> LENGTH: 11
<212> TYPE: PRT
<213> ORGANISM: Artificial Sequence
<220> FEATURE:
<223> OTHER INFORMATION: Synthetic: UC5 VLCDR1 (Kabat)

<400> SEQUENCE: 418

Gln Ala Ser Gln Asp Ile Ser Asn Tyr Leu Asn
1 5 10

<210> SEQ ID NO 419
<211> LENGTH: 7
<212> TYPE: PRT
<213> ORGANISM: Artificial Sequence
<220> FEATURE:
<223> OTHER INFORMATION: Synthetic: UC5 VLCDR2 (Kabat)

<400> SEQUENCE: 419

Asp Ala Ser Thr Leu Glu Thr
1 5

<210> SEQ ID NO 420
<211> LENGTH: 9
<212> TYPE: PRT
<213> ORGANISM: Artificial Sequence
<220> FEATURE:
<223> OTHER INFORMATION: Synthetic: UC5 VLCDR3 (Kabat)

<400> SEQUENCE: 420

Gln Gln Ser Asp Ser Phe Pro Ile Thr
1 5

<210> SEQ ID NO 421
<211> LENGTH: 8
<212> TYPE: PRT
<213> ORGANISM: Artificial Sequence
<220> FEATURE:
<223> OTHER INFORMATION: Synthetic: UC5 VHCDR1 (IMGT)

<400> SEQUENCE: 421

Gly Phe Thr Phe Asn Thr Tyr Ala
1 5

<210> SEQ ID NO 422
<211> LENGTH: 8
<212> TYPE: PRT
<213> ORGANISM: Artificial Sequence
<220> FEATURE:
<223> OTHER INFORMATION: Synthetic: UC5 VHCDR2 (IMGT)

<400> SEQUENCE: 422

Ile Ser Asp Ser Gly Gly Asp Thr
1 5

<210> SEQ ID NO 423
<211> LENGTH: 12
<212> TYPE: PRT
<213> ORGANISM: Artificial Sequence
<220> FEATURE:
<223> OTHER INFORMATION: Synthetic: UC5 VHCDR3 (IMGT)

<400> SEQUENCE: 423

Ala Arg Asp Gly Thr Tyr Ala Ala Arg Phe Asp Tyr
1 5 10

<210> SEQ ID NO 424
<211> LENGTH: 6
<212> TYPE: PRT
<213> ORGANISM: Artificial Sequence
<220> FEATURE:
<223> OTHER INFORMATION: Synthetic: UC5 VLCDR1 (IMGT)

<400> SEQUENCE: 424

Gln Asp Ile Ser Asn Tyr
1 5

<210> SEQ ID NO 425
<211> LENGTH: 3
<212> TYPE: PRT
<213> ORGANISM: Artificial Sequence
<220> FEATURE:
<223> OTHER INFORMATION: Synthetic: UC5 VLCDR2 (IMGT)

<400> SEQUENCE: 425

Asp Ala Ser
1

<210> SEQ ID NO 426
<211> LENGTH: 9
<212> TYPE: PRT
<213> ORGANISM: Artificial Sequence
<220> FEATURE:
<223> OTHER INFORMATION: Synthetic: UC5 VLCDR3 (IMGT)

<400> SEQUENCE: 426

Gln Gln Ser Asp Ser Phe Pro Ile Thr
1 5

<210> SEQ ID NO 427
<211> LENGTH: 119
<212> TYPE: PRT
<213> ORGANISM: Artificial Sequence
<220> FEATURE:
<223> OTHER INFORMATION: Synthetic: UC5 VH

<400> SEQUENCE: 427

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asn Thr Tyr
20 25 30

Ala Met Thr Trp Val Arg Gln Ala Pro Gly Lys Gly Leu Glu Trp Val
35 40 45

Ser Ala Ile Ser Asp Ser Gly Gly Asp Thr Phe Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Gly Thr Tyr Ala Ala Arg Phe Asp Tyr Trp Gly Gln Gly
100 105 110

Thr Leu Val Thr Val Ser Ser
115

<210> SEQ ID NO 428
<211> LENGTH: 107
<212> TYPE: PRT
<213> ORGANISM: Artificial Sequence
<220> FEATURE:
<223> OTHER INFORMATION: Synthetic: UC5 VL

<400> SEQUENCE: 428

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Thr Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Ser Asp Ser Phe Pro Ile
85 90 95

Thr Phe Gly Gln Gly Thr Lys Val Glu Ile Lys
100 105

<210> SEQ ID NO 429
<211> LENGTH: 253
<212> TYPE: PRT
<213> ORGANISM: Artificial Sequence
<220> FEATURE:
<223> OTHER INFORMATION: Synthetic: UC6 (9-1A6) scFv

<400> SEQUENCE: 429

Gln Val Gln Leu Val Gln Ser Gly Ala Glu Val Lys Lys Pro Gly Ser
1 5 10 15

Ser Val Lys Val Ser Cys Lys Ala Ser Gly Asp Ser Phe Asn Asn Phe
20 25 30

Gly Ile Ser Trp Val Arg Gln Ala Pro Gly Gln Gly Leu Glu Trp Met
35 40 45

Gly Gly Ile Val Pro Val Leu Gly Ile Ala Thr Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Ser Ala Trp Tyr Asp Gly Ser Phe Gln Tyr Trp Gly Gln
100 105 110

Gly Thr Leu Val Thr Val Ser Ser Ala Ser Ser Gly Gly Ser Thr Ser
115 120 125

Gly Ser Gly Lys Pro Gly Ser Gly Glu Gly Ser Ser Gly Ser Ala Arg
130 135 140

Glu Ile Val Leu Thr Gln Ser Pro Gly Thr Leu Ser Leu Ser Pro Gly
145 150 155 160

Glu Arg Ala Thr Leu Ser Cys Arg Ala Ser Gln Ser Val Ser Ser Thr
165 170 175

Phe Leu Ala Trp Tyr Gln Gln Lys Pro Gly Gln Ala Pro Arg Leu Leu
180 185 190

Ile Tyr Asp Ala Ser Thr Arg Ala Thr Gly Ile Pro Asp Arg Phe Ser
195 200 205

Gly Ser Asp Ser Gly Thr Asp Phe Thr Leu Thr Ile Ser Arg Leu Glu
210 215 220

Pro Glu Asp Phe Ala Val Tyr Tyr Cys Gln Gln Tyr Asp Ser Trp Pro
225 230 235 240

Phe Thr Phe Gly Gln Gly Thr Lys Val Glu Ile Lys Arg
245 250

<210> SEQ ID NO 430
<211> LENGTH: 7
<212> TYPE: PRT
<213> ORGANISM: Artificial Sequence
<220> FEATURE:
<223> OTHER INFORMATION: Synthetic: UC6 VHCDR1 (Chothia)

<400> SEQUENCE: 430

Gly Asp Ser Phe Asn Asn Phe
1 5

<210> SEQ ID NO 431
<211> LENGTH: 6
<212> TYPE: PRT
<213> ORGANISM: Artificial Sequence
<220> FEATURE:
<223> OTHER INFORMATION: Synthetic: UC6 VHCDR2 (Chothia)

<400> SEQUENCE: 431

Val Pro Val Leu Gly Ile
1 5

<210> SEQ ID NO 432
<211> LENGTH: 11
<212> TYPE: PRT
<213> ORGANISM: Artificial Sequence
<220> FEATURE:
<223> OTHER INFORMATION: Synthetic: UC6 VHCDR3 (Chothia)

<400> SEQUENCE: 432

Gly Ser Ala Trp Tyr Asp Gly Ser Phe Gln Tyr
1 5 10

<210> SEQ ID NO 433
<211> LENGTH: 12
<212> TYPE: PRT
<213> ORGANISM: Artificial Sequence
<220> FEATURE:
<223> OTHER INFORMATION: Synthetic: UC6 VLCDR1 (Chothia)

<400> SEQUENCE: 433

Arg Ala Ser Gln Ser Val Ser Ser Thr Phe Leu Ala
1 5 10

<210> SEQ ID NO 434
<211> LENGTH: 7
<212> TYPE: PRT
<213> ORGANISM: Artificial Sequence
<220> FEATURE:
<223> OTHER INFORMATION: Synthetic: UC6 VLCDR2 (Chothia)

<400> SEQUENCE: 434

Asp Ala Ser Thr Arg Ala Thr
1 5

<210> SEQ ID NO 435
<211> LENGTH: 9
<212> TYPE: PRT
<213> ORGANISM: Artificial Sequence
<220> FEATURE:
<223> OTHER INFORMATION: Synthetic: UC6 VLCDR3 (Chothia)

<400> SEQUENCE: 435

Gln Gln Tyr Asp Ser Trp Pro Phe Thr
1 5

<210> SEQ ID NO 436
<211> LENGTH: 5
<212> TYPE: PRT
<213> ORGANISM: Artificial Sequence
<220> FEATURE:
<223> OTHER INFORMATION: Synthetic: UC6 VHCDR1 (Kabat)

<400> SEQUENCE: 436

Asn Phe Gly Ile Ser
1 5

<210> SEQ ID NO 437
<211> LENGTH: 17
<212> TYPE: PRT
<213> ORGANISM: Artificial Sequence
<220> FEATURE:

<223> OTHER INFORMATION: Synthetic: UC6 VHCDR2 (Kabat)

<400> SEQUENCE: 437

Gly Ile Val Pro Val Leu Gly Ile Ala Thr Tyr Ala Gln Lys Phe Gln
1 5 10 15

Gly

<210> SEQ ID NO 438
<211> LENGTH: 11
<212> TYPE: PRT
<213> ORGANISM: Artificial Sequence
<220> FEATURE:
<223> OTHER INFORMATION: Synthetic: UC6 VHCDR3 (Kabat)

<400> SEQUENCE: 438

Gly Ser Ala Trp Tyr Asp Gly Ser Phe Gln Tyr
1 5 10

<210> SEQ ID NO 439
<211> LENGTH: 12
<212> TYPE: PRT
<213> ORGANISM: Artificial Sequence
<220> FEATURE:
<223> OTHER INFORMATION: Synthetic: UC6 VLCDR1 (Kabat)

<400> SEQUENCE: 439

Arg Ala Ser Gln Ser Val Ser Ser Thr Phe Leu Ala
1 5 10

<210> SEQ ID NO 440
<211> LENGTH: 7
<212> TYPE: PRT
<213> ORGANISM: Artificial Sequence
<220> FEATURE:
<223> OTHER INFORMATION: Synthetic: UC6 VLCDR2 (Kabat)

<400> SEQUENCE: 440

Asp Ala Ser Thr Arg Ala Thr
1 5

<210> SEQ ID NO 441
<211> LENGTH: 9
<212> TYPE: PRT
<213> ORGANISM: Artificial Sequence
<220> FEATURE:
<223> OTHER INFORMATION: Synthetic: UC6 VLCDR3 (Kabat)

<400> SEQUENCE: 441

Gln Gln Tyr Asp Ser Trp Pro Phe Thr
1 5

<210> SEQ ID NO 442
<211> LENGTH: 8
<212> TYPE: PRT
<213> ORGANISM: Artificial Sequence
<220> FEATURE:
<223> OTHER INFORMATION: Synthetic: UC6 VHCDR1 (IMGT)

<400> SEQUENCE: 442

Gly Asp Ser Phe Asn Asn Phe Gly
1 5

<210> SEQ ID NO 443
<211> LENGTH: 8
<212> TYPE: PRT
<213> ORGANISM: Artificial Sequence
<220> FEATURE:
<223> OTHER INFORMATION: Synthetic: UC6 VHCDR2 (IMGT)

<400> SEQUENCE: 443

Ile Val Pro Val Leu Gly Ile Ala
1               5

<210> SEQ ID NO 444
<211> LENGTH: 13
<212> TYPE: PRT
<213> ORGANISM: Artificial Sequence
<220> FEATURE:
<223> OTHER INFORMATION: Synthetic: UC6 VHCDR3 (IMGT)

<400> SEQUENCE: 444

Ala Arg Gly Ser Ala Trp Tyr Asp Gly Ser Phe Gln Tyr
1               5                   10

<210> SEQ ID NO 445
<211> LENGTH: 7
<212> TYPE: PRT
<213> ORGANISM: Artificial Sequence
<220> FEATURE:
<223> OTHER INFORMATION: Synthetic: UC6 VLCDR1 (IMGT)

<400> SEQUENCE: 445

Gln Ser Val Ser Ser Thr Phe
1               5

<210> SEQ ID NO 446
<211> LENGTH: 3
<212> TYPE: PRT
<213> ORGANISM: Artificial Sequence
<220> FEATURE:
<223> OTHER INFORMATION: Synthetic: UC6 VLCDR2 (IMGT)

<400> SEQUENCE: 446

Asp Ala Ser
1

<210> SEQ ID NO 447
<211> LENGTH: 9
<212> TYPE: PRT
<213> ORGANISM: Artificial Sequence
<220> FEATURE:
<223> OTHER INFORMATION: Synthetic: UC6 VLCDR3 (IMGT)

<400> SEQUENCE: 447

Gln Gln Tyr Asp Ser Trp Pro Phe Thr
1               5

<210> SEQ ID NO 448
<211> LENGTH: 120
<212> TYPE: PRT
<213> ORGANISM: Artificial Sequence
<220> FEATURE:
<223> OTHER INFORMATION: Synthetic: UC6 VH

<400> SEQUENCE: 448

Gln Val Gln Leu Val Gln Ser Gly Ala Glu Val Lys Lys Pro Gly Ser
1               5                   10                  15

Ser Val Lys Val Ser Cys Lys Ala Ser Gly Asp Ser Phe Asn Asn Phe
            20                  25                  30

Gly Ile Ser Trp Val Arg Gln Ala Pro Gly Gln Gly Leu Glu Trp Met
        35                  40                  45

```
Gly Gly Ile Val Pro Val Leu Gly Ile Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Ala Trp Tyr Asp Gly Ser Phe Gln Tyr Trp Gly Gln
            100                 105                 110

Gly Thr Leu Val Thr Val Ser Ser
        115                 120


<210> SEQ ID NO 449
<211> LENGTH: 108
<212> TYPE: PRT
<213> ORGANISM: Artificial Sequence
<220> FEATURE:
<223> OTHER INFORMATION: Synthetic: UC6 VL

<400> SEQUENCE: 449

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Phe Leu Ala Trp Tyr Gln Gln Lys Pro Gly Gln Ala Pro Arg Leu Leu
        35                  40                  45

Ile Tyr Asp Ala Ser Thr Arg Ala Thr Gly Ile Pro Asp Arg Phe Ser
    50                  55                  60

Gly Ser Asp Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Ser Trp Pro
                85                  90                  95

Phe Thr Phe Gly Gln Gly Thr Lys Val Glu Ile Lys
            100                 105


<210> SEQ ID NO 450
<211> LENGTH: 256
<212> TYPE: PRT
<213> ORGANISM: Artificial Sequence
<220> FEATURE:
<223> OTHER INFORMATION: Synthetic: UC7 (9-1B5) scFv

<400> SEQUENCE: 450

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Tyr
            20                  25                  30

Gly Val Ser Trp Val Arg Gln Ala Pro Gly Gln Gly Leu Glu Trp Met
        35                  40                  45

Gly Arg Ile Val Pro Val Phe Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Ser Pro Tyr Val Thr Tyr Ser Ser Tyr Tyr Phe Asp Tyr
            100                 105                 110

Trp Gly Gln Gly Thr Leu Val Thr Val Ser Ser Ala Ser Ser Gly Gly
        115                 120                 125
```

```
Ser Thr Ser Gly Ser Gly Lys Pro Gly Ser Gly Glu Gly Ser Ser Gly
    130                 135                 140

Ser Ala Arg Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175

Ser Asn Asn Phe Leu Ala Trp Tyr Gln Gln Lys Pro Gly Gln Ala Pro
            180                 185                 190

Arg Leu Leu Ile Tyr Asp Ala Ser Thr Arg Ala Thr Gly Ile Pro Asp
        195                 200                 205

Arg Phe Ser Gly Ser Gly Ser Gly Thr Asp Phe Thr Leu Thr Ile Ser
    210                 215                 220

Arg Leu Glu Pro Glu Asp Phe Ala Val Tyr Tyr Cys Gln Gln Tyr Gly
225                 230                 235                 240

Ser Trp Pro Ile Thr Phe Gly Gln Gly Thr Lys Val Glu Ile Lys Arg
                245                 250                 255


<210> SEQ ID NO 451
<211> LENGTH: 7
<212> TYPE: PRT
<213> ORGANISM: Artificial Sequence
<220> FEATURE:
<223> OTHER INFORMATION: Synthetic: UC7 VHCDR1 (Chothia)

<400> SEQUENCE: 451

Gly Asp Thr Phe Ser Ser Tyr
1               5


<210> SEQ ID NO 452
<211> LENGTH: 6
<212> TYPE: PRT
<213> ORGANISM: Artificial Sequence
<220> FEATURE:
<223> OTHER INFORMATION: Synthetic: UC7 VHCDR2 (Chothia)

<400> SEQUENCE: 452

Val Pro Val Phe Gly Ile
1               5


<210> SEQ ID NO 453
<211> LENGTH: 14
<212> TYPE: PRT
<213> ORGANISM: Artificial Sequence
<220> FEATURE:
<223> OTHER INFORMATION: Synthetic: UC7 VHCDR3 (Chothia)

<400> SEQUENCE: 453

Gln Ser Pro Tyr Val Thr Tyr Ser Ser Tyr Tyr Phe Asp Tyr
1               5                   10


<210> SEQ ID NO 454
<211> LENGTH: 12
<212> TYPE: PRT
<213> ORGANISM: Artificial Sequence
<220> FEATURE:
<223> OTHER INFORMATION: Synthetic: UC7 VLCDR1 (Chothia)

<400> SEQUENCE: 454

Arg Ala Ser Gln Ser Val Ser Asn Asn Phe Leu Ala
1               5                   10


<210> SEQ ID NO 455
```

<211> LENGTH: 7
<212> TYPE: PRT
<213> ORGANISM: Artificial Sequence
<220> FEATURE:
<223> OTHER INFORMATION: Synthetic: UC7 VLCDR2 (Chothia)

<400> SEQUENCE: 455

Asp Ala Ser Thr Arg Ala Thr
1 5

<210> SEQ ID NO 456
<211> LENGTH: 9
<212> TYPE: PRT
<213> ORGANISM: Artificial Sequence
<220> FEATURE:
<223> OTHER INFORMATION: Synthetic: UC7 VLCDR3 (Chothia)

<400> SEQUENCE: 456

Gln Gln Tyr Gly Ser Trp Pro Ile Thr
1 5

<210> SEQ ID NO 457
<211> LENGTH: 5
<212> TYPE: PRT
<213> ORGANISM: Artificial Sequence
<220> FEATURE:
<223> OTHER INFORMATION: Synthetic: UC7 VHCDR1 (Kabat)

<400> SEQUENCE: 457

Ser Tyr Gly Val Ser
1 5

<210> SEQ ID NO 458
<211> LENGTH: 17
<212> TYPE: PRT
<213> ORGANISM: Artificial Sequence
<220> FEATURE:
<223> OTHER INFORMATION: Synthetic: UC7 VHCDR2 (Kabat)

<400> SEQUENCE: 458

Arg Ile Val Pro Val Phe Gly Ile Ala Asn Tyr Ala Gln Lys Phe Gln
1 5 10 15

Gly

<210> SEQ ID NO 459
<211> LENGTH: 14
<212> TYPE: PRT
<213> ORGANISM: Artificial Sequence
<220> FEATURE:
<223> OTHER INFORMATION: Synthetic: UC7 VHCDR3 (Kabat)

<400> SEQUENCE: 459

Gln Ser Pro Tyr Val Thr Tyr Ser Ser Tyr Tyr Phe Asp Tyr
1 5 10

<210> SEQ ID NO 460
<211> LENGTH: 12
<212> TYPE: PRT
<213> ORGANISM: Artificial Sequence
<220> FEATURE:
<223> OTHER INFORMATION: Synthetic: UC7 VLCDR1 (Kabat)

<400> SEQUENCE: 460

Arg Ala Ser Gln Ser Val Ser Asn Asn Phe Leu Ala
1 5 10

<210> SEQ ID NO 461
<211> LENGTH: 7
<212> TYPE: PRT
<213> ORGANISM: Artificial Sequence
<220> FEATURE:
<223> OTHER INFORMATION: Synthetic: UC7 VLCDR2 (Kabat)

<400> SEQUENCE: 461

Asp Ala Ser Thr Arg Ala Thr
1               5

<210> SEQ ID NO 462
<211> LENGTH: 9
<212> TYPE: PRT
<213> ORGANISM: Artificial Sequence
<220> FEATURE:
<223> OTHER INFORMATION: Synthetic: UC7 VLCDR3 (Kabat)

<400> SEQUENCE: 462

Gln Gln Tyr Gly Ser Trp Pro Ile Thr
1               5

<210> SEQ ID NO 463
<211> LENGTH: 8
<212> TYPE: PRT
<213> ORGANISM: Artificial Sequence
<220> FEATURE:
<223> OTHER INFORMATION: Synthetic: UC7 VHCDR1 (IMGT)

<400> SEQUENCE: 463

Gly Asp Thr Phe Ser Ser Tyr Gly
1               5

<210> SEQ ID NO 464
<211> LENGTH: 8
<212> TYPE: PRT
<213> ORGANISM: Artificial Sequence
<220> FEATURE:
<223> OTHER INFORMATION: Synthetic: UC7 VHCDR2 (IMGT)

<400> SEQUENCE: 464

Ile Val Pro Val Phe Gly Ile Ala
1               5

<210> SEQ ID NO 465
<211> LENGTH: 16
<212> TYPE: PRT
<213> ORGANISM: Artificial Sequence
<220> FEATURE:
<223> OTHER INFORMATION: Synthetic: UC7 VHCDR3 (IMGT)

<400> SEQUENCE: 465

Ala Arg Gln Ser Pro Tyr Val Thr Tyr Ser Ser Tyr Tyr Phe Asp Tyr
1               5                   10                  15

<210> SEQ ID NO 466
<211> LENGTH: 7
<212> TYPE: PRT
<213> ORGANISM: Artificial Sequence
<220> FEATURE:
<223> OTHER INFORMATION: Synthetic: UC7 VLCDR1 (IMGT)

<400> SEQUENCE: 466

Gln Ser Val Ser Asn Asn Phe
1               5

<210> SEQ ID NO 467

<211> LENGTH: 3
<212> TYPE: PRT
<213> ORGANISM: Artificial Sequence
<220> FEATURE:
<223> OTHER INFORMATION: Synthetic: UC7 VLCDR2 (IMGT)

<400> SEQUENCE: 467

Asp Ala Ser
1

<210> SEQ ID NO 468
<211> LENGTH: 9
<212> TYPE: PRT
<213> ORGANISM: Artificial Sequence
<220> FEATURE:
<223> OTHER INFORMATION: Synthetic: UC7 VLCDR3 (IMGT)

<400> SEQUENCE: 468

Gln Gln Tyr Gly Ser Trp Pro Ile Thr
1 5

<210> SEQ ID NO 469
<211> LENGTH: 123
<212> TYPE: PRT
<213> ORGANISM: Artificial Sequence
<220> FEATURE:
<223> OTHER INFORMATION: Synthetic: UC7 VH

<400> SEQUENCE: 469

Gln Val Gln Leu Val Gln Ser Gly Ala Glu Val Lys Lys Pro Gly Ser
1 5 10 15

Ser Val Lys Val Ser Cys Lys Ala Ser Gly Asp Thr Phe Ser Ser Tyr
20 25 30

Gly Val Ser Trp Val Arg Gln Ala Pro Gly Gln Gly Leu Glu Trp Met
35 40 45

Gly Arg Ile Val Pro Val Phe Gly Ile Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gln Ser Pro Tyr Val Thr Tyr Ser Ser Tyr Tyr Phe Asp Tyr
100 105 110

Trp Gly Gln Gly Thr Leu Val Thr Val Ser Ser
115 120

<210> SEQ ID NO 470
<211> LENGTH: 108
<212> TYPE: PRT
<213> ORGANISM: Artificial Sequence
<220> FEATURE:
<223> OTHER INFORMATION: Synthetic: UC7 VL

<400> SEQUENCE: 470

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Asn Asn
20 25 30

Phe Leu Ala Trp Tyr Gln Gln Lys Pro Gly Gln Ala Pro Arg Leu Leu
35 40 45

Ile Tyr Asp Ala Ser Thr Arg Ala Thr Gly Ile Pro Asp Arg Phe Ser
50 55 60

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Trp Pro
                85                  90                  95

Ile Thr Phe Gly Gln Gly Thr Lys Val Glu Ile Lys
            100                 105


<210> SEQ ID NO 471
<211> LENGTH: 256
<212> TYPE: PRT
<213> ORGANISM: Artificial Sequence
<220> FEATURE:
<223> OTHER INFORMATION: Synthetic: UC 8 (9-2A4) scFv

<400> SEQUENCE: 471

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Asn Tyr
            20                  25                  30

Gly Phe Ser Trp Val Arg Gln Ala Pro Gly Gln Gly Leu Glu Trp Met
        35                  40                  45

Gly Gly Ile Val Pro Val Phe Gly Ile Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Tyr Tyr Pro Asp Asp Pro Arg Tyr Phe Glu Tyr
            100                 105                 110

Trp Gly Gln Gly Thr Leu Val Thr Val Ser Ser Ala Ser Ser Gly Gly
        115                 120                 125

Ser Thr Ser Gly Ser Gly Lys Pro Gly Ser Gly Glu Gly Ser Ser Gly
    130                 135                 140

Ser Ala Arg Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175

Ser Ser Thr Phe Leu Ala Trp Tyr Gln Gln Lys Pro Gly Gln Ala Pro
            180                 185                 190

Arg Leu Leu Ile Tyr Ala Ala Ser Ser Arg Ala Thr Gly Ile Pro Asp
        195                 200                 205

Arg Phe Ser Gly Ser Gly Ser Gly Thr Asp Phe Thr Leu Thr Ile Ser
    210                 215                 220

Arg Leu Glu Pro Glu Asp Phe Ala Val Tyr Tyr Cys Gln Gln Tyr Gly
225                 230                 235                 240

Ser Trp Pro Leu Thr Phe Gly Gln Gly Thr Lys Val Glu Ile Lys Arg
                245                 250                 255


<210> SEQ ID NO 472
<211> LENGTH: 7
<212> TYPE: PRT
<213> ORGANISM: Artificial Sequence
<220> FEATURE:
<223> OTHER INFORMATION: Synthetic: UC8 VHCDR1 (Chothia)

<400> SEQUENCE: 472

Gly Asp Thr Phe Ser Asn Tyr
```

1 5

<210> SEQ ID NO 473
<211> LENGTH: 6
<212> TYPE: PRT
<213> ORGANISM: Artificial Sequence
<220> FEATURE:
<223> OTHER INFORMATION: Synthetic: UC8 VHCDR2 (Chothia)

<400> SEQUENCE: 473

Val Pro Val Phe Gly Ile
1 5

<210> SEQ ID NO 474
<211> LENGTH: 14
<212> TYPE: PRT
<213> ORGANISM: Artificial Sequence
<220> FEATURE:
<223> OTHER INFORMATION: Synthetic: UC8 VHCDR3 (Chothia)

<400> SEQUENCE: 474

Asp Tyr Ser Tyr Tyr Pro Asp Asp Pro Arg Tyr Phe Glu Tyr
1 5 10

<210> SEQ ID NO 475
<211> LENGTH: 12
<212> TYPE: PRT
<213> ORGANISM: Artificial Sequence
<220> FEATURE:
<223> OTHER INFORMATION: Synthetic: UC8 VLCDR1 (Chothia)

<400> SEQUENCE: 475

Arg Ala Ser Gln Ser Val Ser Ser Thr Phe Leu Ala
1 5 10

<210> SEQ ID NO 476
<211> LENGTH: 7
<212> TYPE: PRT
<213> ORGANISM: Artificial Sequence
<220> FEATURE:
<223> OTHER INFORMATION: Synthetic: UC8 VLCDR2 (Chothia)

<400> SEQUENCE: 476

Ala Ala Ser Ser Arg Ala Thr
1 5

<210> SEQ ID NO 477
<211> LENGTH: 9
<212> TYPE: PRT
<213> ORGANISM: Artificial Sequence
<220> FEATURE:
<223> OTHER INFORMATION: Synthetic: UC8 VLCDR3 (Chothia)

<400> SEQUENCE: 477

Gln Gln Tyr Gly Ser Trp Pro Leu Thr
1 5

<210> SEQ ID NO 478
<211> LENGTH: 5
<212> TYPE: PRT
<213> ORGANISM: Artificial Sequence
<220> FEATURE:
<223> OTHER INFORMATION: Synthetic: UC8 VHCDR1 (Kabat)

<400> SEQUENCE: 478

Asn Tyr Gly Phe Ser
1 5

<210> SEQ ID NO 479
<211> LENGTH: 17
<212> TYPE: PRT
<213> ORGANISM: Artificial Sequence
<220> FEATURE:
<223> OTHER INFORMATION: Synthetic: UC8 VHCDR2 (Kabat)

<400> SEQUENCE: 479

Gly Ile Val Pro Val Phe Gly Ile Ala Thr Tyr Ala Gln Lys Phe Gln
1 5 10 15

Gly

<210> SEQ ID NO 480
<211> LENGTH: 14
<212> TYPE: PRT
<213> ORGANISM: Artificial Sequence
<220> FEATURE:
<223> OTHER INFORMATION: Synthetic: UC8 VHCDR3 (Kabat)

<400> SEQUENCE: 480

Asp Tyr Ser Tyr Tyr Pro Asp Asp Pro Arg Tyr Phe Glu Tyr
1 5 10

<210> SEQ ID NO 481
<211> LENGTH: 12
<212> TYPE: PRT
<213> ORGANISM: Artificial Sequence
<220> FEATURE:
<223> OTHER INFORMATION: Synthetic: UC8 VLCDR1 (Kabat)

<400> SEQUENCE: 481

Arg Ala Ser Gln Ser Val Ser Ser Thr Phe Leu Ala
1 5 10

<210> SEQ ID NO 482
<211> LENGTH: 7
<212> TYPE: PRT
<213> ORGANISM: Artificial Sequence
<220> FEATURE:
<223> OTHER INFORMATION: Synthetic: UC8 VLCDR2 (Kabat)

<400> SEQUENCE: 482

Ala Ala Ser Ser Arg Ala Thr
1 5

<210> SEQ ID NO 483
<211> LENGTH: 9
<212> TYPE: PRT
<213> ORGANISM: Artificial Sequence
<220> FEATURE:
<223> OTHER INFORMATION: Synthetic: UC8 VLCDR3 (Kabat)

<400> SEQUENCE: 483

Gln Gln Tyr Gly Ser Trp Pro Leu Thr
1 5

<210> SEQ ID NO 484
<211> LENGTH: 8
<212> TYPE: PRT
<213> ORGANISM: Artificial Sequence
<220> FEATURE:
<223> OTHER INFORMATION: Synthetic: UC8 VHCDR1 (IMGT)

<400> SEQUENCE: 484

Gly Asp Thr Phe Ser Asn Tyr Gly 1 5

<210> SEQ ID NO 485
<211> LENGTH: 8
<212> TYPE: PRT
<213> ORGANISM: Artificial Sequence
<220> FEATURE:
<223> OTHER INFORMATION: Synthetic: UC8 VHCDR2 (IMGT)

<400> SEQUENCE: 485

Ile Val Pro Val Phe Gly Ile Ala
1 5

<210> SEQ ID NO 486
<211> LENGTH: 16
<212> TYPE: PRT
<213> ORGANISM: Artificial Sequence
<220> FEATURE:
<223> OTHER INFORMATION: Synthetic: UC8 VHCDR3 (IMGT)

<400> SEQUENCE: 486

Ala Arg Asp Tyr Ser Tyr Tyr Pro Asp Asp Pro Arg Tyr Phe Glu Tyr
1 5 10 15

<210> SEQ ID NO 487
<211> LENGTH: 7
<212> TYPE: PRT
<213> ORGANISM: Artificial Sequence
<220> FEATURE:
<223> OTHER INFORMATION: Synthetic: UC8 VLCDR1 (IMGT)

<400> SEQUENCE: 487

Gln Ser Val Ser Ser Thr Phe
1 5

<210> SEQ ID NO 488
<211> LENGTH: 3
<212> TYPE: PRT
<213> ORGANISM: Artificial Sequence
<220> FEATURE:
<223> OTHER INFORMATION: Synthetic: UC8 VLCDR2 (IMGT)

<400> SEQUENCE: 488

Ala Ala Ser
1

<210> SEQ ID NO 489
<211> LENGTH: 9
<212> TYPE: PRT
<213> ORGANISM: Artificial Sequence
<220> FEATURE:
<223> OTHER INFORMATION: Synthetic: UC8 VLCDR3 (IMGT)

<400> SEQUENCE: 489

Gln Gln Tyr Gly Ser Trp Pro Leu Thr
1 5

<210> SEQ ID NO 490
<211> LENGTH: 123
<212> TYPE: PRT
<213> ORGANISM: Artificial Sequence
<220> FEATURE:
<223> OTHER INFORMATION: Synthetic: UC8 VH

<400> SEQUENCE: 490

Gln Val Gln Leu Val Gln Ser Gly Ala Glu Val Lys Lys Pro Gly Ser
1 5 10 15

Ser Val Lys Val Ser Cys Lys Ala Ser Gly Asp Thr Phe Ser Asn Tyr
20 25 30

Gly Phe Ser Trp Val Arg Gln Ala Pro Gly Gln Gly Leu Glu Trp Met
35 40 45

Gly Gly Ile Val Pro Val Phe Gly Ile Ala Thr Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Tyr Ser Tyr Tyr Pro Asp Asp Pro Arg Tyr Phe Glu Tyr
100 105 110

Trp Gly Gln Gly Thr Leu Val Thr Val Ser Ser
115 120

<210> SEQ ID NO 491
<211> LENGTH: 108
<212> TYPE: PRT
<213> ORGANISM: Artificial Sequence
<220> FEATURE:
<223> OTHER INFORMATION: Synthetic: UC8 VL

<400> SEQUENCE: 491

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Thr
20 25 30

Phe Leu Ala Trp Tyr Gln Gln Lys Pro Gly Gln Ala Pro Arg Leu Leu
35 40 45

Ile Tyr Ala Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Trp Pro
85 90 95

Leu Thr Phe Gly Gln Gly Thr Lys Val Glu Ile Lys
100 105

<210> SEQ ID NO 492
<211> LENGTH: 108
<212> TYPE: PRT
<213> ORGANISM: Artificial Sequence
<220> FEATURE:
<223> OTHER INFORMATION: Synthetic

<400> SEQUENCE: 492

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Thr Asn Phe
20 25 30

Leu Asn Trp Tyr Gln Gln Lys Pro Gly Lys Ala Pro Lys Leu Leu Ile
35 40 45

Tyr Asp Ala Ser Thr Leu Gln Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Ser Asp Ser Tyr Pro Ile

-continued

```
                85                  90                  95

Thr Phe Gly Gln Gly Thr Lys Val Glu Ile Lys Arg
            100                 105


<210> SEQ ID NO 493
<211> LENGTH: 108
<212> TYPE: PRT
<213> ORGANISM: Artificial Sequence
<220> FEATURE:
<223> OTHER INFORMATION: Synthetic

<400> SEQUENCE: 493

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Phe
            20                  25                  30

Leu Asn Trp Tyr Gln Gln Lys Pro Gly Lys Ala Pro Lys Leu Leu Ile
        35                  40                  45

Tyr Asp Ala Ser Arg Arg Arg Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Ser Tyr Pro Ile
                85                  90                  95

Thr Phe Gly Gln Gly Thr Lys Val Glu Ile Lys Arg
            100                 105
```